(12) United States Patent
Moon

(10) Patent No.: US 10,927,103 B1
(45) Date of Patent: Feb. 23, 2021

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventor: Doo-Hyeon Moon, Gyeonggi-do (KR)

(73) Assignee: Rohm and Haas Electronic Materials Korea Ltd., Seoul (KR)

(*) Notice: Subject to any disclaimer, the term of this patent is extended or adjusted under 35 U.S.C. 154(b) by 0 days.

(21) Appl. No.: 16/897,422

(22) Filed: Jun. 10, 2020

Related U.S. Application Data

(62) Division of application No. 16/088,919, filed as application No. PCT/KR2017/002823 on Mar. 16, 2017.

(30) Foreign Application Priority Data

Apr. 8, 2016 (KR) .......... 10-2016-0043403
Feb. 24, 2017 (KR) .......... 10-2017-0024534

(51) Int. Cl.
| | | |
|---|---|---|
| *C07D 413/10* | (2006.01) | |
| *C07D 417/10* | (2006.01) | |
| *C09K 11/06* | (2006.01) | |
| *H01L 51/54* | (2006.01) | |
| *H01L 51/00* | (2006.01) | |
| *H01L 51/50* | (2006.01) | |

(52) U.S. Cl.
CPC ......... *C07D 413/10* (2013.01); *C07D 417/10* (2013.01); *C09K 11/06* (2013.01); *H01L 51/0067* (2013.01); *H01L 51/0071* (2013.01); *H01L 51/5056* (2013.01)

(58) Field of Classification Search
CPC .... C07D 417/10; C07D 413/10; C09K 11/06; H01L 51/0067; H01L 51/0071; H01L 51/5066
USPC .......... 544/150, 217; 548/150, 217
See application file for complete search history.

(56) References Cited

U.S. PATENT DOCUMENTS

| | | |
|---|---|---|
| 7,420,065 B2 | 9/2008 | Yoshida et al. |
| 9,136,481 B2 | 9/2015 | Kang et al. |
| 9,163,004 B2 | 10/2015 | Kwak et al. |
| 2005/0007938 A1 | 1/2005 | Shinotsuka |
| 2009/0278115 A1 | 11/2009 | Hosokawa et al. |
| 2012/0031309 A1 | 2/2012 | Buckland et al. |
| 2018/0258053 A1 | 9/2018 | Wendeborn et al. |
| 2019/0148645 A1* | 5/2019 | Moon ............... C07D 417/10 544/216 |

FOREIGN PATENT DOCUMENTS

| | | |
|---|---|---|
| EP | 1593675 A1 | 11/2009 |
| KR | 10-2015-0136033 A1 | 12/2004 |

OTHER PUBLICATIONS

Atzrodt et al. Angew. Chem. Int. Ed. 2007, 46, 7744-7765.*
Supplementary European Search Report for EPO application No. 17779286.8; dated Mar. 16, 2017.

* cited by examiner

Primary Examiner — Venkataraman Balasubramanian
(74) Attorney, Agent, or Firm — S. Matthew Cairns

(57) ABSTRACT

The present disclosure relates to an organic electroluminescent compound and an organic electroluminescent device comprising the same. The organic electroluminescent compound of the present disclosure provides an organic electroluminescent device having high efficiency and/or long lifespan.

9 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting device with the advantages of providing a wider viewing angle, a greater contrast ratio, and a faster response time. The first organic EL device was developed by Eastman Kodak, by using small aromatic diamine molecules and aluminum complexes as materials for forming a light-emitting layer (see Appl. Phys. Lett. 51, 913, 1987).

An organic EL device changes electric energy into light by the injection of a charge into an organic light-emitting material, and commonly comprises an anode, a cathode, and an organic layer formed between the two electrodes. The organic layer of the organic EL device may be composed of a hole injection layer, a hole transport layer, an electron blocking layer, a light-emitting layer (containing host and dopant materials), an electron buffer layer, a hole blocking layer, an electron transport layer, an electron injection layer, etc.; the materials used in the organic layer can be classified into a hole injection material, a hole transport material, an electron blocking material, a light-emitting material, an electron buffer material, a hole blocking material, an electron transport material, an electron injection material, etc., depending on functions. In the organic EL device, holes from an anode and electrons from a cathode are injected into a light-emitting layer by electric voltage, and an exciton having high energy is produced by the recombination of the holes and electrons. The organic light-emitting compound moves into an excited state by the energy and emits light from energy when the organic light-emitting compound returns to the ground state from the excited state.

The most important factor determining luminous efficiency in an organic EL device is light-emitting materials. The light-emitting materials are required to have the following features: high quantum efficiency, high movement degree of an electron and a hole, and uniformity and stability of the formed light-emitting material layer. The light-emitting material is classified into blue, green, and red light-emitting materials according to the light-emitting color, and further includes yellow or orange light-emitting materials. Furthermore, the light-emitting material is classified into a host material and a dopant material in a functional aspect. Recently, an urgent task is the development of an organic EL device having high efficiency and/or long lifespan. In particular, the development of highly excellent light-emitting material over conventional materials is urgently required, considering the EL properties necessary for medium- and large-sized OLED panels. For this, preferably, as a solvent in a solid state and an energy transmitter, a host material should have high purity and a suitable molecular weight in order to be deposited under vacuum. Furthermore, a host material is required to have high glass transition temperature and pyrolysis temperature for guaranteeing thermal stability, high electrochemical stability for long lifespan, easy formability of an amorphous thin film, good adhesion with adjacent layers, and no movement between layers.

Further, the electron buffer layer is equipped to improve a problem of light-emitting luminance reduction which may occur due to the change of current properties in the device when the device is exposed to a high temperature during a process of producing panels. Thus, the properties of the compounds comprised in the electron buffer layer are important. In addition, the compound used for the electron buffer layer performs a role of controlling an electron injection by the electron withdrawing characteristics and the electron affinity LUMO (lowest unoccupied molecular orbital) energy level, and thus performs a role to improve the efficiency and lifespan of the organic electroluminescent device.

Meanwhile, in an organic EL device, an electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as $Alq_3$ are excellent in transporting electrons, and thus have been conventionally used as an electron transport material. However, $Alq_3$ has problems in that it moves to other layers and shows reduction of color purity when used in blue light-emitting devices. Therefore, new electron transport materials have been required, which do not have the above problems, are highly electron-affinitive, and quickly transport electrons in organic EL devices to provide organic EL devices having high luminous efficiency.

Korean Patent No. 1297158 discloses a compound wherein a heteroaryl is bonded to a carbon position other than a naphthalene ring in a naphthoxazole structure via an arylene as a linker; Korean Patent Appln. Laying-Open No. KR 2008-0028424 A discloses a naphthoimidazole derivative; European Patent Application Publication No. EP 1593675 A1 discloses a compound wherein an amine is bonded to a carbon position of a benzene ring, which is directly fused with an oxazole in a naphthoxazole structure, via arylene as a linker; and Korean Patent No. 1202349 discloses a benzoindene derivative. However, the above references fail to disclose a compound wherein a heteroaryl is bonded to a carbon position of a benzene ring, which is not directly fused with an oxazole in a naphthoxazole structure, directly or via an arylene as a linker.

In addition, Korean Patent Appln. Laying-Open No. KR 2015-0136033 A discloses a compound wherein a heteroaryl is bonded to a carbon position of a benzene ring, which is not directly fused with an oxazole in a naphthoxazole structure, directly or via an arylene as a linker. However, the compound disclosed in KR 2015-0136033 A is different from the compound of the present disclosure in the position of the substituents.

DISCLOSURE OF THE INVENTION

Problems to be Solved

The objective of the present disclosure is to provide an organic electroluminescent compound effective to produce an organic electroluminescent device having relatively low driving voltage and/or excellent luminous efficiency.

Solution to Problems

The present inventors found that the above objective can be achieved by an organic electroluminescent compound represented by the following formula 1:

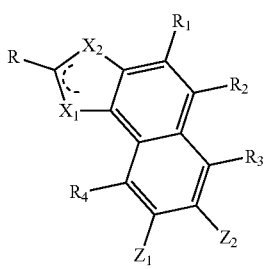

(1)

wherein $X_1$ and $X_2$ each independently represent N, O, or S, with the proviso, when $X_1$ represents N, $X_2$ represents O or S, and when $X_1$ represents O or S, $X_2$ represents N;

$Z_1$ and $Z_2$ each independently represent hydrogen, deuterium, or -$L_1$-Het, with the proviso, at least one of $Z_1$ and $Z_2$ represents -$L_1$-Het;

R represents a substituted or unsubstituted (C6-C30)aryl, or a substituted or unsubstituted 3- to 30-membered heteroaryl;

$R_1$ to $R_4$ each independently represent hydrogen, deuterium, a substituted or unsubstituted (C1-C10)alkyl, a substituted or unsubstituted (C6-C30)aryl, or a substituted or unsubstituted 3- to 30-membered heteroaryl;

$L_1$ represents a direct bond, a substituted or unsubstituted (C6-C30)arylene, or a substituted or unsubstituted 3- to 30-membered heteroarylene;

Het represents a substituted or unsubstituted 3- to 30-membered heteroaryl; and the heteroaryl(ene) contains at least one heteroatom selected from B, N, O, S, Si, and P.

Effects of the Invention

By using the organic electroluminescent compound according to the present disclosure, an organic EL device with relatively low driving voltage and/or excellent luminous efficiency is provided. The organic electroluminescent compound according to the present disclosure may be used as an electron buffer material to provide an organic EL device with excellent driving voltage and/or luminous efficiency characteristics, and it may be used as an electron transport material to provide excellent effects in driving voltage, luminous efficiency, and/or in an aspect of color coordinates of a device. In addition, the organic electroluminescent compound according to the present disclosure may also be used as a phosphorescent host.

EMBODIMENTS OF THE INVENTION

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound represented by formula 1 may be comprised in at least one layer constituting an organic electroluminescent device, and may be comprised in an electron buffer layer as an electron buffer material and/or an electron transport layer as an electron transport material, but is not limited thereto.

Hereinafter, the organic electroluminescent compound represented by formula 1 will be described in detail.

Herein, "(C1-C30)alkyl" is meant to be a linear or branched alkyl having 1 to 30 carbon atoms constituting the chain, in which the number of carbon atoms is preferably 1 to 10, more preferably 1 to 6, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "3- to 7-membered heterocycloalkyl" is a cycloalkyl having at least one heteroatom selected from the group consisting of B, N, O, S, Si, and P, preferably O, S, and N, and 3 to 7 ring backbone atoms, and includes tetrahydrofuran, pyrrolidine, thiolan, tetrahydropyran, etc. "(C6-C30)aryl(ene)" is a monocyclic or fused ring derived from an aromatic hydrocarbon having 6 to 30 ring backbone carbon atoms, in which the number of ring backbone carbon atoms is preferably 6 to 20, more preferably 6 to 15, and includes phenyl, biphenyl, terphenyl, naphthyl, binaphthyl, phenylnaphthyl, naphthyl phenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc. "3- to 30-membered heteroaryl(ene)" is an aryl group having at least one, preferably 1 to 4 heteroatoms selected from the group consisting of B, N, O, S, Si, and P, and 3 to 30 ring backbone atoms, in which the number of ring backbone atoms is preferably 3 to 20, more preferably 5 to 15; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzonaphthothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Halogen" includes F, Cl, Br, and I.

The compound of formula 1 may be represented by the following formula 2 or 3:

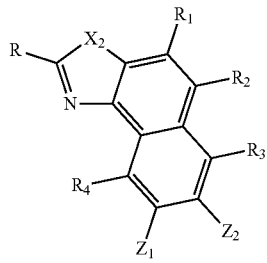
(2)

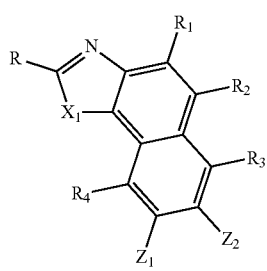
(3)

wherein $X_1$, $X_2$, $Z_1$, $Z_2$, R, and $R_1$ to $R_4$ are as defined in formula 1.

Also, the compound of formula 2 or 3 may be represented by any one of the following formulae 4 to 7:

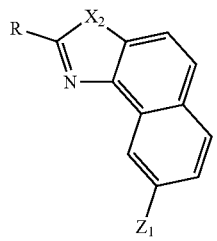
(4)

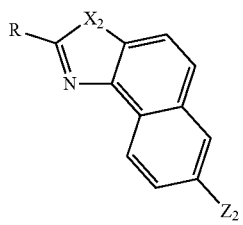
(5)

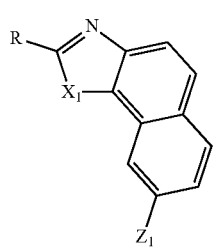
(6)

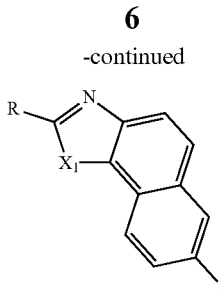
(7)

wherein $X_1$, $X_2$, $Z_1$, $Z_2$, and R are as defined in formula 1.

Herein, "substituted" in the expression "substituted or unsubstituted" means that a hydrogen atom in a certain functional group is replaced with another atom or functional group, i.e., a substituent. The substituents of the substituted alkyl, the substituted aryl(ene), and the substituted heteroaryl(ene) in R, $R_1$ to $R_4$, $L_1$, and Het in formula 1 each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a 3- to 30-membered heteroaryl, a tri(C1-C30)alkylsilyl, a tri(C6-C30)arylsilyl, a di(C1-C30)alkyl(C6-C30)arylsilyl, a (C1—C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl; and preferably each independently are a (C1-C6)alkyl or a (C6-C12)aryl.

In formula 1, $X_1$ and $X_2$ each independently represent N, O, or S, with the proviso, when $X_1$ represents N, $X_2$ represents O or S, and when $X_1$ represents O or S, $X_2$ represents N.

$Z_1$ and $Z_2$ each independently represent hydrogen, deuterium, or -$L_1$-Het, with the proviso, at least one of $Z_1$ and $Z_2$ represents -$L_1$-Het.

R represents a substituted or unsubstituted (C6-C30)aryl, or a substituted or unsubstituted 3- to 30-membered heteroaryl; preferably represents a substituted or unsubstituted (C6-C18)aryl, or a substituted or unsubstituted 5- to 18-membered heteroaryl; and more preferably represents an unsubstituted (C6-C18)aryl, or an unsubstituted 5- to 18-membered heteroaryl.

$R_1$ to $R_4$ each independently represent hydrogen, deuterium, a substituted or unsubstituted (C1-C10)alkyl, a substituted or unsubstituted (C6-C30)aryl, or a substituted or unsubstituted 3- to 30-membered heteroaryl; and preferably each independently represent hydrogen.

$L_1$ represents a direct bond, a substituted or unsubstituted (C6-C30)arylene, or a substituted or unsubstituted 3- to 30-membered heteroarylene; preferably represents a direct bond, a substituted or unsubstituted (C6-C18)arylene, or a substituted or unsubstituted 5- to 18-membered heteroarylene; and more preferably represents a direct bond, a (C6-C18)arylene unsubstituted or substituted with a (C1-C6)alkyl, or an unsubstituted 5- to 18-membered heteroarylene.

Het represents a substituted or unsubstituted 3- to 30-membered heteroaryl; preferably represents a substituted or unsubstituted 5- to 18-membered heteroaryl; and more preferably represents a 5- to 18-membered heteroaryl unsubstituted or substituted with a (C6-C12)aryl.

Specifically, Het may be a substituted or unsubstituted pyridine, a substituted or unsubstituted pyrimidine, a substituted or unsubstituted triazine, a substituted or unsubstituted quinoline, a substituted or unsubstituted isoquinoline, a substituted or unsubstituted quinazoline, a substituted or unsubstituted quinoxaline, a substituted or unsubstituted triazole, a substituted or unsubstituted pyrazole, a substituted or unsubstituted benzofuran, a substituted or unsubstituted dibenzofuran, a substituted or unsubstituted benzothiophene, or a substituted or unsubstituted dibenzothiophene.

According to one embodiment of the present disclosure, in formula 1, $X_1$ and $X_2$ each independently represent N, O, or S, with the proviso, when $X_1$ represents N, $X_2$ represents O or S, and when $X_1$ represents O or S, $X_2$ represents N; $Z_1$ and $Z_2$ each independently represent hydrogen or -$L_1$-Het, with the proviso, at least one of $Z_1$ and $Z_2$ represents -$L_1$-Het; R represents a substituted or unsubstituted (C6-C18)aryl, or a substituted or unsubstituted 5- to 18-membered heteroaryl; $R_1$ to $R_4$ each independently represent hydrogen; $L_1$ represents a direct bond, a substituted or unsubstituted (C6-C18)arylene, or a substituted or unsubstituted 5- to 18-membered heteroarylene; and Het represents a substituted or unsubstituted 5- to 18-membered heteroaryl.

According to another embodiment of the present disclosure, in formula 1, $X_1$ and $X_2$ each independently represent N, O, or S, with the proviso, when $X_1$ represents N, $X_2$ represents O or S, and when $X_1$ represents O or S, $X_2$ represents N; $Z_1$ and $Z_2$ each independently represent hydrogen or -$L_1$-Het, with the proviso, at least one of $Z_1$ and $Z_2$ represents -$L_1$-Het; R represents an unsubstituted (C6-C18)aryl, or an unsubstituted 5- to 18-membered heteroaryl; $R_1$ to $R_4$ each independently represent hydrogen; $L_1$ represents a direct bond, a (C6-C18)arylene unsubstituted or substituted with a (C1-C6)alkyl, or an unsubstituted 5- to 18-membered heteroarylene; and Het represents a 5- to 18-membered heteroaryl unsubstituted or substituted with a (C6-C12)aryl.

The organic electroluminescent compound represented by formula 1 may be selected from the group consisting of the following compounds, but is not limited thereto:

C-1

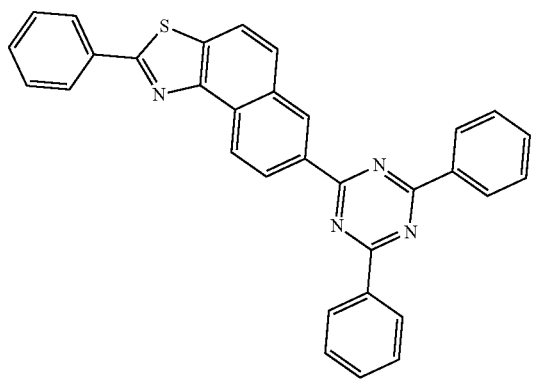

-continued

C-2

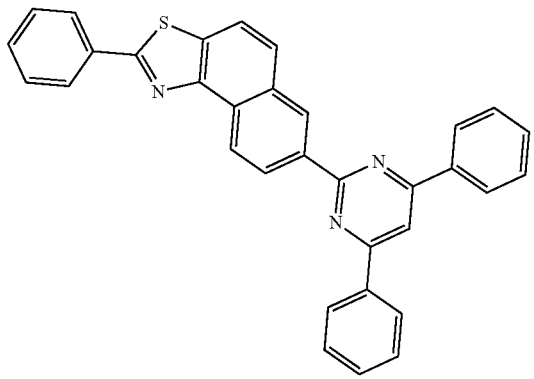

C-3

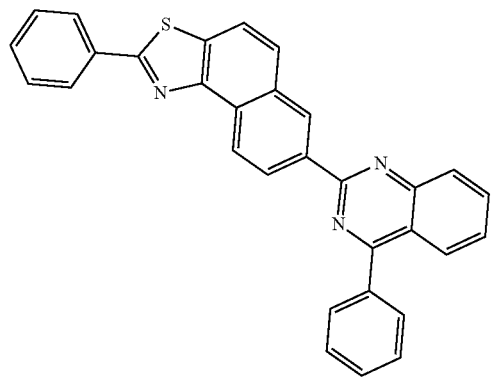

C-4

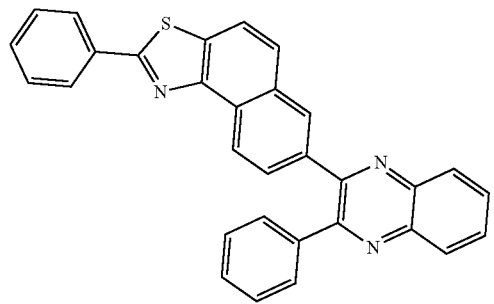

C-5

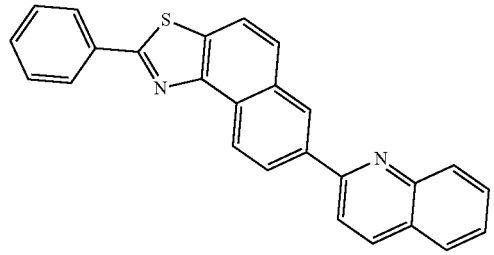

C-6

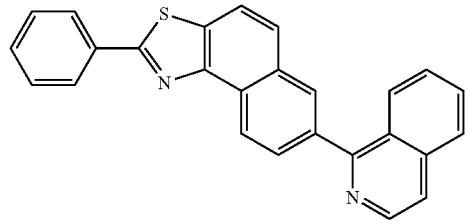

C-7
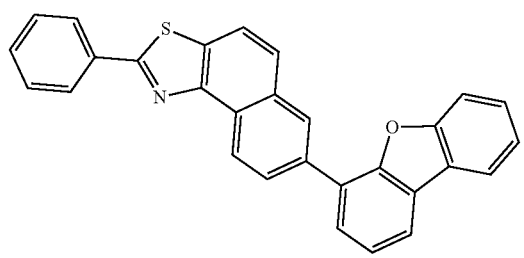
C-8
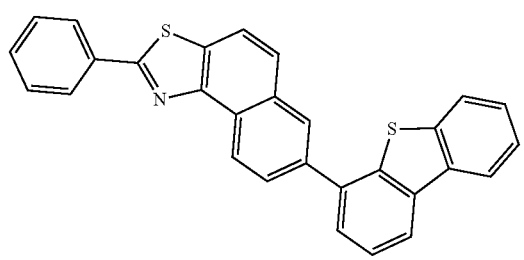
C-9
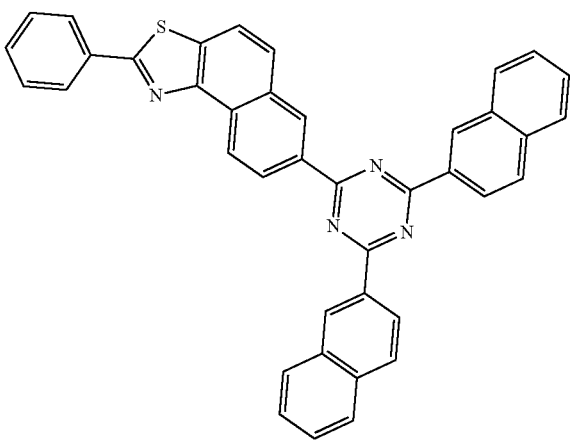
C-10
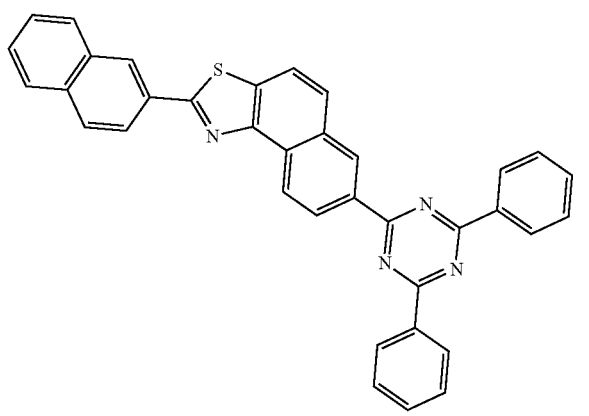
C-11
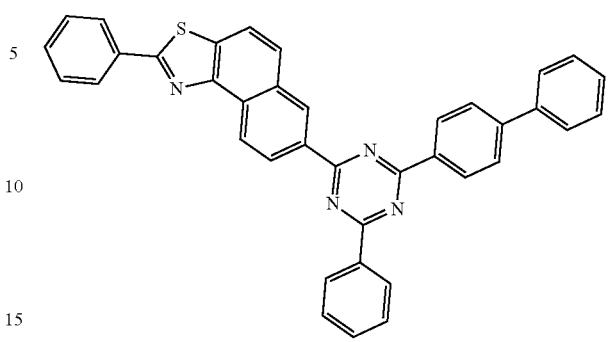
C-12
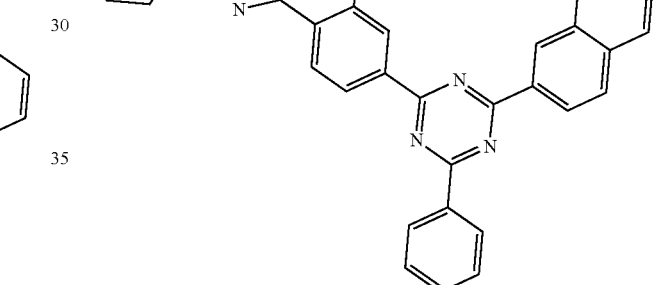
C-13
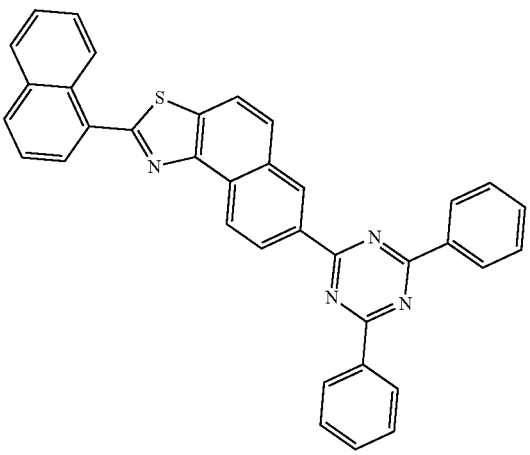

-continued
C-14
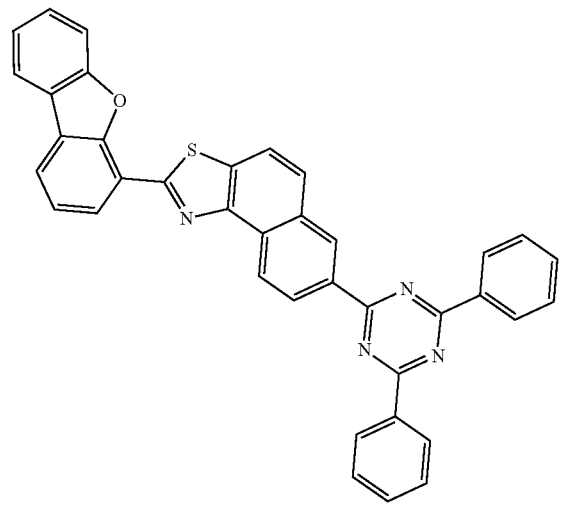
C-15
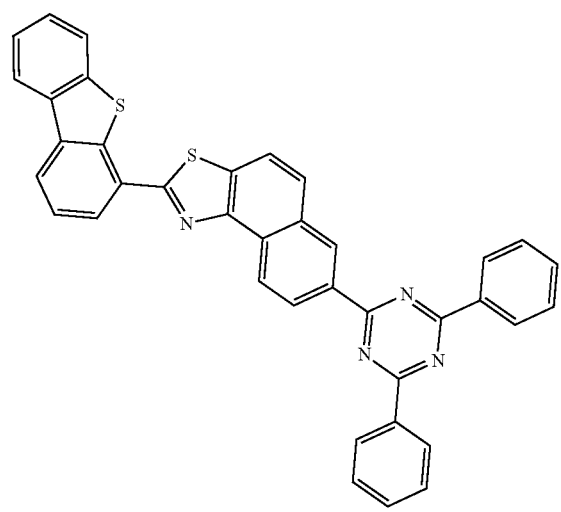
C-16
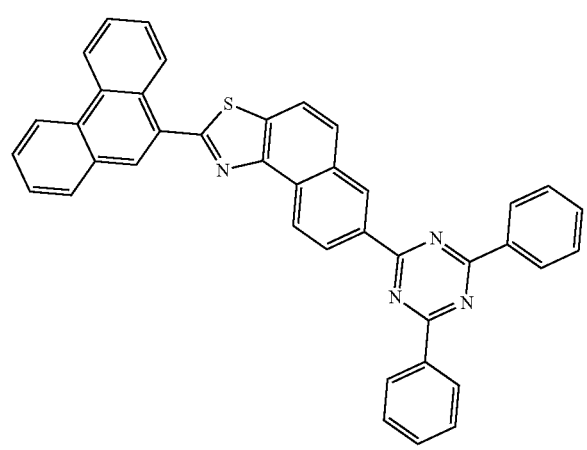
-continued
C-17
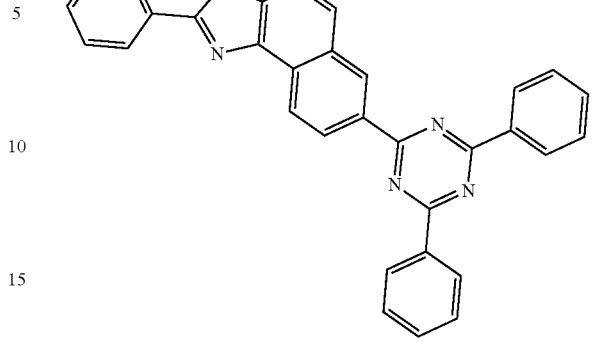
C-18
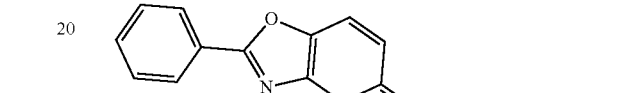
C-19
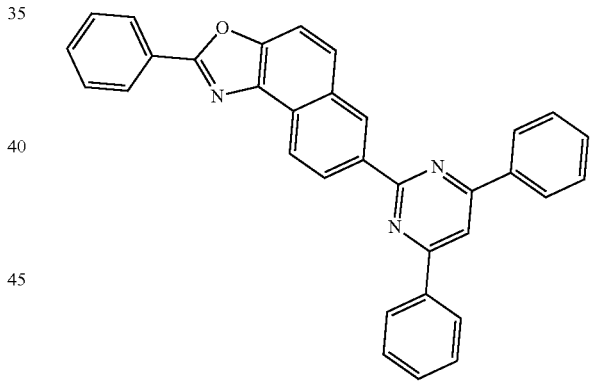
C-20
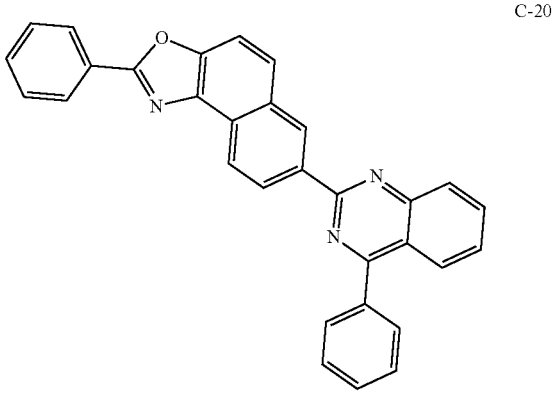

C-21
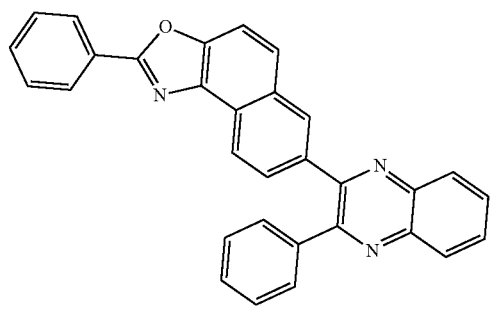
C-22
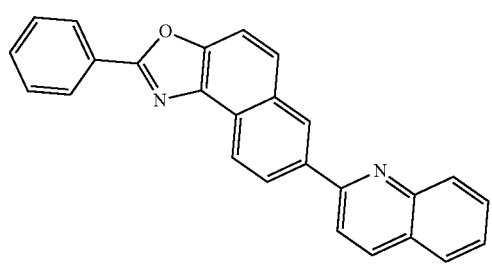
C-23
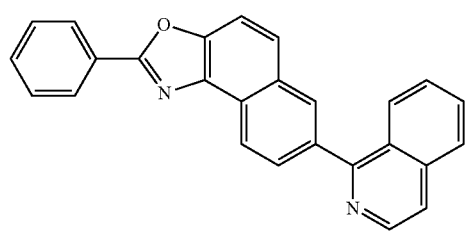
C-24
C-25
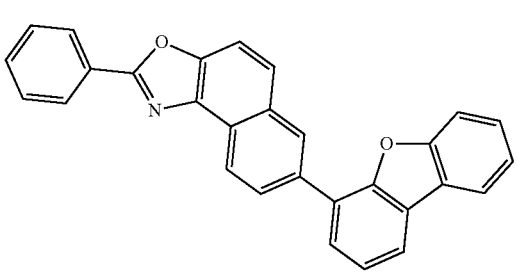
C-26
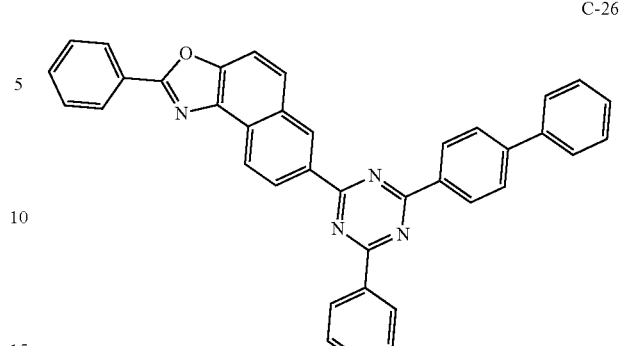
C-27
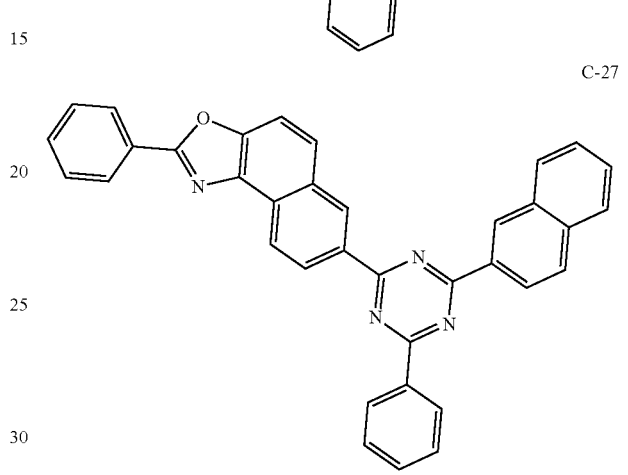
C-28
C-29
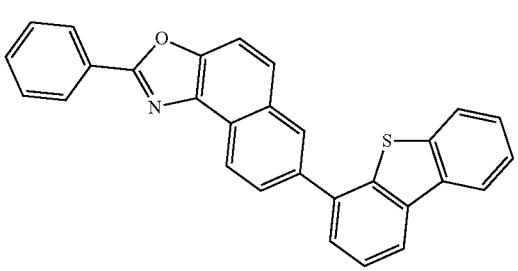

-continued
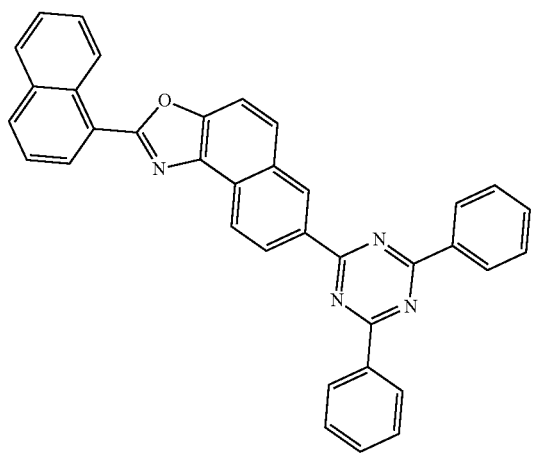
C-30
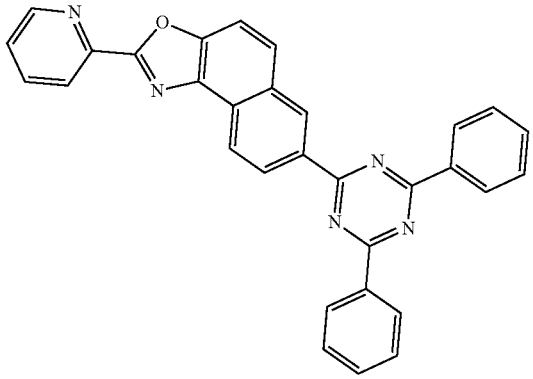
C-33
C-31
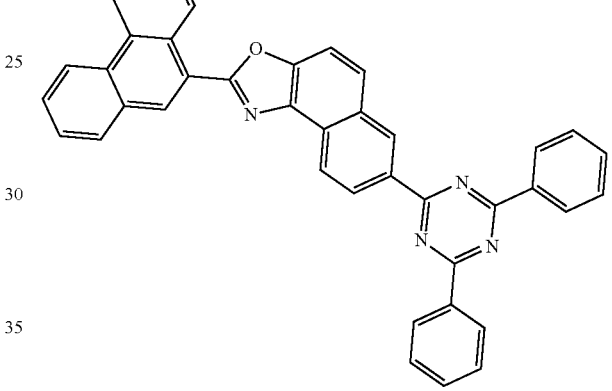
C-34
C-32
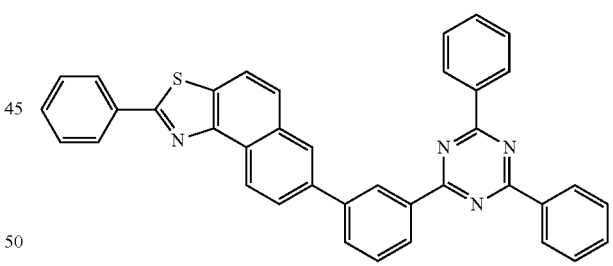
C-35
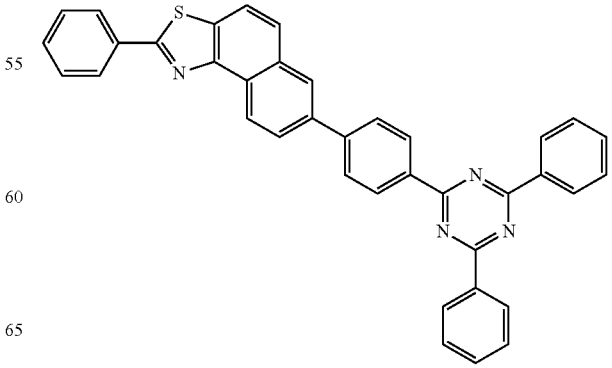
C-36

C-37
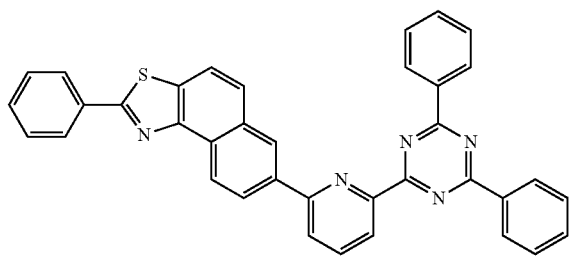
C-38
C-39
C-40
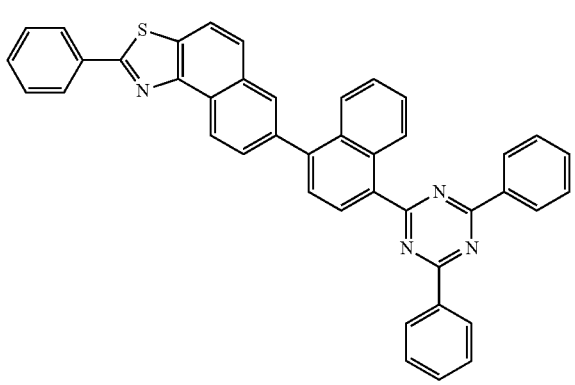
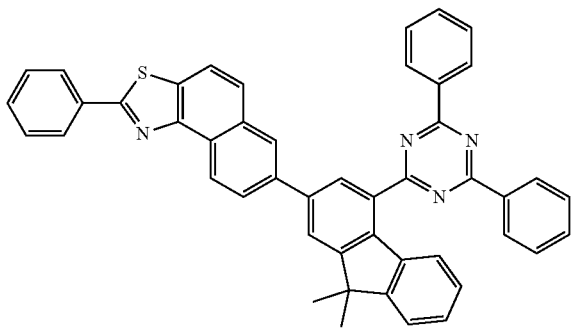
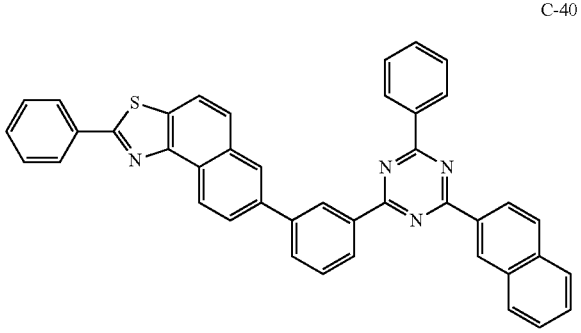
C-41
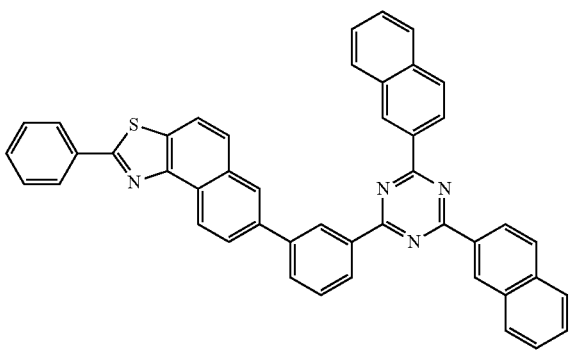
C-42
C-43
C-44

-continued
C-45
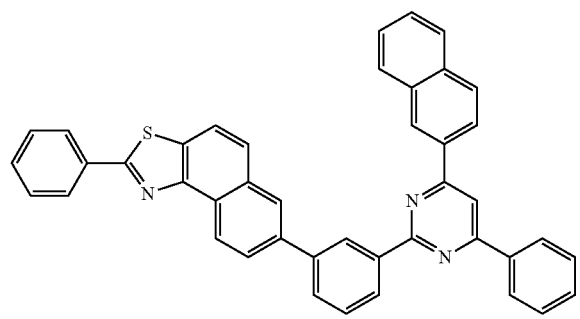
C-46
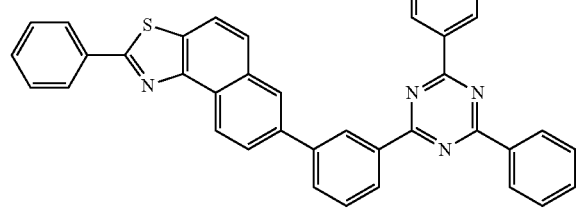
C-47
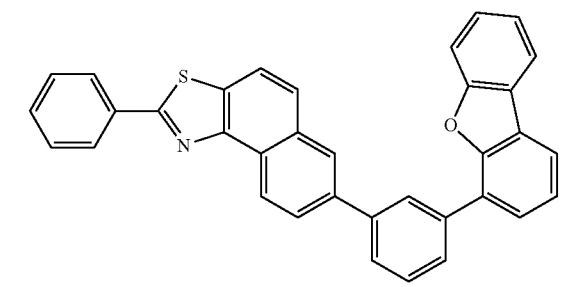
C-48
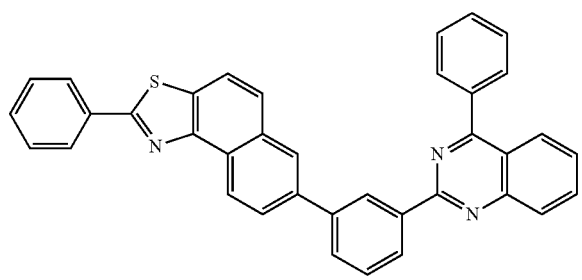
C-49
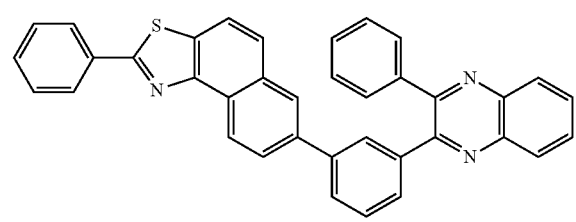
-continued
C-50
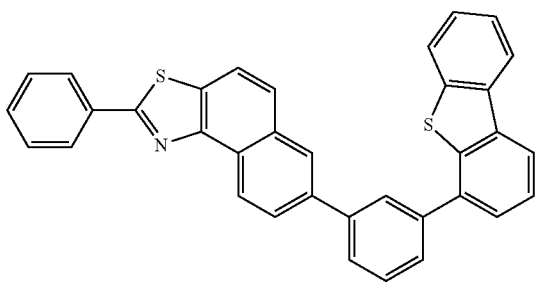
C-51
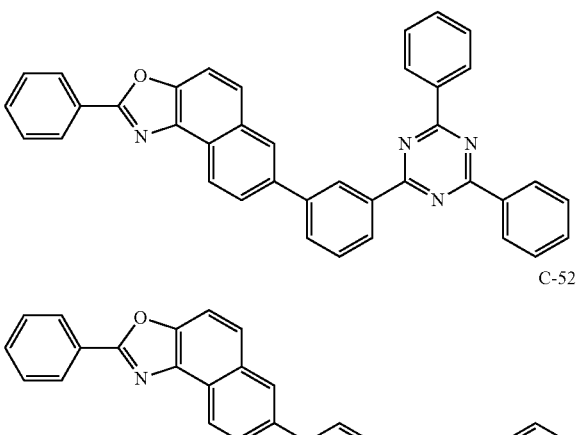
C-52
C-53
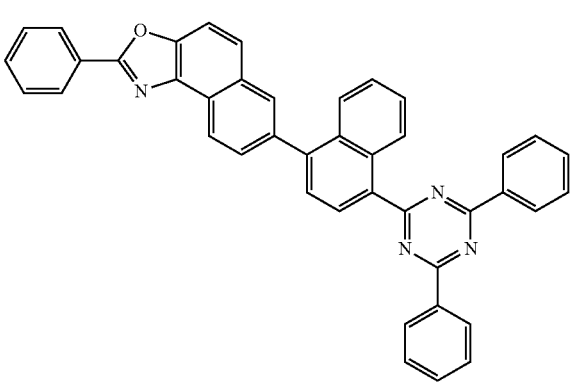
C-54
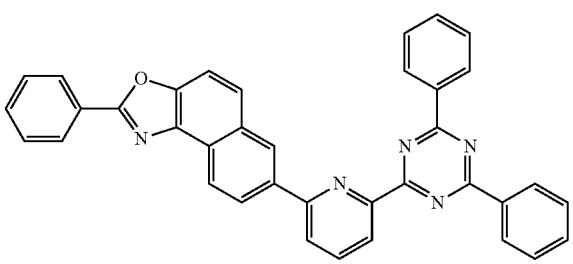

C-55
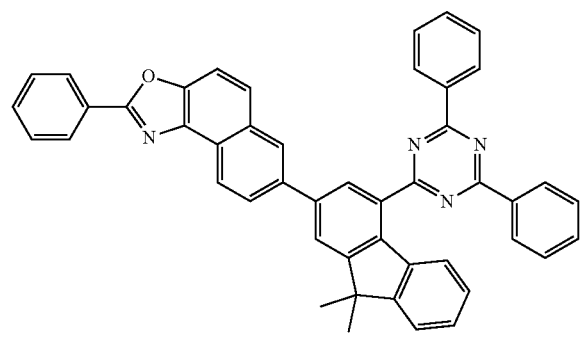
C-59
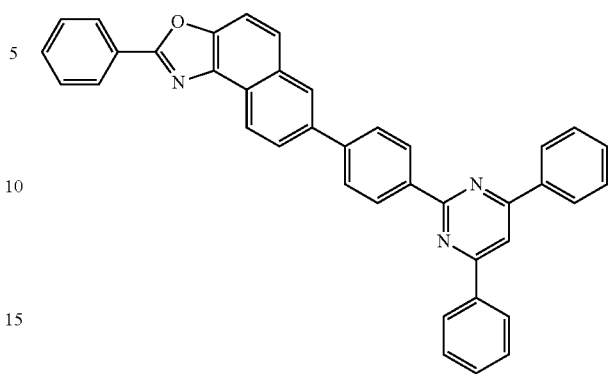
C-56
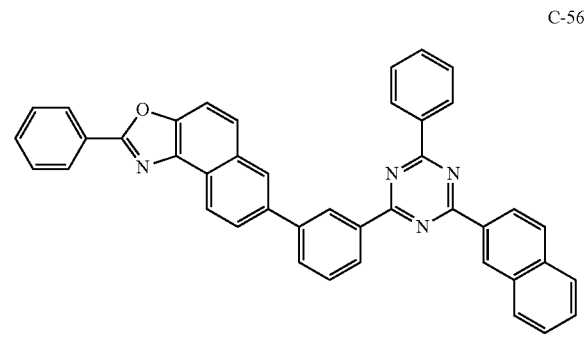
C-60
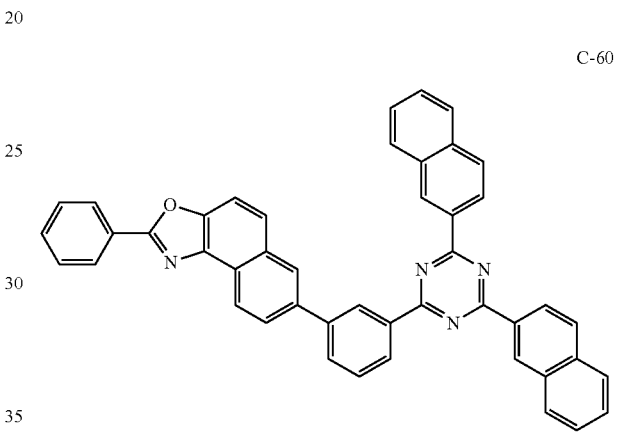
C-57
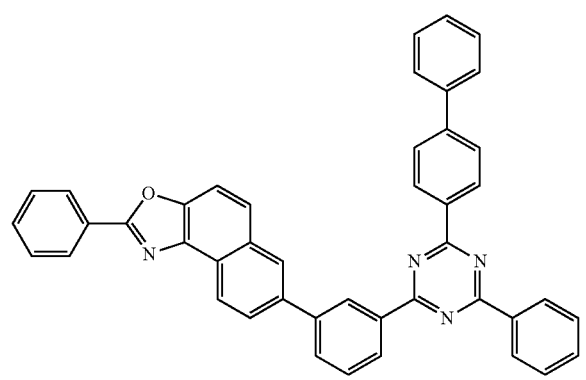
C-61
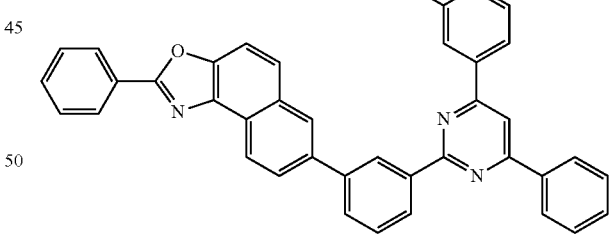
C-58
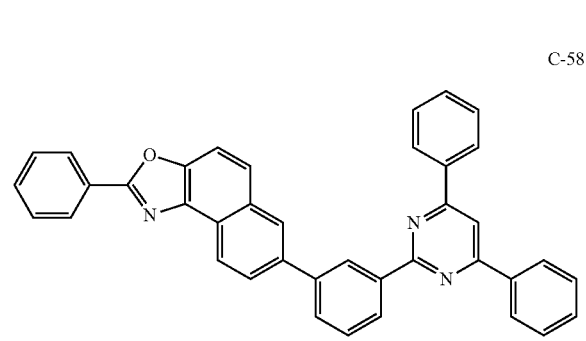
C-62
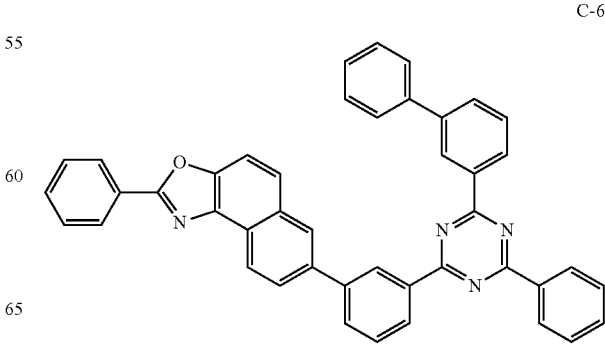

C-63
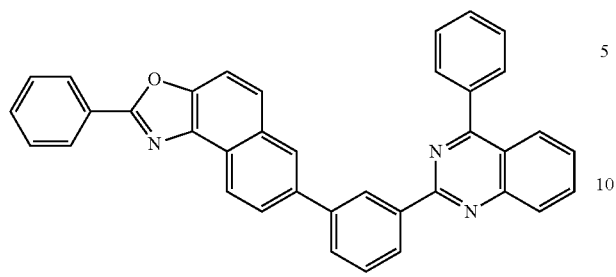
C-64
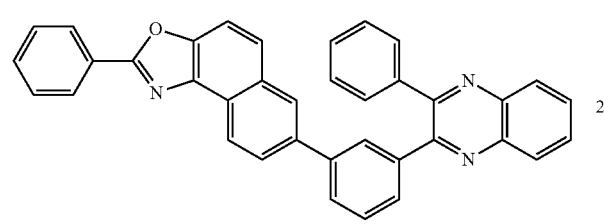
C-65
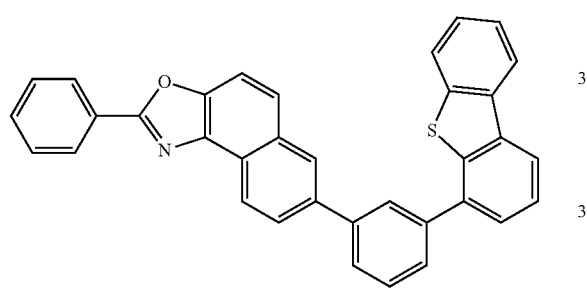
C-66
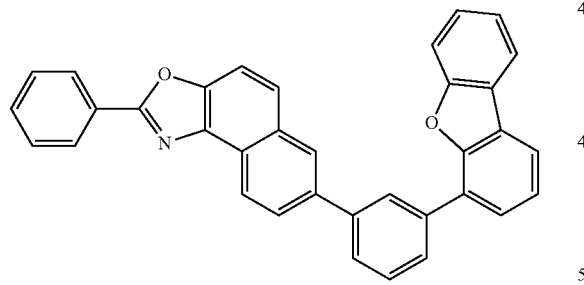
C-67
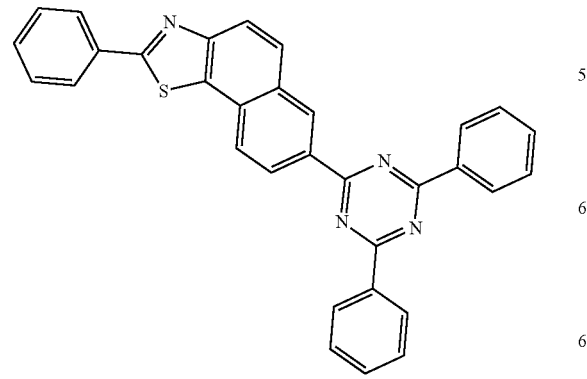
C-68
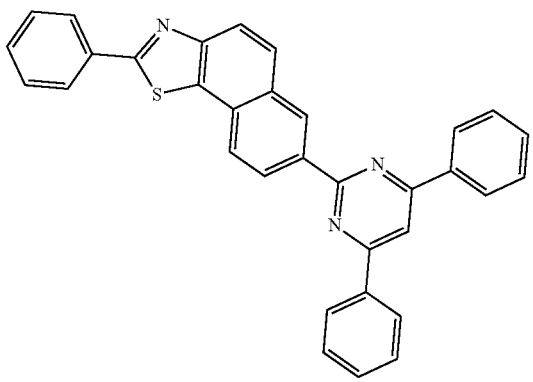
C-69
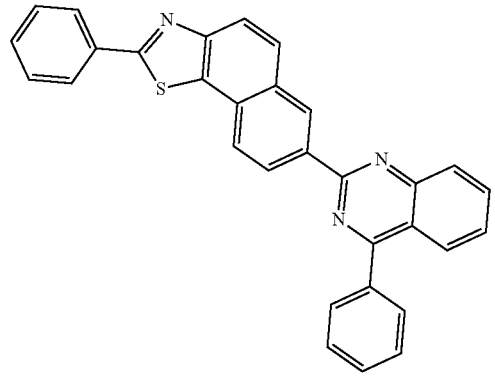
C-70
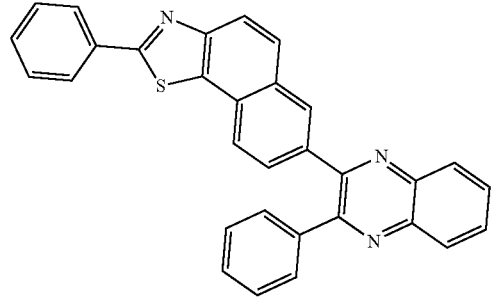
C-71
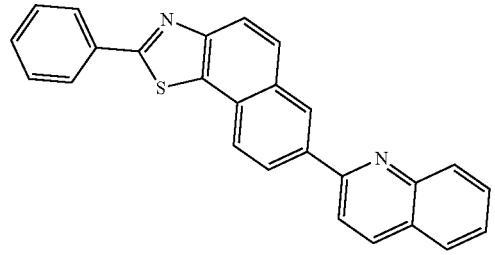
C-72
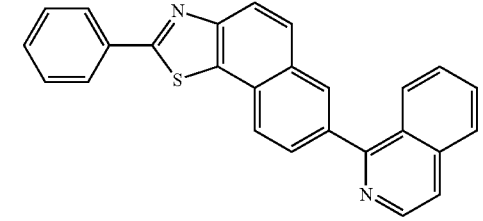

-continued
C-73
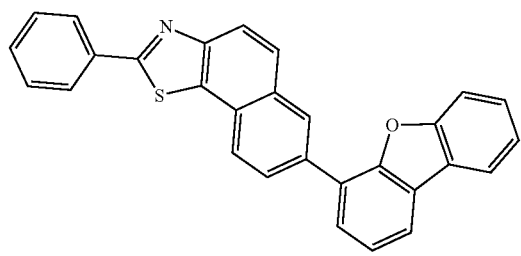
C-74
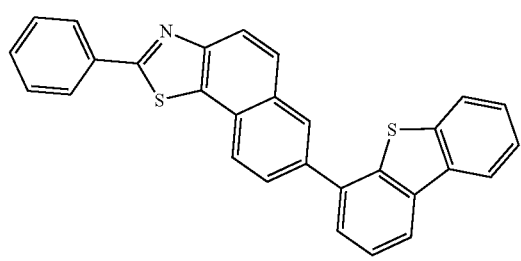
C-75
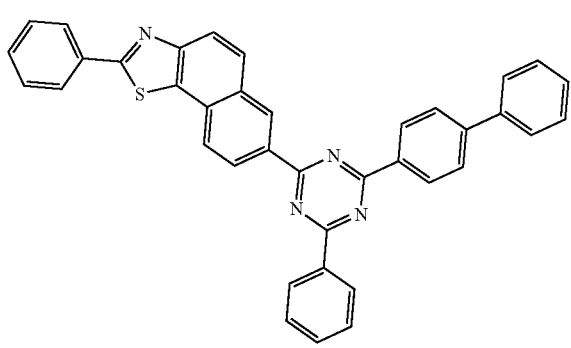
C-76
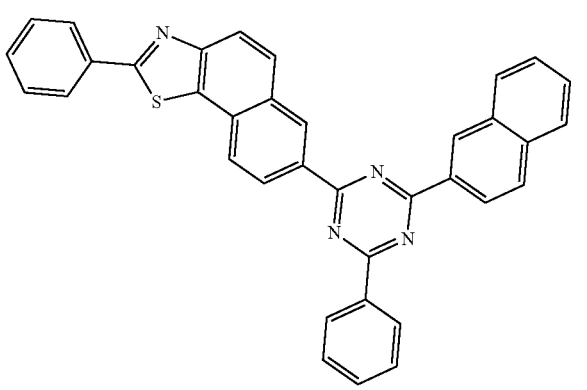
-continued
C-77
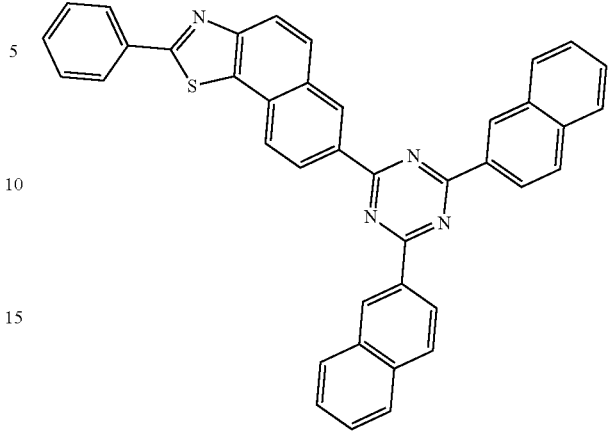
C-78
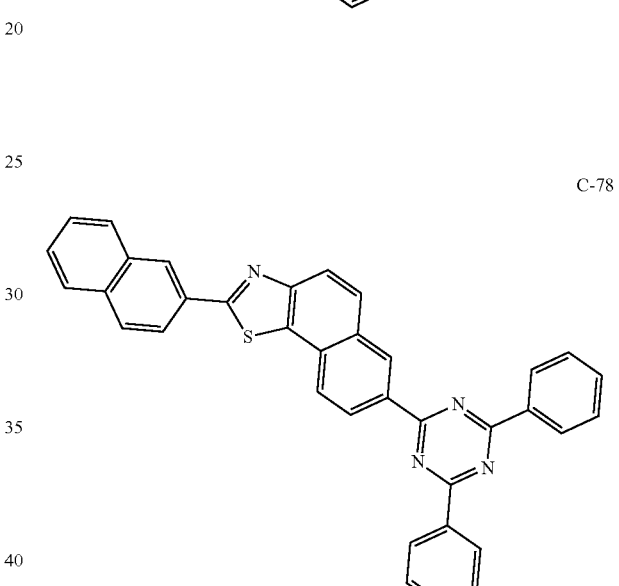
C-79
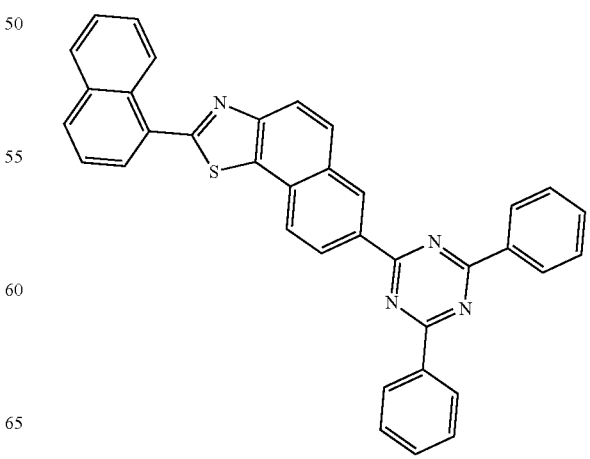

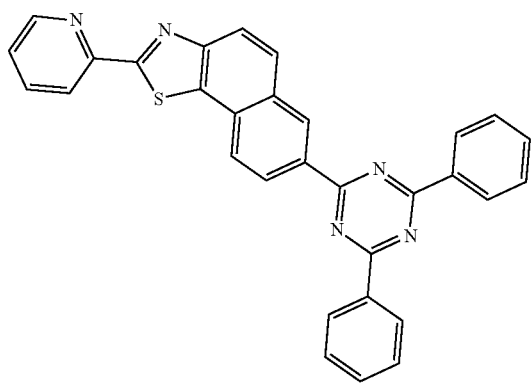
C-80
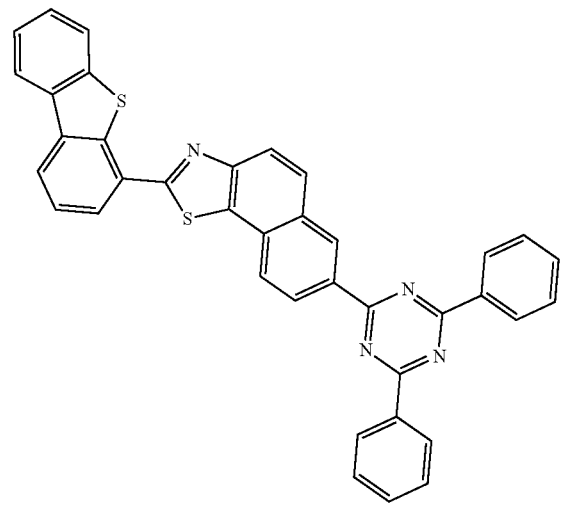
C-83
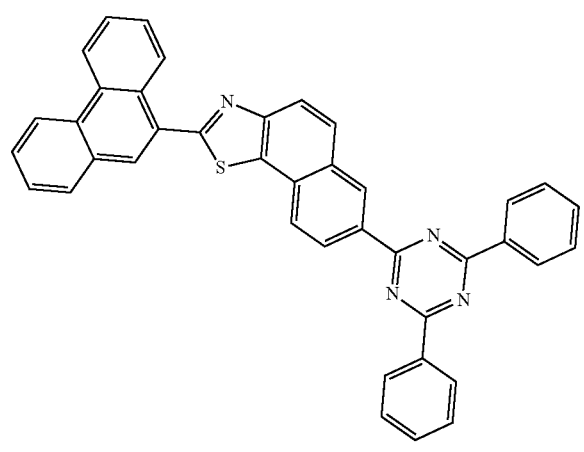
C-81
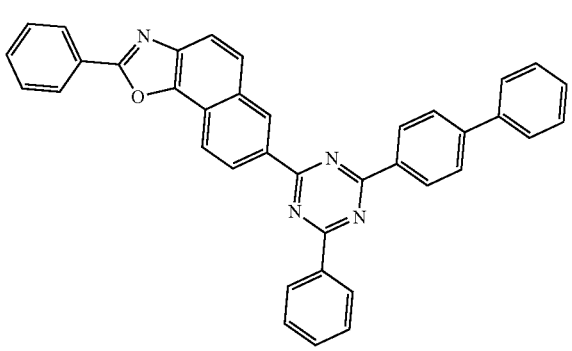
C-84
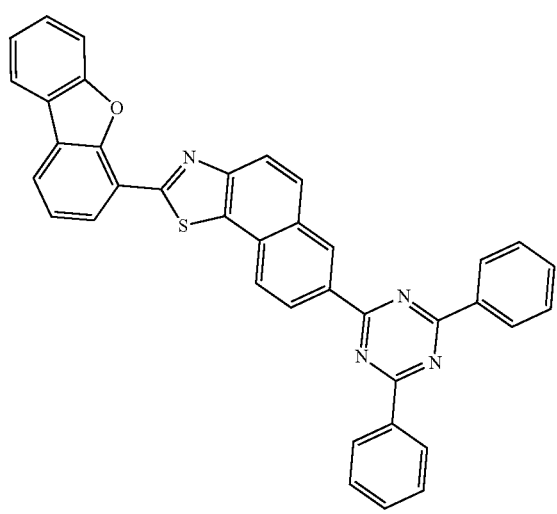
C-82
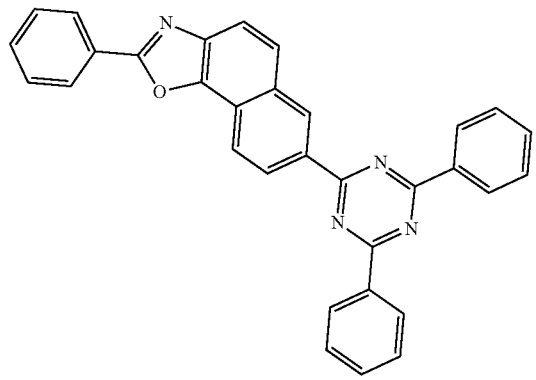
C-85

C-86
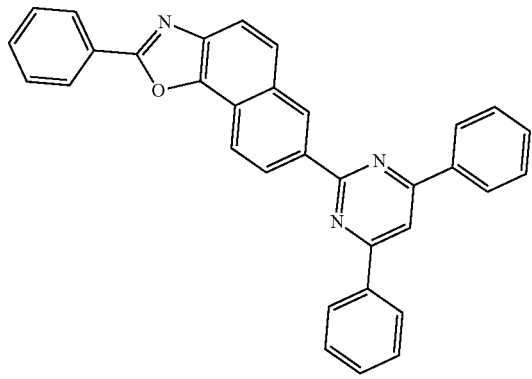
C-91
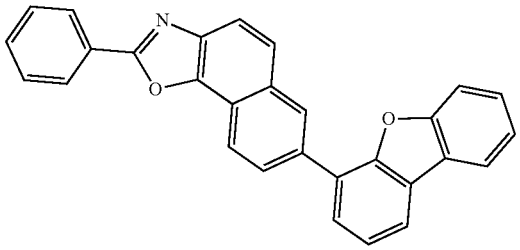
C-87
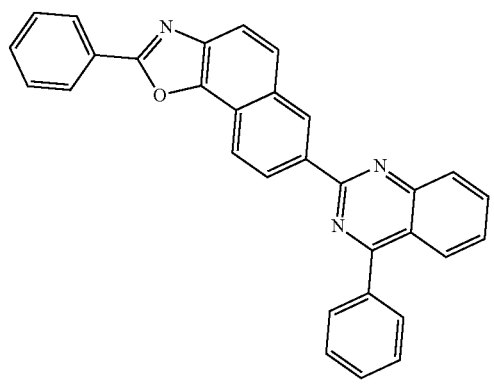
C-92
C-88
C-93
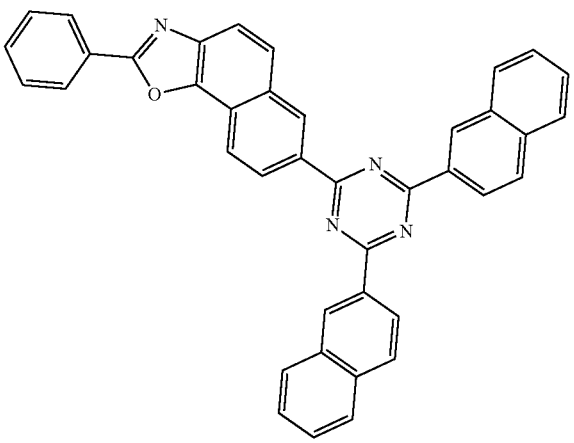
C-89
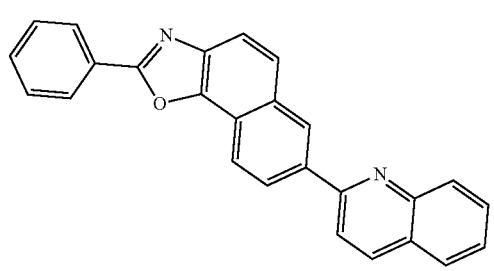
C-90
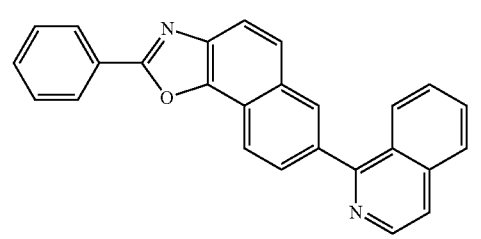
C-94
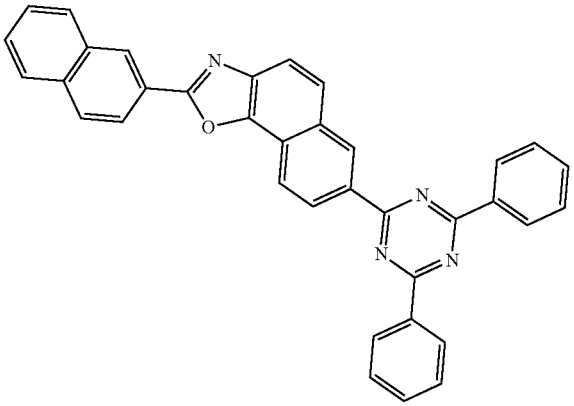

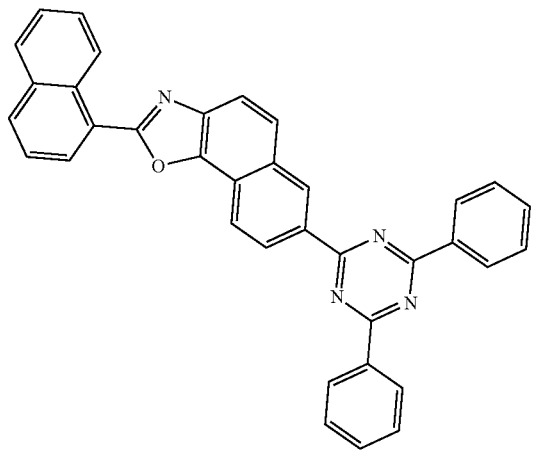
C-95
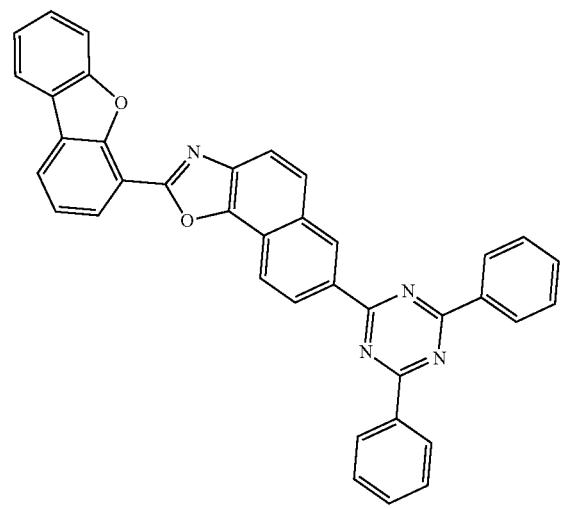
C-99
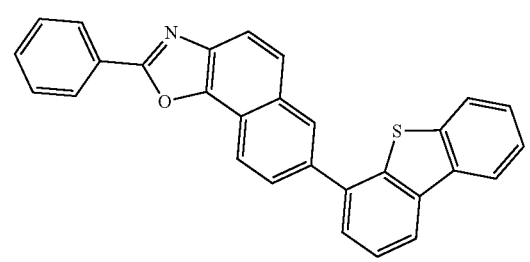
C-96
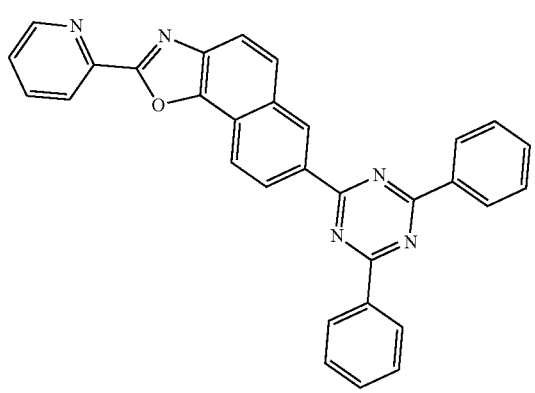
C-97
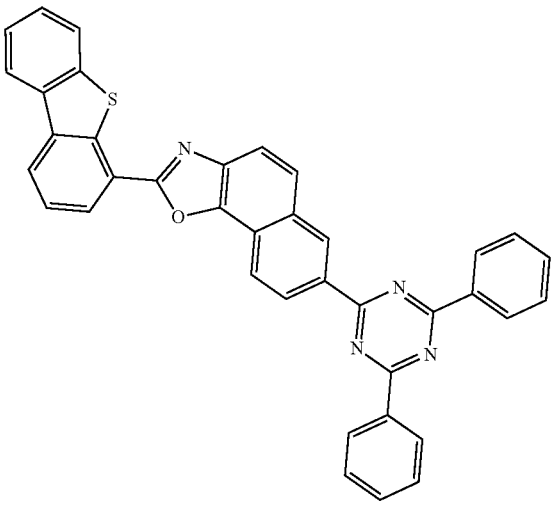
C-100
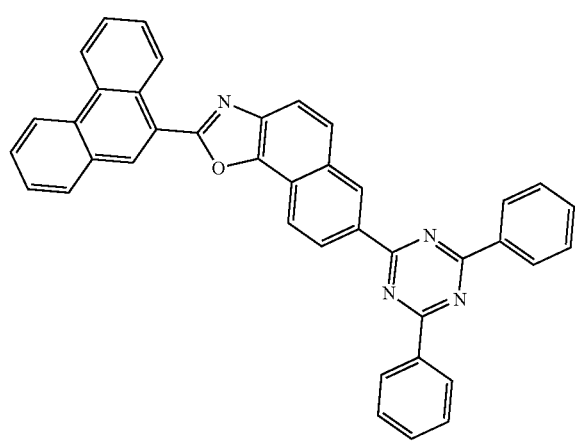
C-98
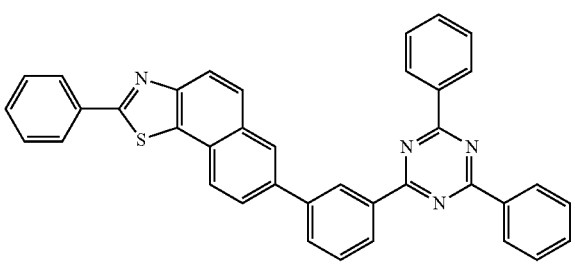
C-101

-continued
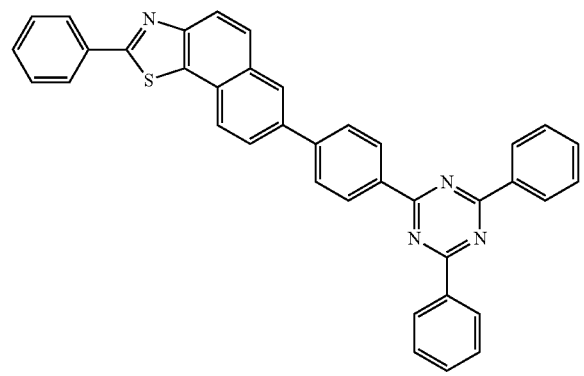
C102
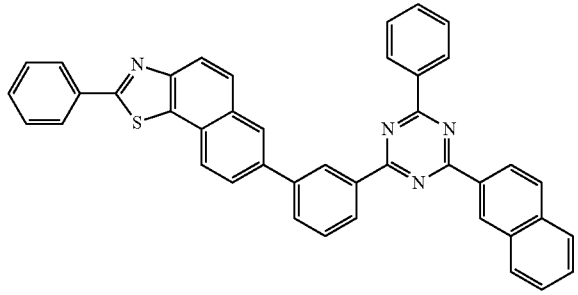
C-106
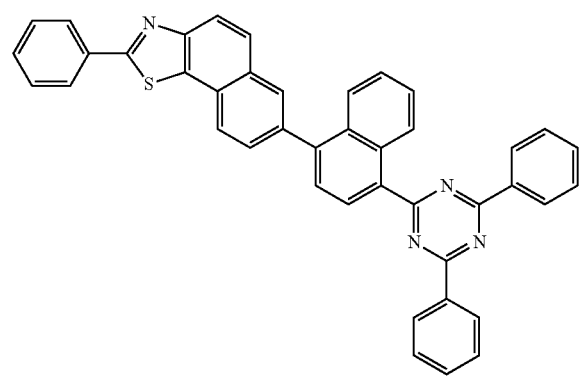
C-103
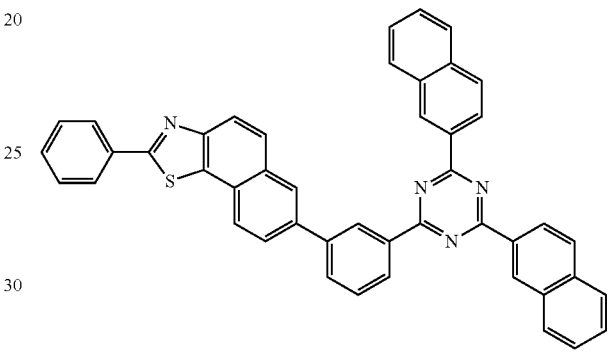
C-107
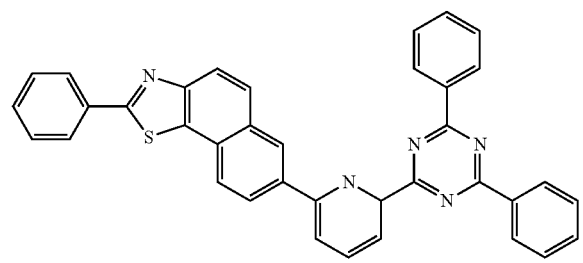
C-104
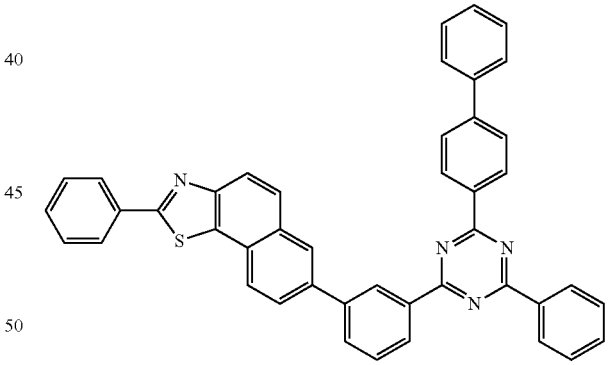
C-108
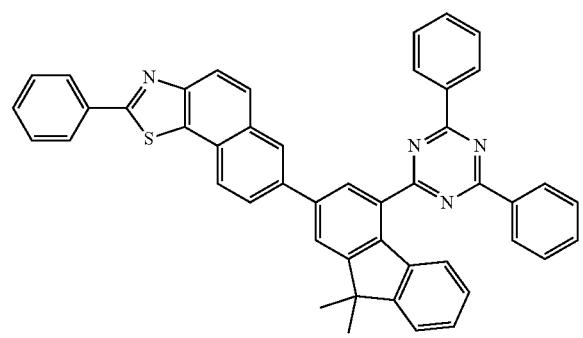
C-105
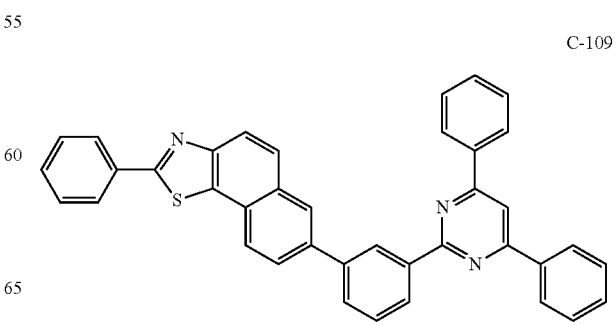
C-109

C-110
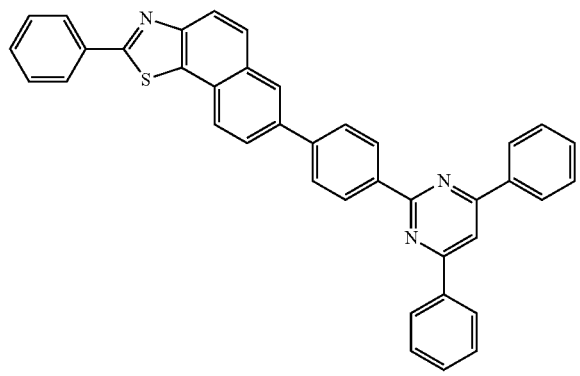
C-115
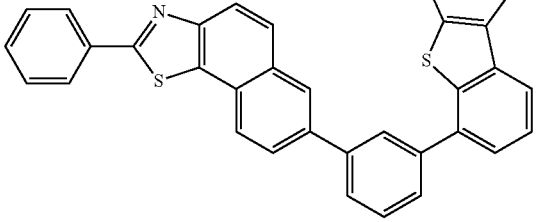
C-111
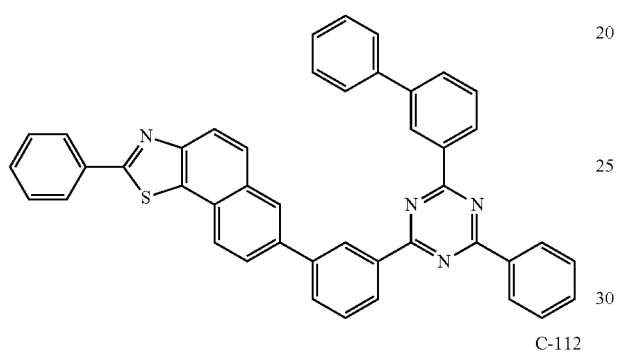
C-116
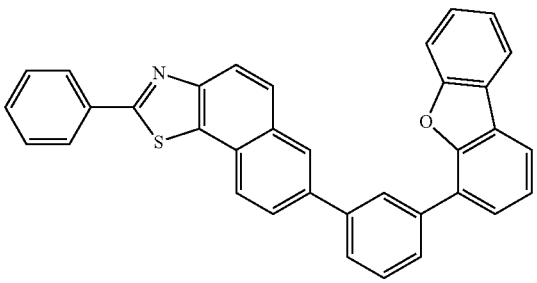
C-112
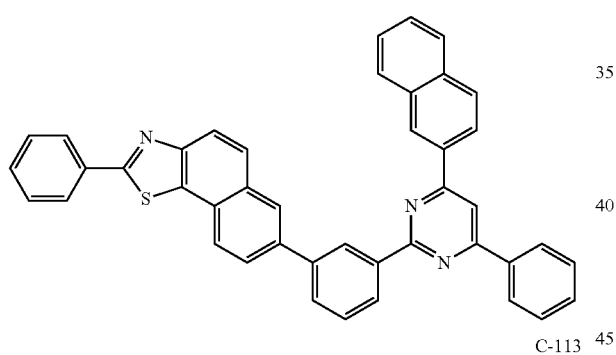
C-117
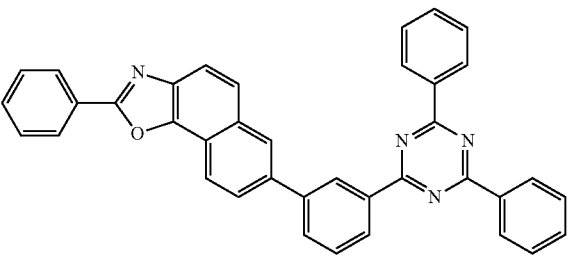
C-113
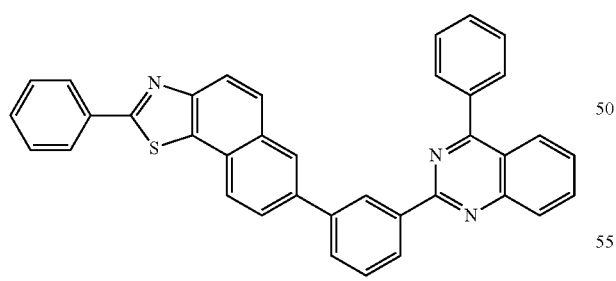
C-118
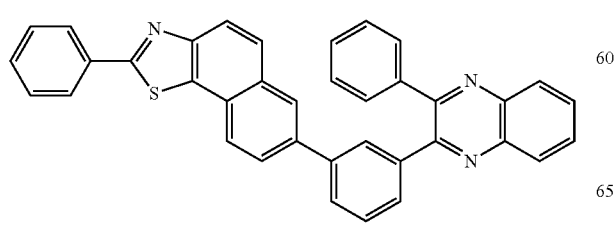
C-114

C-119
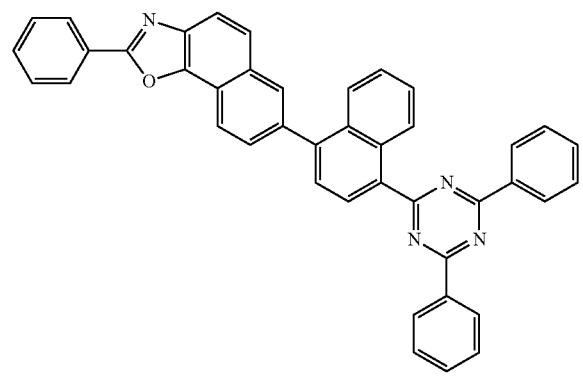
C-120
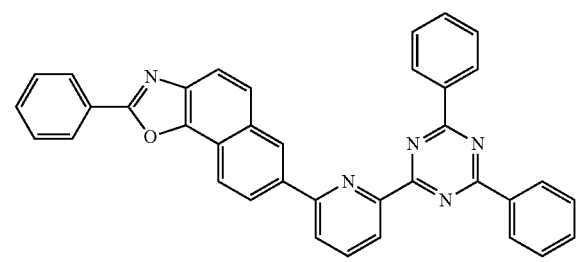
C-121
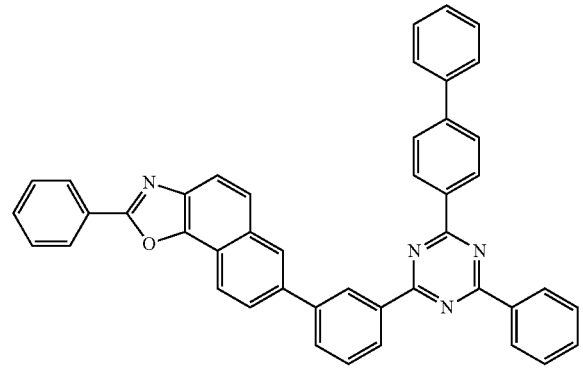
C-122
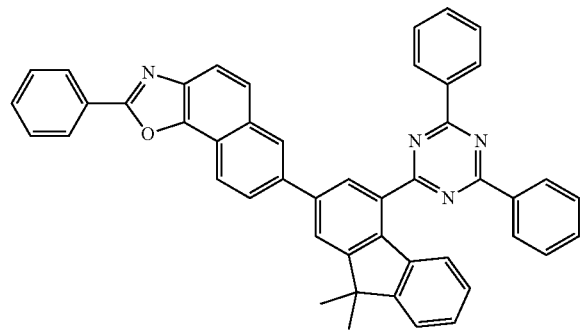
C-123
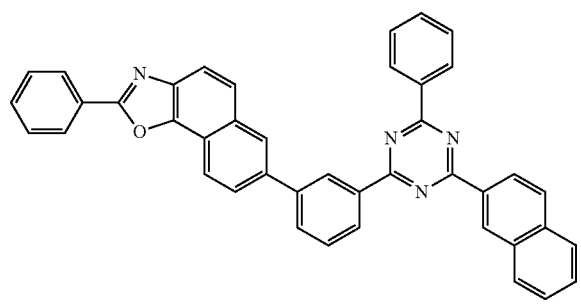
C-124
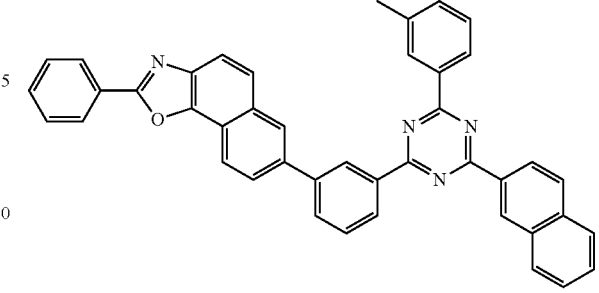
C-125
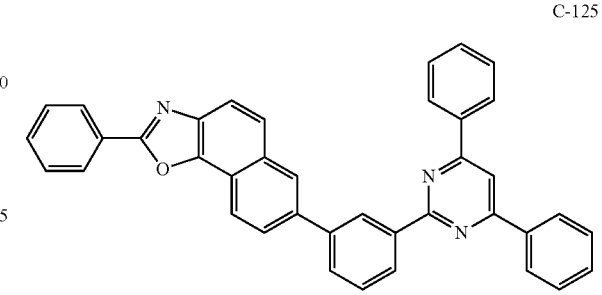
C-126
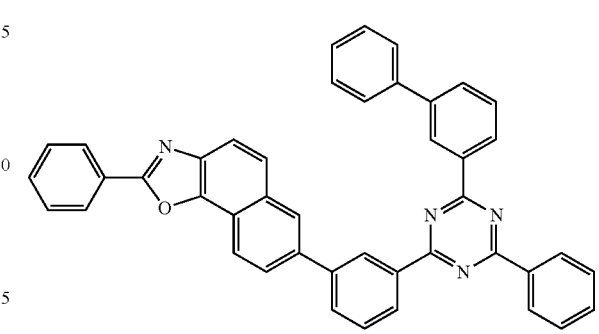

C-127
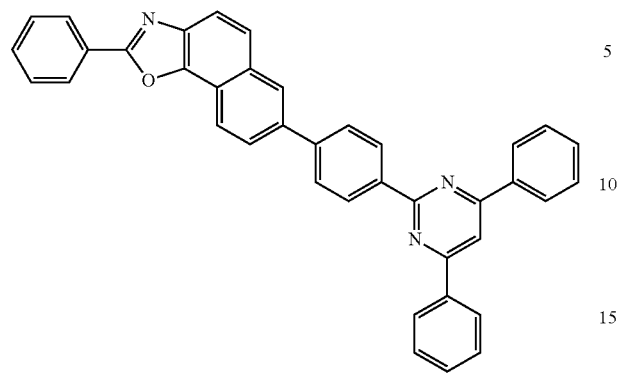
C-128
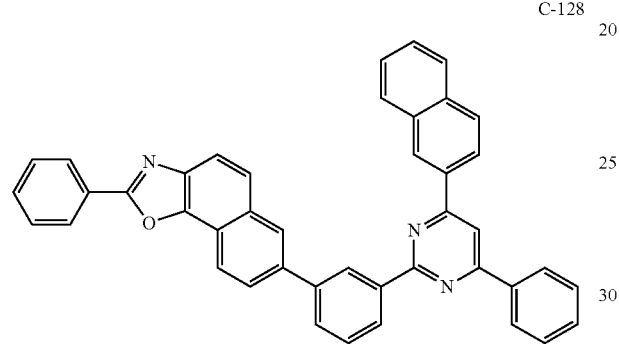
C-129
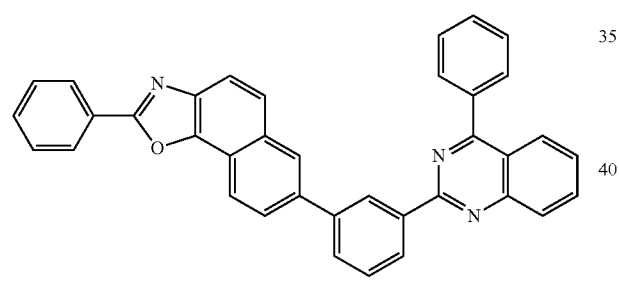
C-130
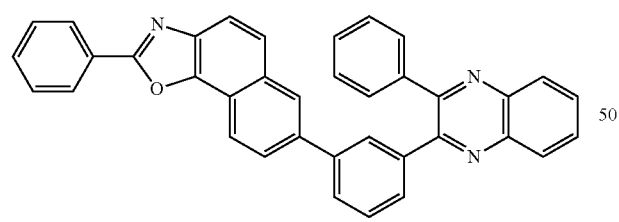
C-131
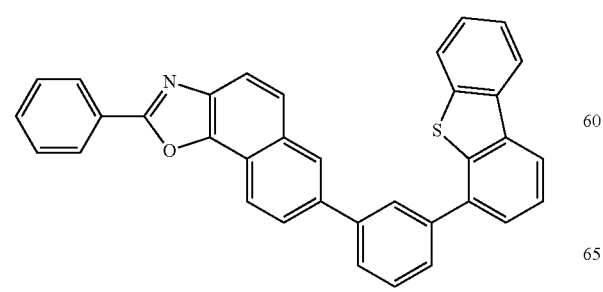
C-132
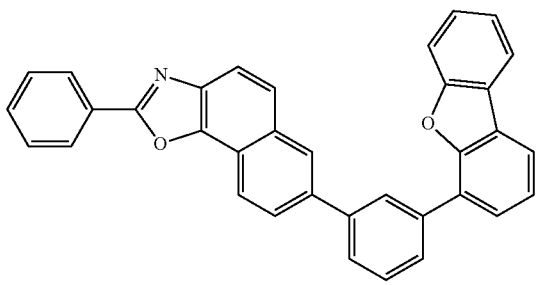
C-133
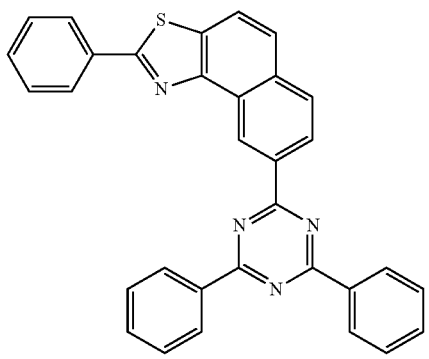
C-134
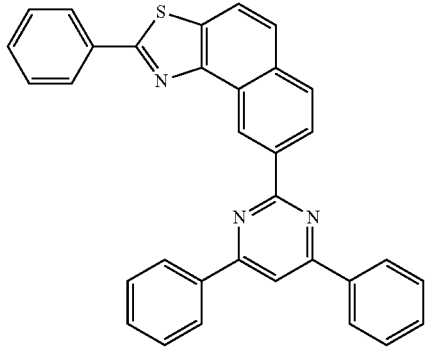
C-135
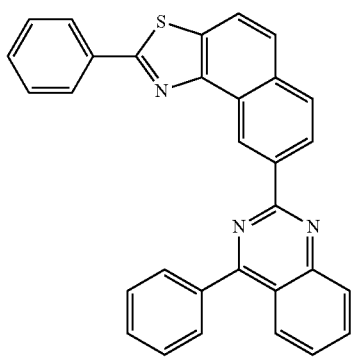

-continued
C-136
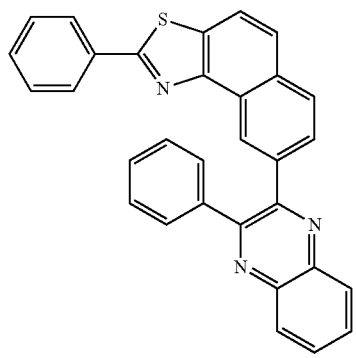
C-137
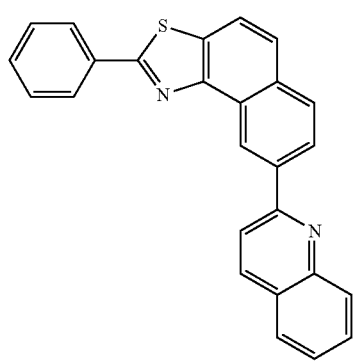
C-138
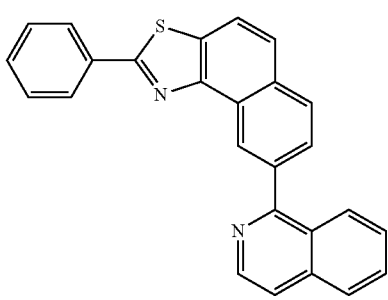
C-139
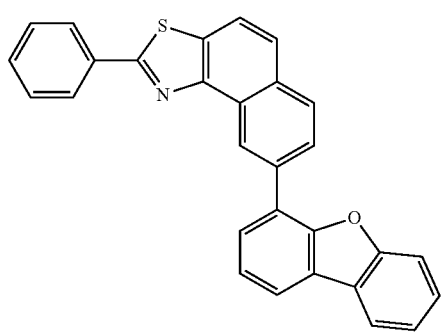
-continued
C-140
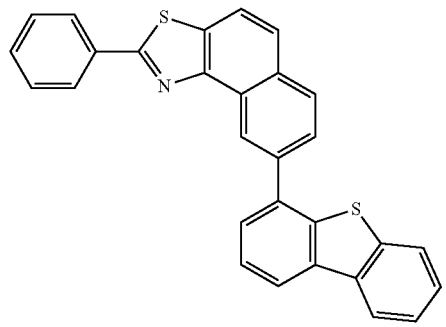
C-141
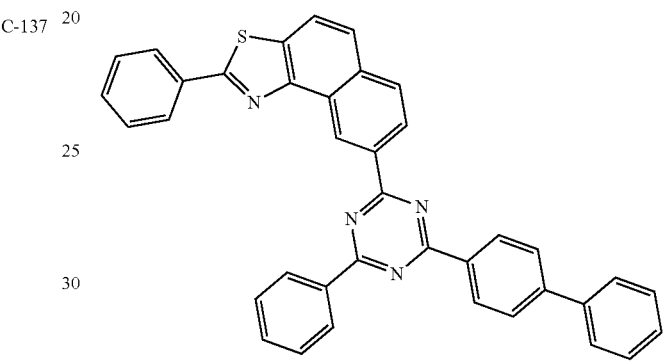
C-142
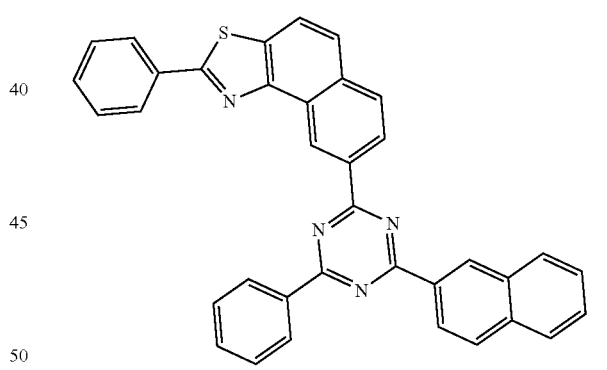
C-143
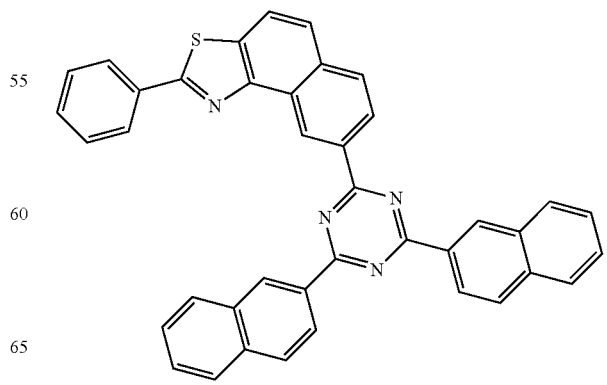

C-144
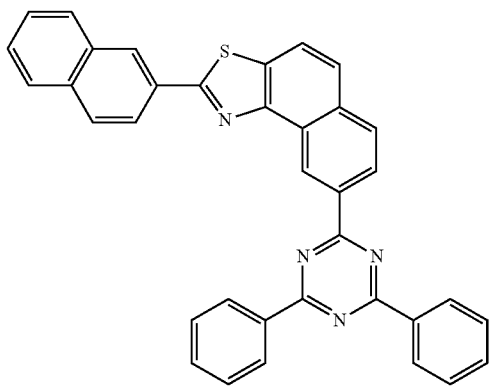
C-145
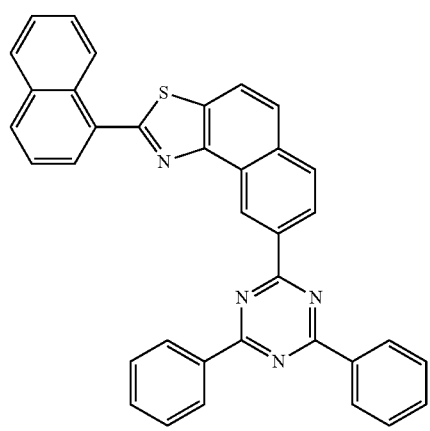
C-146
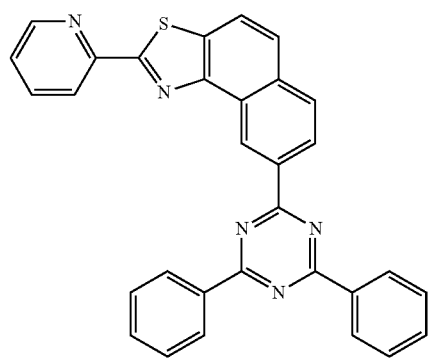
C-147
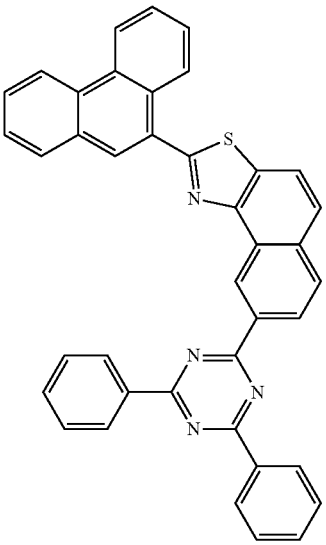
C-148
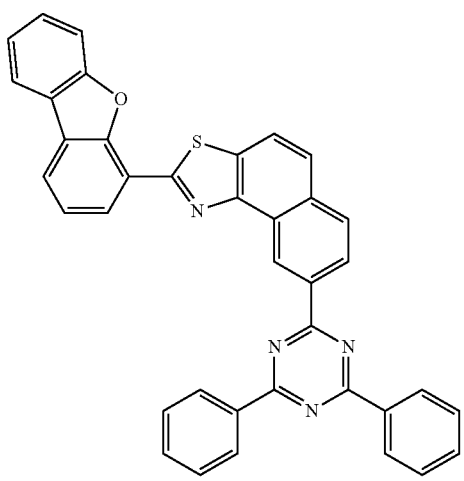
C-149
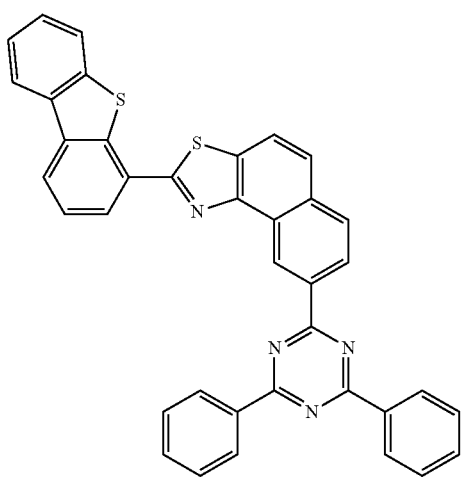

C-150
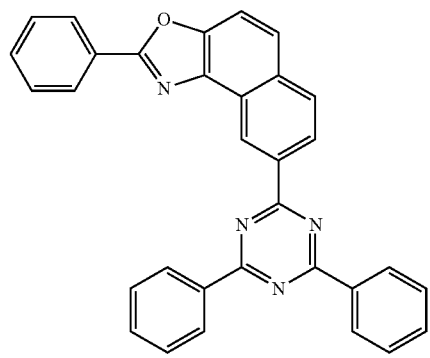
C-151
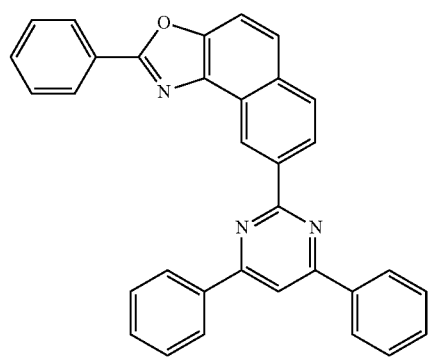
C-152
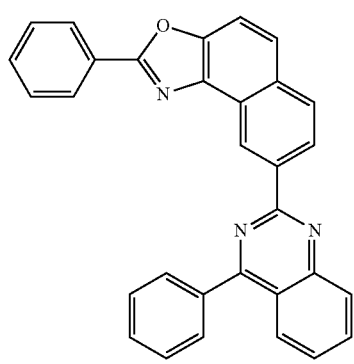
C-153
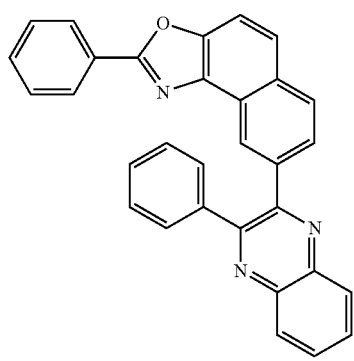
C-154
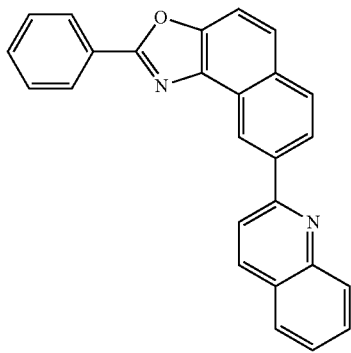
C-155
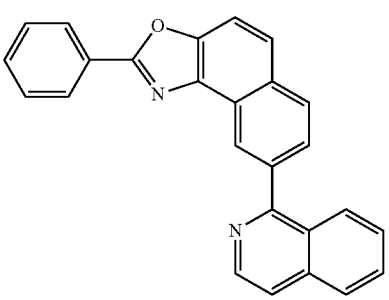
C-156
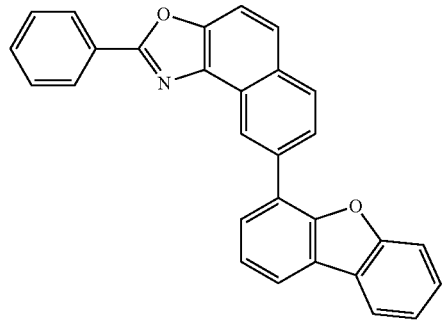
C-157
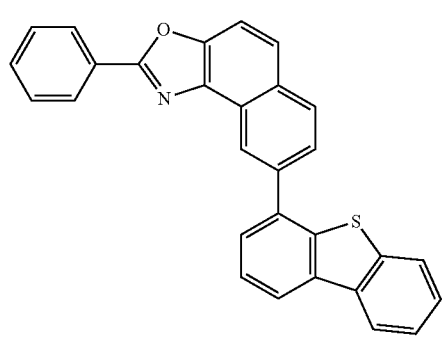

C-158
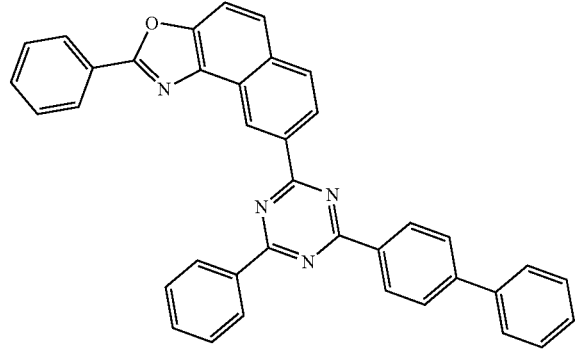
C-159
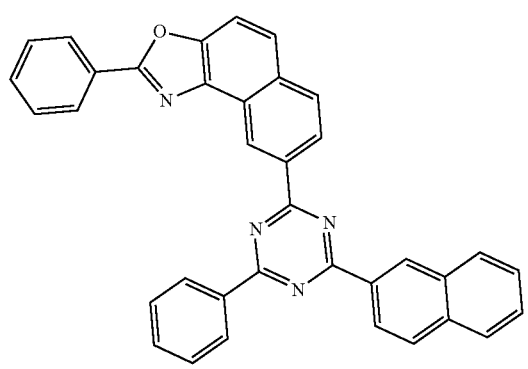
C-160
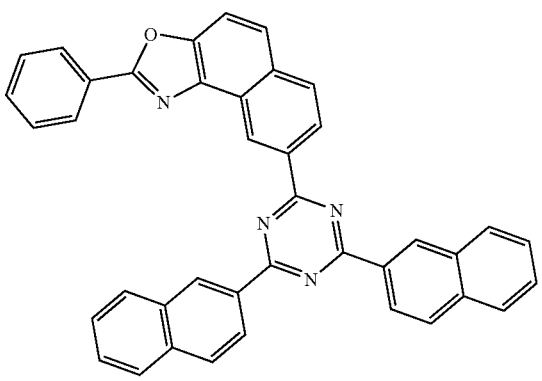
C-161
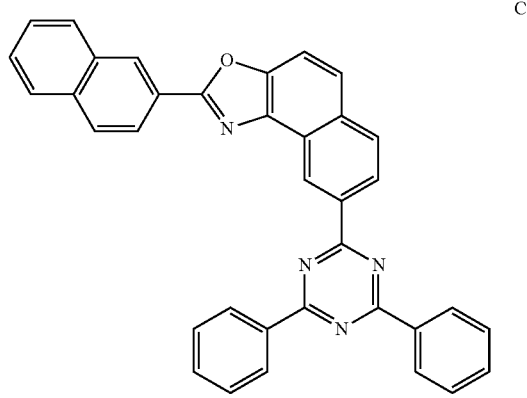
C-162
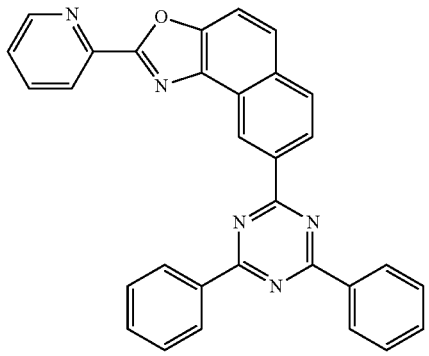
C-163
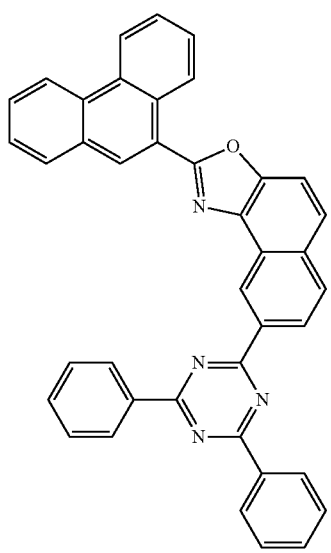
C-164
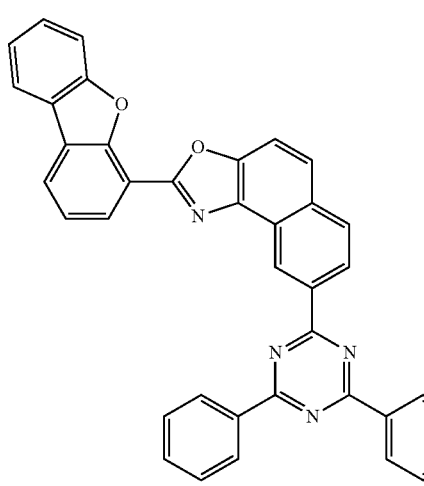

C-165
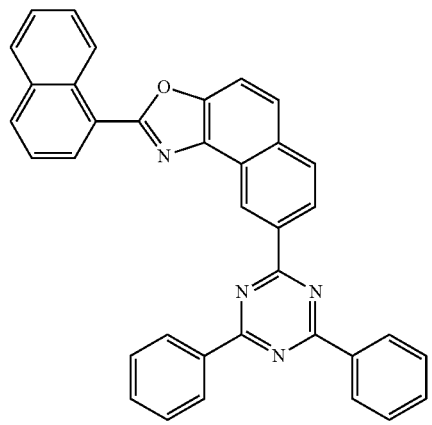
C-166
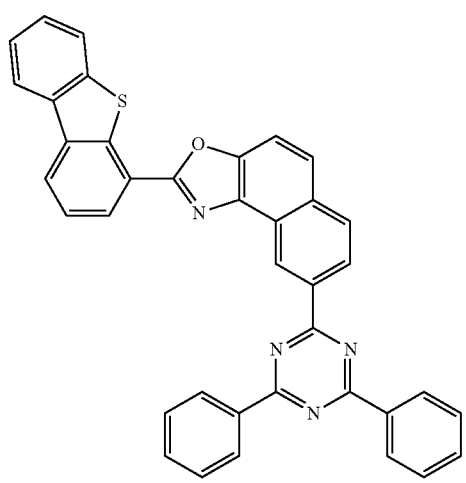
C-167
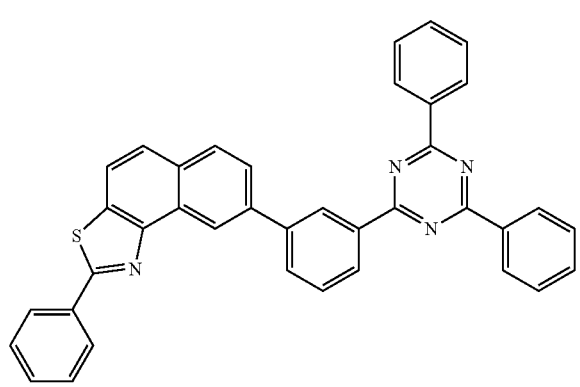
C-168
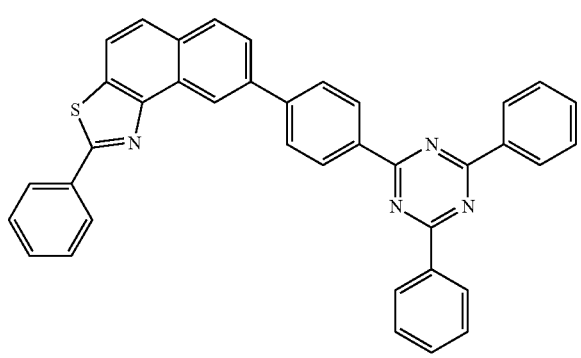
C-169
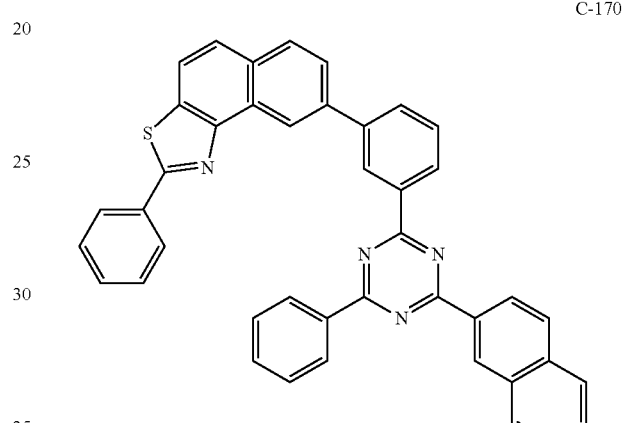
C-170
C-171
C-172

C-173
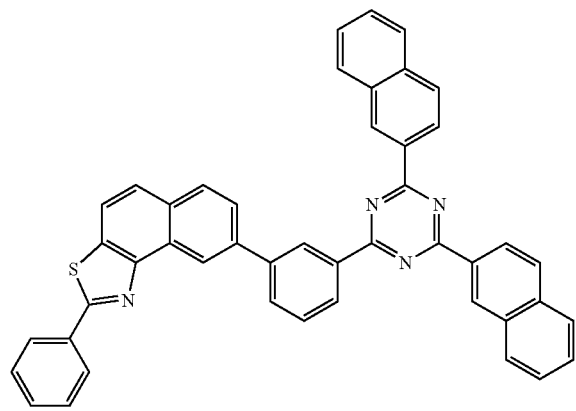
C-174
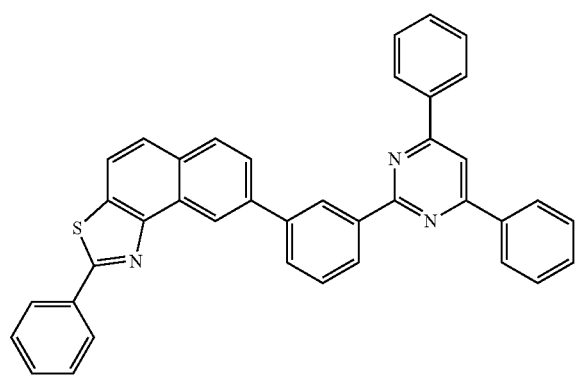
C-175
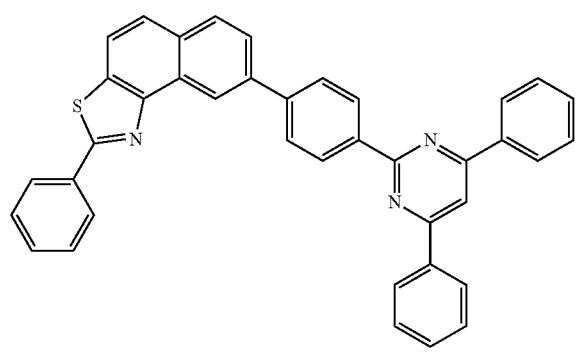
C-176
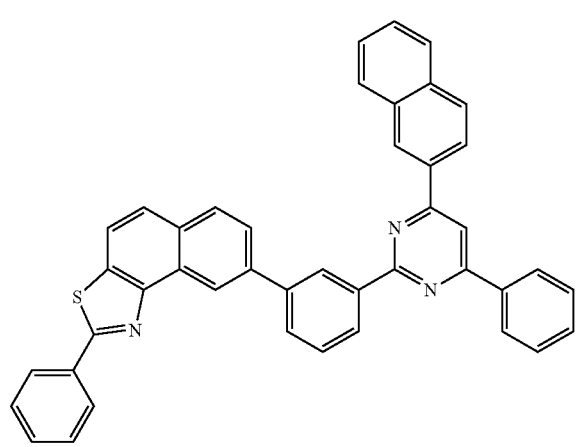
C-177
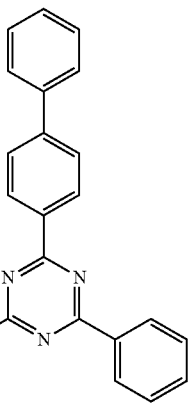
C-178
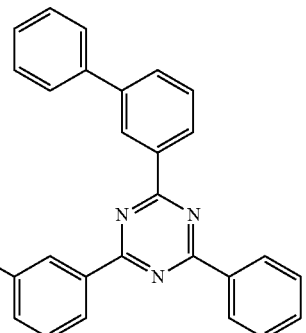
C-179

-continued
C-180
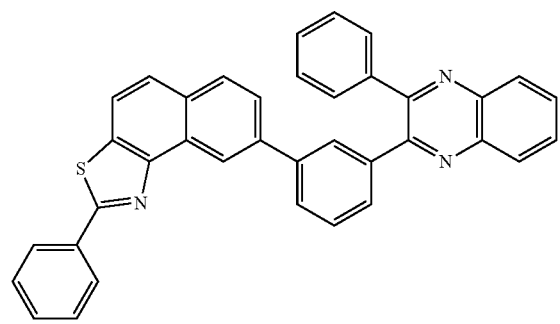
C-181
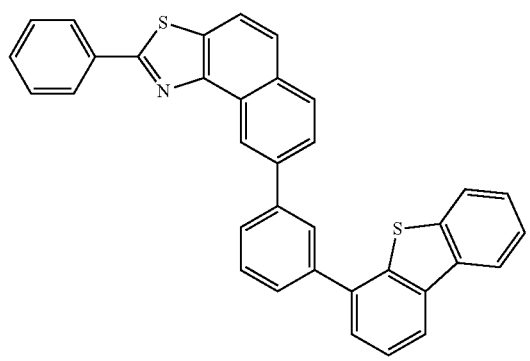
C-182
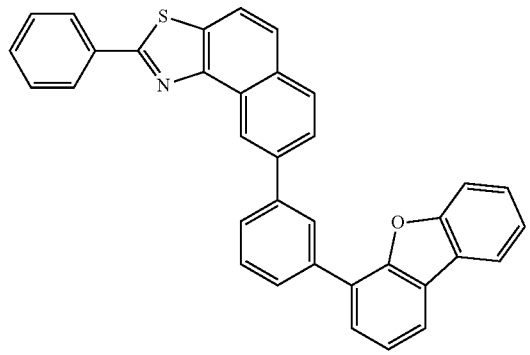
C-183
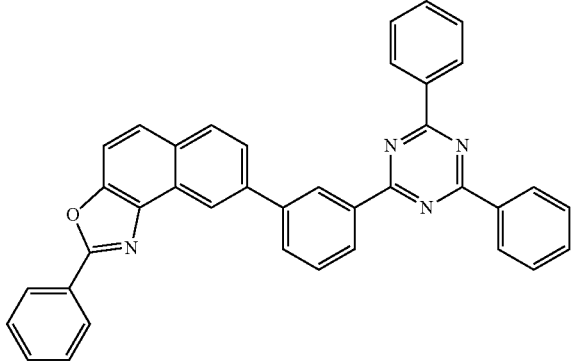
-continued
C-184
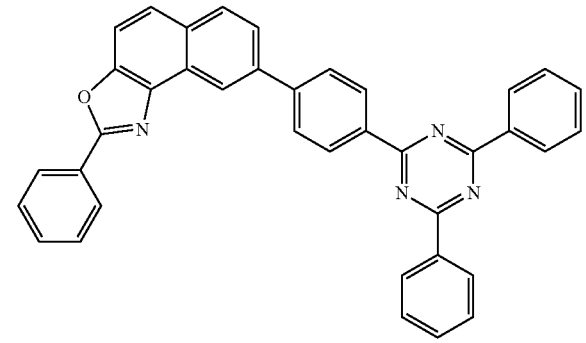
C-185
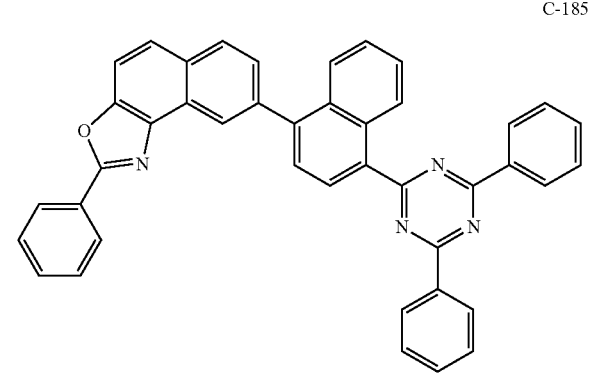
C-186
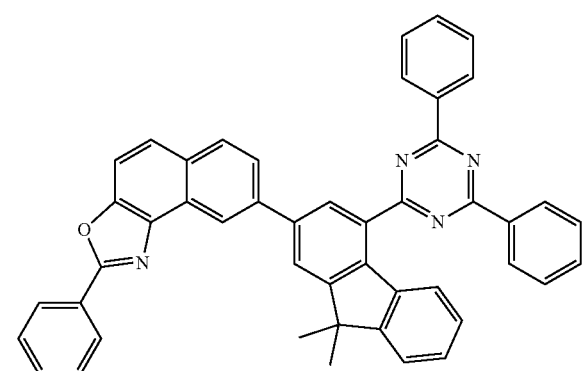
C-187
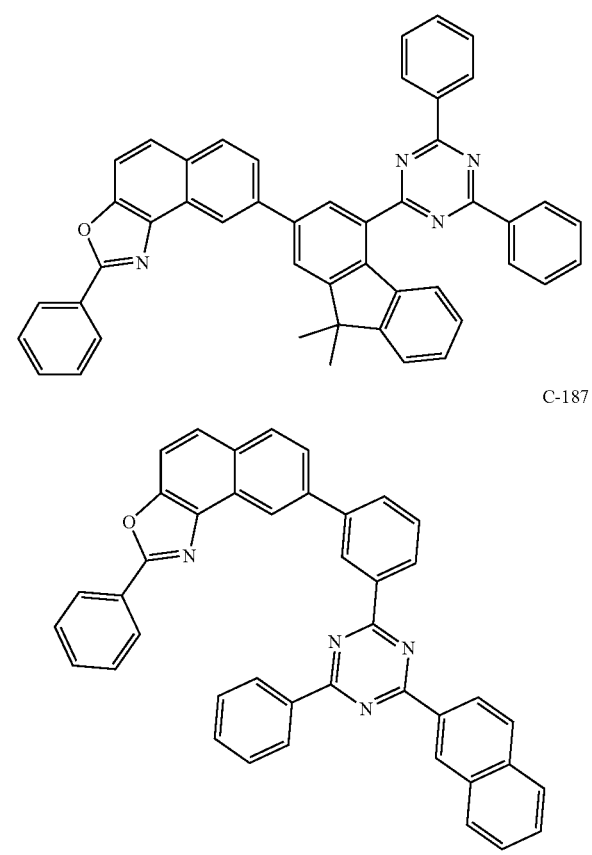

-continued
C-188
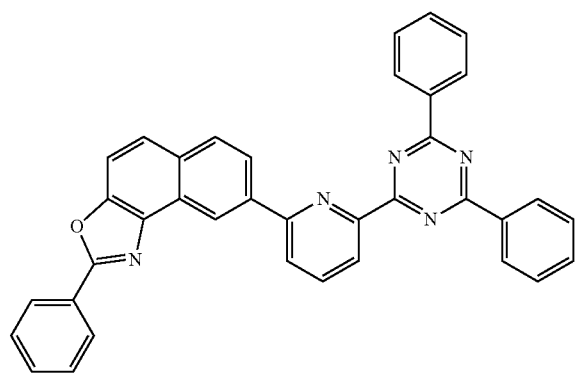
C-189
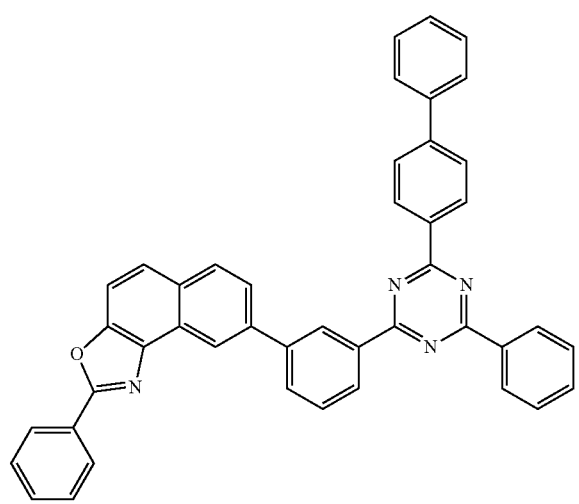
C-190
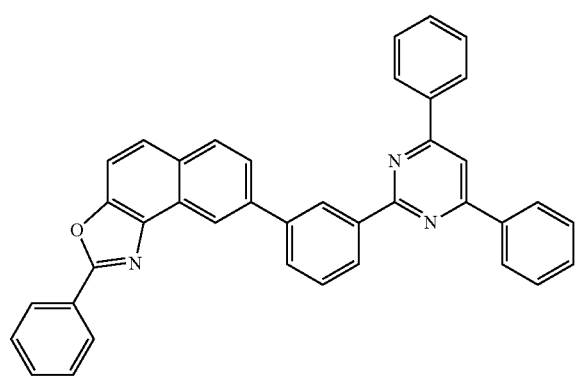
-continued
C-191
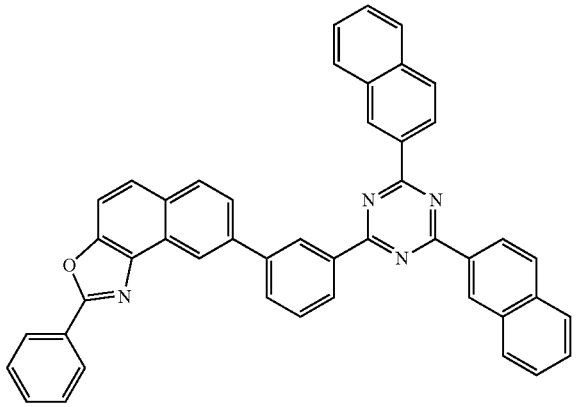
C-192
C-193
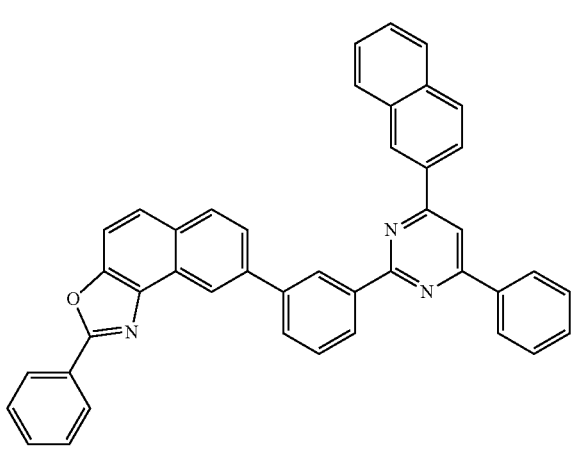

C-194
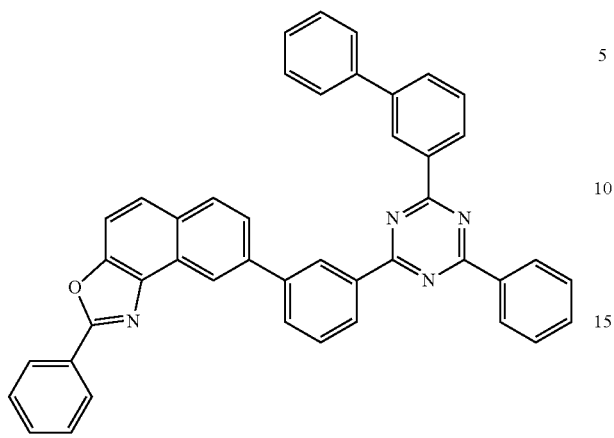
C-195
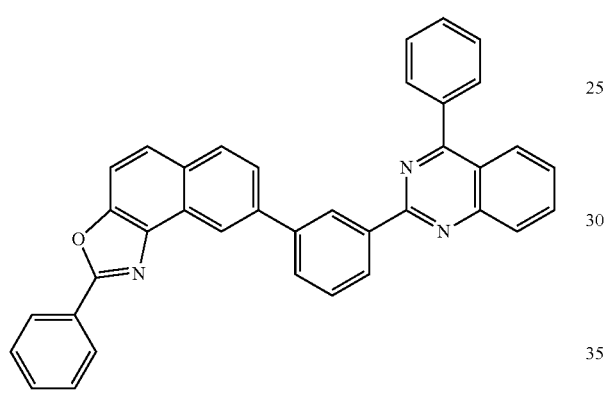
C-196
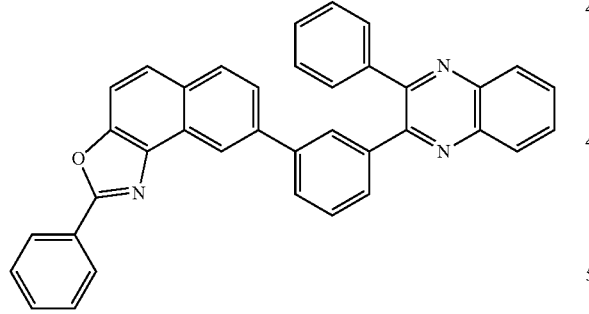
C-197
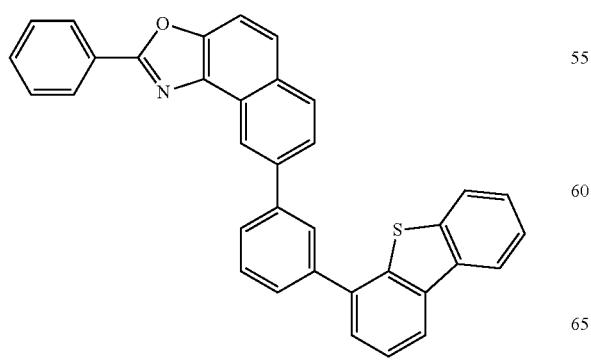
C-198
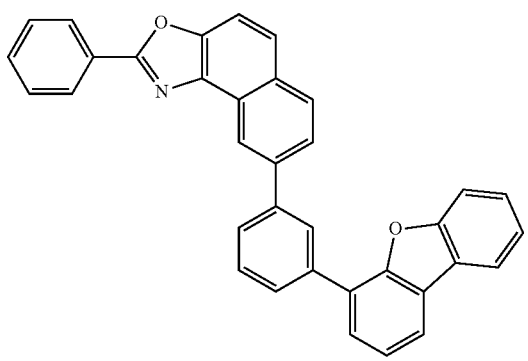
C-199
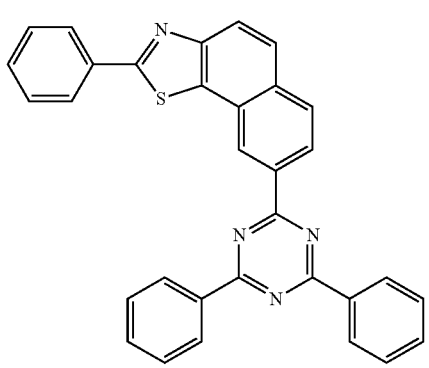
C-200
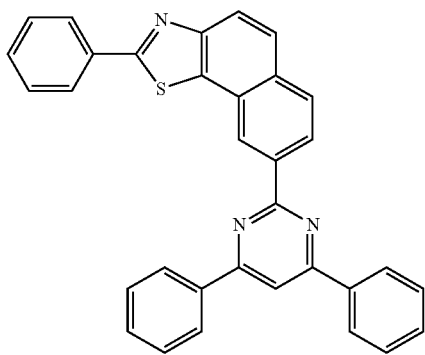
C-201
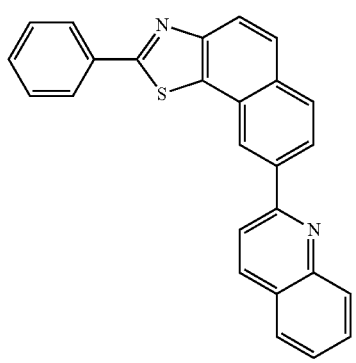

C-202 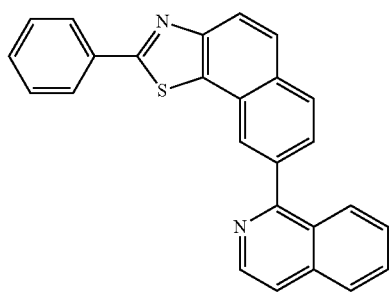
C-206 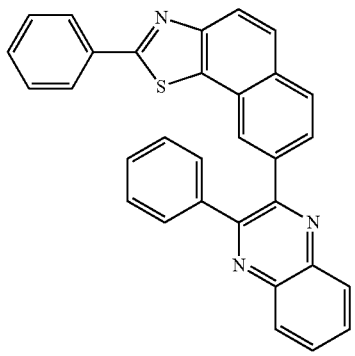
C-203 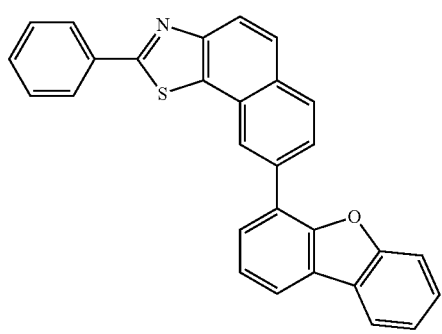
C-207 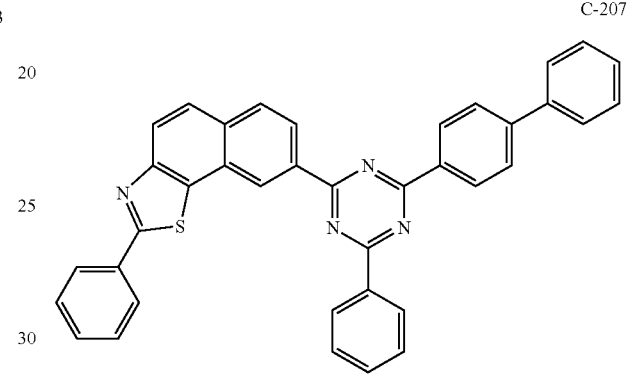
C-204 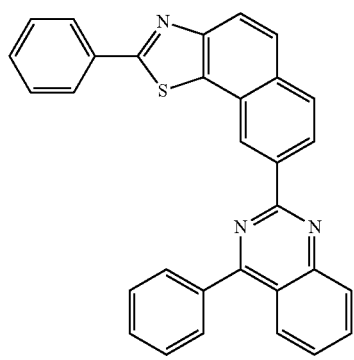
C-208 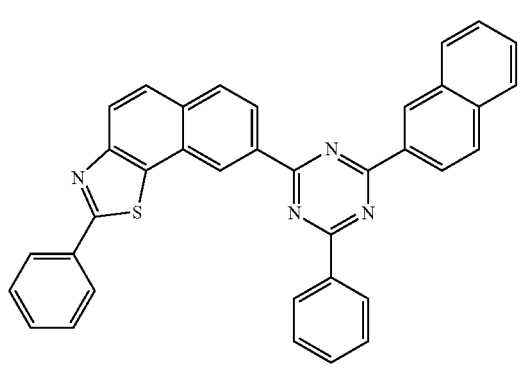
C-205 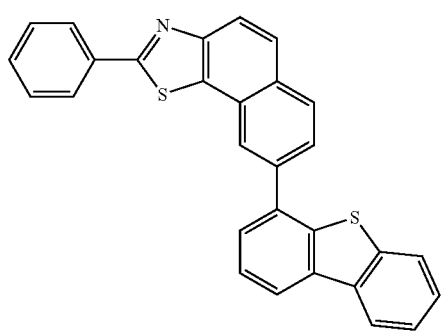
C-209 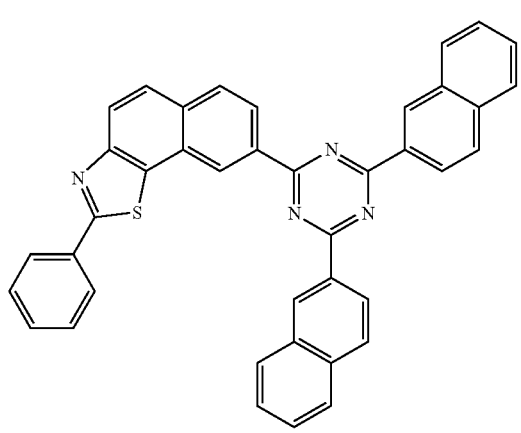

-continued
C-210
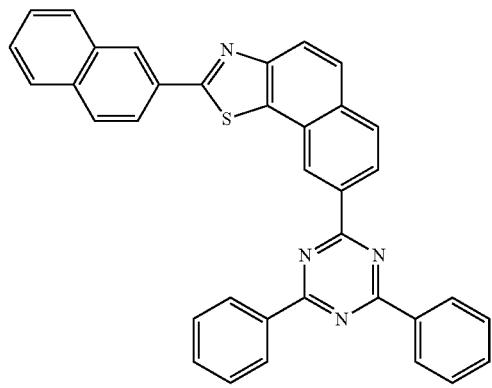
C-211
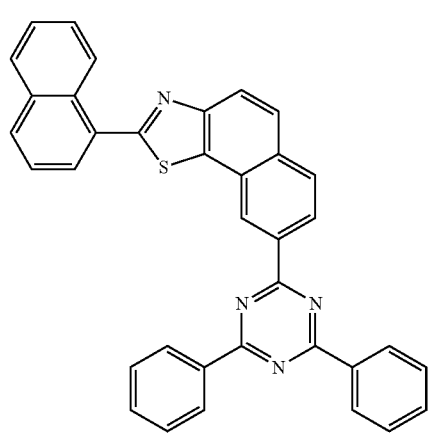
C-212
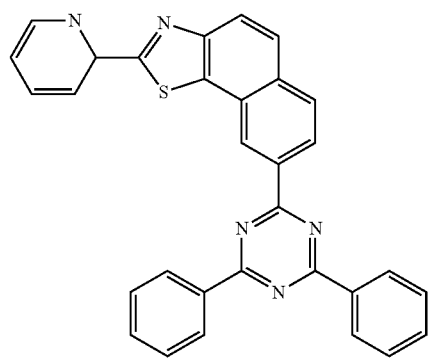
-continued
C-213
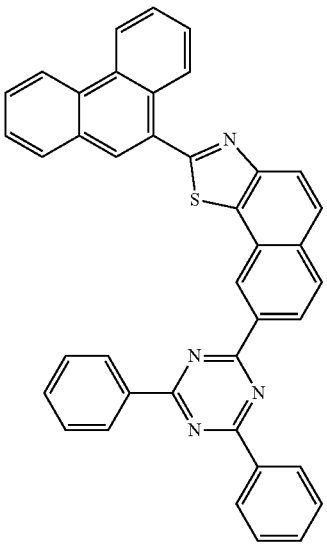
C-214
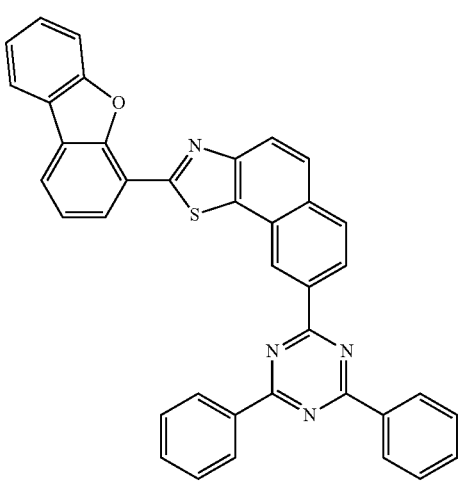
C-215
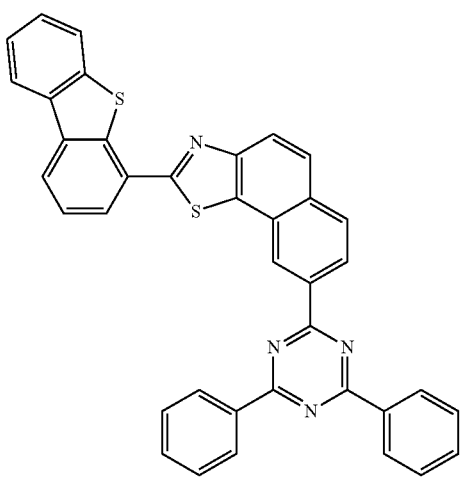

-continued
C-216
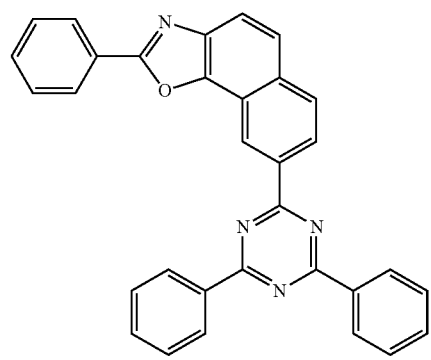
C-217
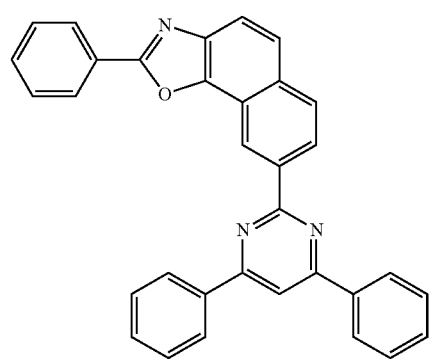
C-218
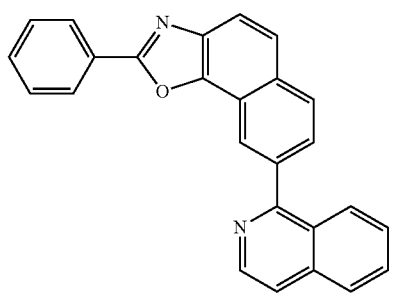
C-219
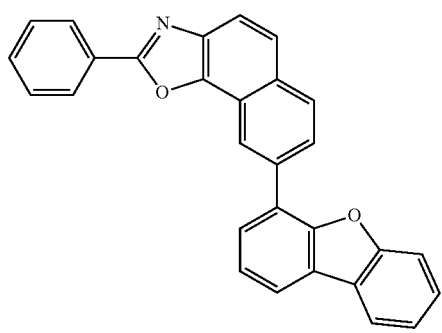
-continued
C-220
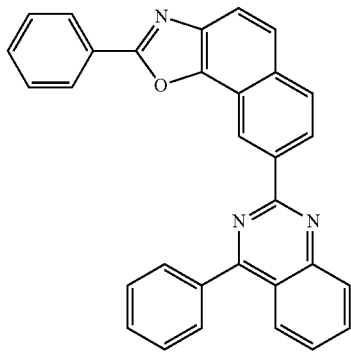
C-221
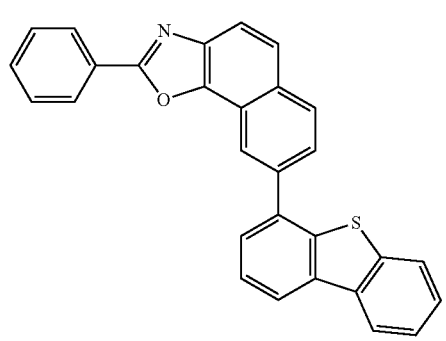
C-222
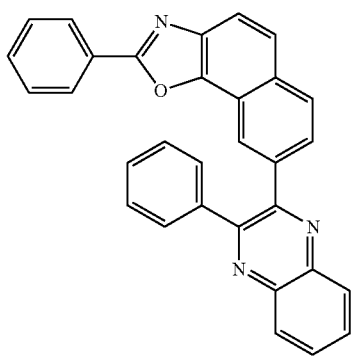
C-223
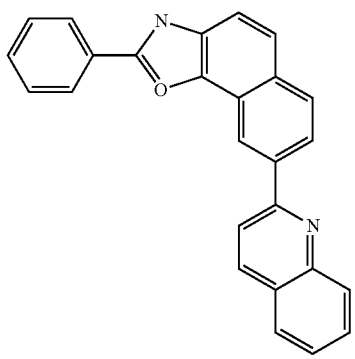

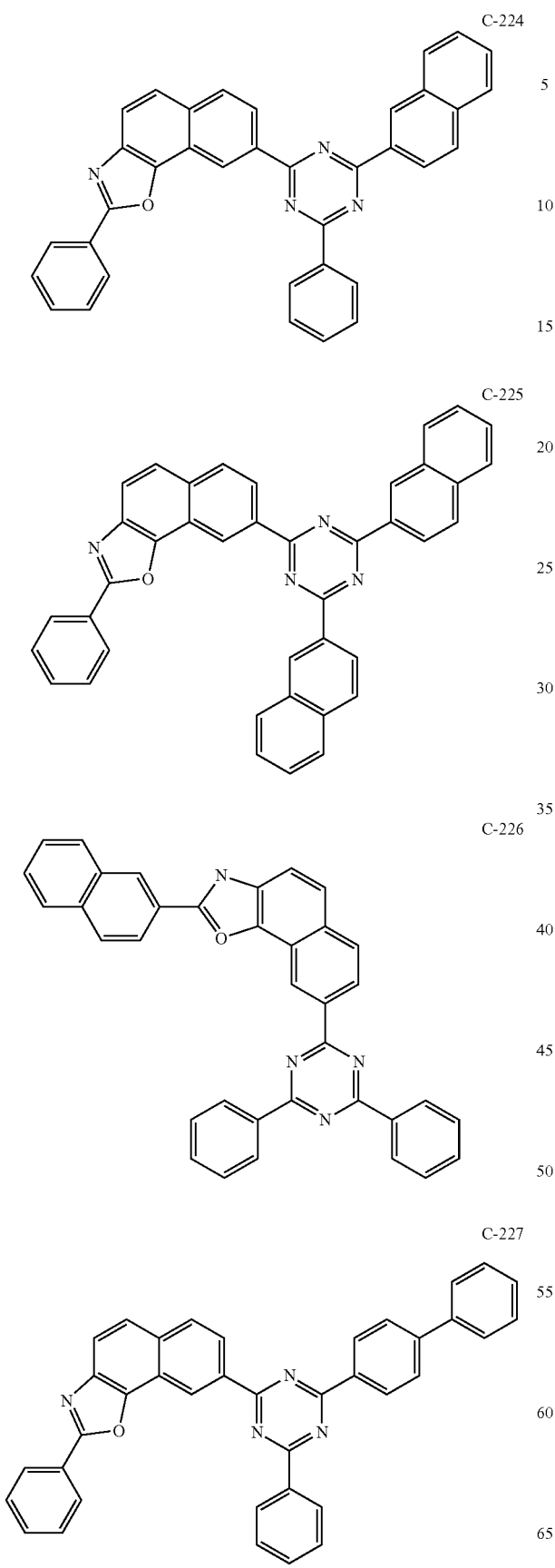
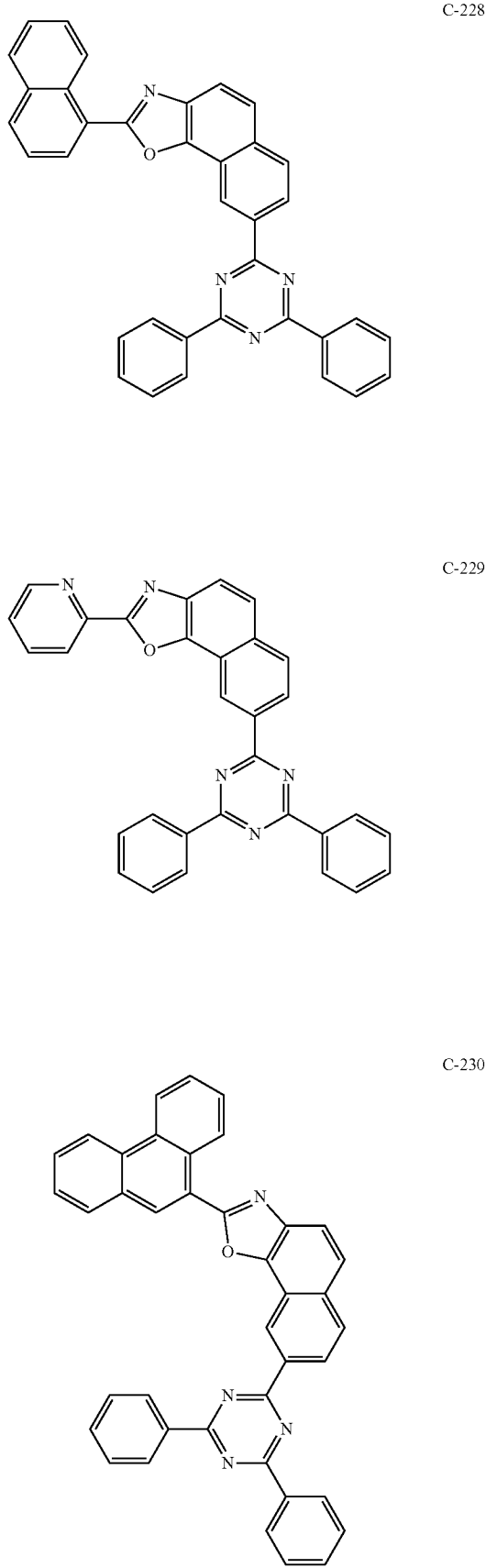

-continued
C-231
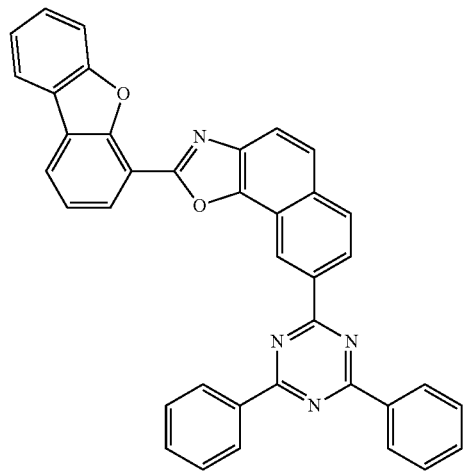
C-232
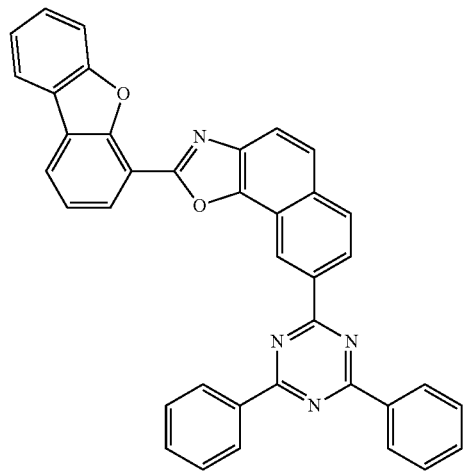
C-233
-continued
C-234
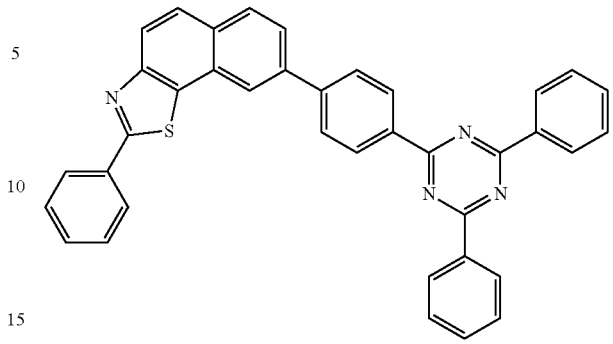
C-235
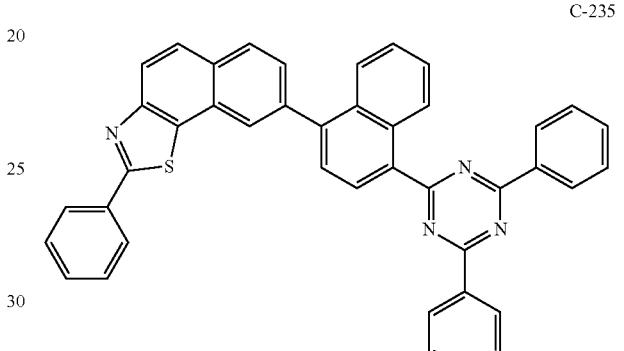
C-236
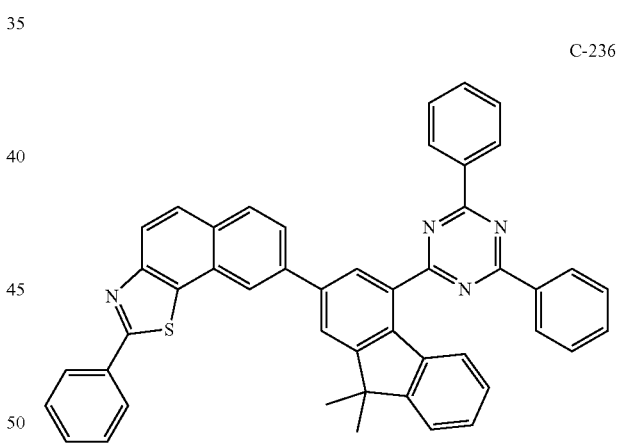
C-237
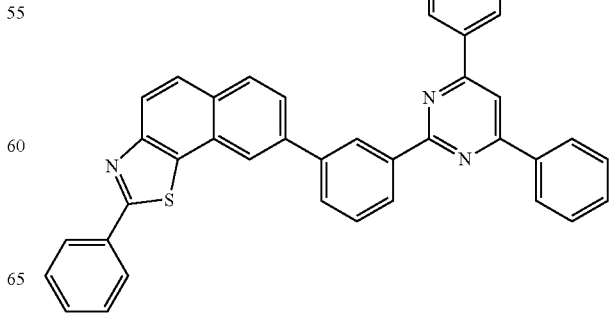

C-238
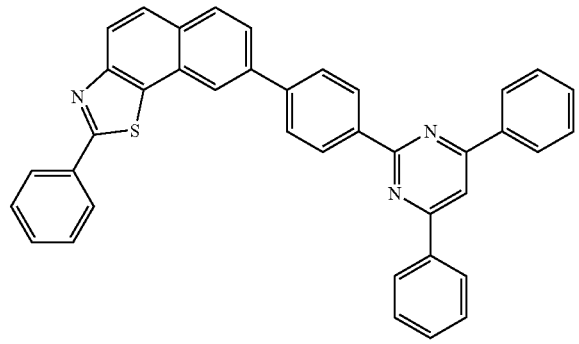
C-242
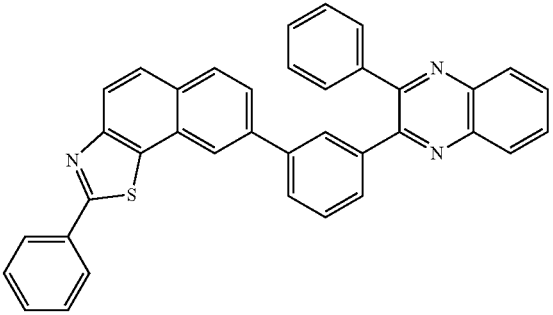
C-239
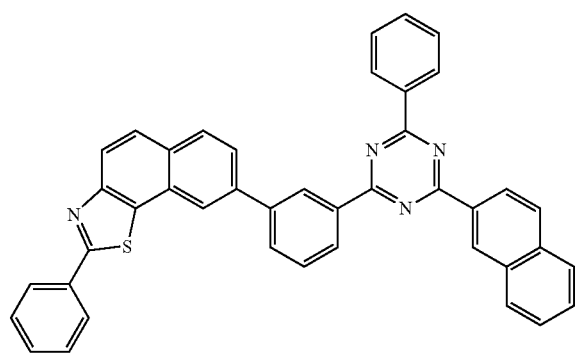
C-243
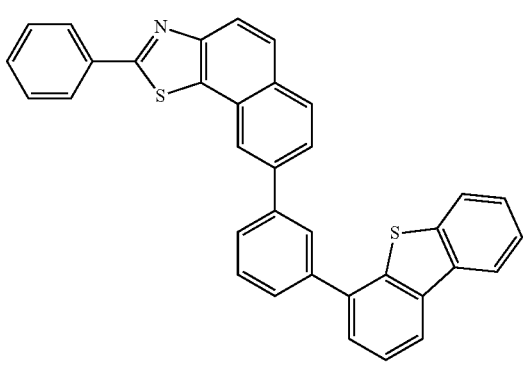
C-240
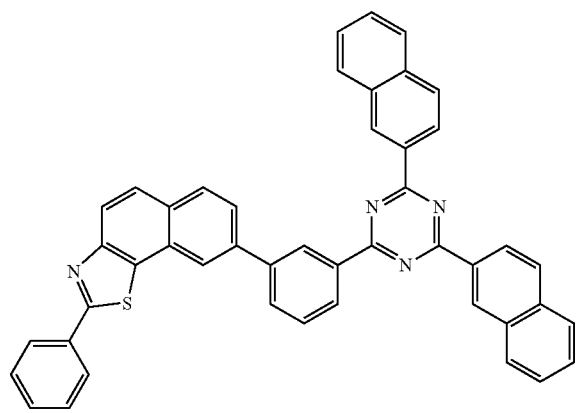
C-244
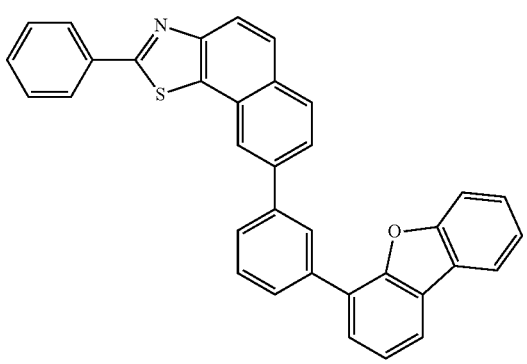
C-41
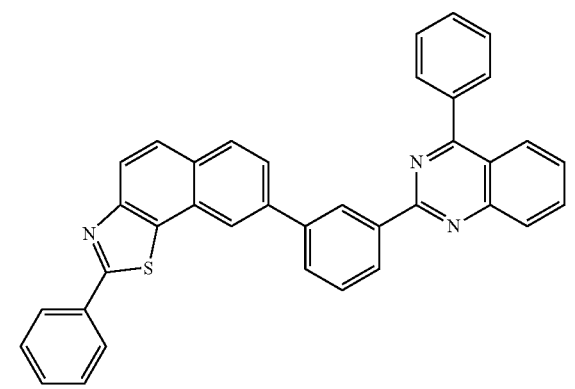
C-245
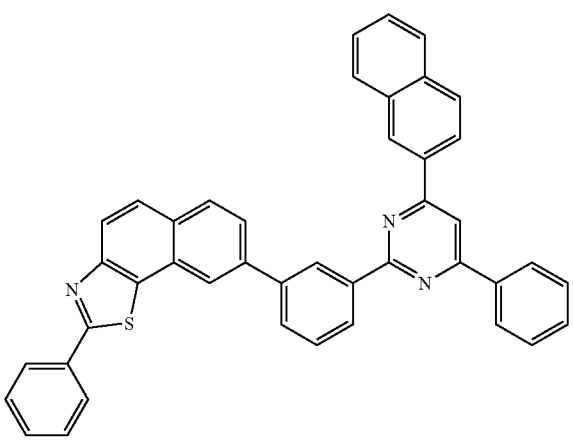

-continued
C-246
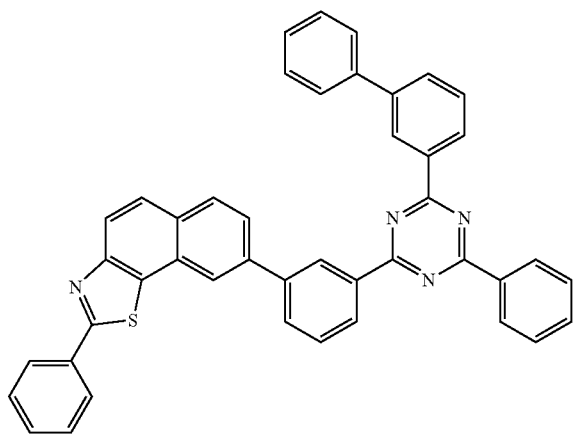
C-247
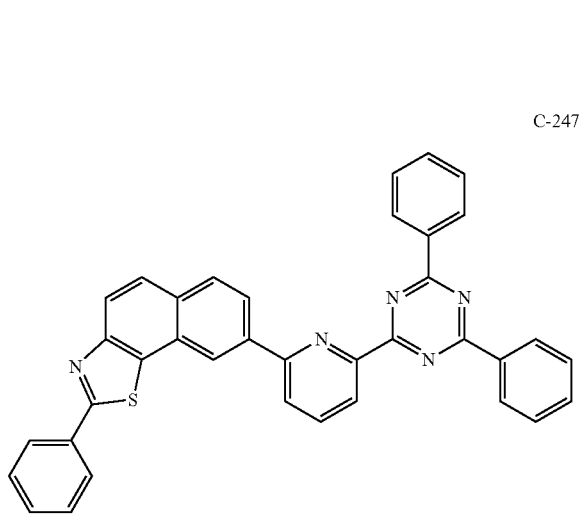
C-248
-continued
C-249
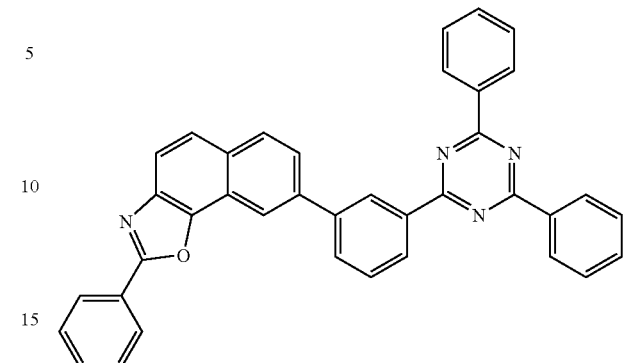
C-250
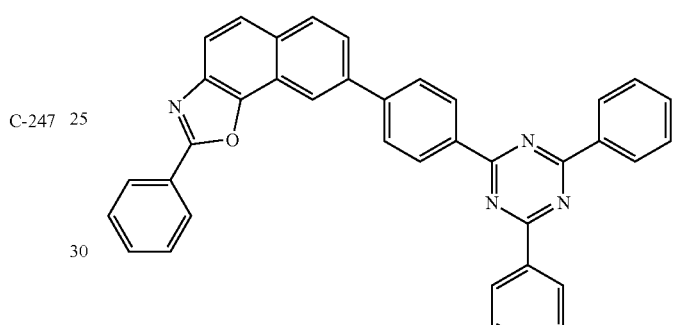
C-251
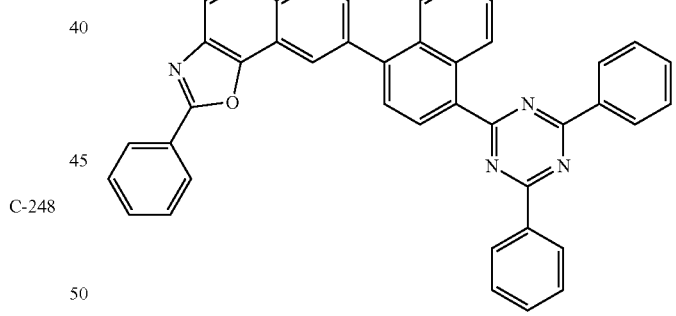
C-252
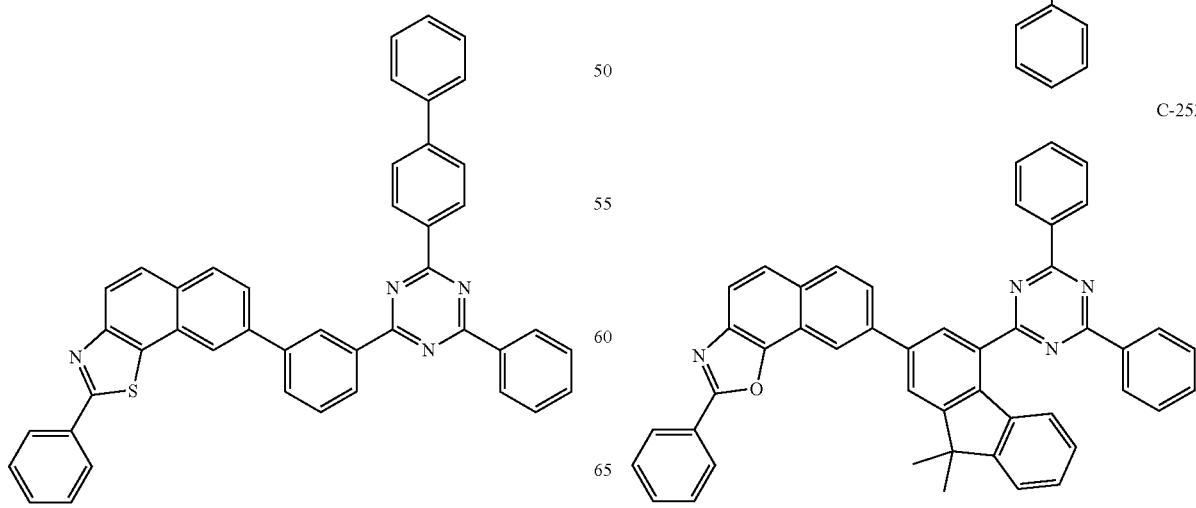

C-253
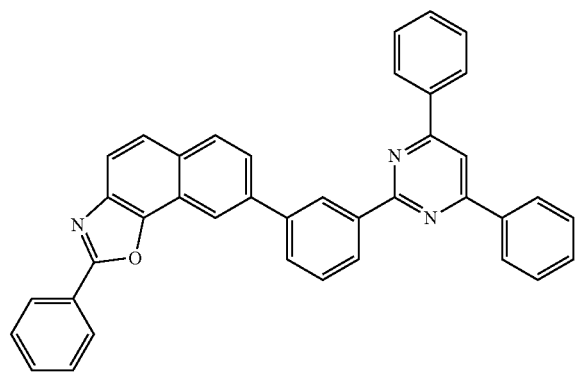
C-254
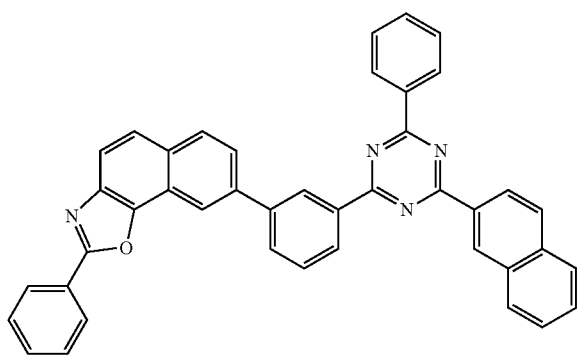
C-255
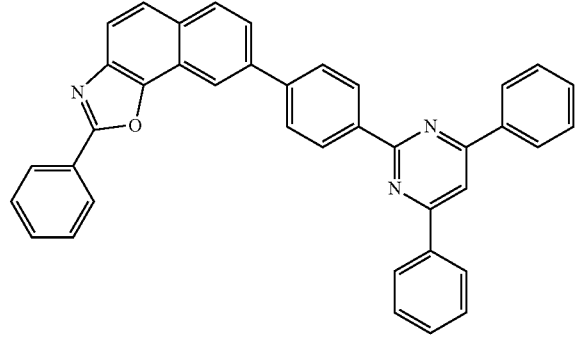
C-256
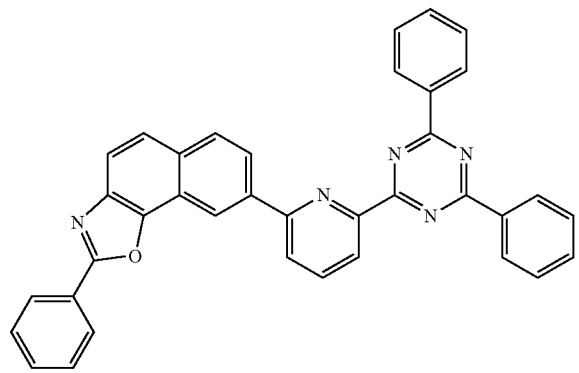
C-257
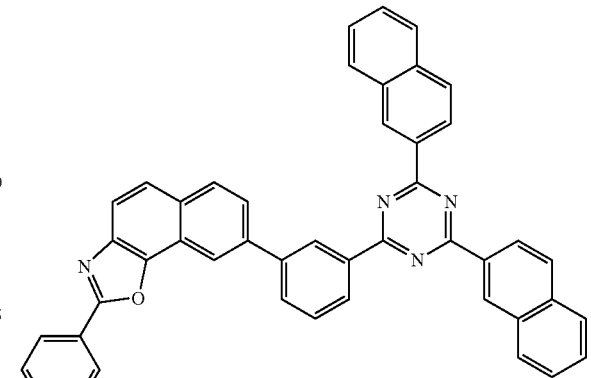
C-258
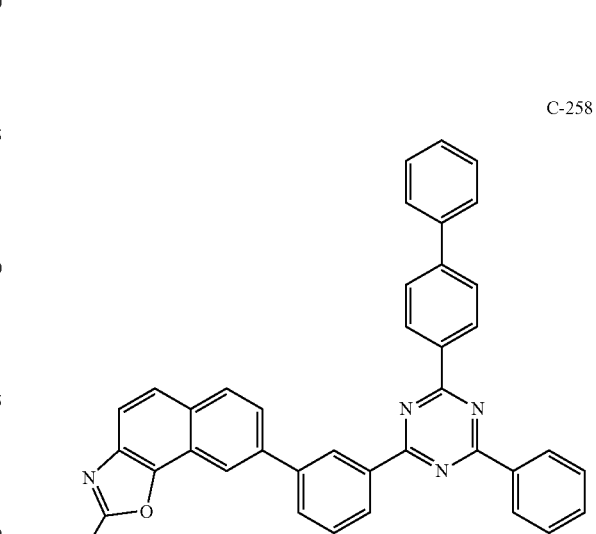
C-259
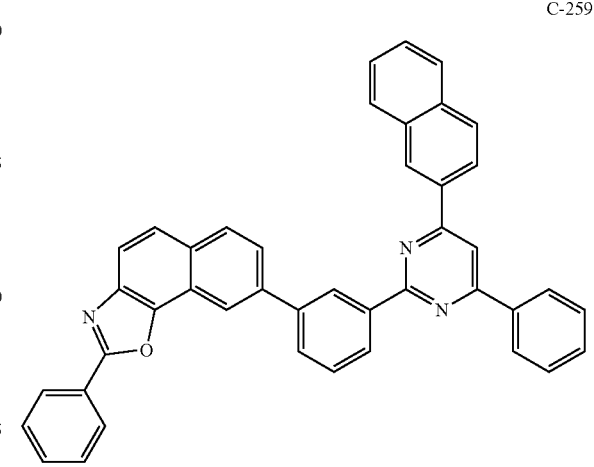

C-260
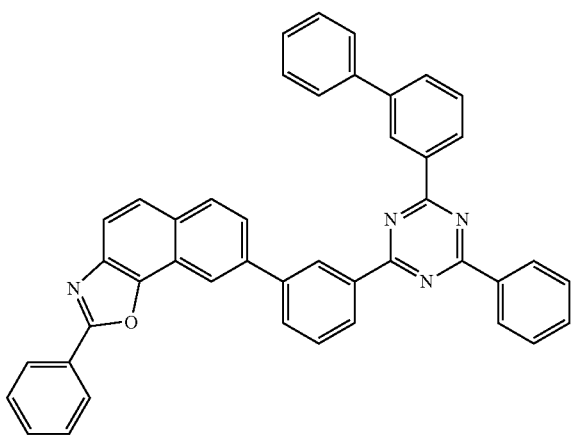
C-261
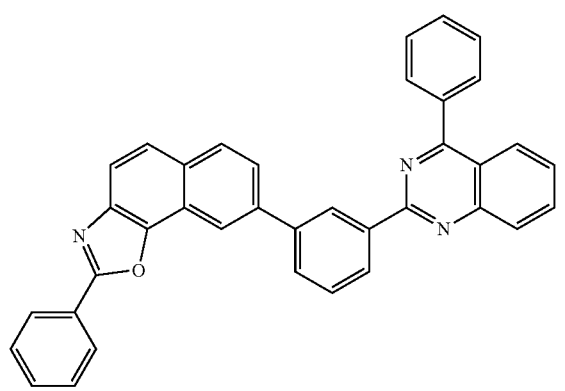
C-262
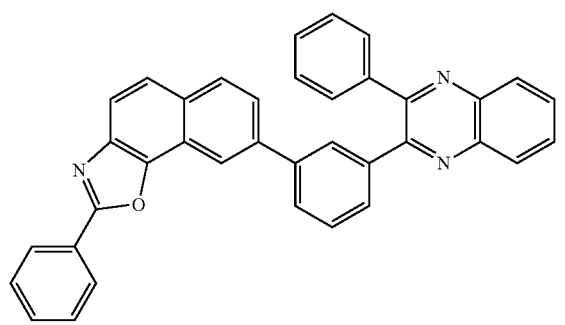
C-263
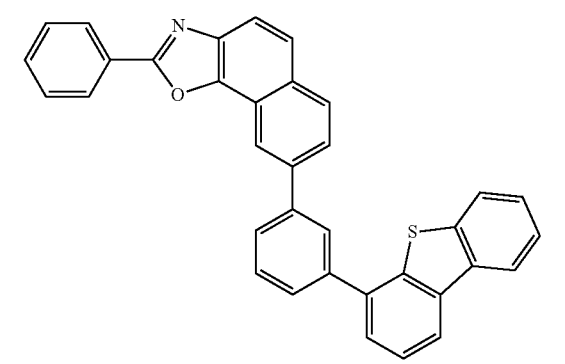
C-264
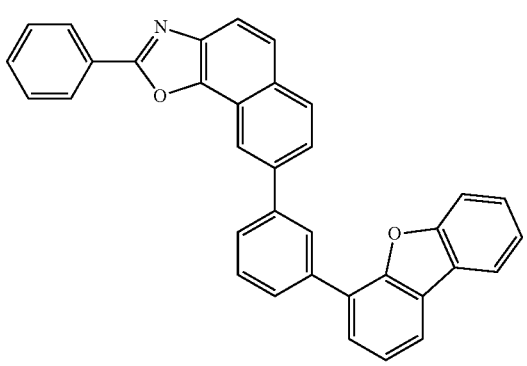
The organic electroluminescent compound according to the present disclosure can be prepared by known methods to one skilled in the art, and can be prepared, for example, according to the following reaction scheme:
Reaction Scheme 1
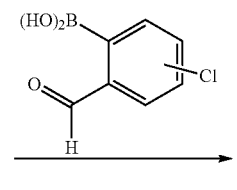
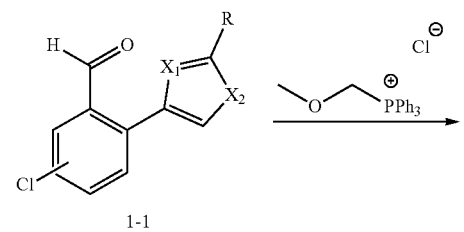
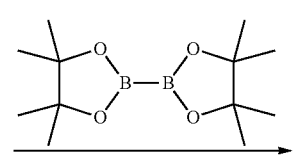

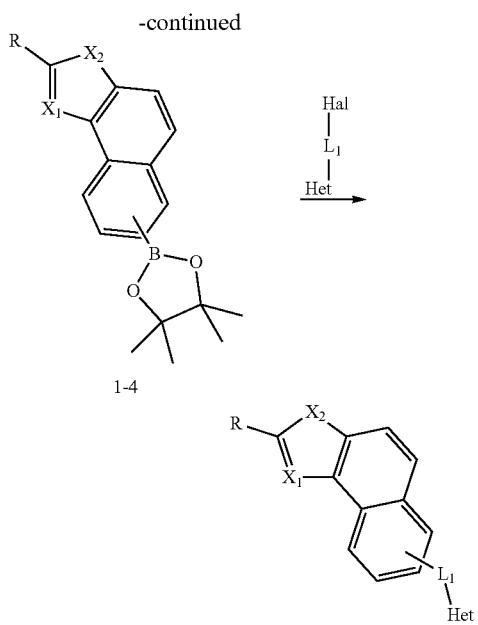

wherein $X_1$, $X_2$, R, $L_1$, and Het are as defined in formula 1, and Hal represents a halogen. The present disclosure provides an organic electroluminescent material comprising the organic electroluminescent compound of formula 1, and an organic EL device comprising the material.

The material can be comprised of the organic electroluminescent compound of the present disclosure alone, or can be a mixture or composition for an organic electroluminescent material which further comprises conventional materials generally included in organic electroluminescent materials.

The organic electroluminescent device according to the present disclosure may comprise a first electrode, a second electrode, and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic electroluminescent compound of formula 1 may be comprised in at least one layer of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer, preferably in at least one layer of the light-emitting layer, the electron buffer layer, and the electron transport layer. When used in the light-emitting layer, the organic electroluminescent compound of formula 1 may be comprised as a phosphorescent host material; when used in the electron buffer layer, the organic electroluminescent compound of formula 1 may be comprised as an electron buffer material; and when used in the electron transport layer, the organic electroluminescent compound of formula 1 may be comprised as an electron transport material.

The light-emitting layer may comprise at least one host and at least one dopant. The light-emitting layer emits light, which may be a single layer or multi-layers having two or more layers. The doping concentration of the dopant compound to the host compound in the light-emitting layer is preferably less than 20 wt %.

Preferably, the light-emitting layer may comprise at least one dopant, and, if necessary, may further comprise another compound besides the organic electroluminescent compound of formula 1 as a host material. When the organic electroluminescent compound of formula 1 is comprised as a host material, the weight ratio of the compound of formula 1 (first host material) to the other compound besides the compound of formula 1 (second host material) is in the range of 1:99 to 99:1.

The host material consisting of another compound besides the compound of formula 1 can be used of any of the known hosts. In terms of luminous efficiency, the host material consisting of another compound besides the compound of formula 1 may be preferably selected from the group consisting of the compounds represented by the following formulae 11 to 16:

 (11)

 (12)

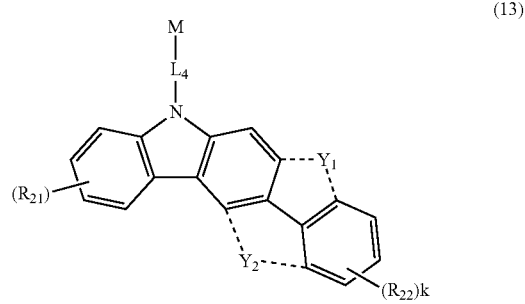 (13)

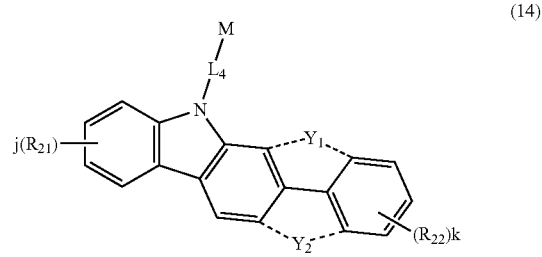 (14)

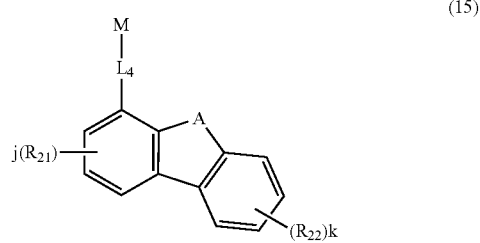 (15)

wherein

Cz represents the following structure:

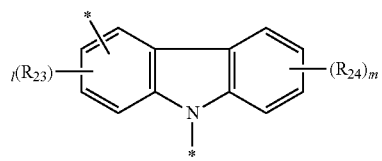

A represents —O— or —S—; and $R_{21}$ to $R_{24}$, each independently, represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, or —$SiR_{25}R_{26}R_{27}$; in which $R_{25}$ to $R_{27}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted (5- to 30-membered)heteroarylene; M represents a substituted or unsubstituted (C6-C30)aryl, or a substituted or unsubstituted (5- to 30-membered)heteroaryl; $Y_1$ and $Y_2$, each independently, represent —O—, —S—, —$NR_{31}$— or —$CR_{32}R_{33}$—, with the proviso that $Y_1$ and $Y_2$ are not present simultaneously; $R_{31}$ to $R_{33}$, each independently, represent a substituted or unsubstituted (C1-C30)alkyl, a substituted or unsubstituted (C6-C30)aryl, or a substituted or unsubstituted (5- to 30-membered)heteroaryl; $R_{32}$ and $R_{33}$ may be the same or different; h and i, each independently, represent an integer of 1 to 3; j, k, l, and m, each independently, represent an integer of 0 to 4; where if h, i, j, k, l, or m represents an integer of 2 or more, each (Cz-$L_a$), each (Cz), each $R_{21}$, each $R_{22}$, each $R_{23}$, or each $R_{24}$ may be the same or different;

(16)

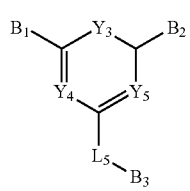

wherein $Y_3$ to $Y_5$, each independently, represent $CR_{34}$ or N, in which $R_{34}$ represents hydrogen, a substituted or unsubstituted (C1-C30)alkyl, a substituted or unsubstituted (C6-C30)aryl, or a substituted or unsubstituted (5- to 30-membered)heteroaryl;

$B_1$ and $B_2$, each independently, represent hydrogen, a substituted or unsubstituted (C6-C30)aryl, or a substituted or unsubstituted (5- to 30-membered)heteroaryl;

$B_3$ represents a substituted or unsubstituted (C6-C30)aryl, or a substituted or unsubstituted (5- to 30-membered)heteroaryl; and $L_5$ represents a single bond, a substituted or unsubstituted (C6-C30)arylene, or a substituted or unsubstituted (5- to 30-membered)heteroarylene.

Specifically, the preferred examples of the second host material are as follows, but are not limited thereto.

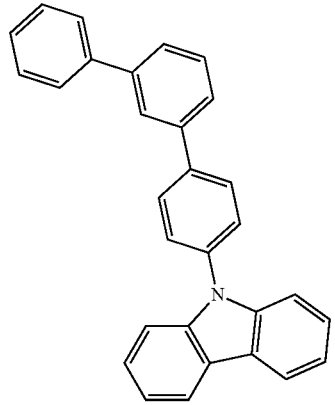
B-1

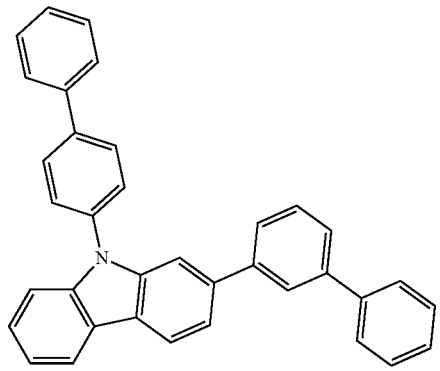
B-2

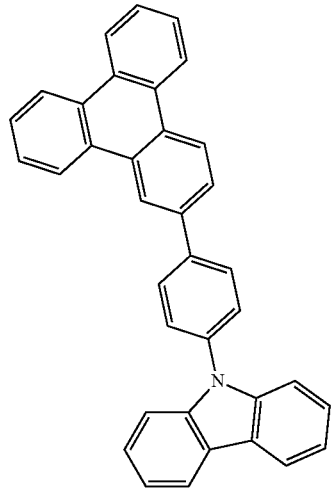
B-3

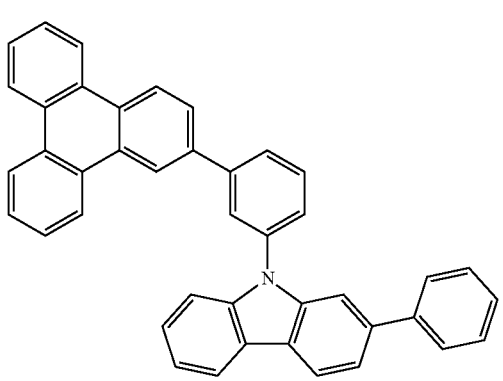
B-4

B-5
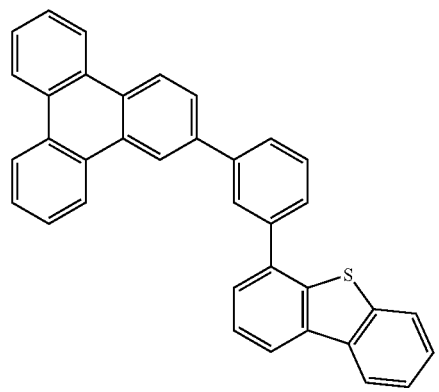
B-6
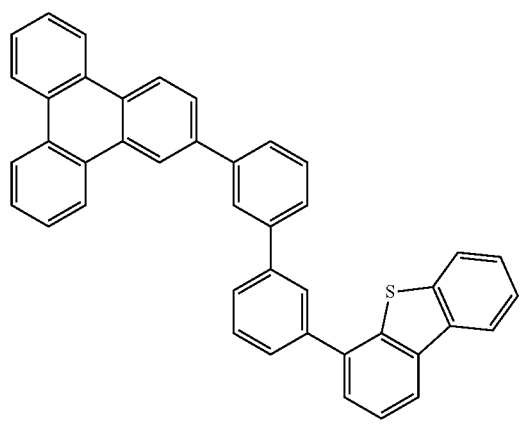
B-7
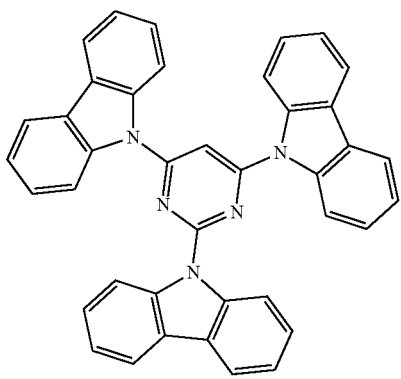
B-8
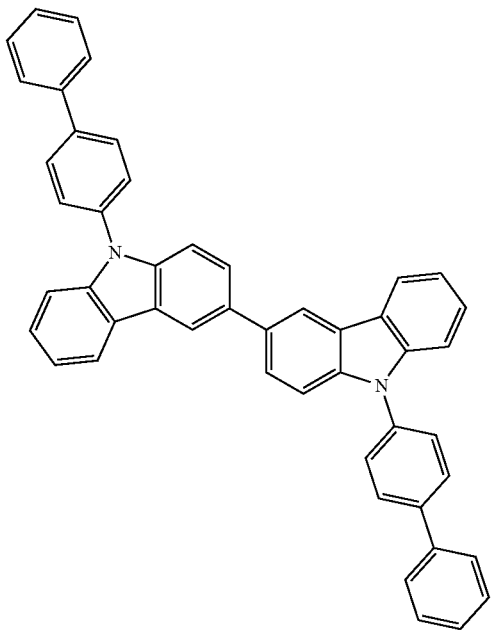
B-9
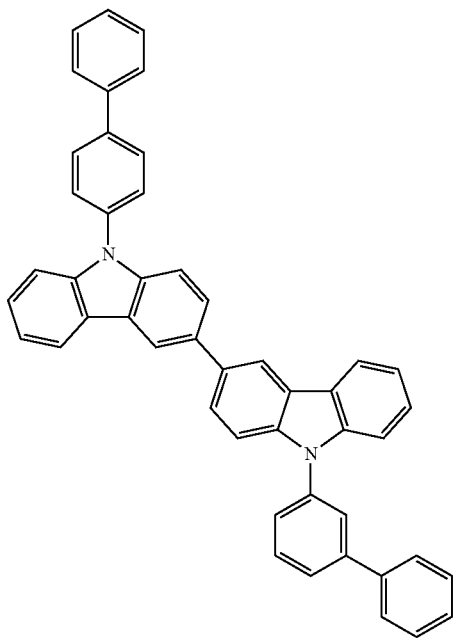

B-10
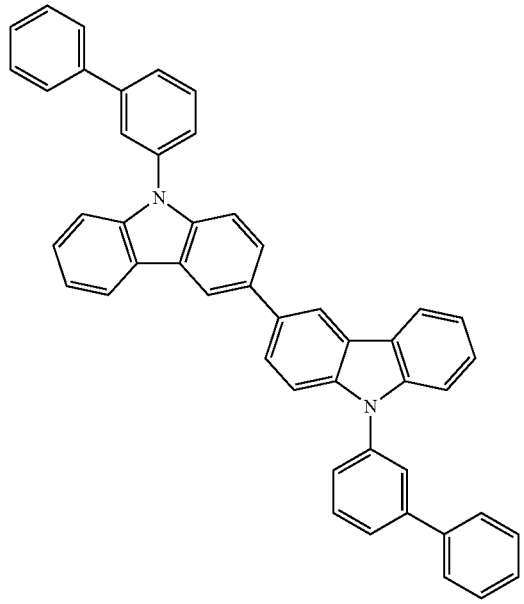
B-12
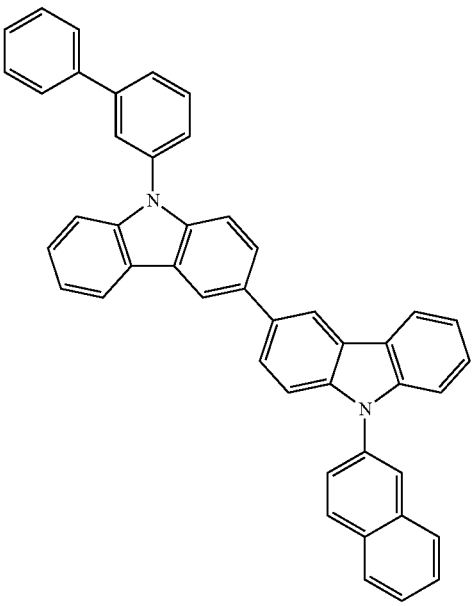
B-13
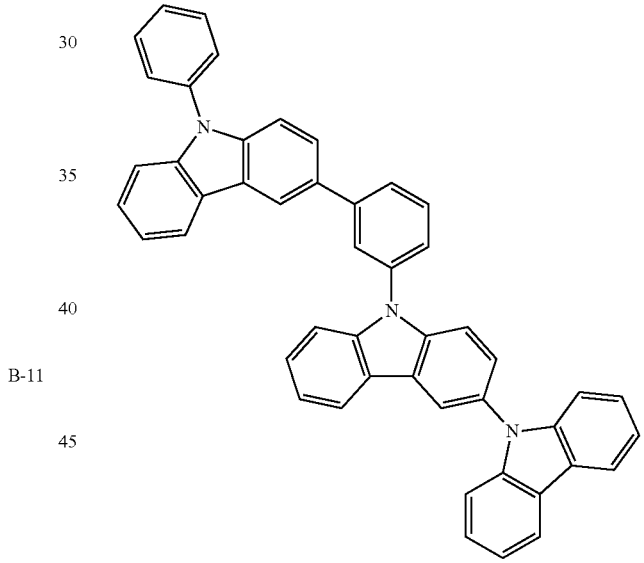
B-11
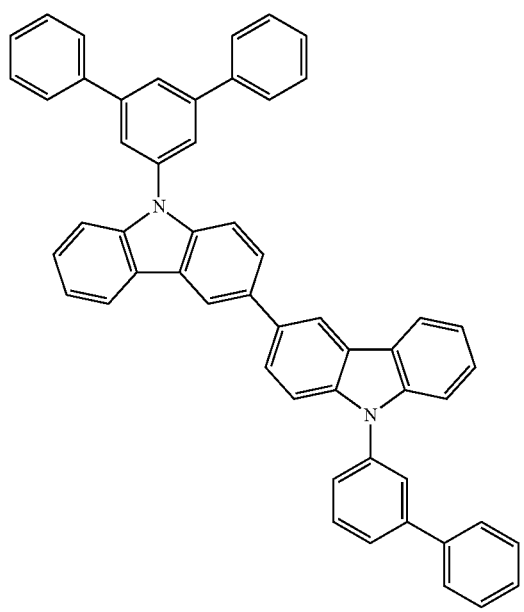
B-14
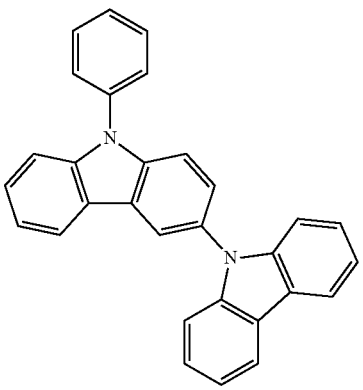

B-15
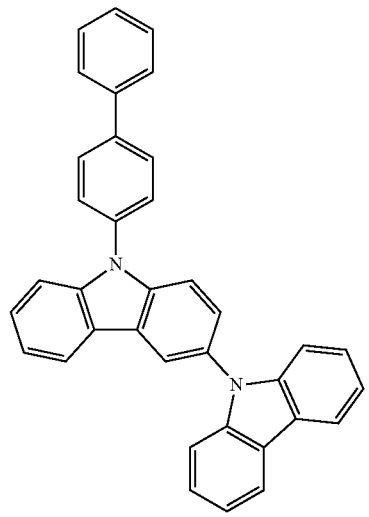
B-16
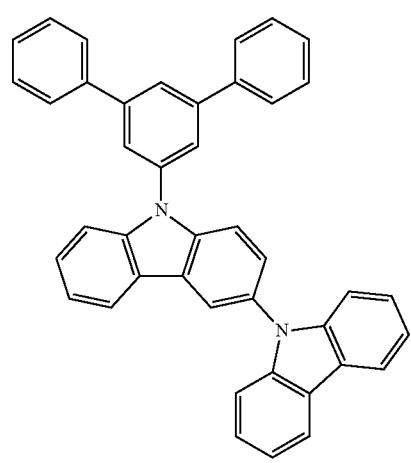
B-17
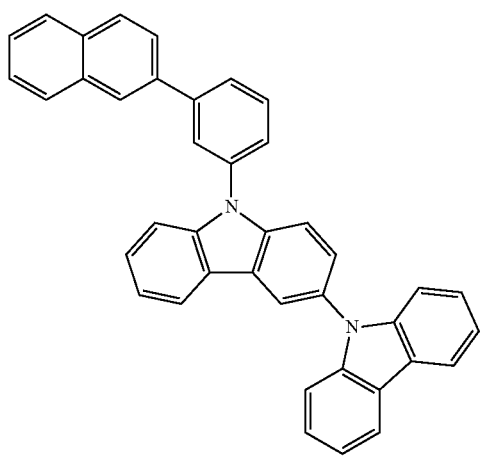
B-18
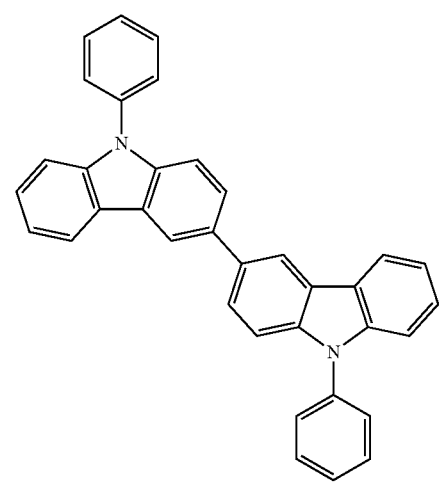
B-19
B-20
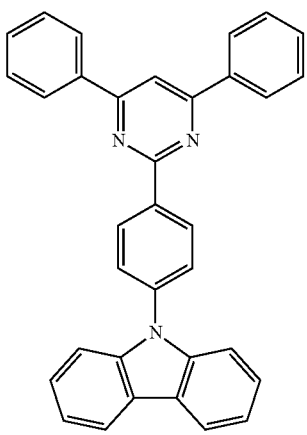

B-21
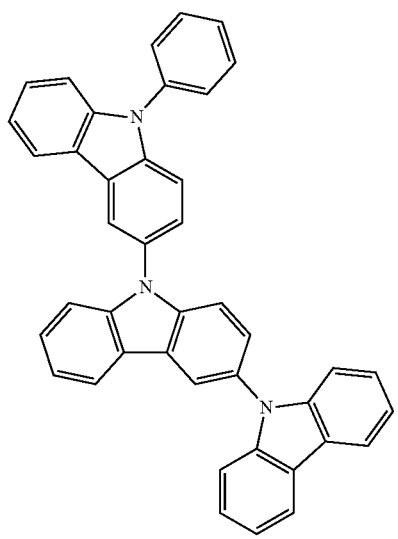
B-23
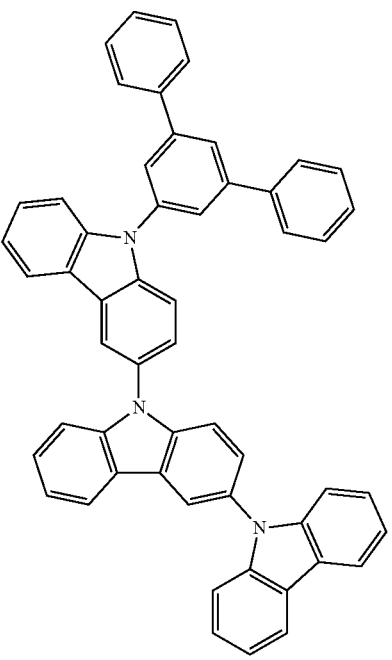
B-22
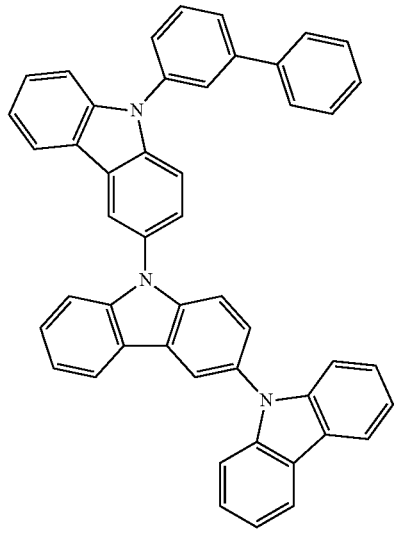
B-24
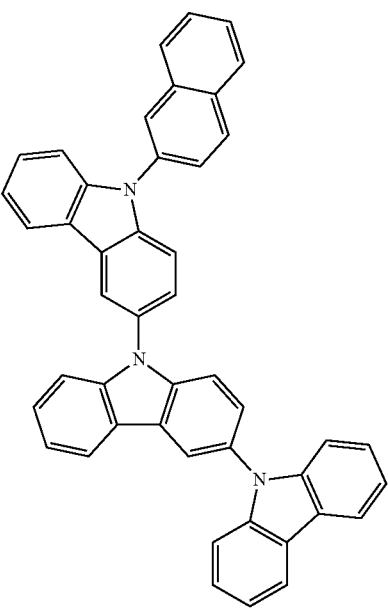

B-25
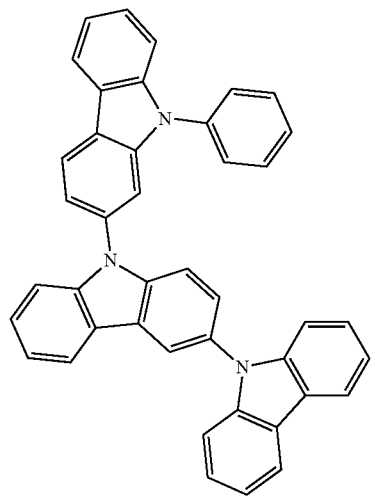
B-26
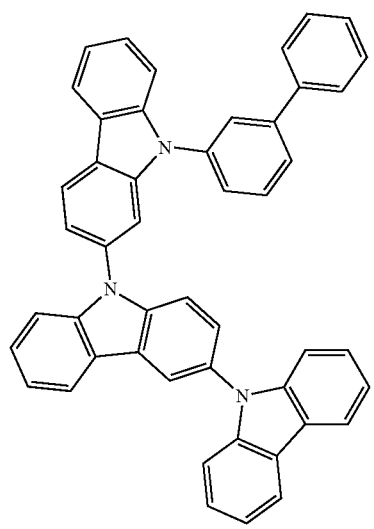
B-27
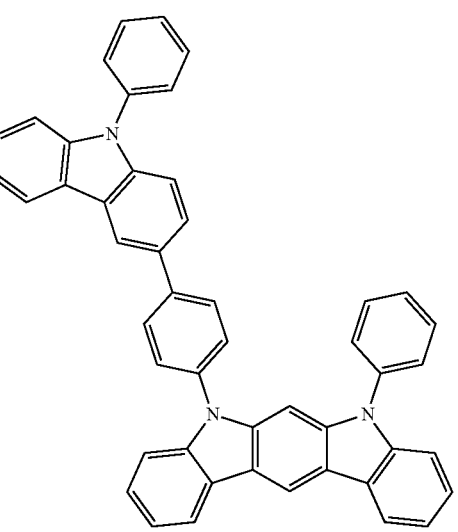
B-28
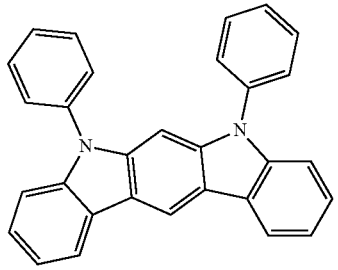
B-29
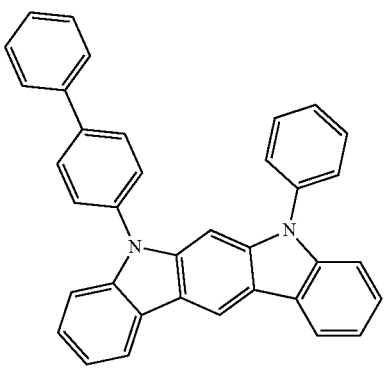
B-30
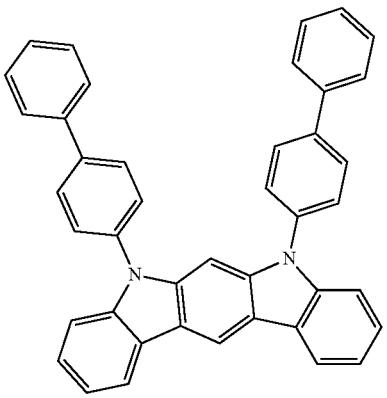
B-31
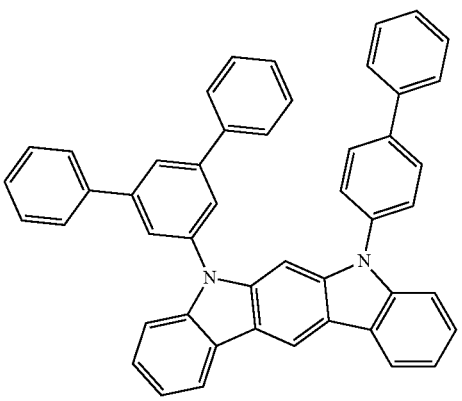

B-32
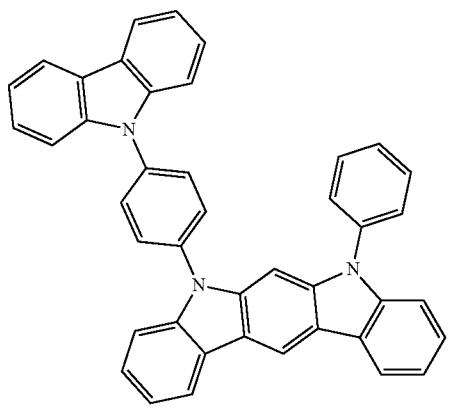
B-33
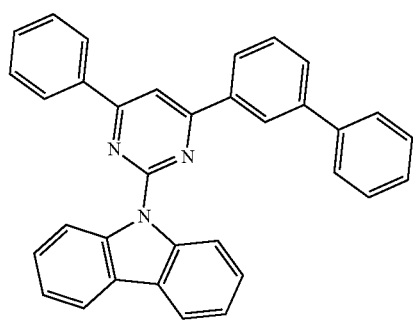
B-34
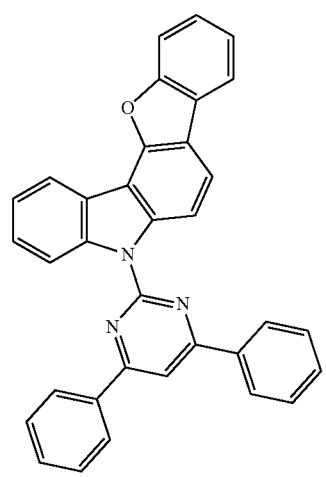
B-35
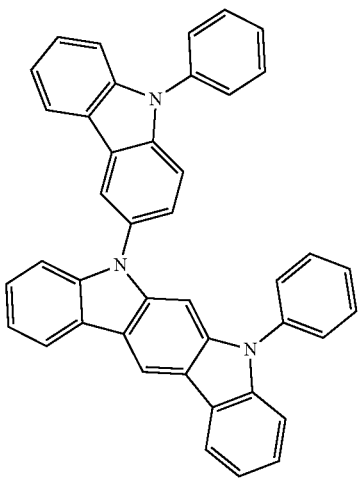
B-36
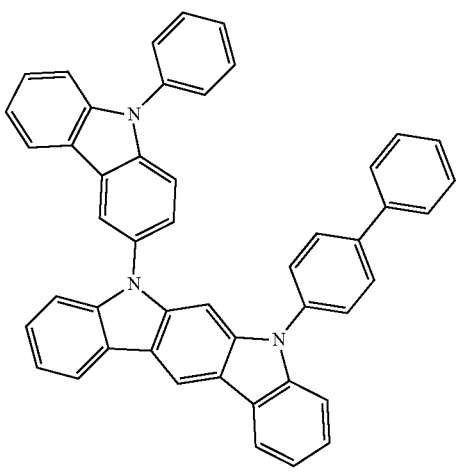
B-37
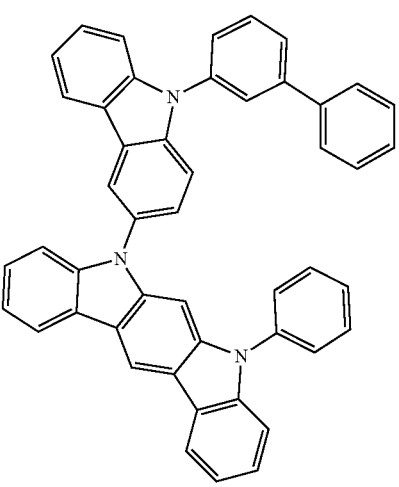

B-38
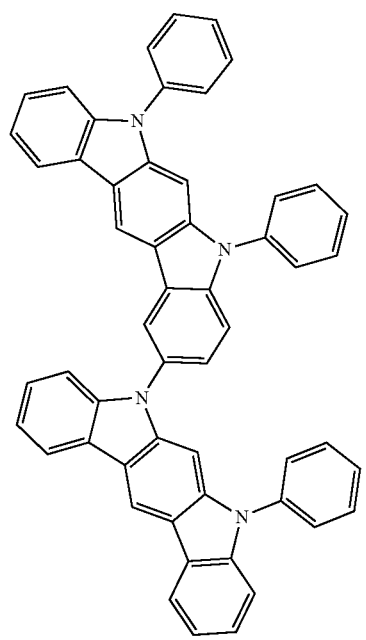
B-39
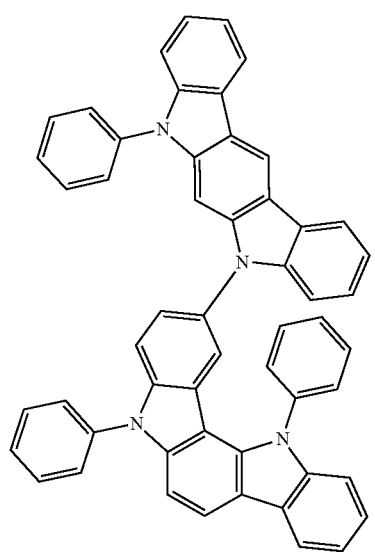
B-40
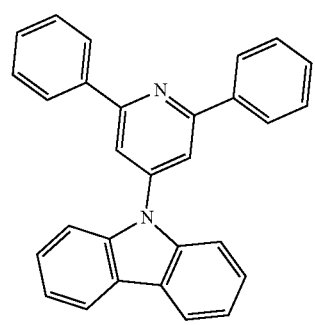
B-41
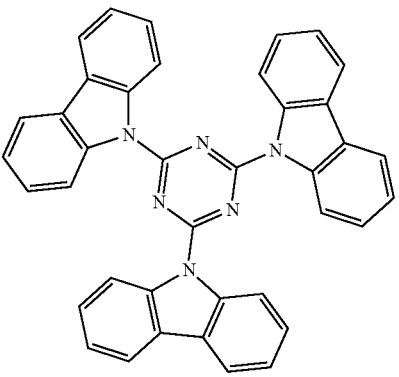
B-42
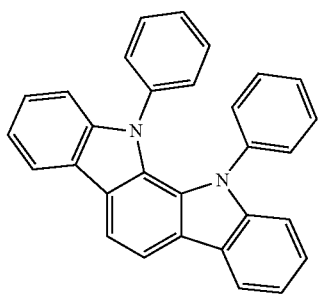
B-43
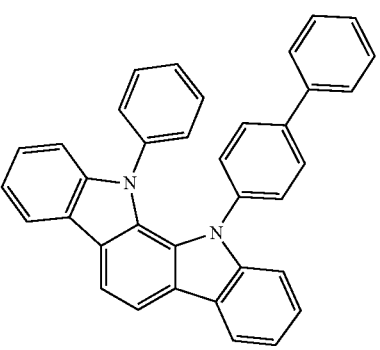
B-44
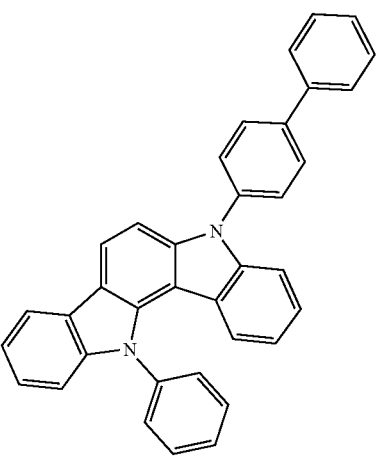

B-45
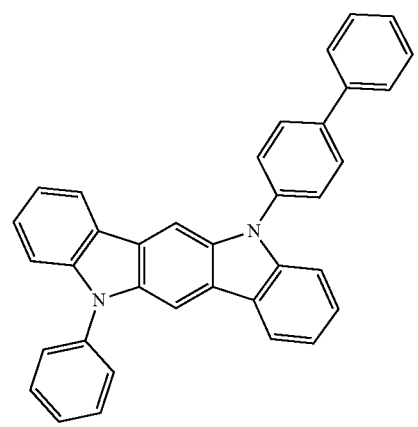
B-46
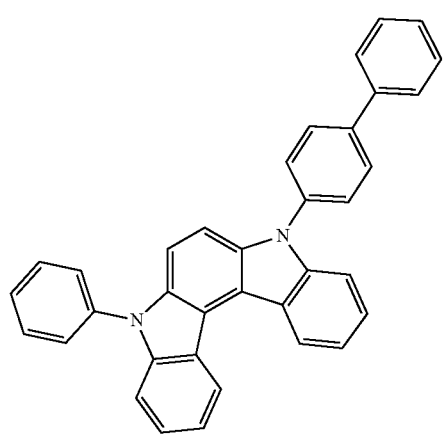
B-47
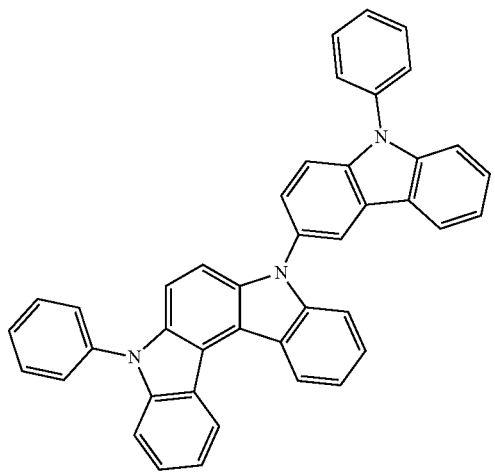
B-48
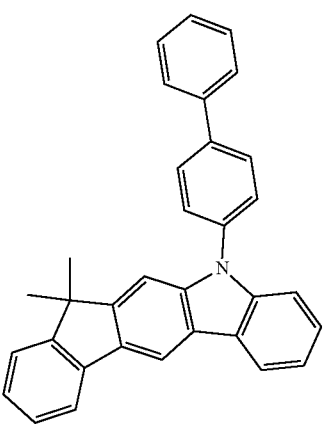
B-49
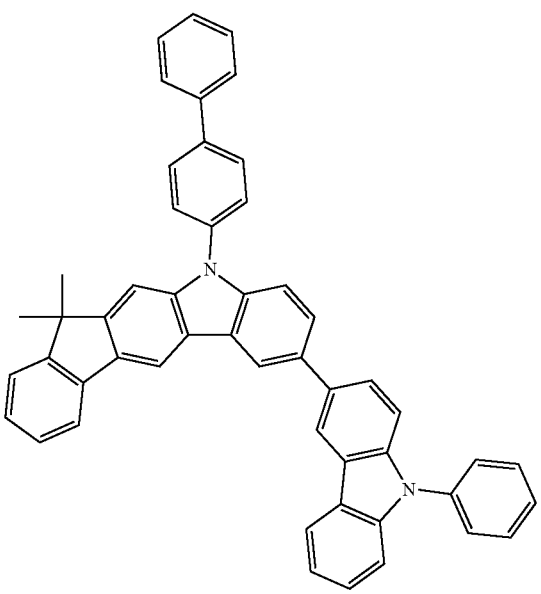
B-50

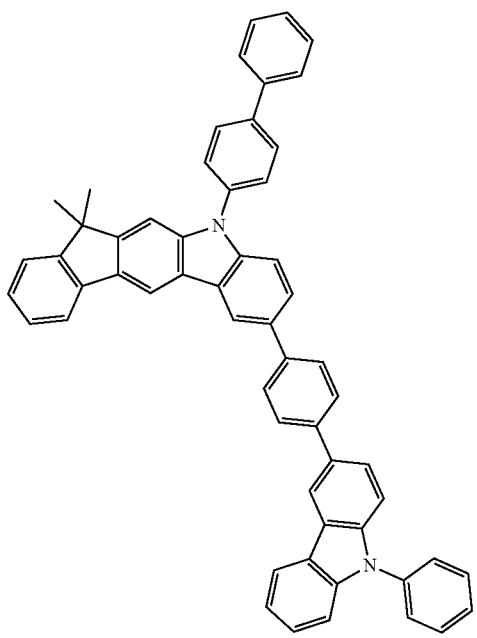
B-51
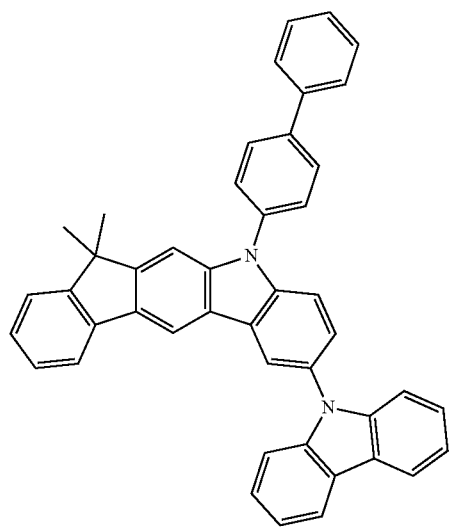
B-52
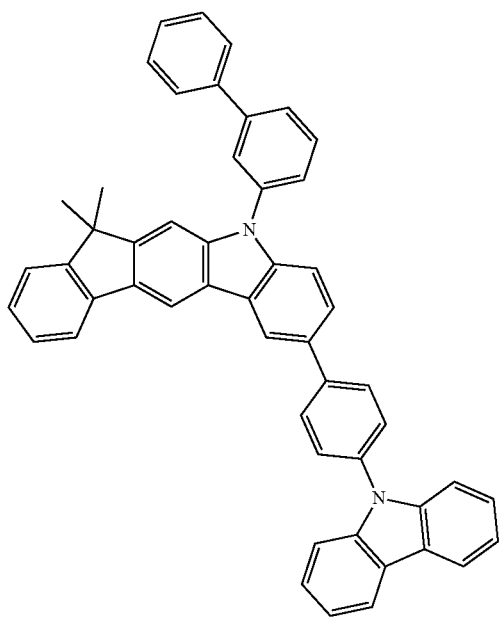
B-53
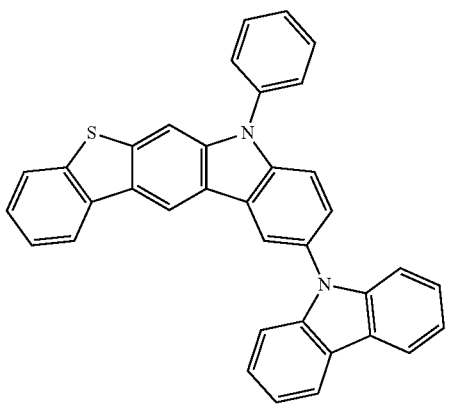
B-54
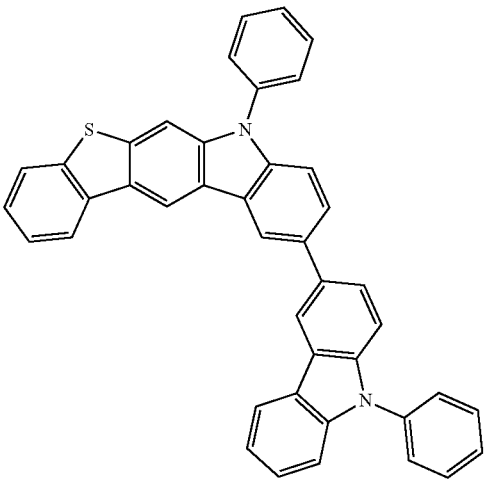
B-55

B-56
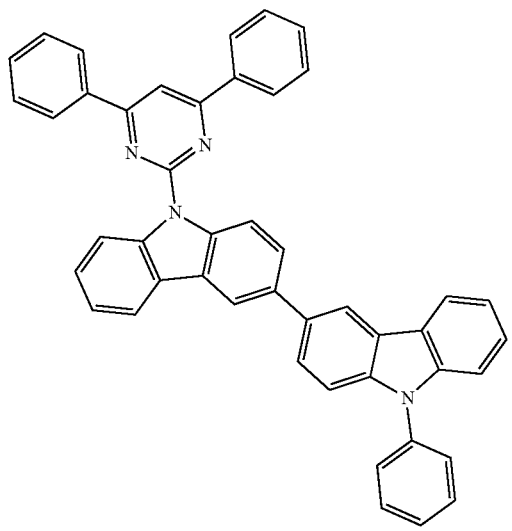
B-57
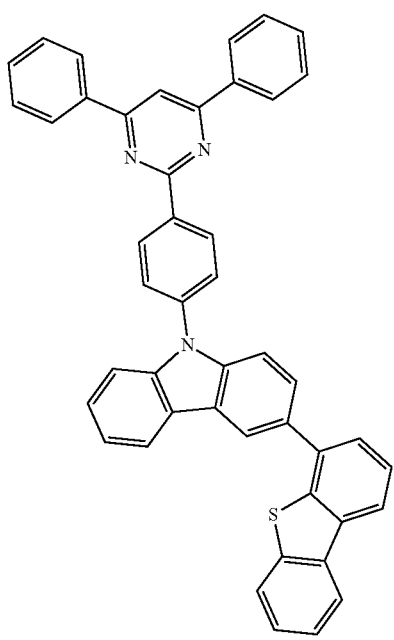
B-58
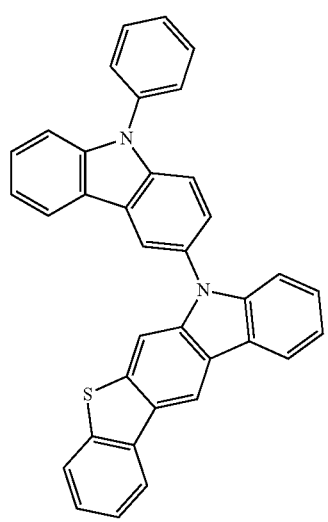
B-59
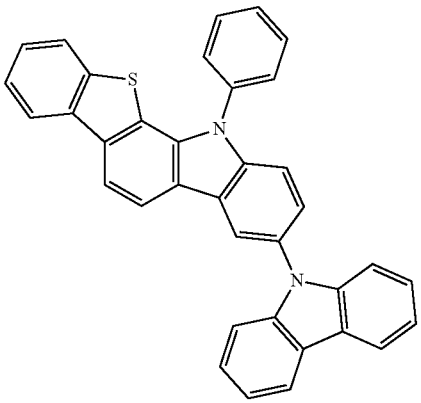
B-60
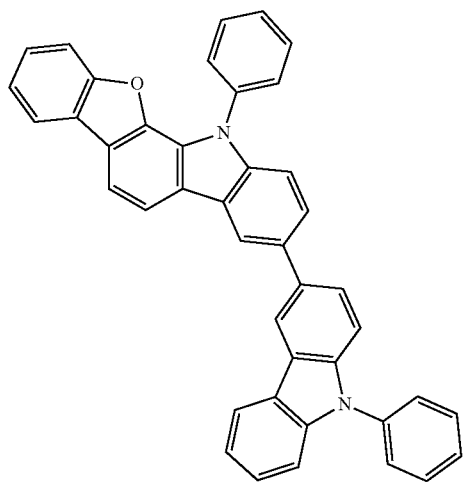
B-61
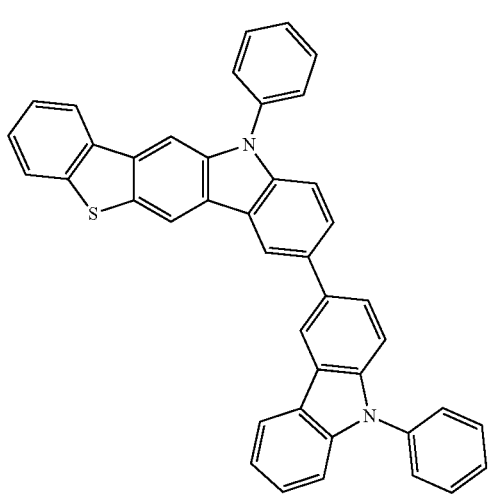

B-62
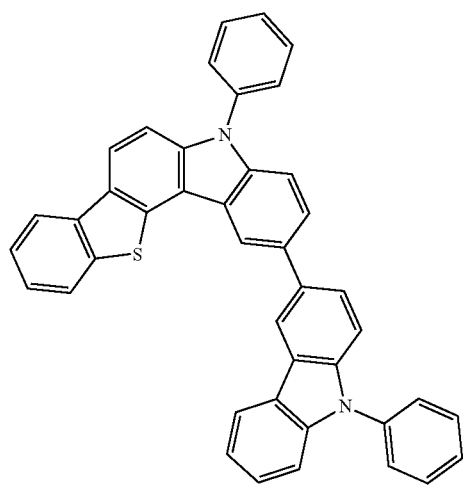
B-64
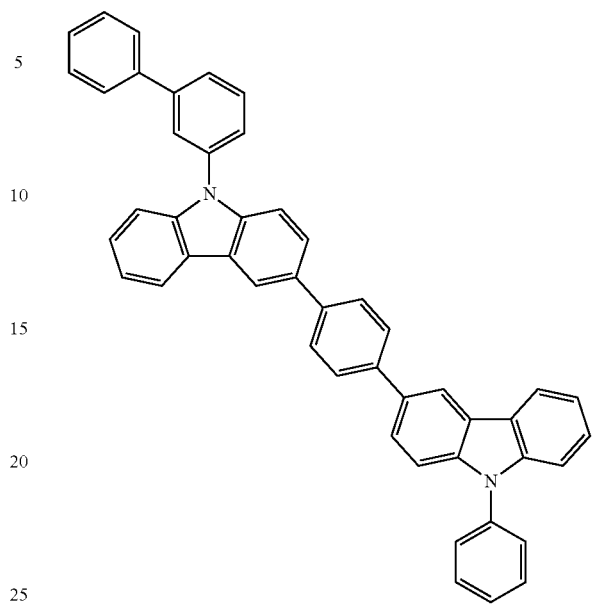
B-63
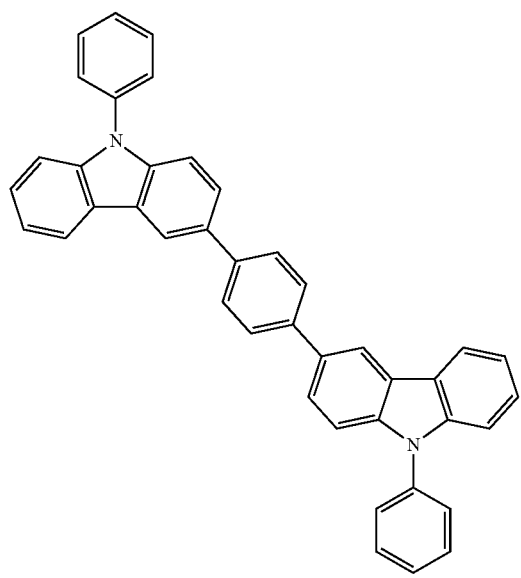
B-65
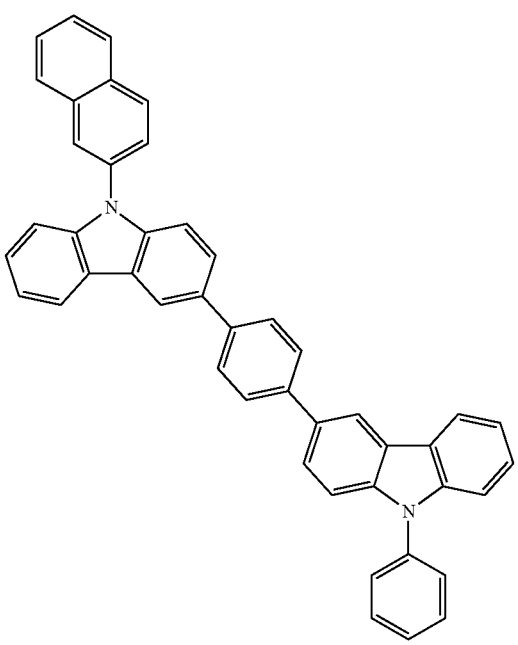

B-66
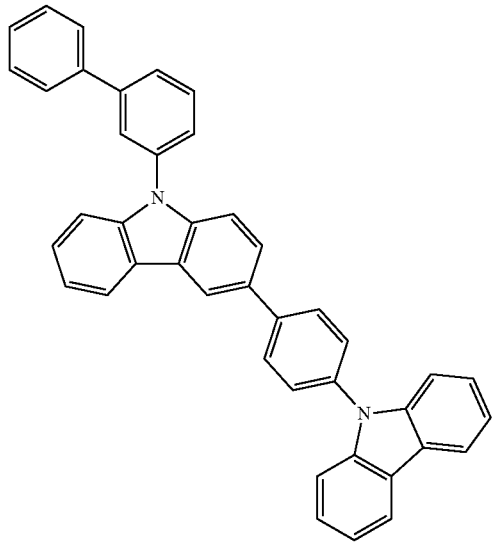
B-67
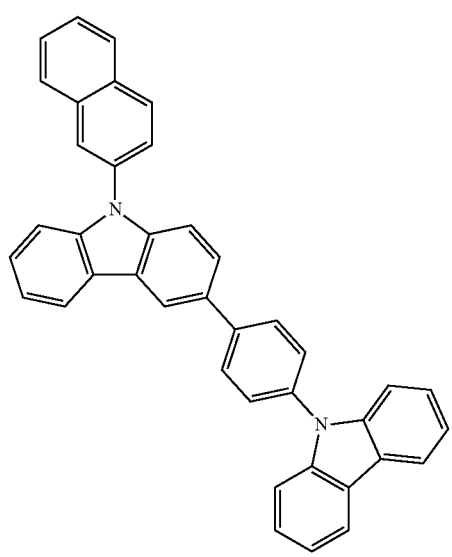
B-68
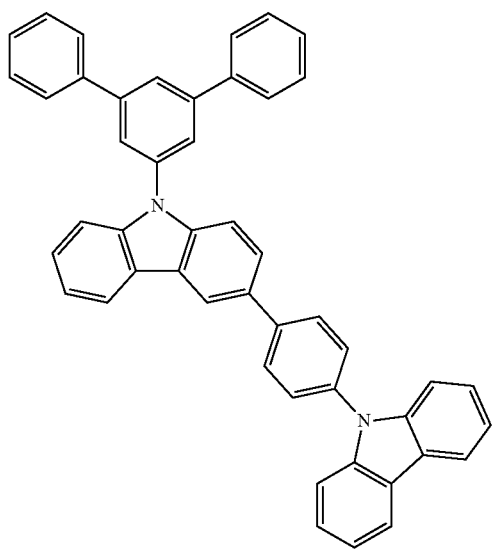
B-69
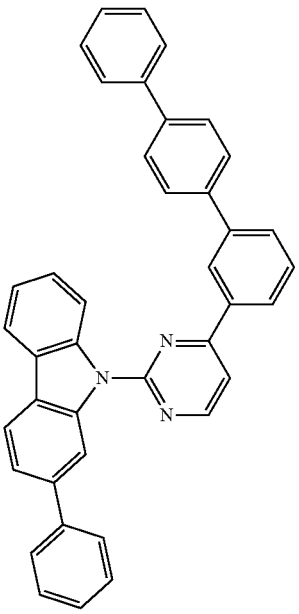
B-70
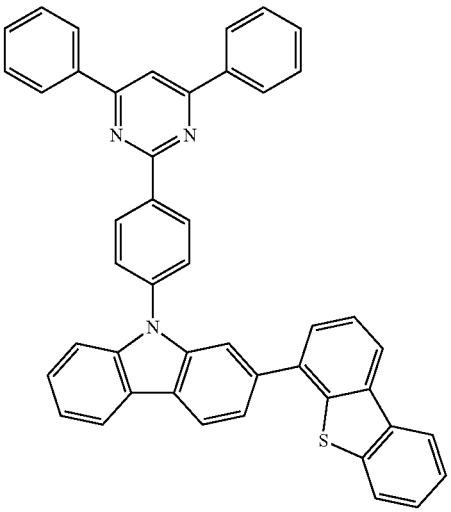
B-71
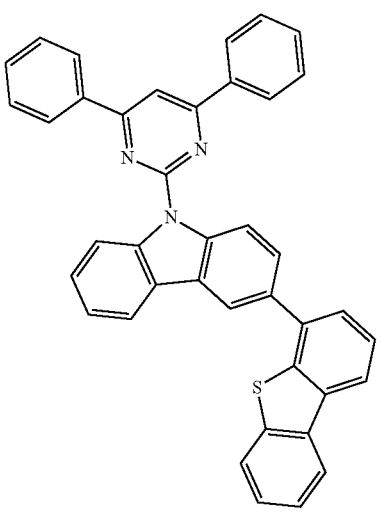

B-72
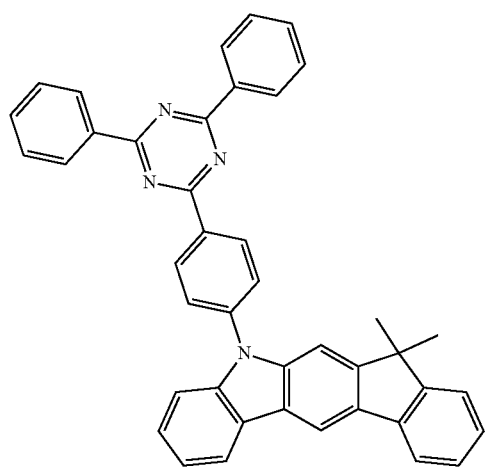
B-75
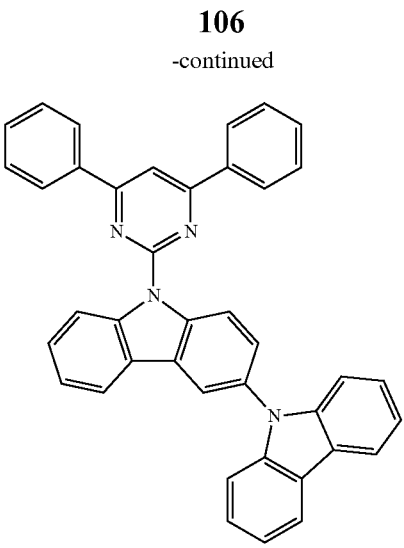
B-73
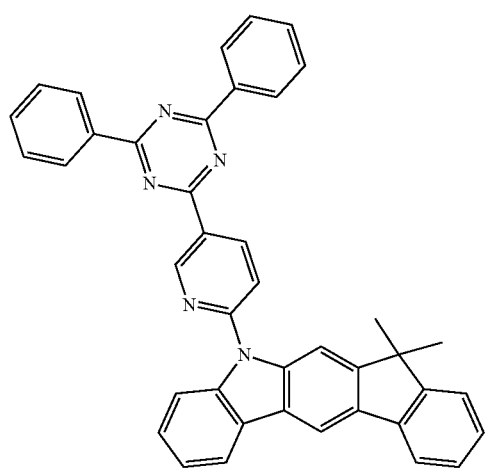
B-76
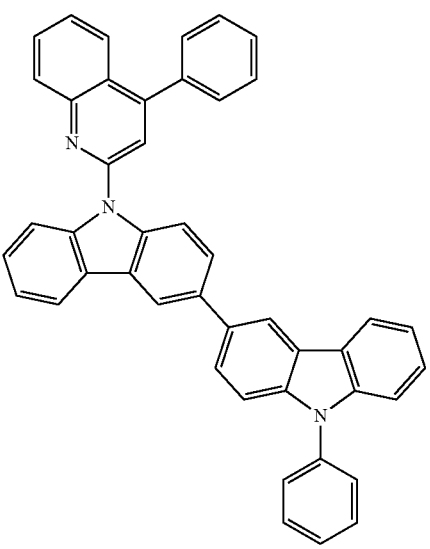
B-74
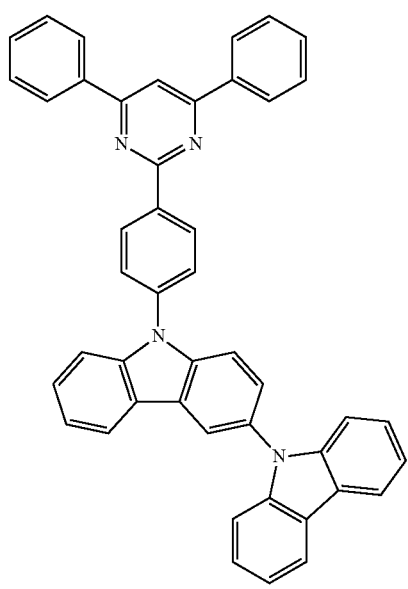
B-77
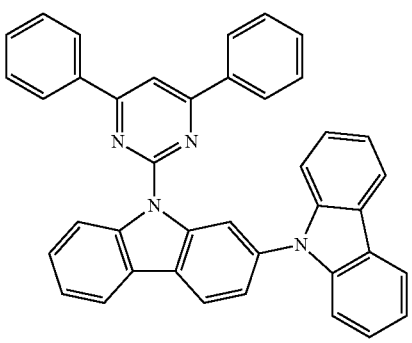

B-78
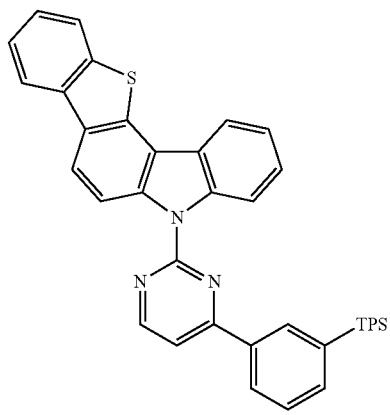
B-79
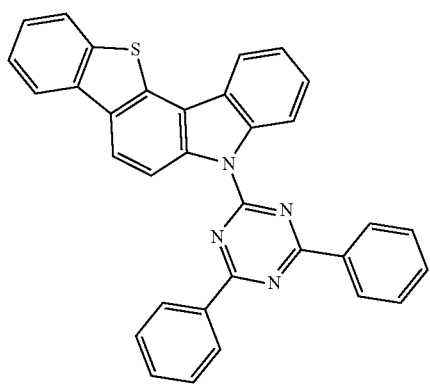
B-80
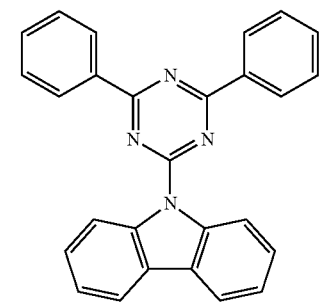
B-81
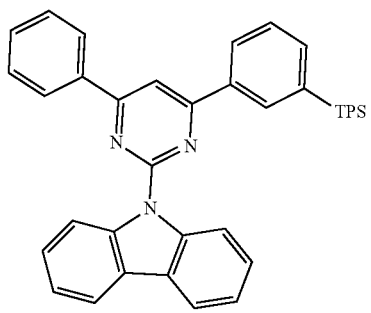
B-82
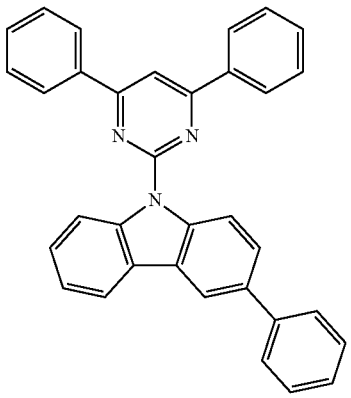
B-83
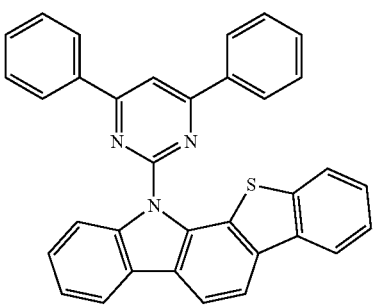
B-84
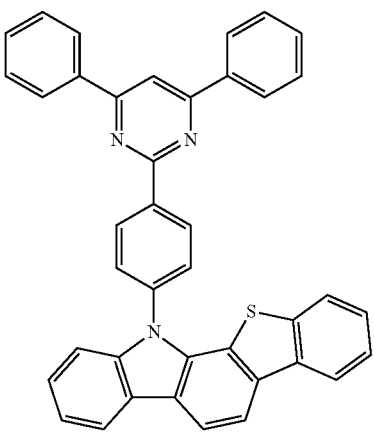
B-85
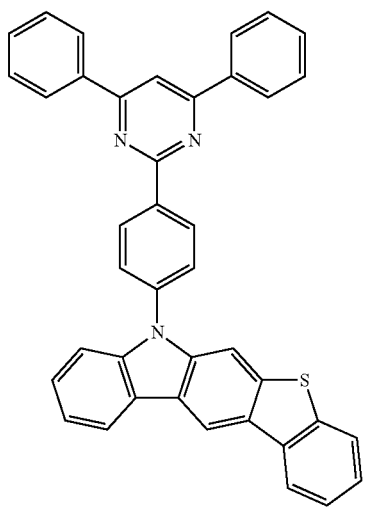

B-86
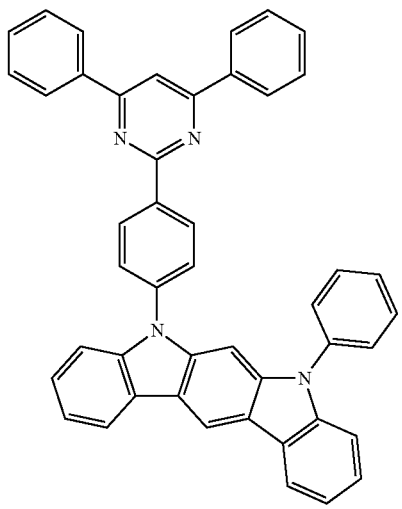
B-89
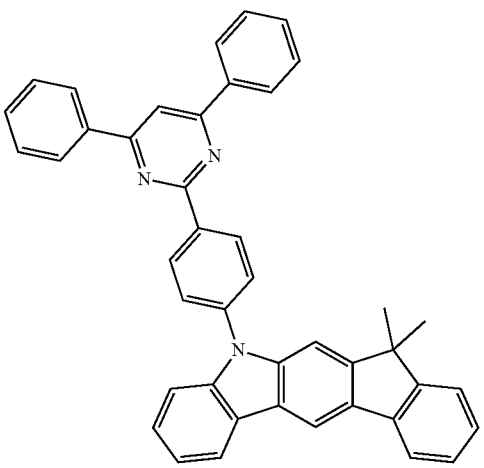
B-87
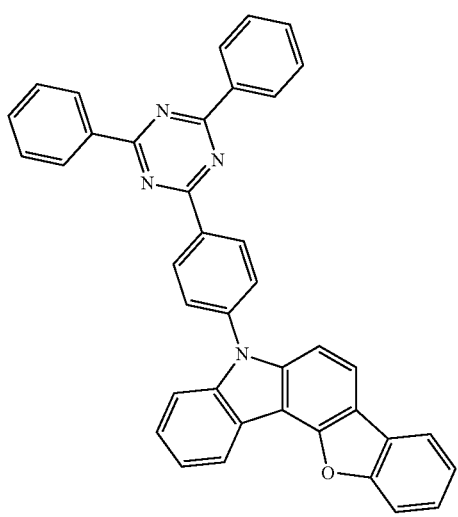
B-90
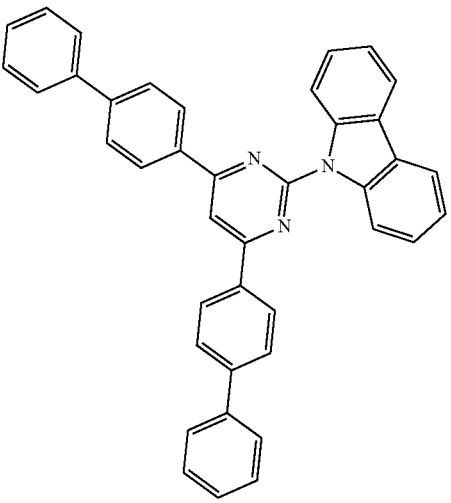
B-88
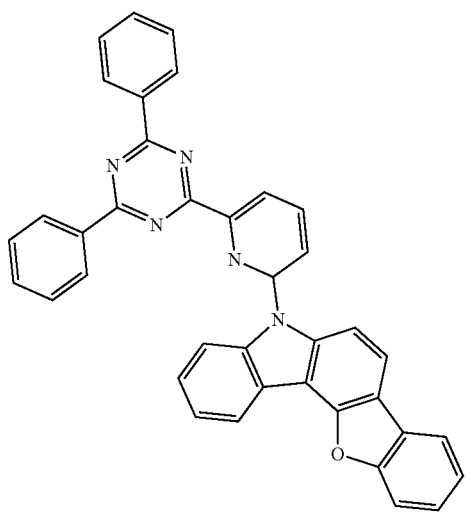
B-91
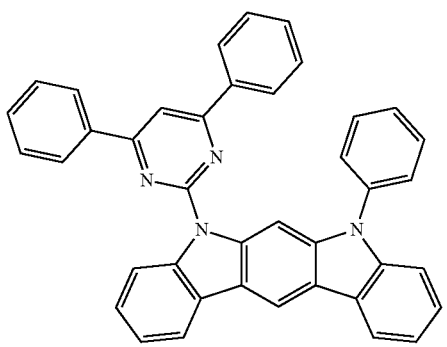

B-92
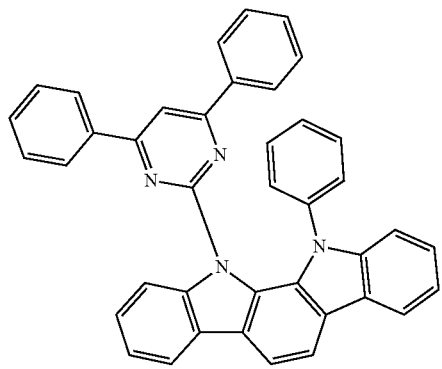
B-93
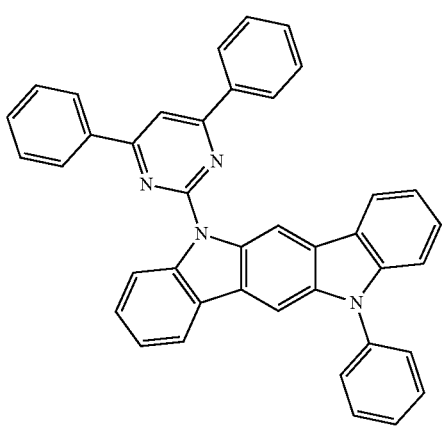
B-94
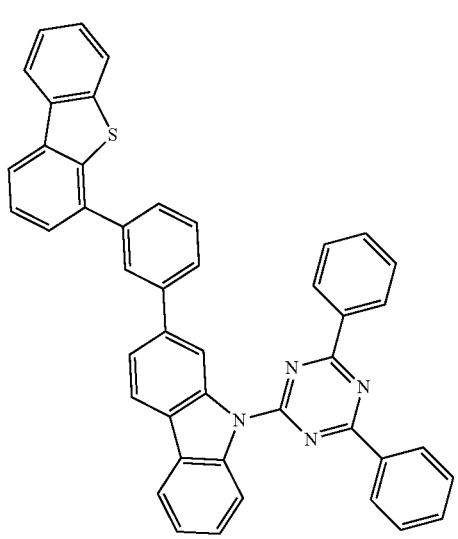
B-95
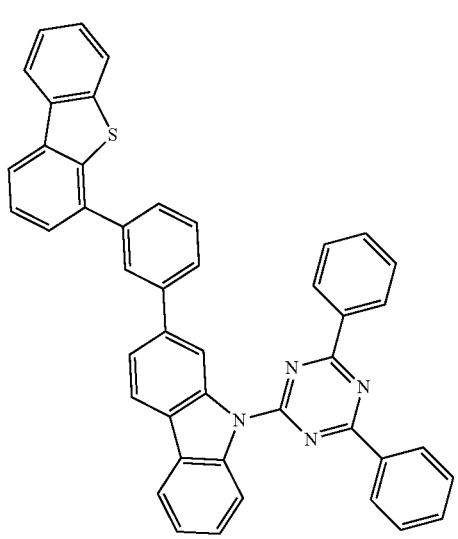
B-96
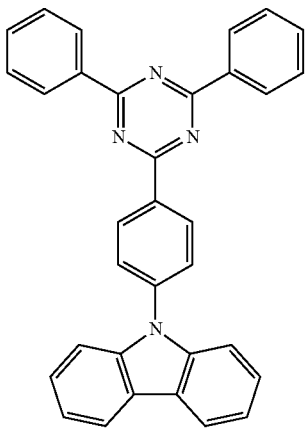
B-97
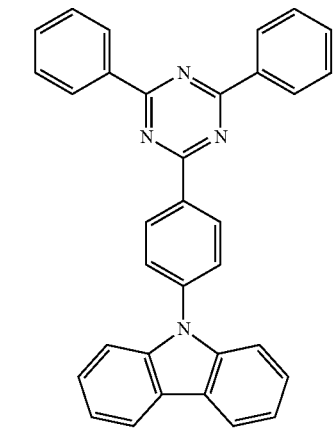
B-98
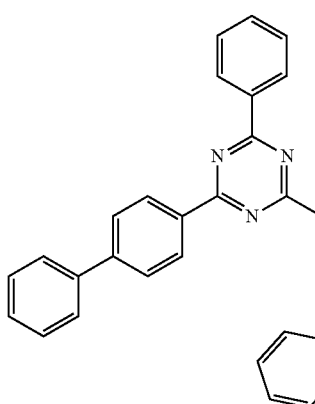

B-99
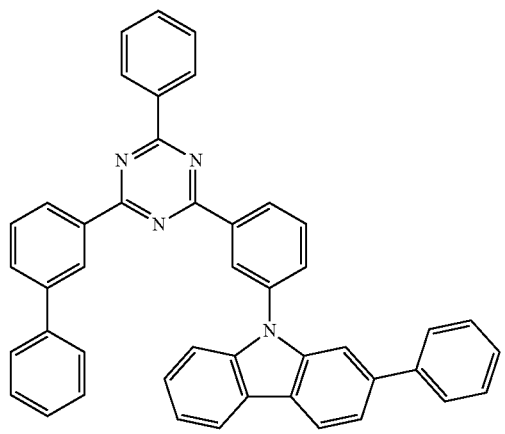
B-100
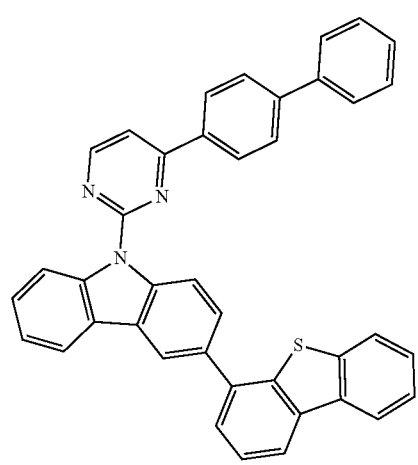
B-101
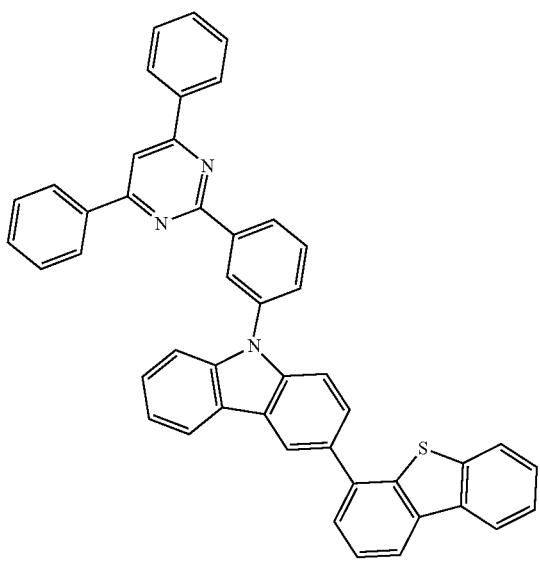
B-102
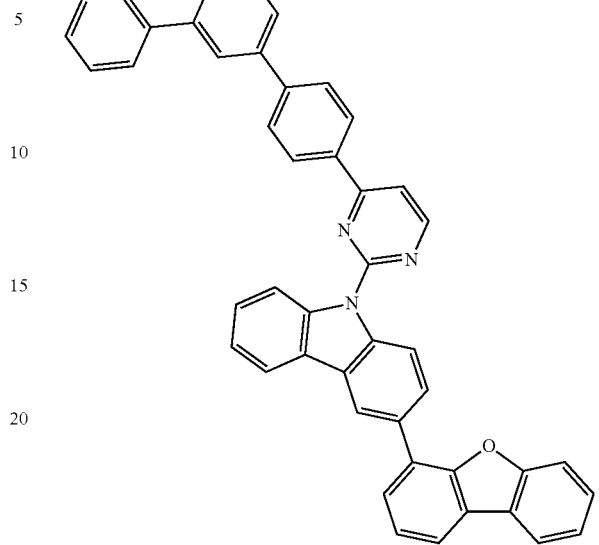
B-103
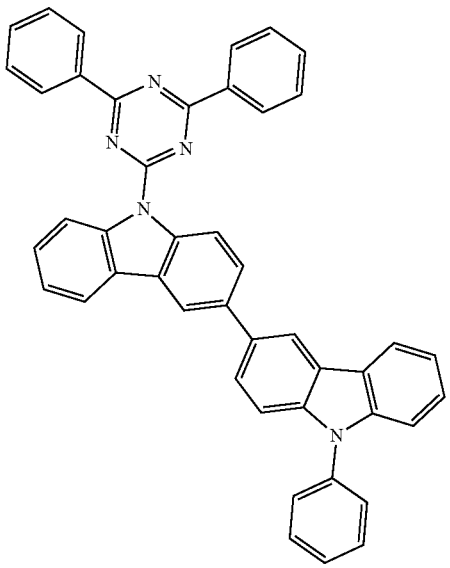

B-104
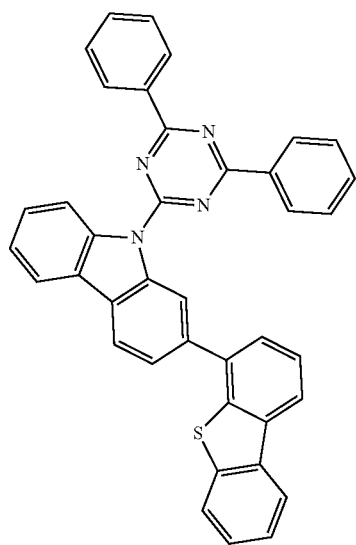
B-105
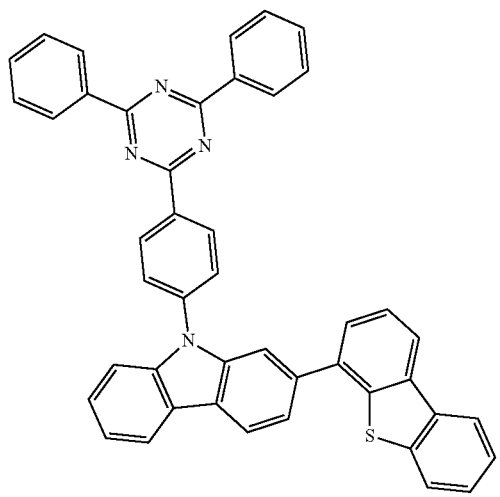
B-106
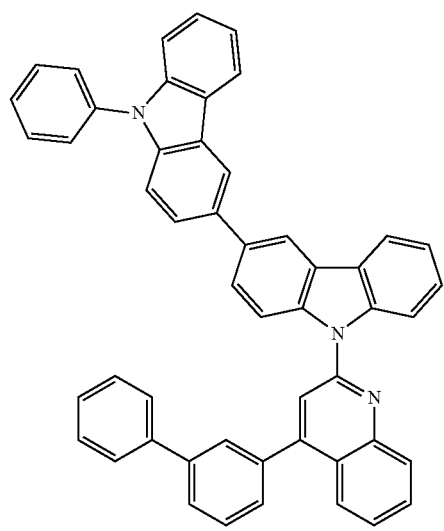
B-107
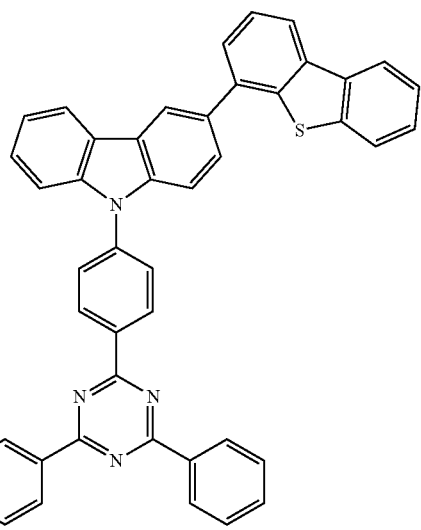
B-108
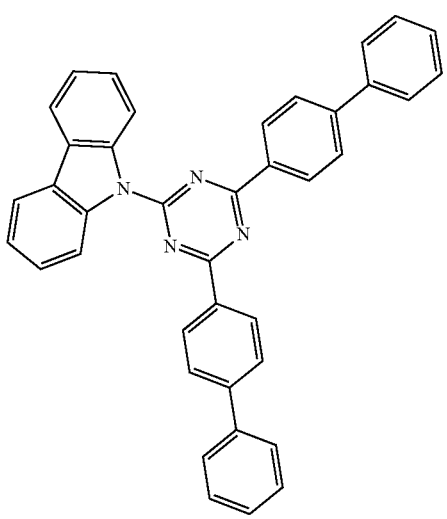
B-109
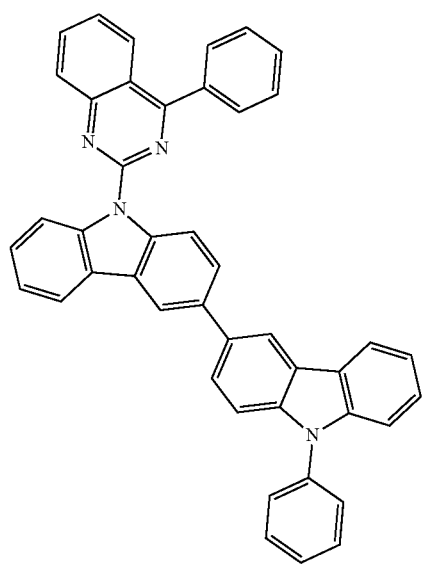

B-110
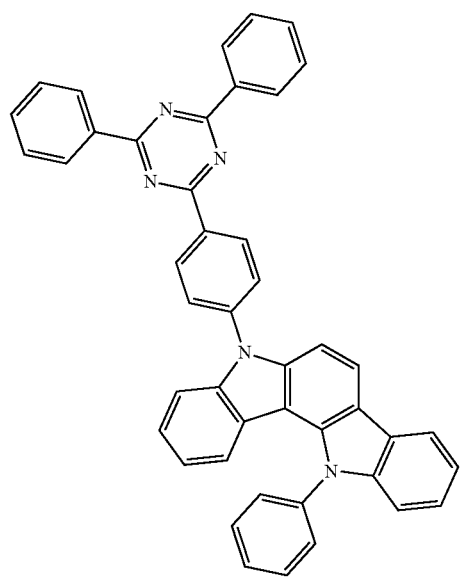
B-111
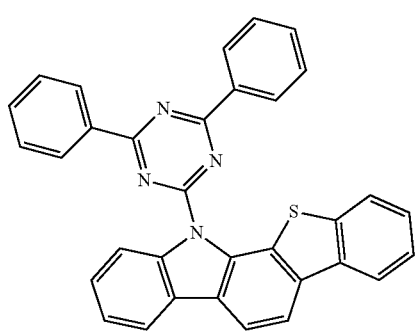
B-112
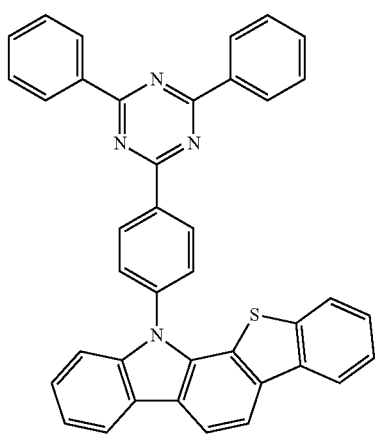
B-113
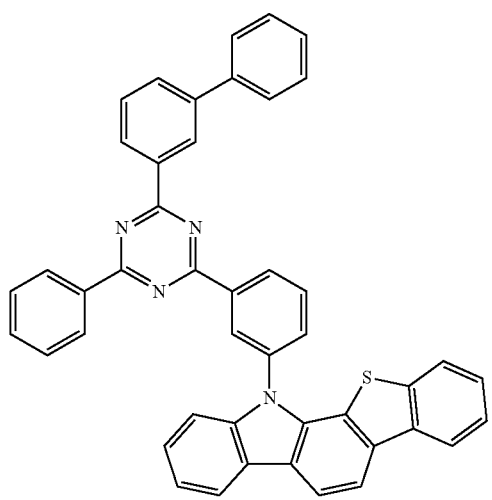
B-114
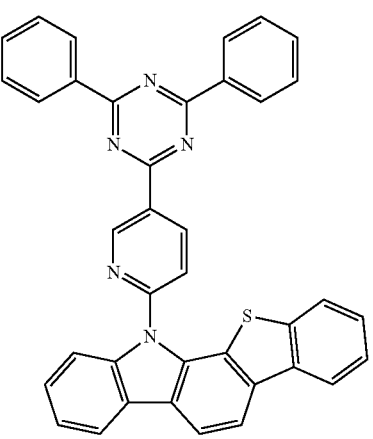
B-115
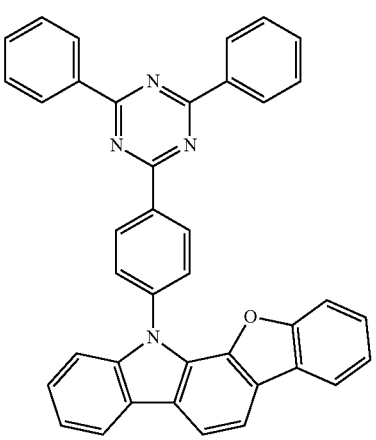

B-116
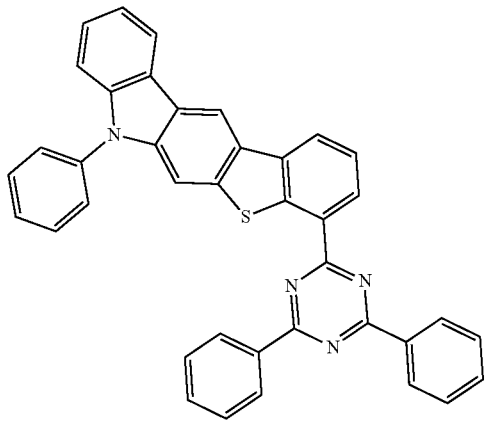
B-117
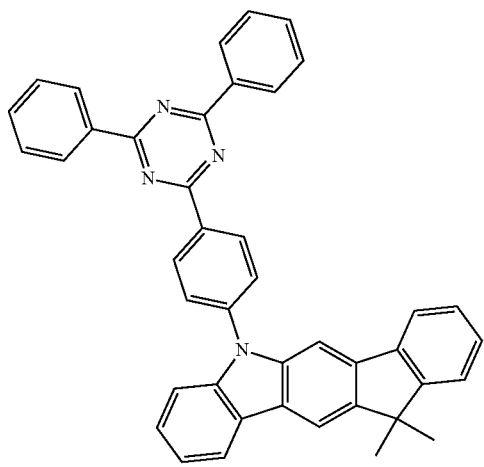
B-118
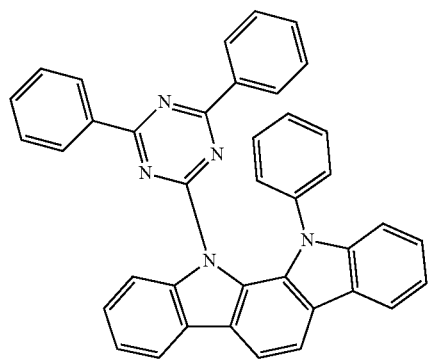
B-119
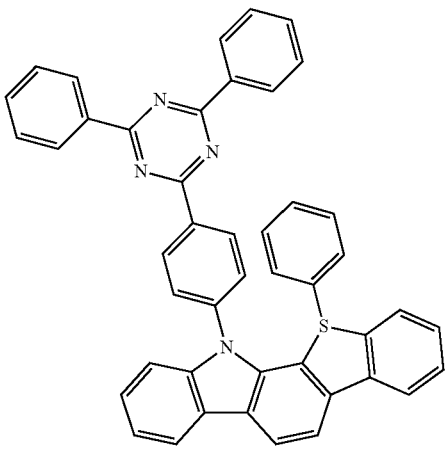
B-120
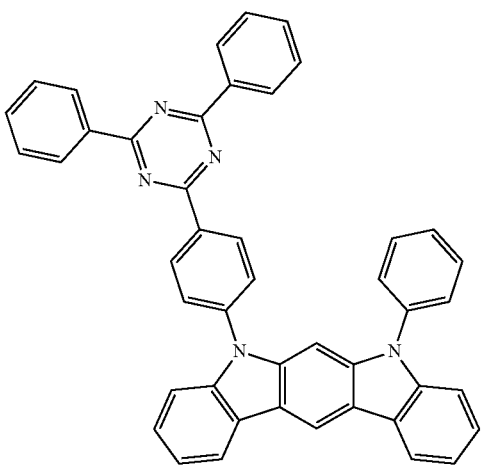
B-121
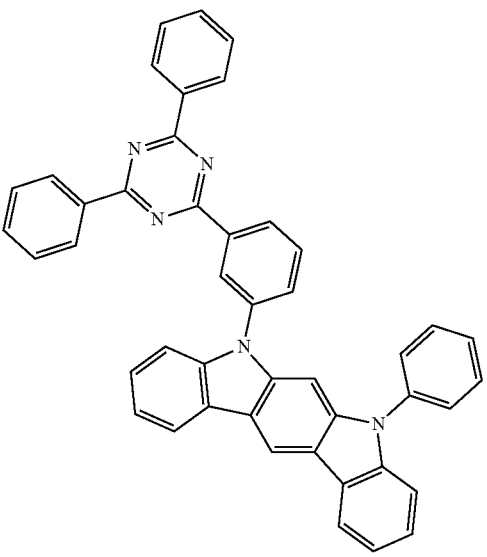

B-122
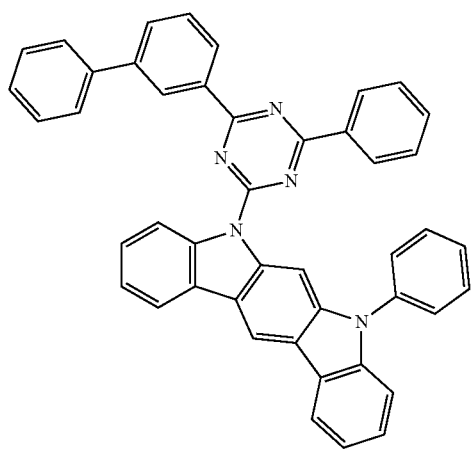
B-125
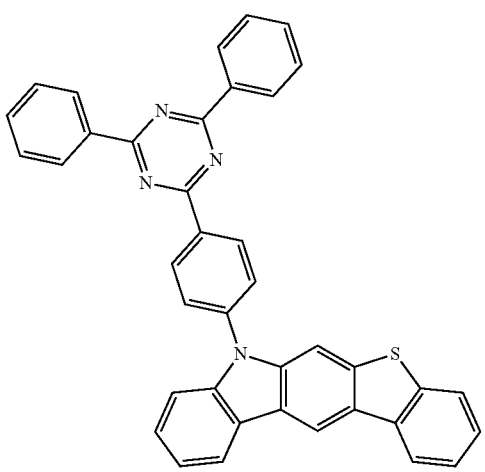
B-123
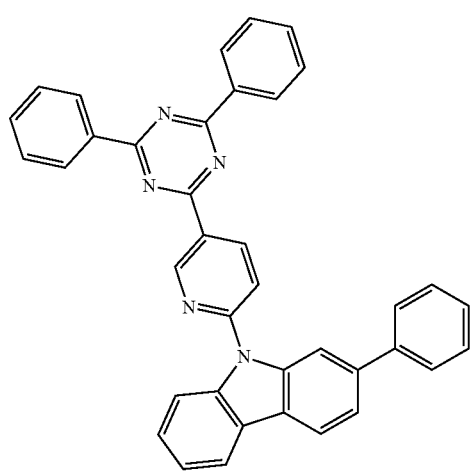
B-126
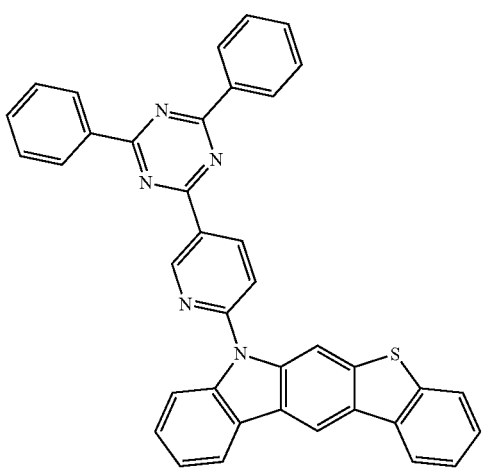
B-124
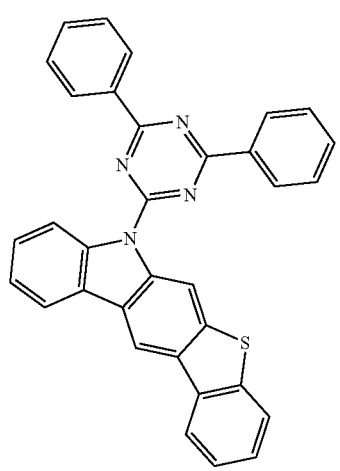
B-127
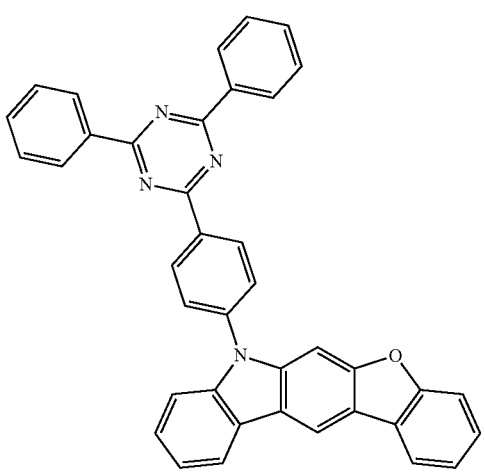

B-128
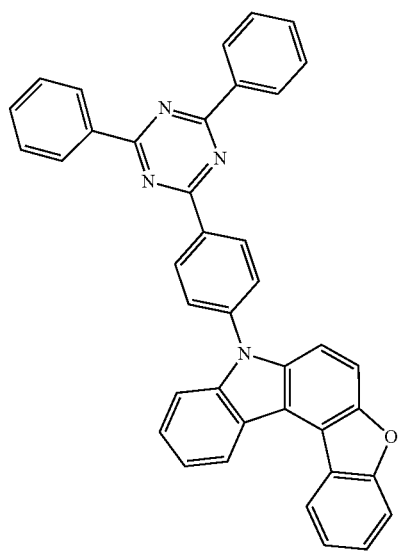
B-129
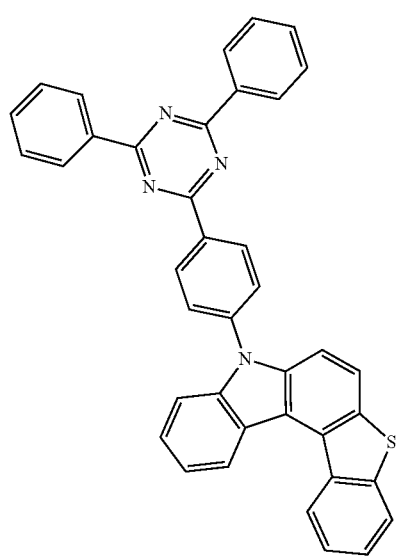
B-130
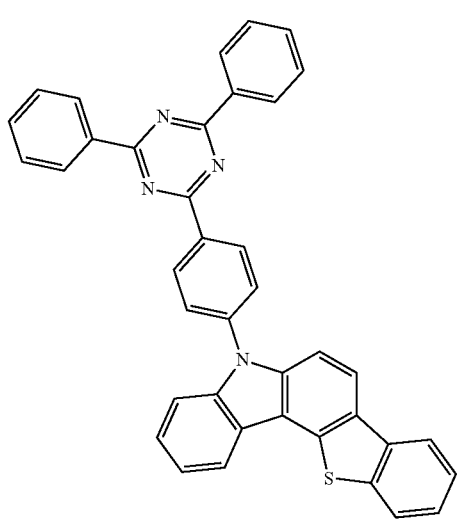
B-131
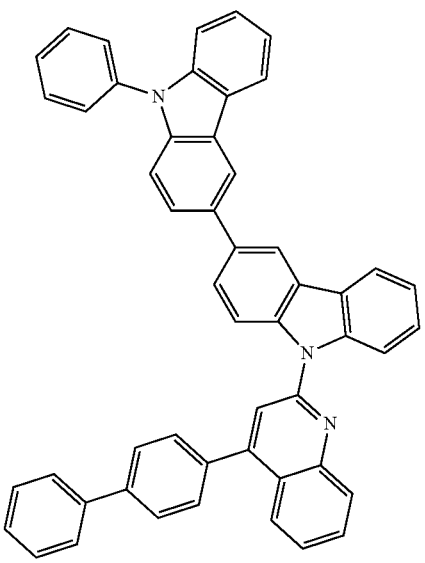
B-132
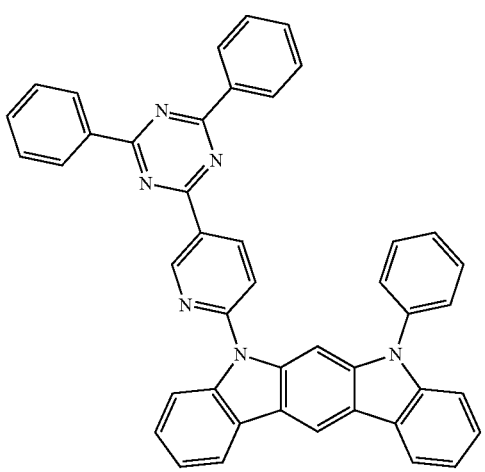
B-133
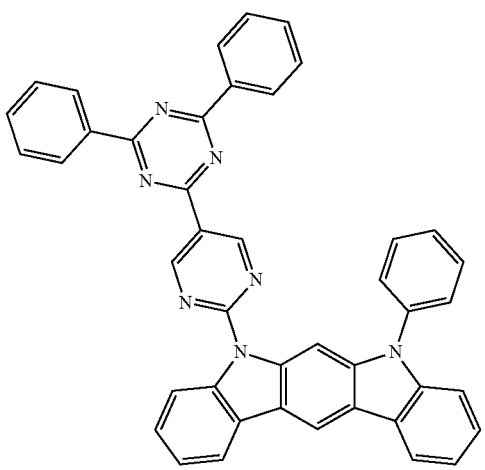

-continued
B-134
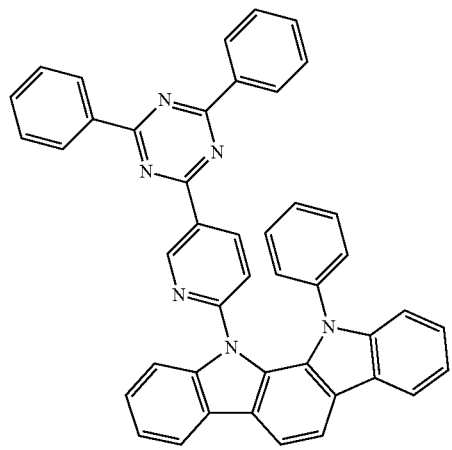
B-135
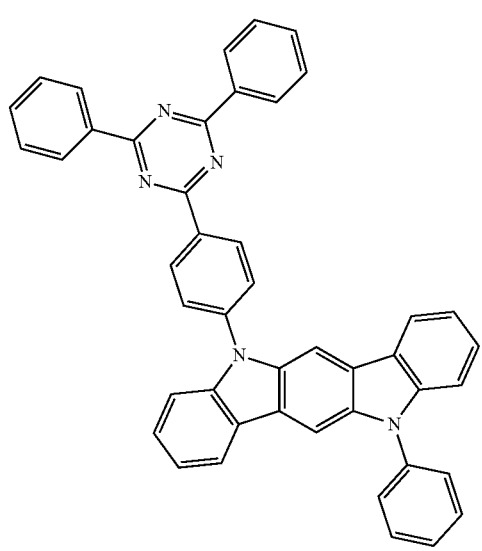
B-136
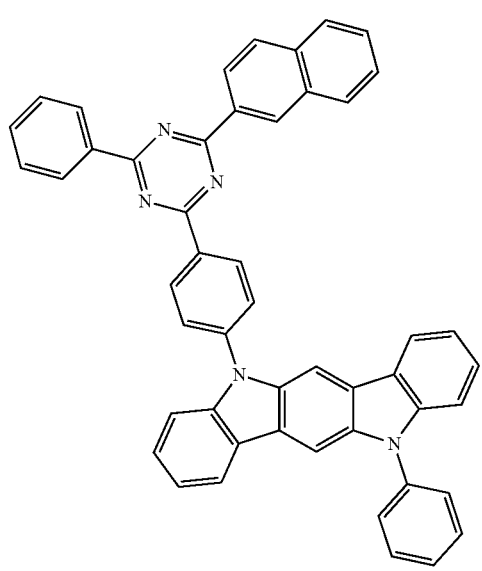
-continued
B-137
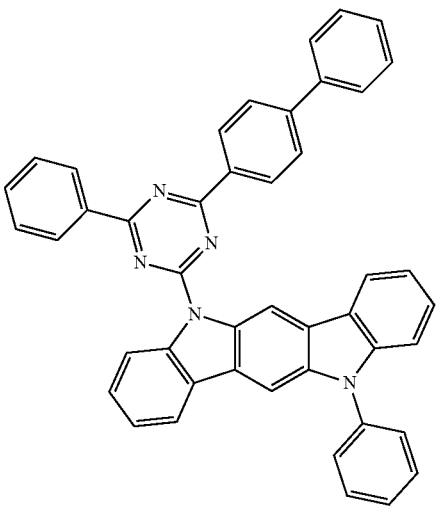
B-138
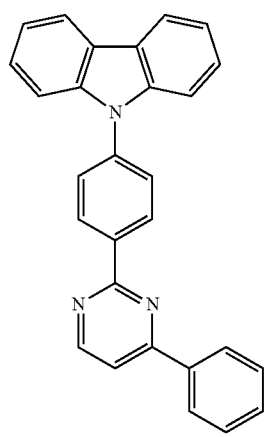
B-139
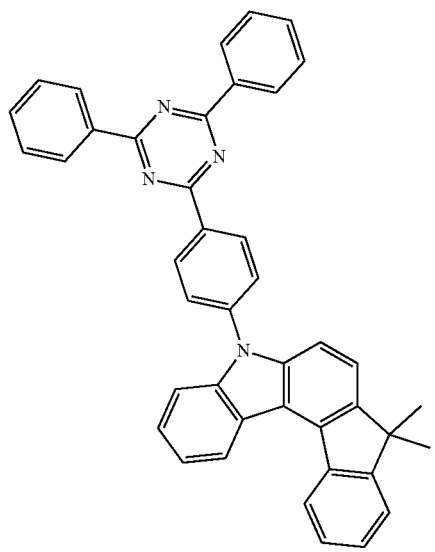

B-140
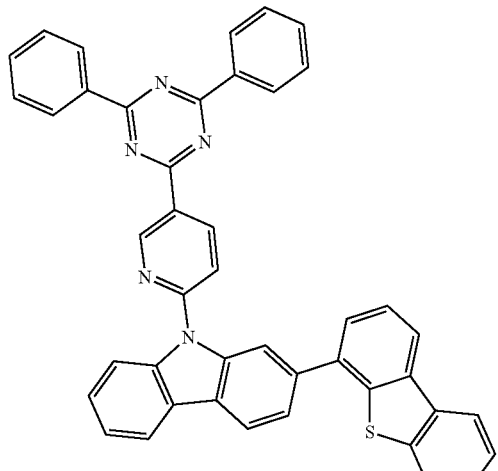
B-141
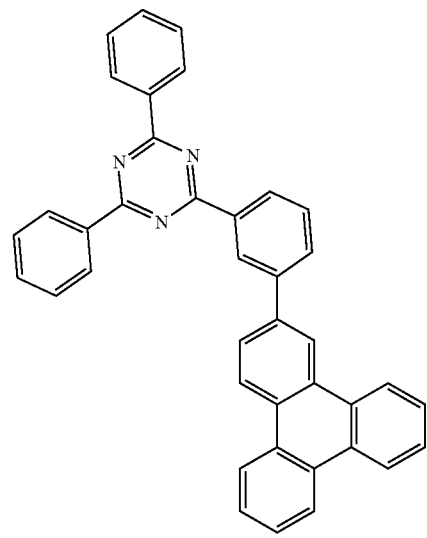
B-142
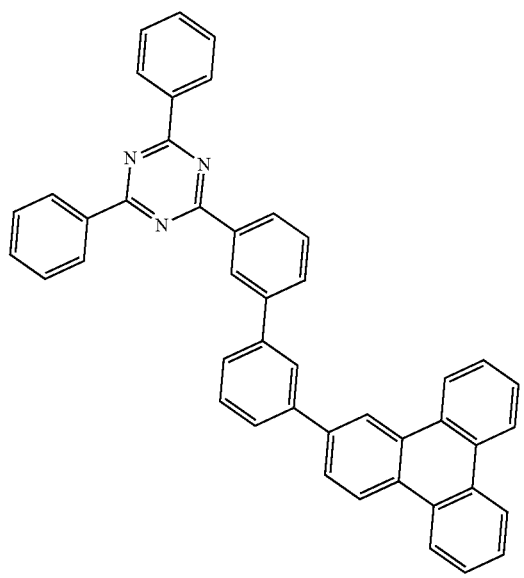
B-143
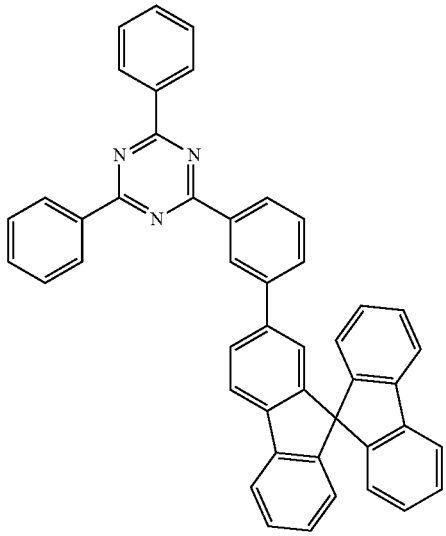
B-144
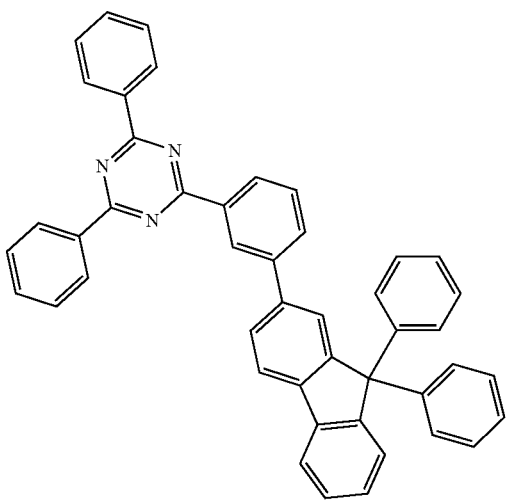
B-145
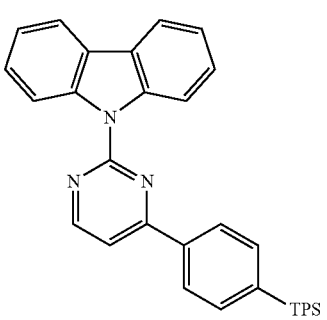

B-146 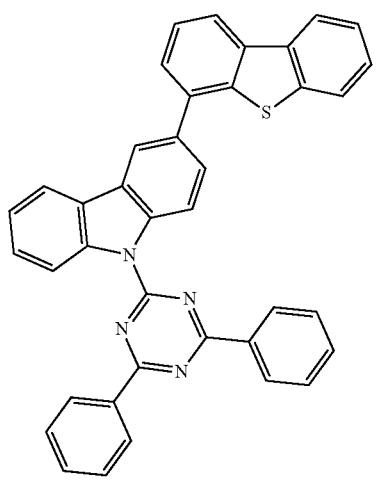
B-147 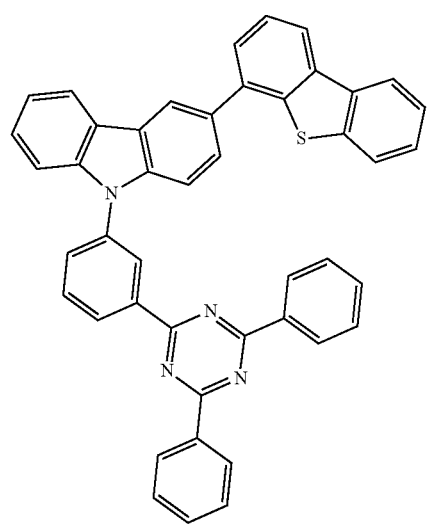
B-148 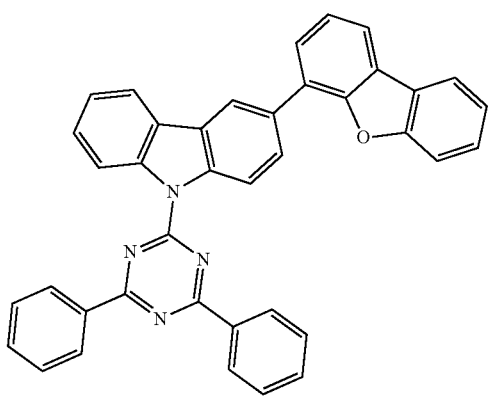
B-149 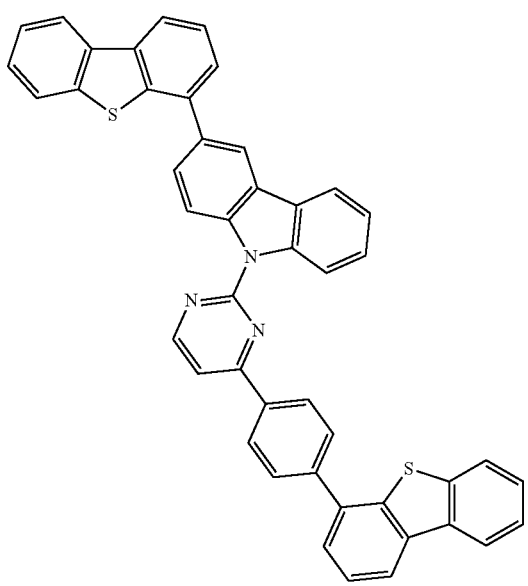
B-150 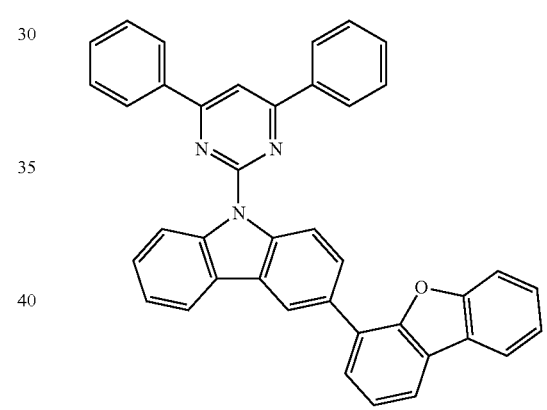
B-151 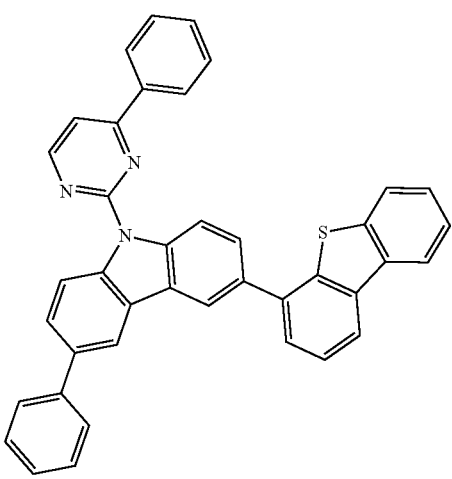

B-152
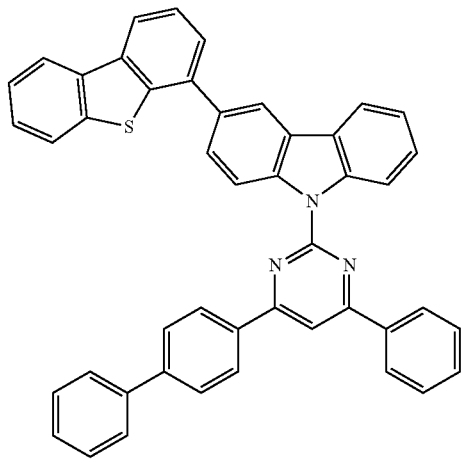
B-153
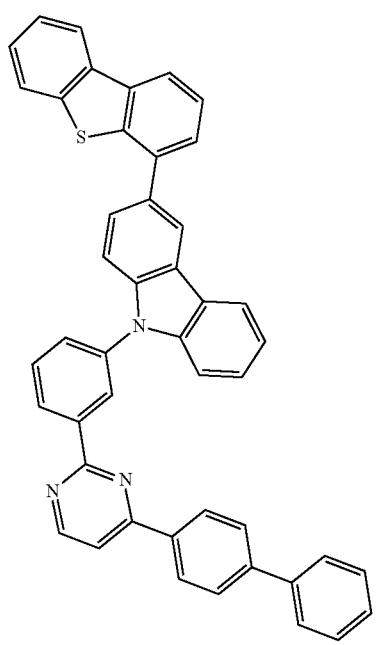
B-154
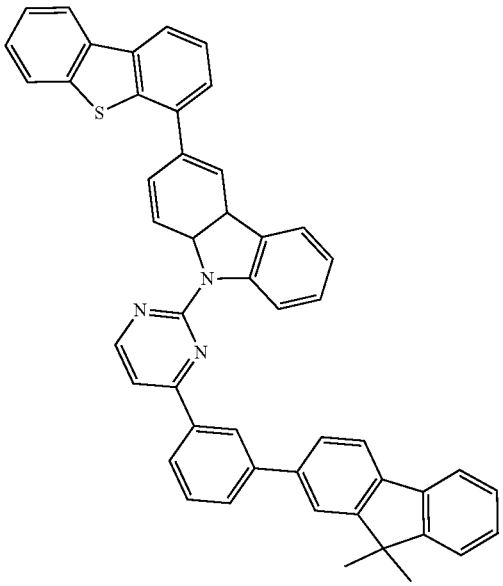
B-155
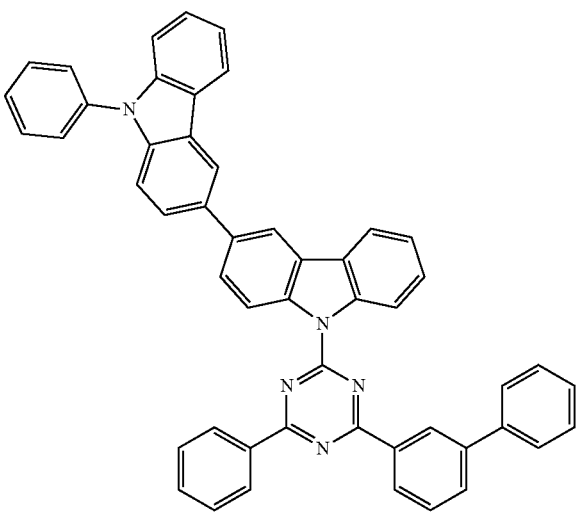

B-156
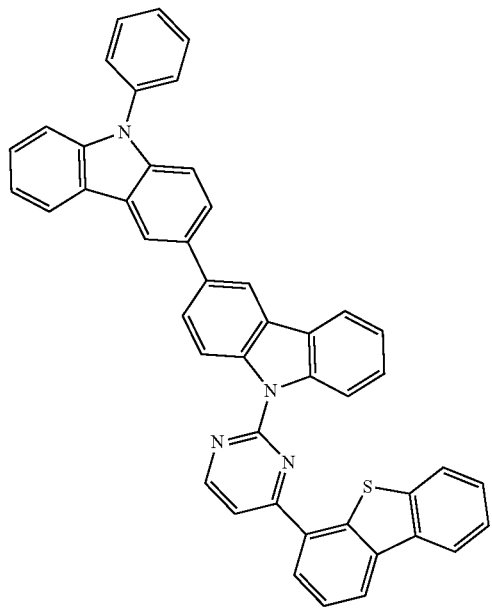
B-158
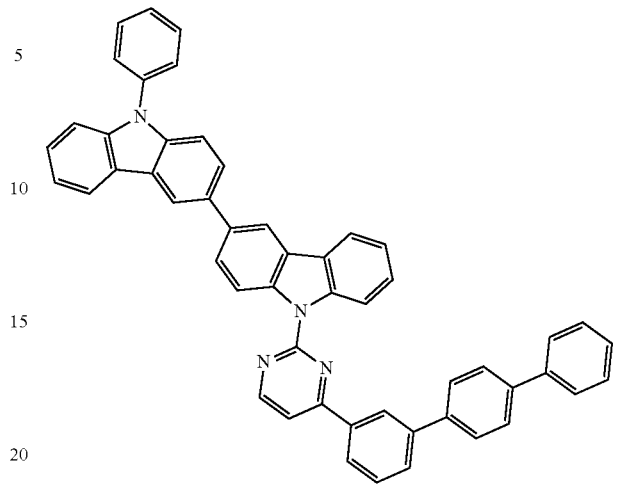
B-157
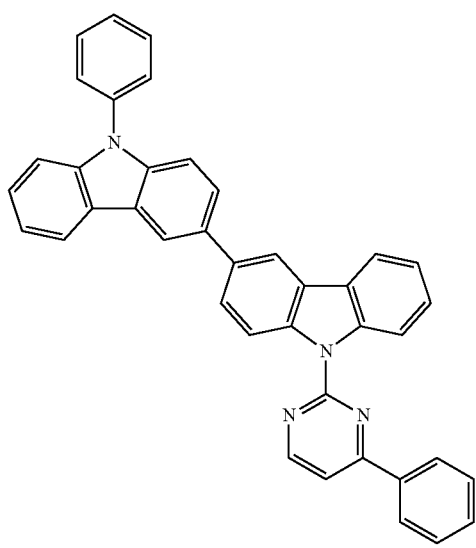
B-159
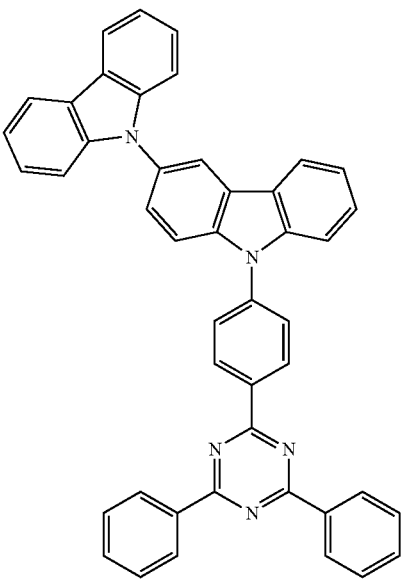

B-160
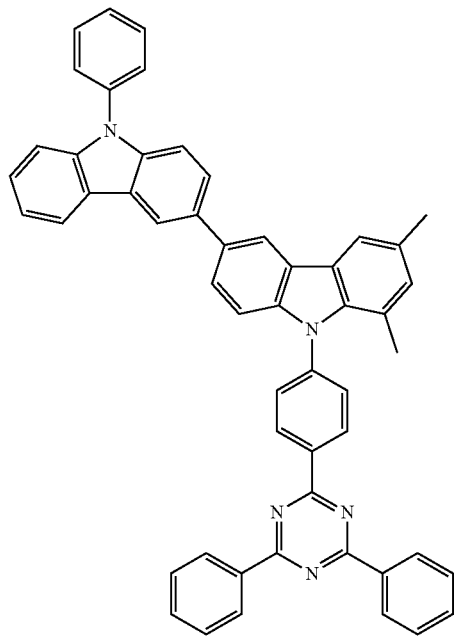
B-161
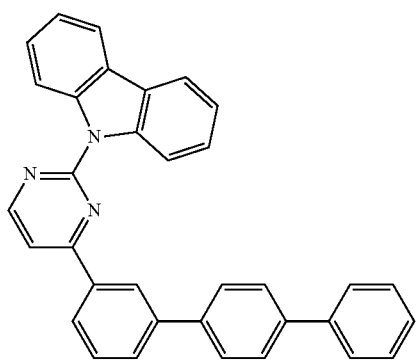
B-162
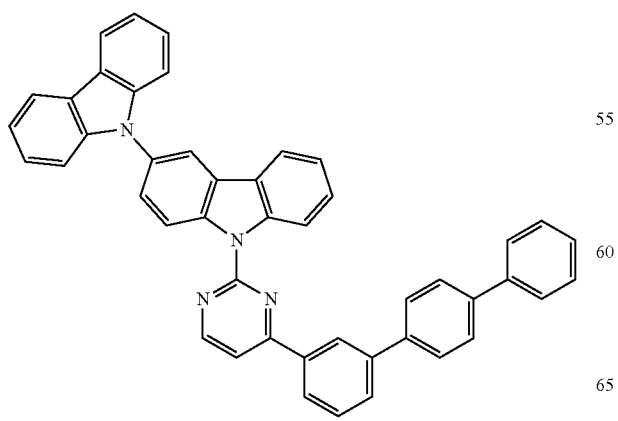
B-163
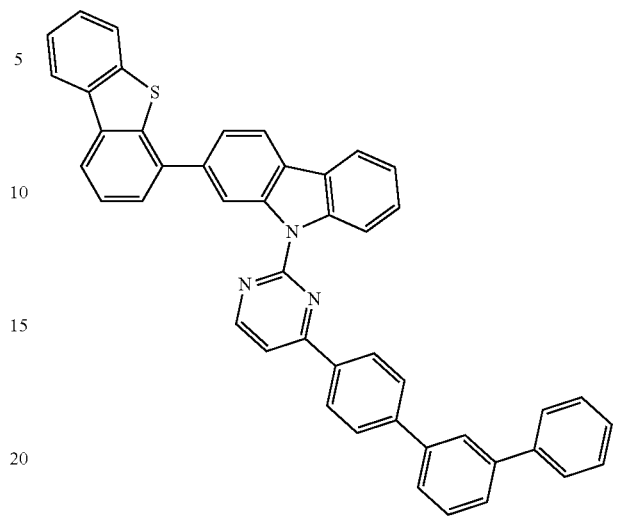
B-164
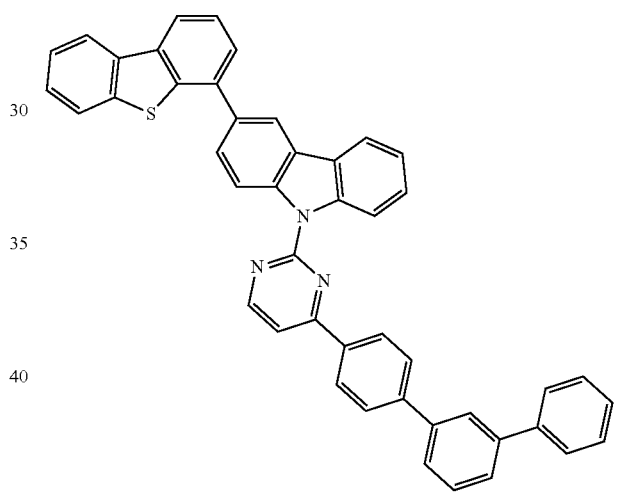
B-165
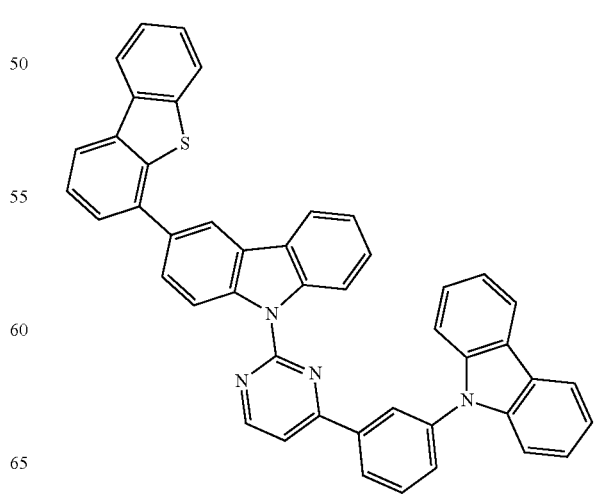

B-166
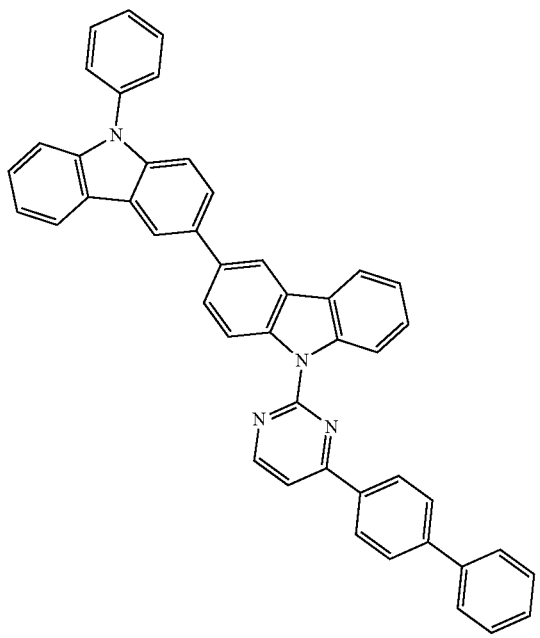
B-167
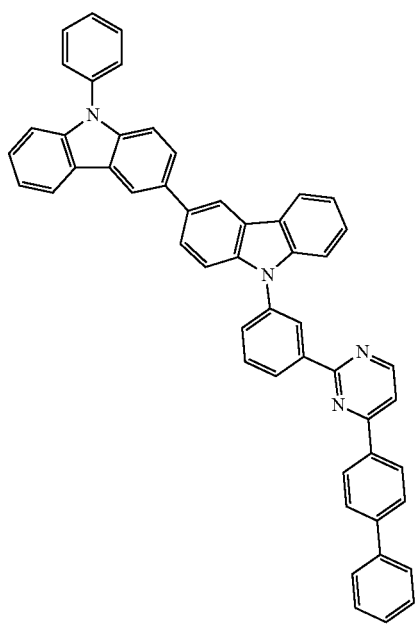
B-168
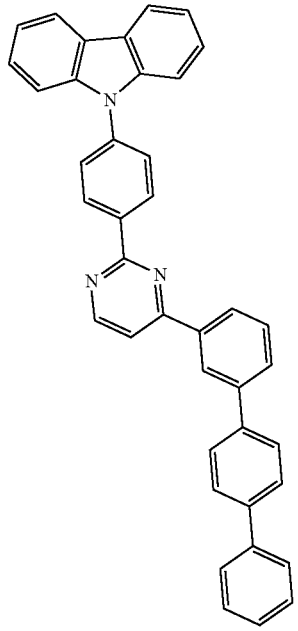
B-169
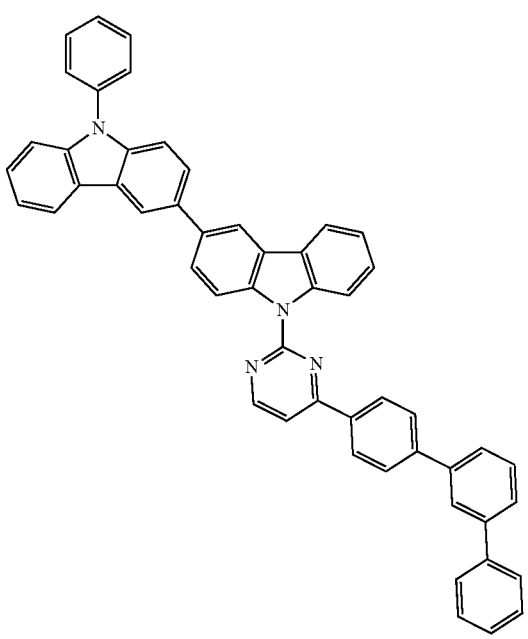

B-170
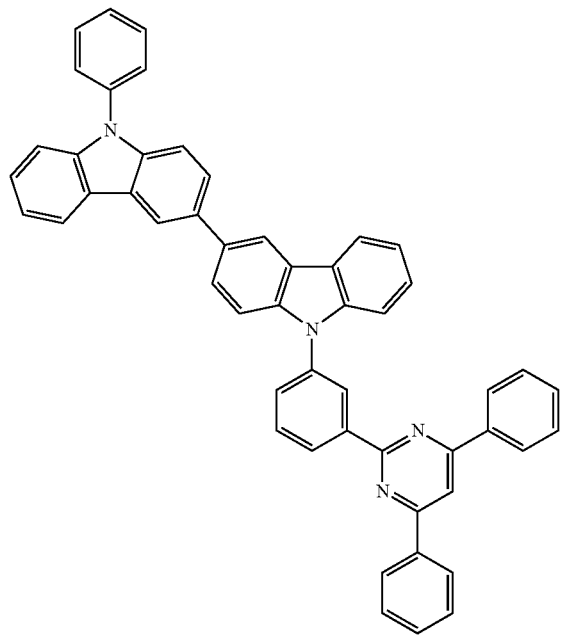
B-172
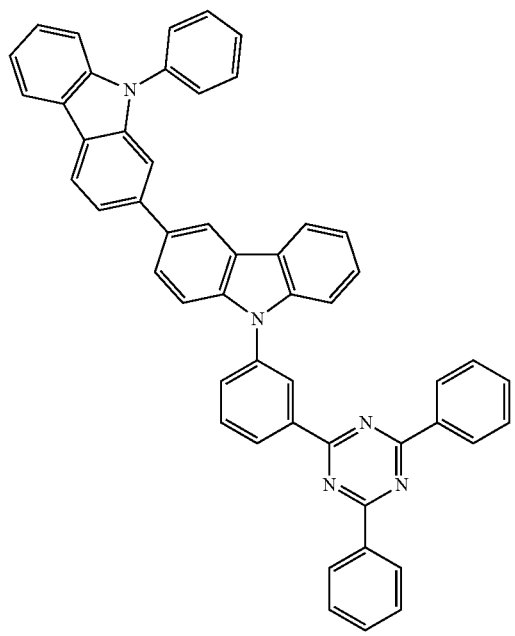
B-171
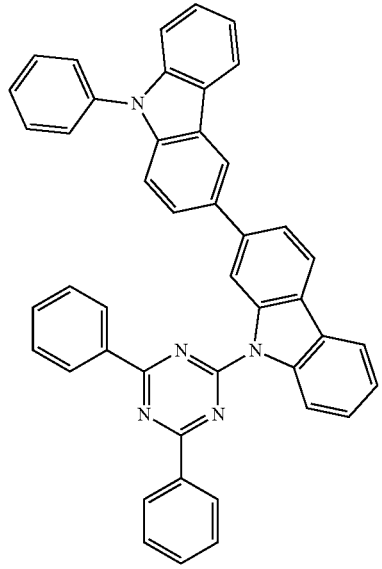
B-173
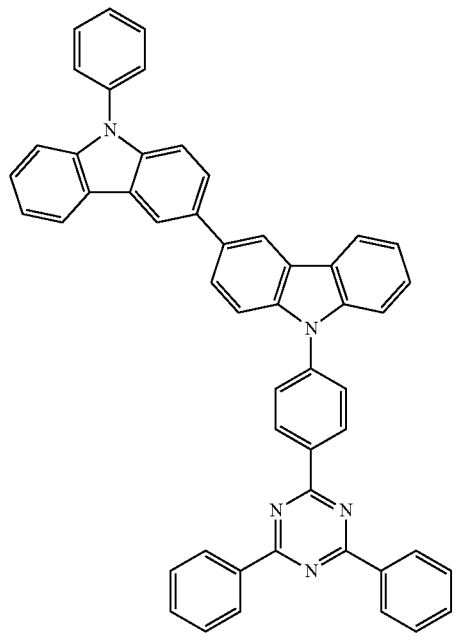

B-174
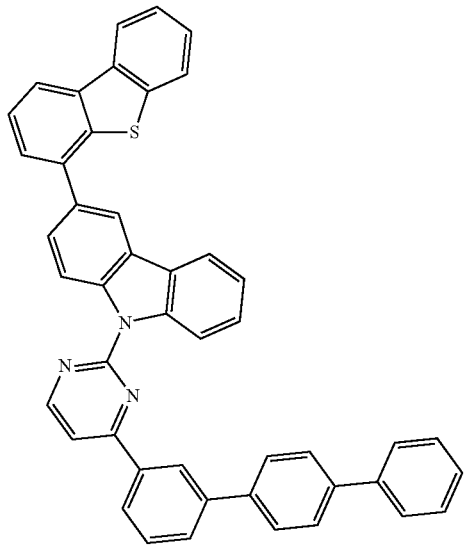
B-176
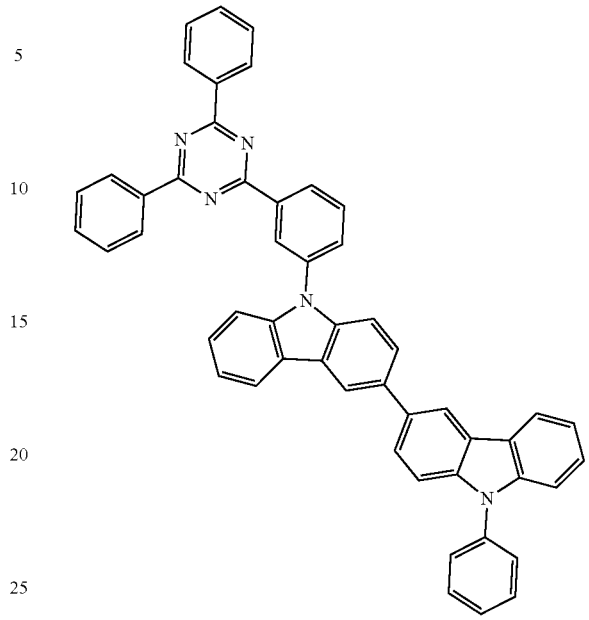
B-175
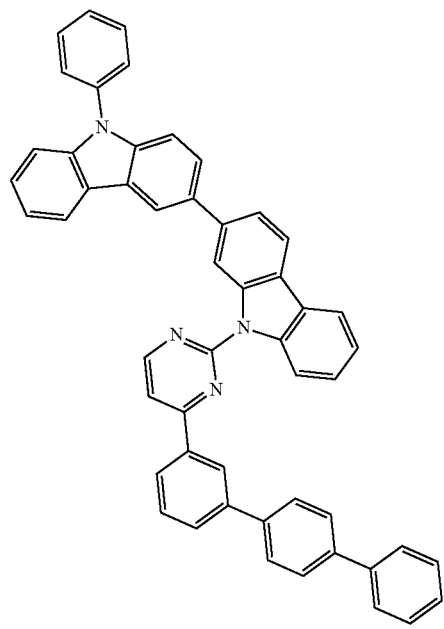
B-177
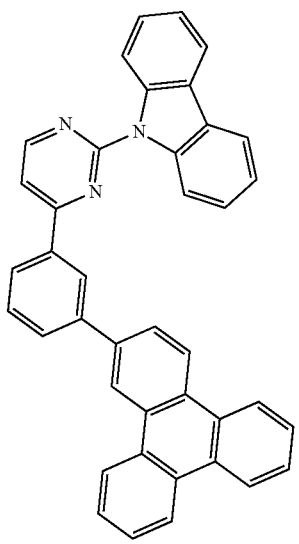

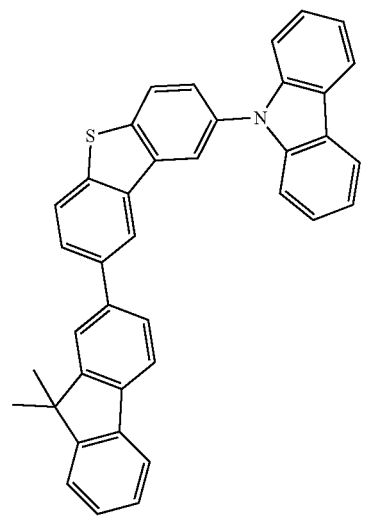
B-178
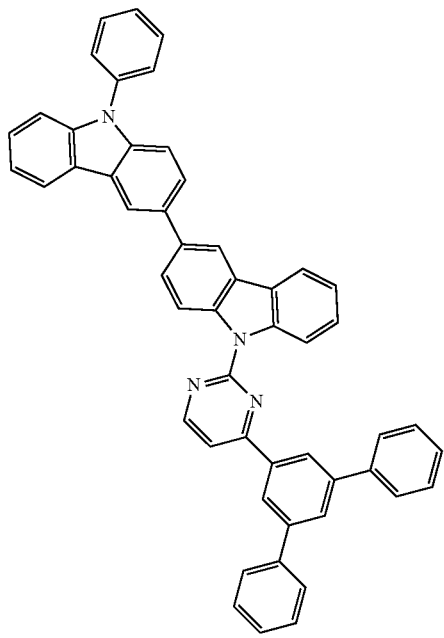
B-180
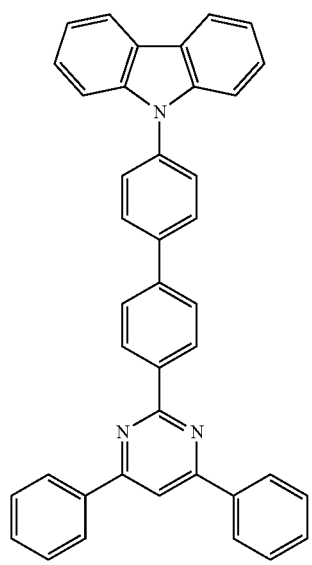
B-179
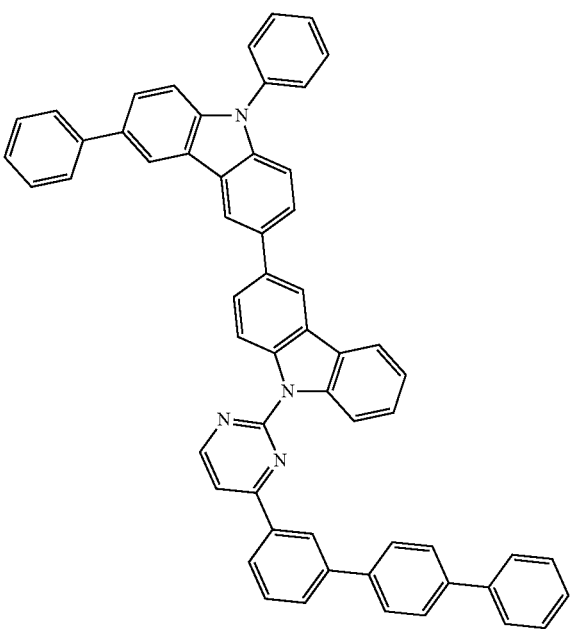
B-181

B-182
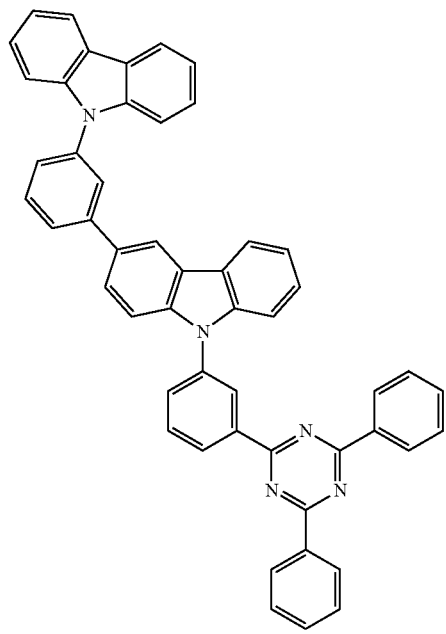
B-184
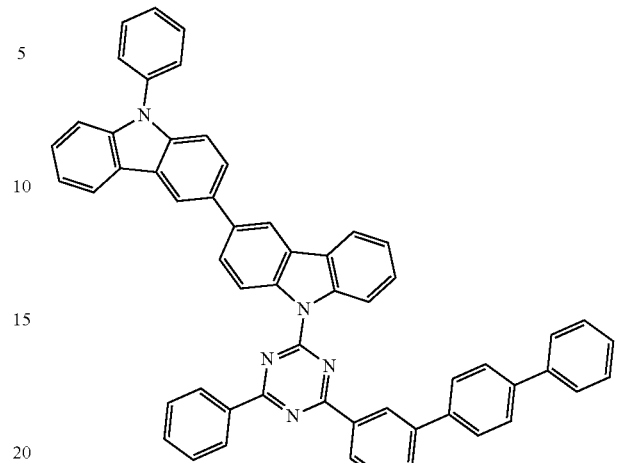
B-185
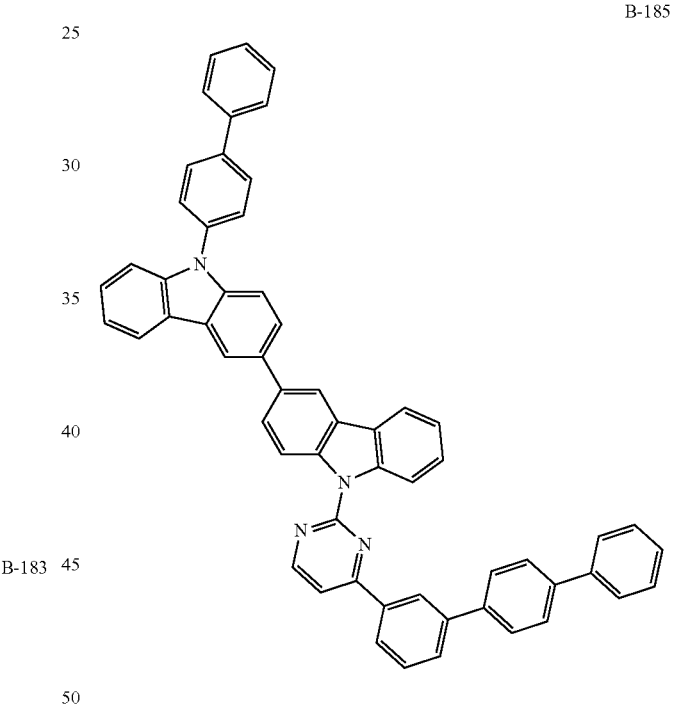
B-183
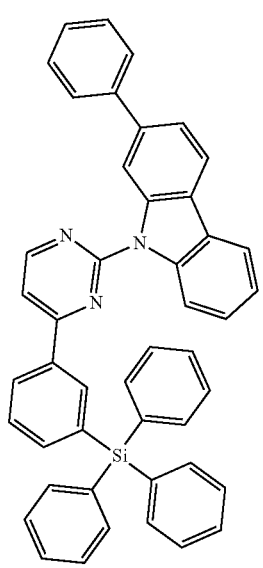
B-186

B-187
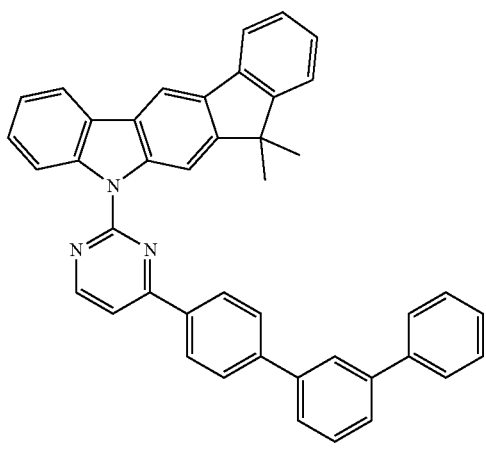
B-188
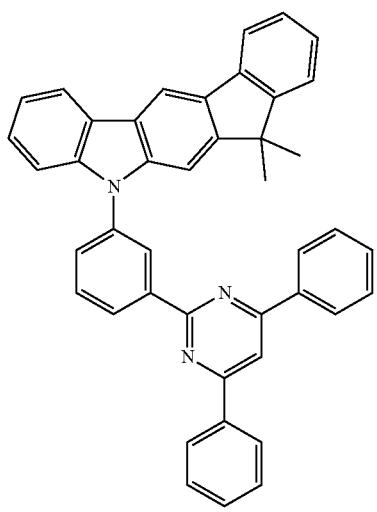
B-189
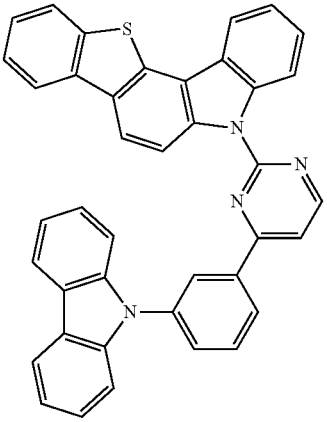
B-190
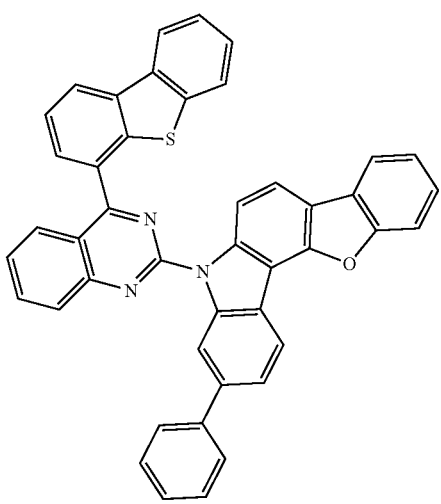
B-191
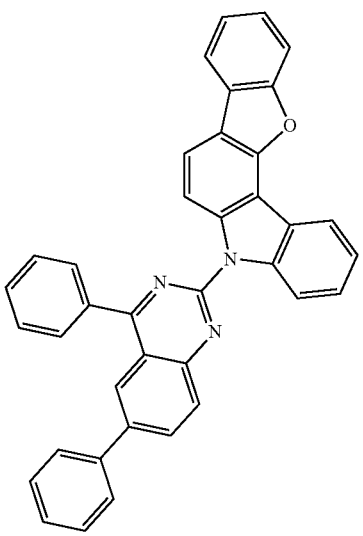
B-192

B-193

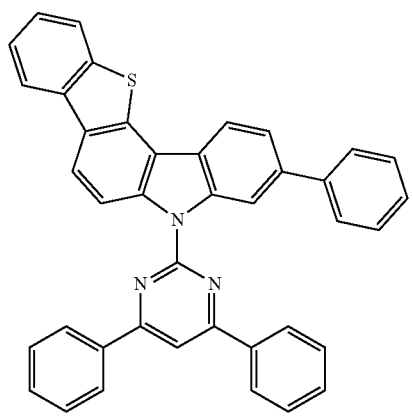

B-196

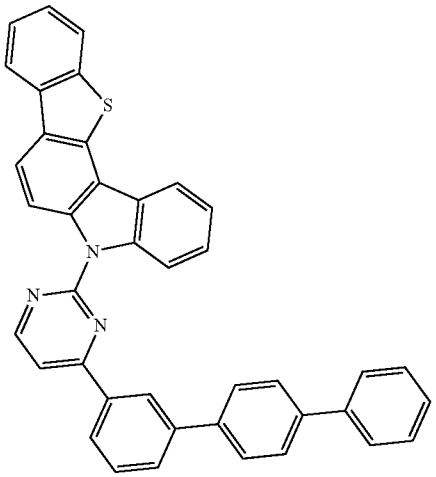

B-194

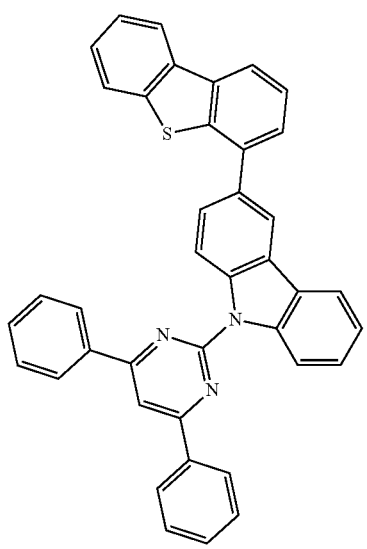

B-197

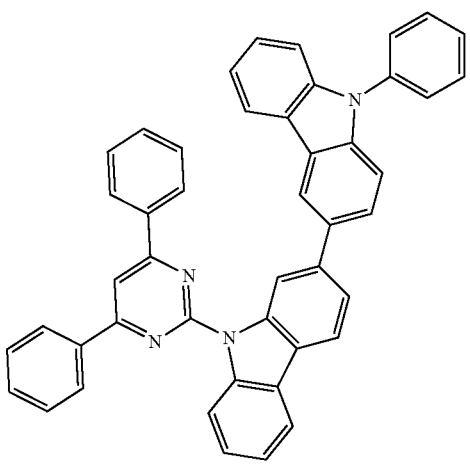

B-195

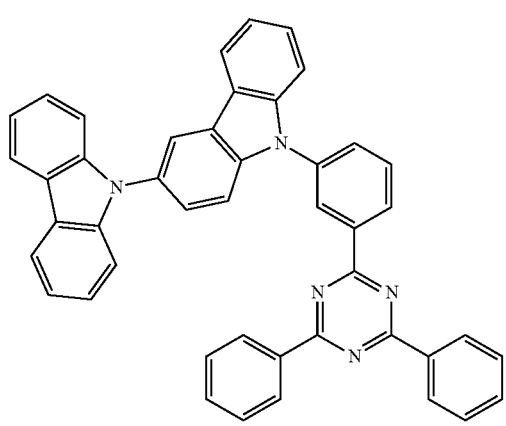

[wherein, TPS represents a triphenylsilyl group.]

When the compound of the present disclosure is used as a host, one or more phosphorescent dopants may be preferably used as a dopant. The phosphorescent dopant material is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant may comprise a compound selected from the group consisting of the compounds represented by the following formulae 101 to 104, but is not limited thereto.

(101)
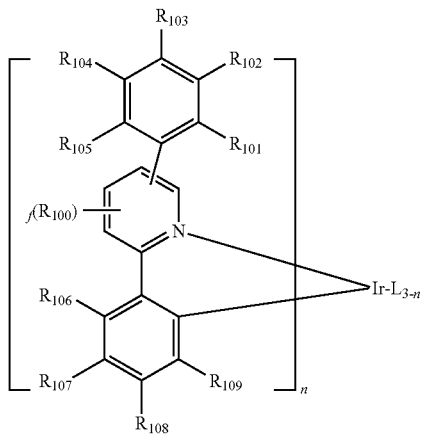

(102)
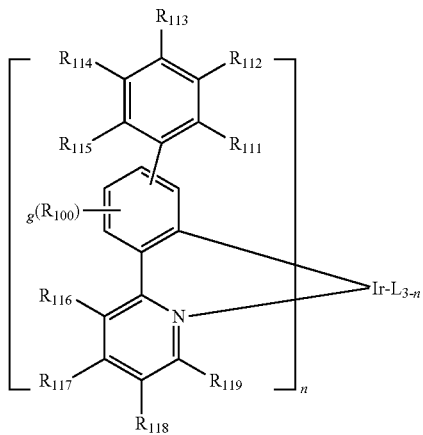

(103)
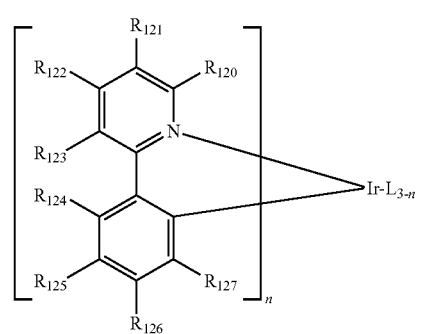

(104)
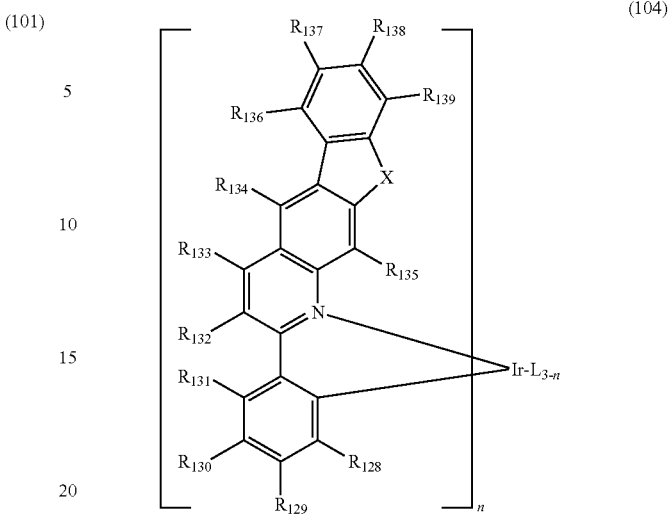

wherein, L is selected from the following structures:

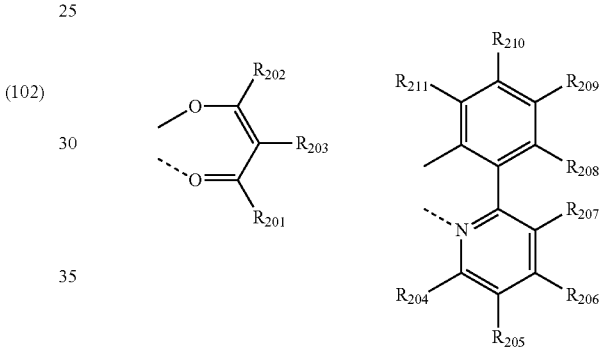

$R_{100}$, $R_{134}$, and $R_{135}$, each independently, represent hydrogen, deuterium, a substituted or unsubstituted (C1-C30)alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a cyano, or a substituted or unsubstituted (C1-C30)alkoxy; adjacent substituents of $R_{106}$ to $R_{109}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl; and adjacent substituents of $R_{120}$ to $R_{123}$ may be linked to each other to form a substituted or unsubstituted fused ring, e.g., a quinoline unsubstituted or substituted with an alkyl or an aryl;

$R_{124}$ to $R_{133}$ and $R_{136}$ to $R_{139}$, each independently, represent hydrogen, deuterium, a halogen, a substituted or unsubstituted (C1-C30)alkyl, or a substituted or unsubstituted (C6-C30)aryl; and adjacent substituents of $R_{124}$ to $R_{127}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

X represents $CR_{11}R_{12}$, O, or S;

$R_{11}$ and $R_{12}$, each independently, represent a substituted or unsubstituted (C1-C10)alkyl, or a substituted or unsubstituted (C6-C30)aryl;

$R_{201}$ to $R_{211}$, each independently, represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; and adjacent substituents of $R_{208}$ to $R_{211}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

f and g, each independently, represent an integer of 1 to 3; where f or g is an integer of 2 or more, each $R_{100}$ may be the same or different; and n represents an integer of 1 to 3.

The specific examples of the dopant compound are as follows:

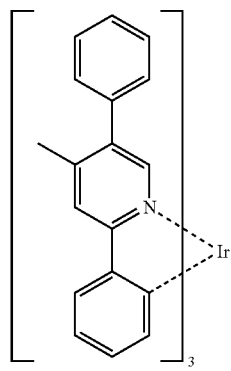

D-1

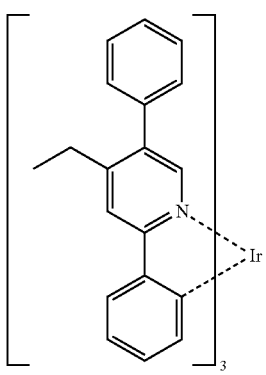

D-2

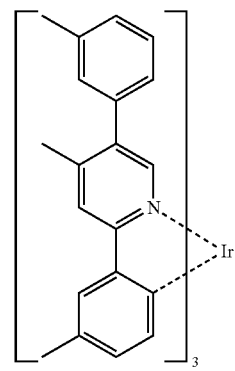

D-3

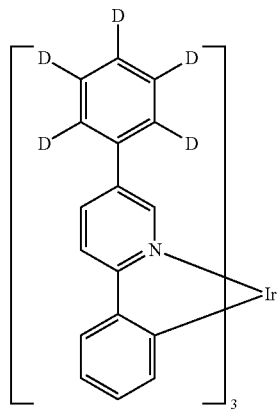

D-4

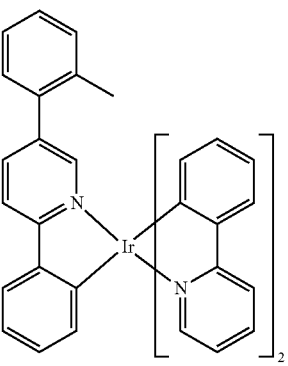

D-5

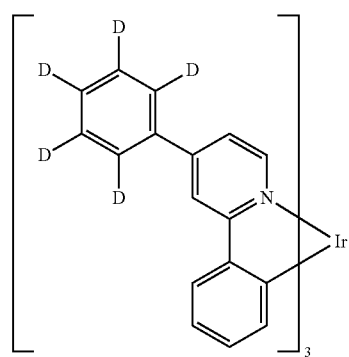

D-6

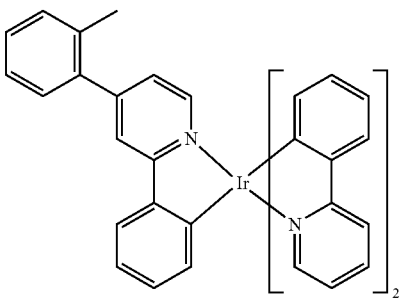

D-7

-continued
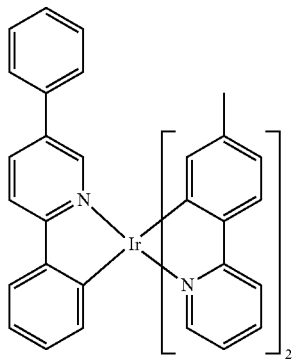
D-8
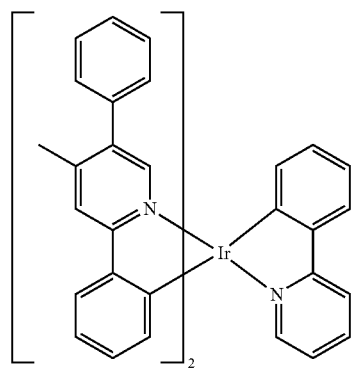
D-9
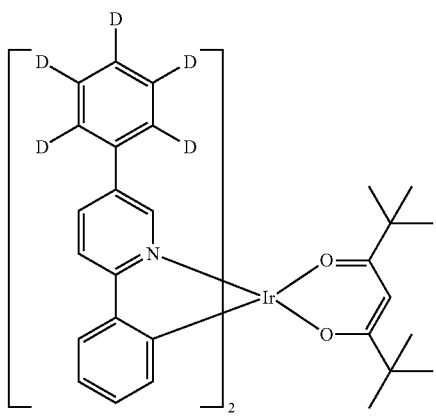
D-10
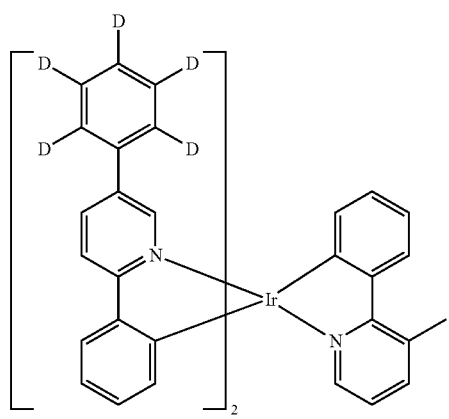
D-11
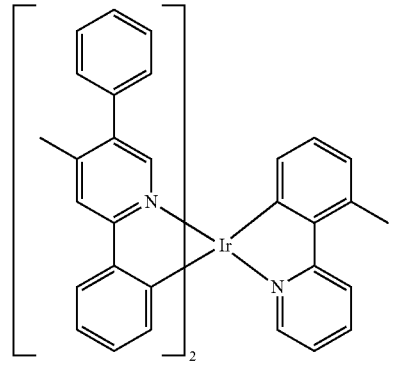
D-12
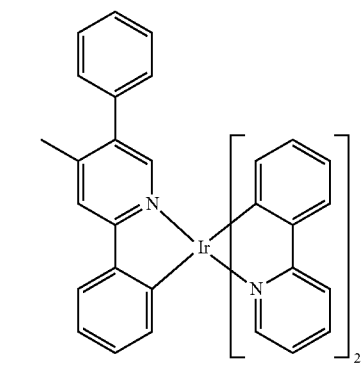
D-13
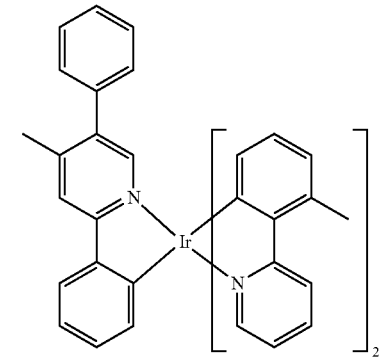
D-14
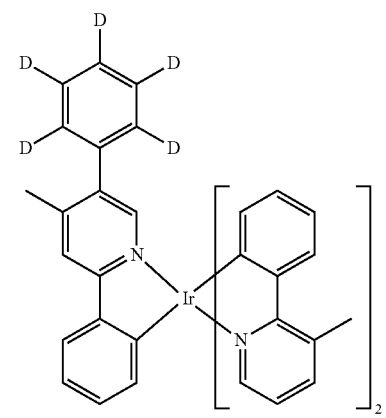
D-15

D-16
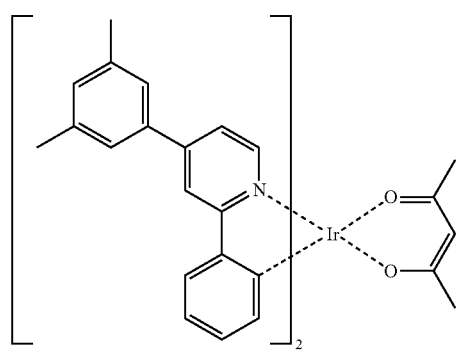
D-17
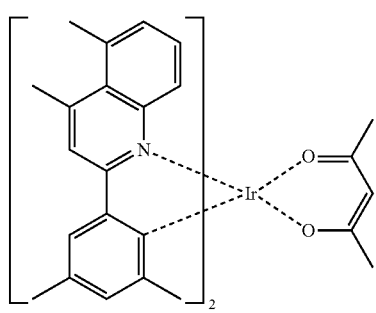
D-18
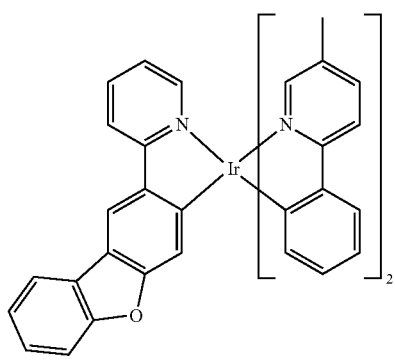
D-19
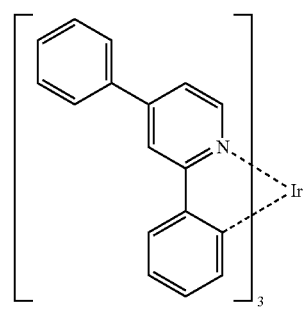
D-20
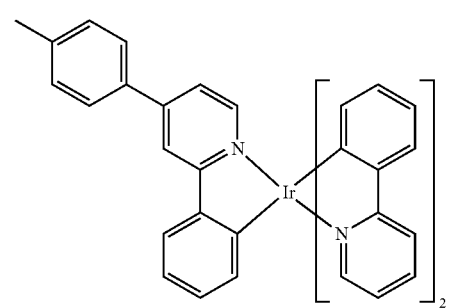
D-21
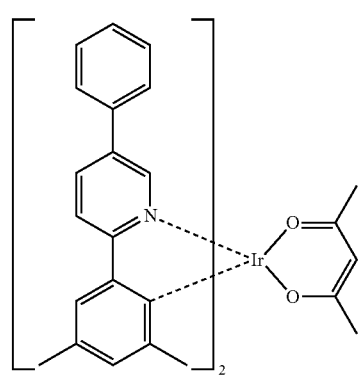
D-22
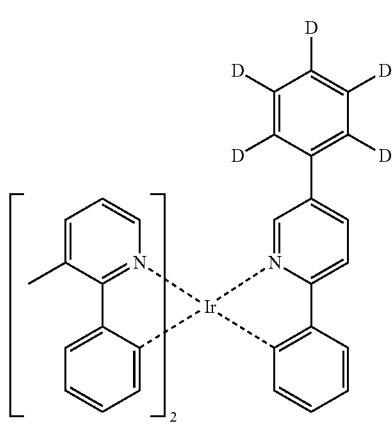
D-23
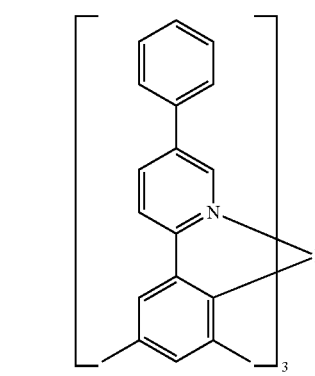
D-24
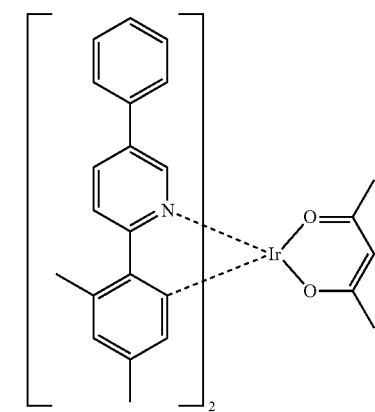

-continued
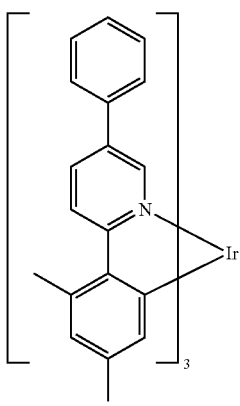
D-25
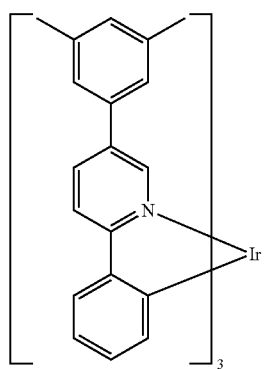
D-26
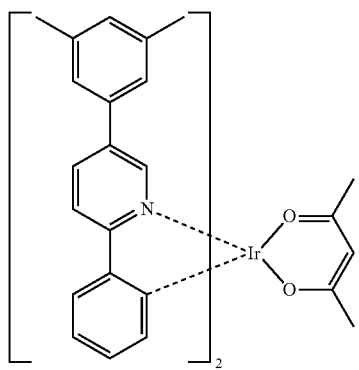
D-27
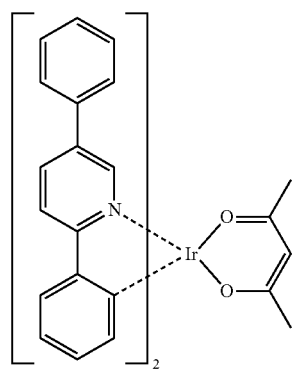
D-28
-continued
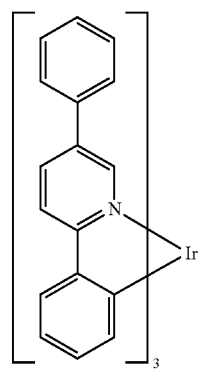
D-29
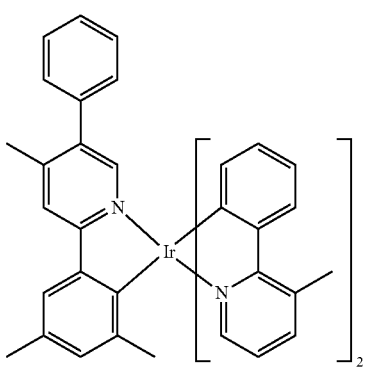
D-30
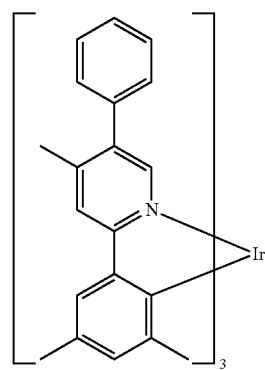
D-31
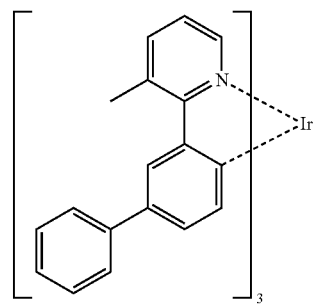
D-32

D-33 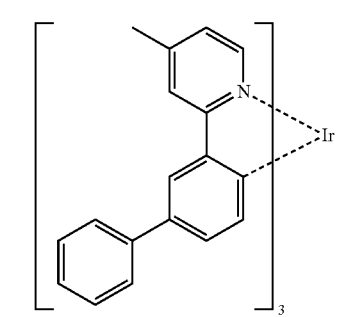
D-34 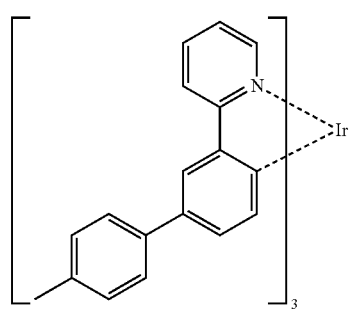
D-35 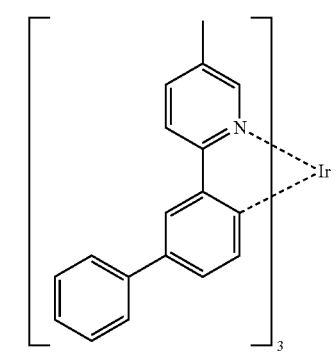
D-36 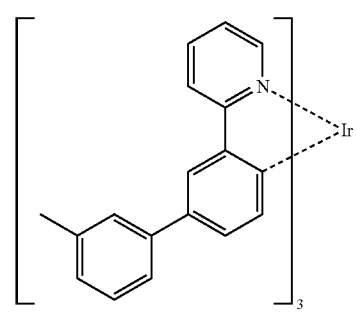
D-37 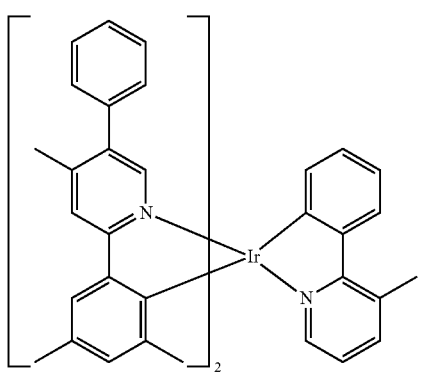
D-38 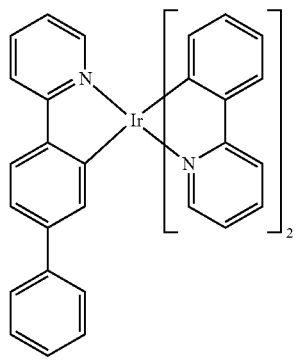
D-39 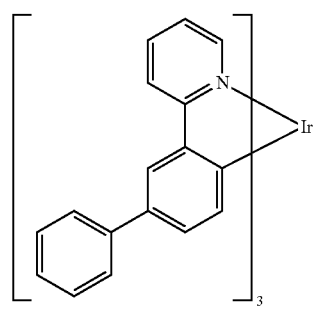
D-40 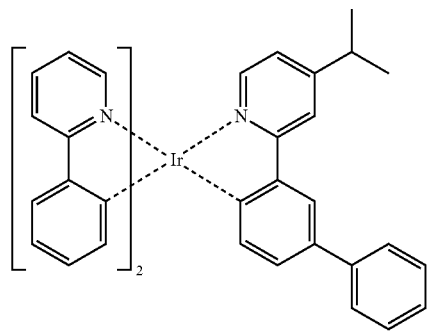
D-41 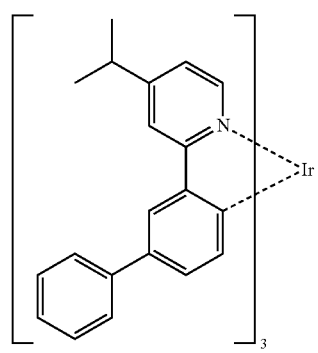
D-42 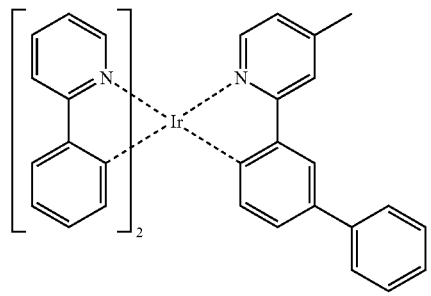

-continued
D-43
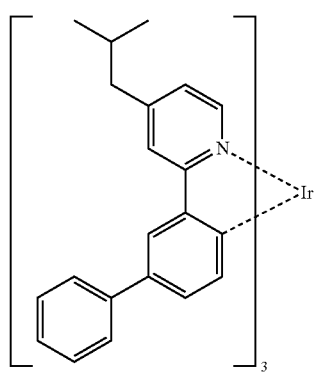
D-44
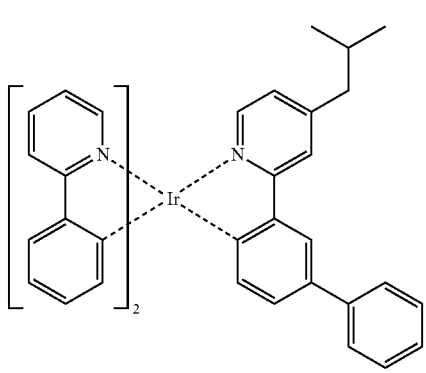
D-45
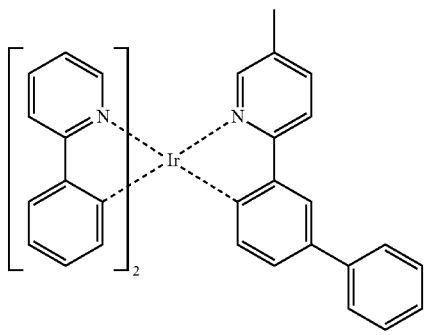
D-46
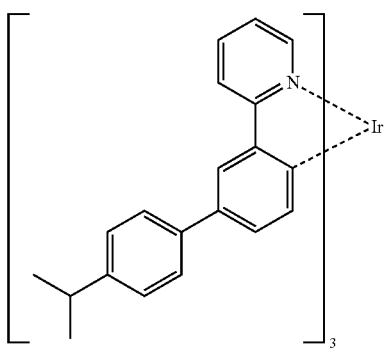
-continued
D-47
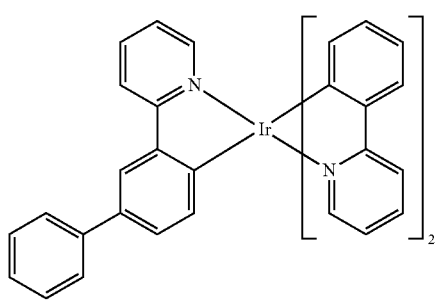
D-48
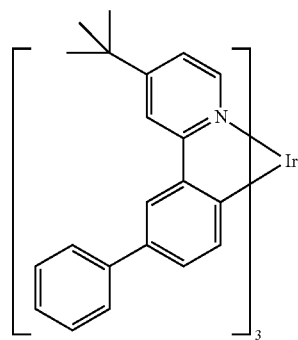
D-49
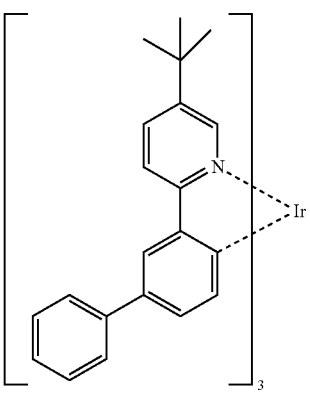
D-50
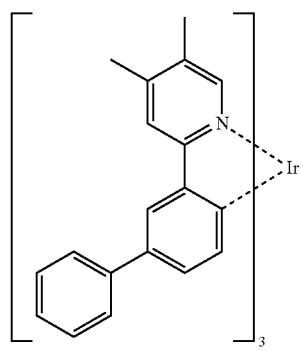

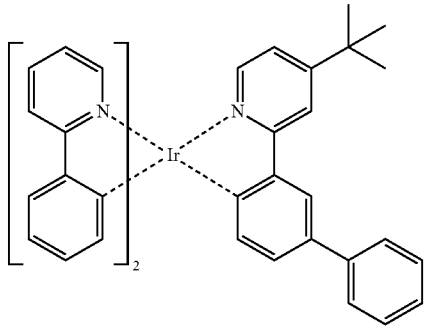
D-51
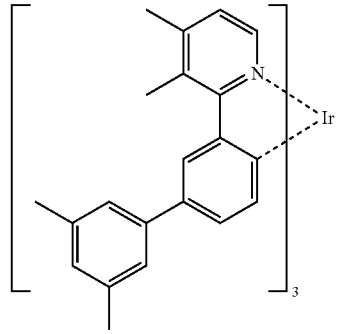
D-55
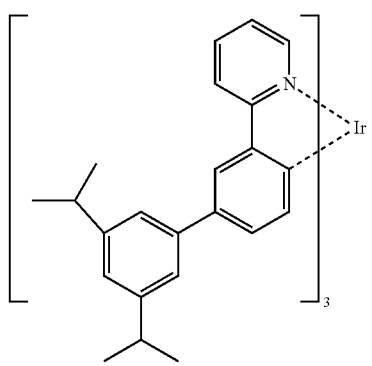
D-52
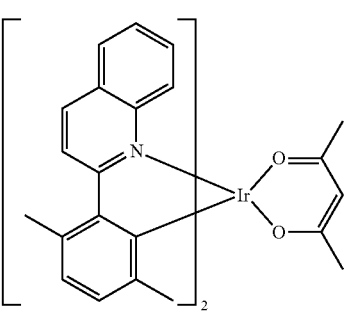
D-56
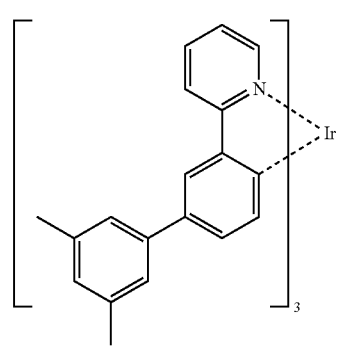
D-53
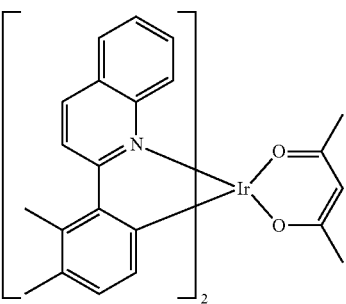
D-57
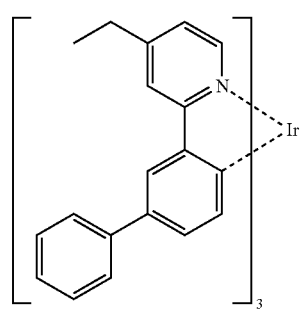
D-54
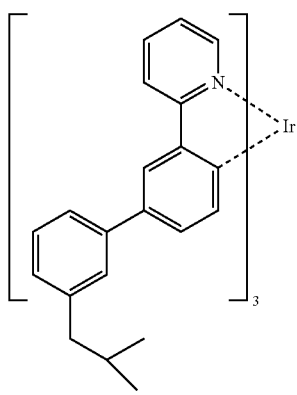
D-58

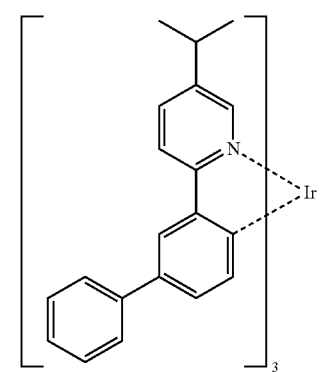
D-59
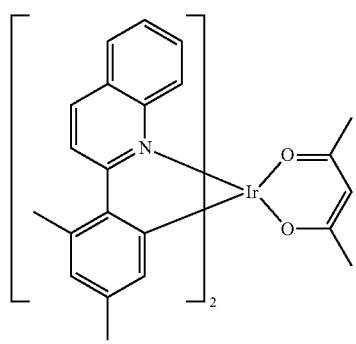
D-60
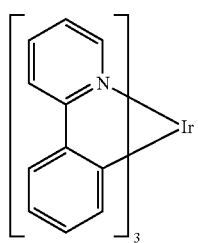
D-61
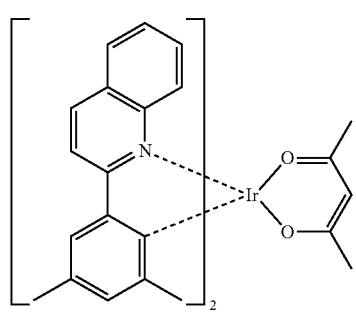
D-62
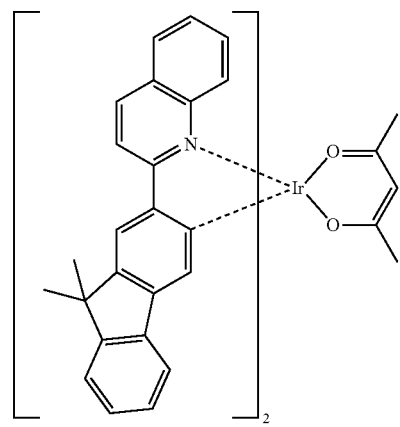
D-63
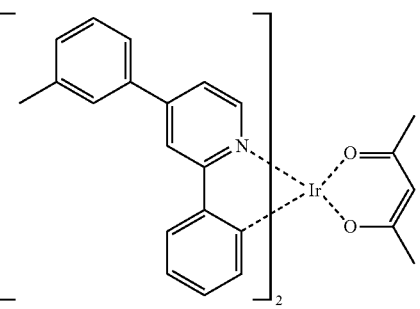
D-64
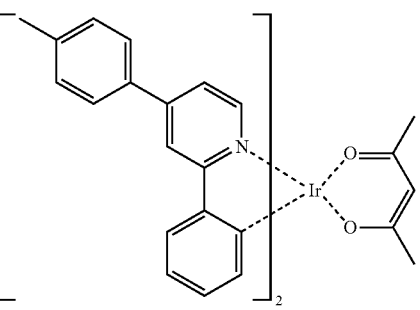
D-65
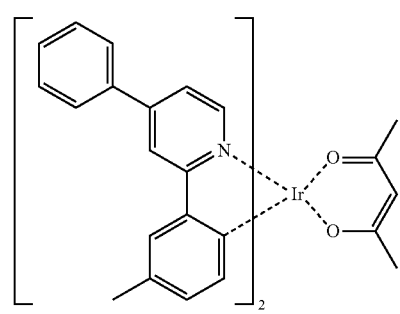
D-66
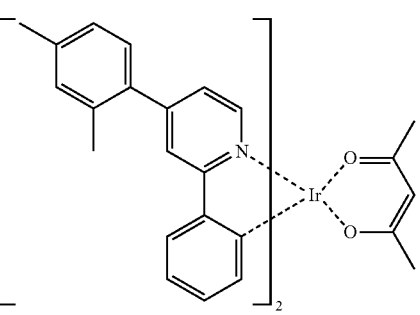
D-67

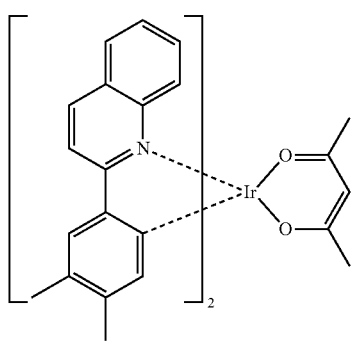
D-68
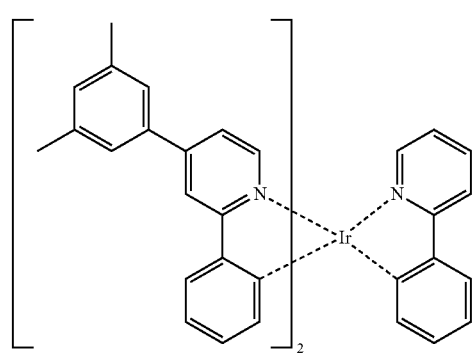
D-72
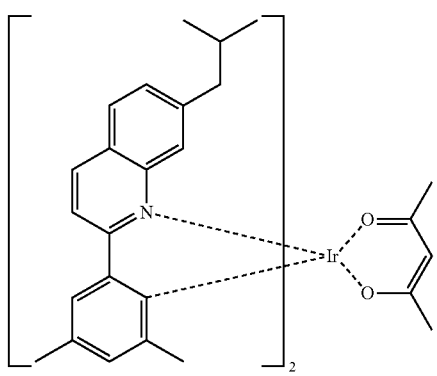
D-69
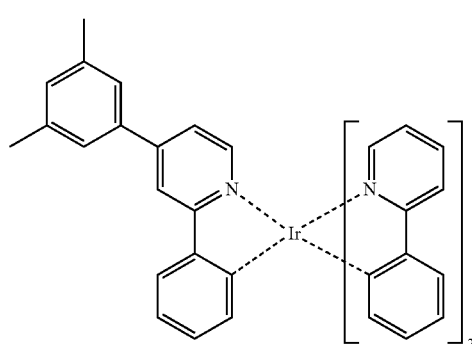
D-73
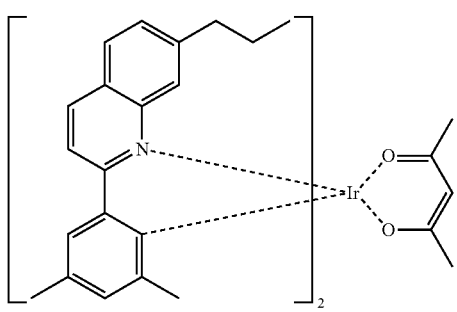
D-70
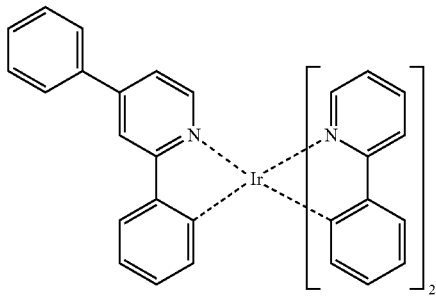
D-74
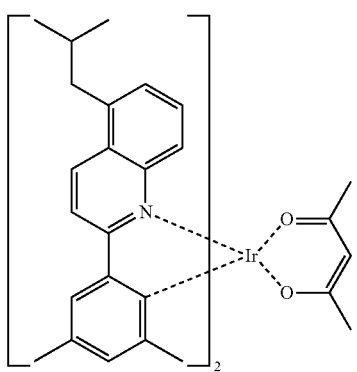
D-71
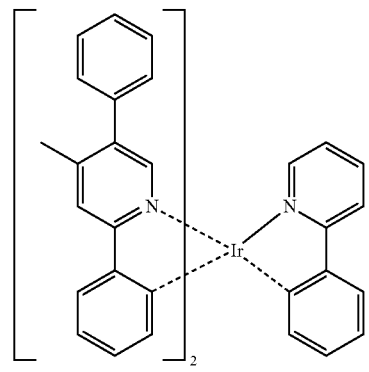
D-75

-continued
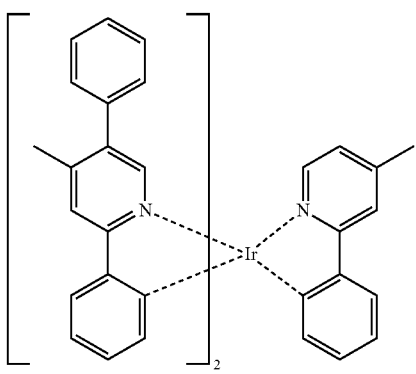
D-76
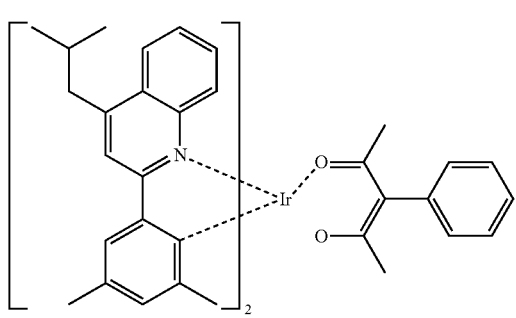
D-77
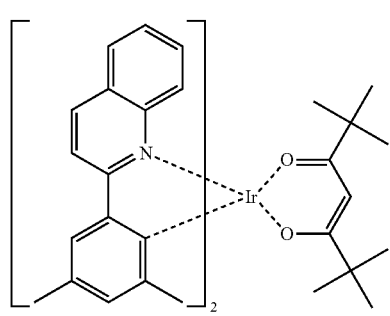
D-78
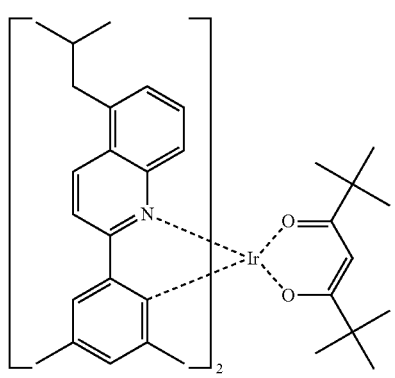
D-79
-continued
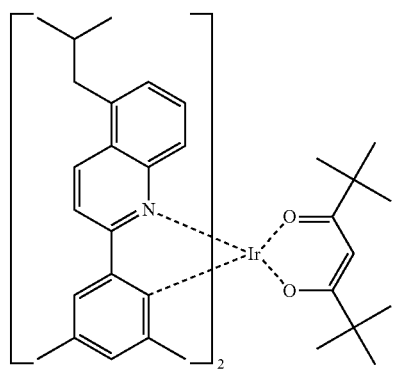
D-79
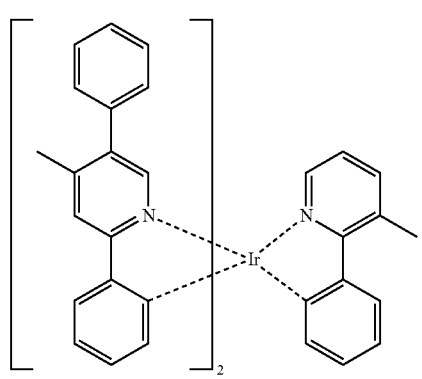
D-80
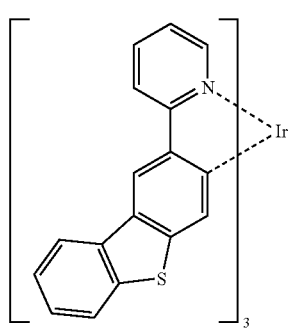
D-81
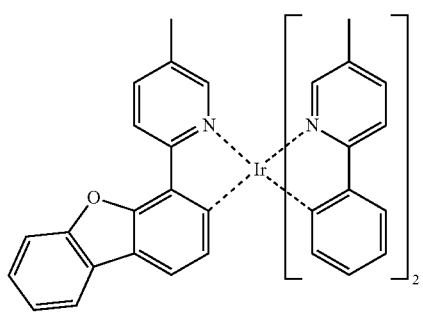
D-82

D-83 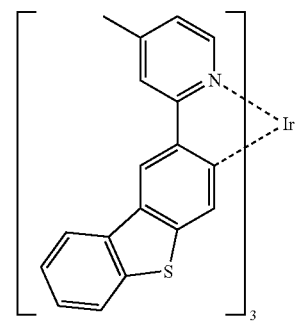
D-84 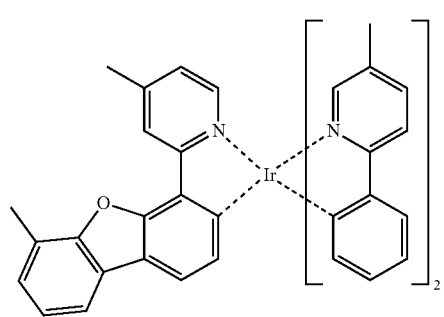
D-85 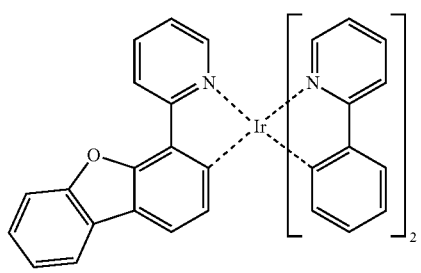
D-86 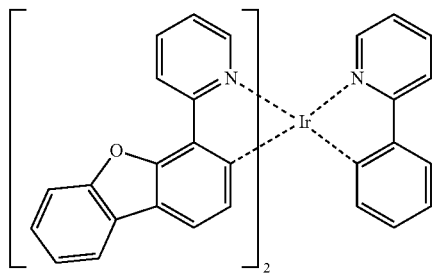
D-87 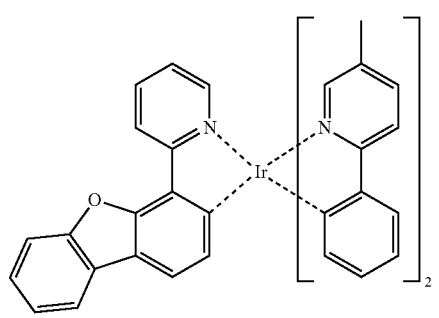
D-88 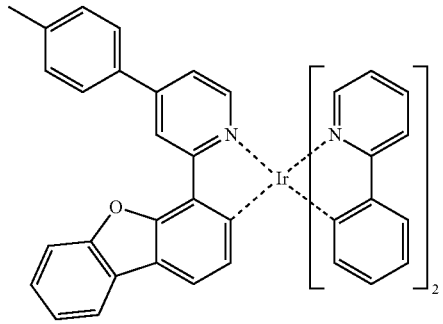
D-89 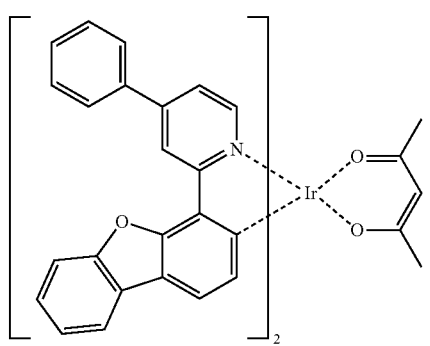
D-90 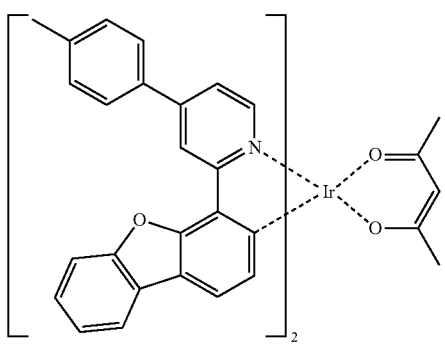
D-91 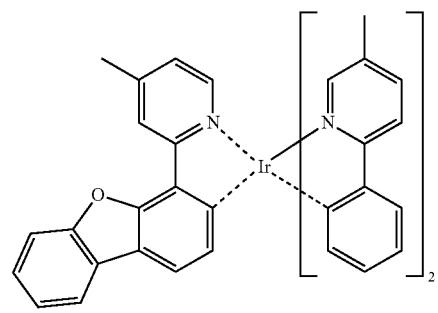
D-92 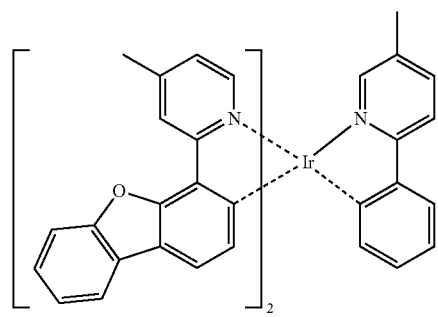

D-93
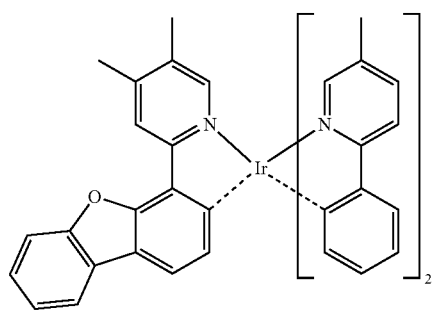
D-94
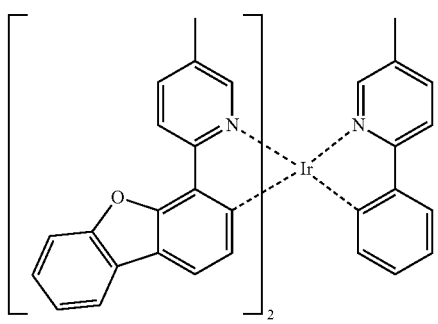
D-95
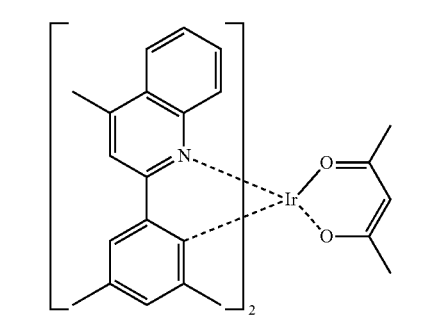
D-96
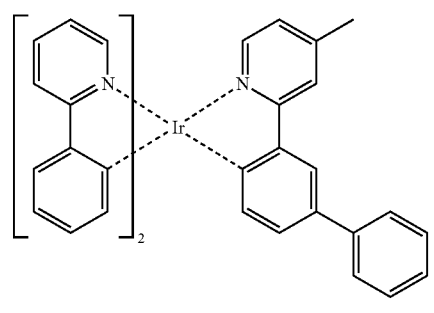
D-97
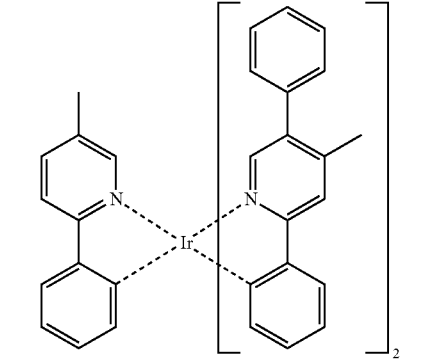
D-98
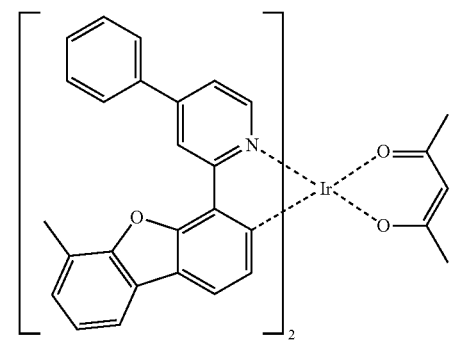
D-99
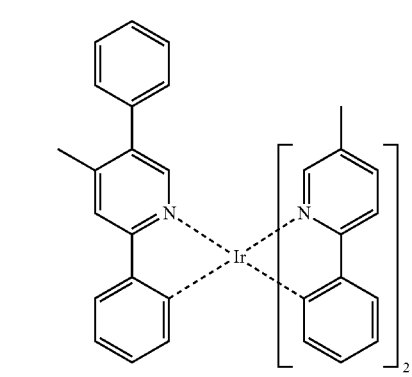
D-100
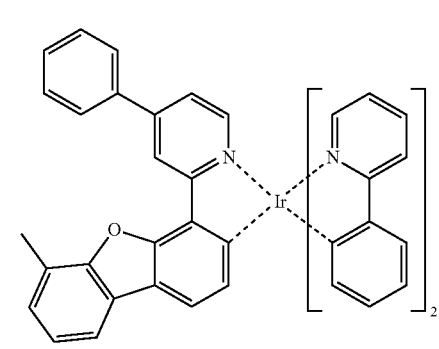
D-101
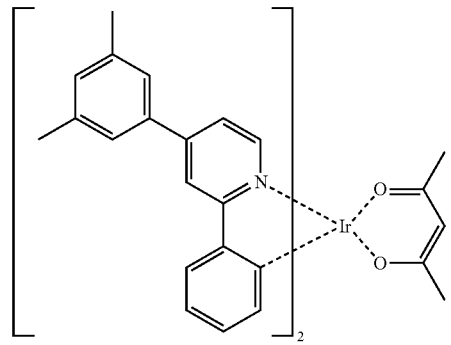

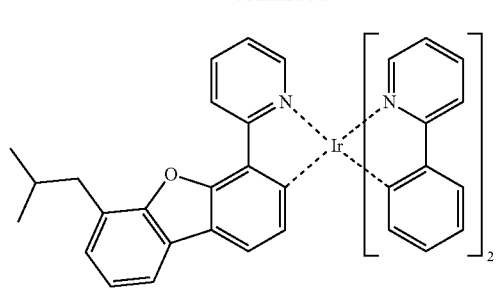
D-102
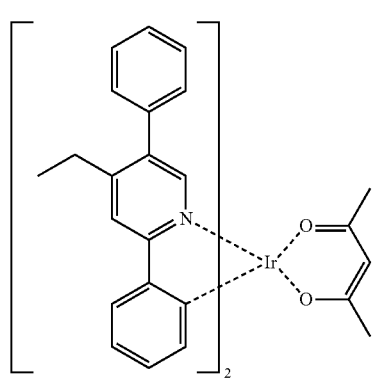
D-103
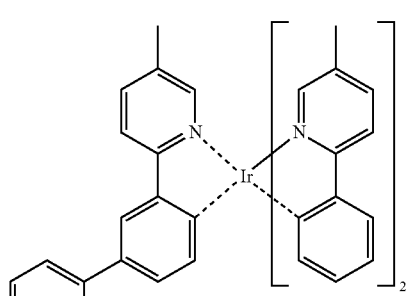
D-104
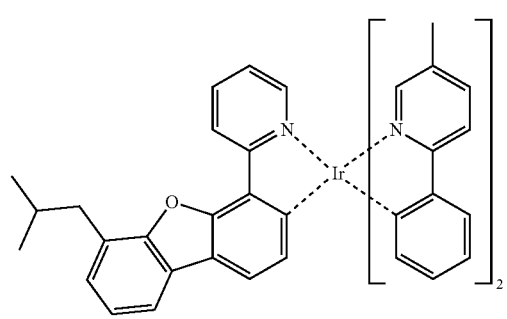
D-105
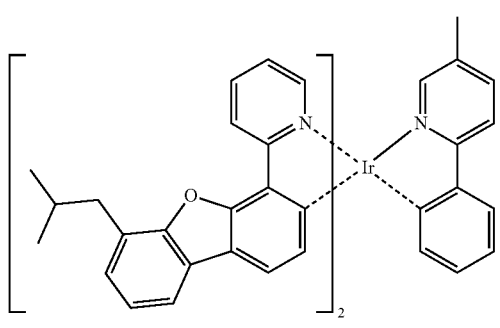
D-106
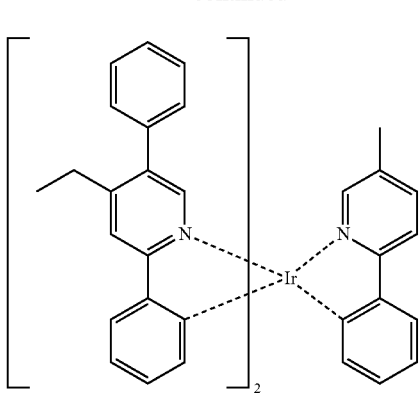
D-107
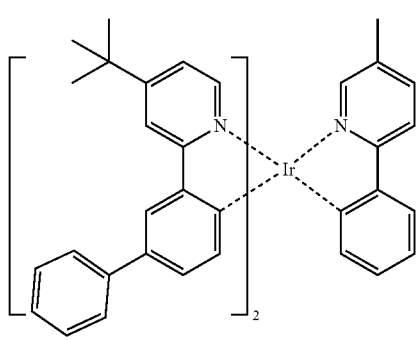
D-108
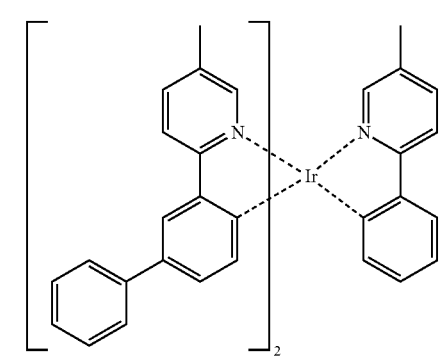
D-109
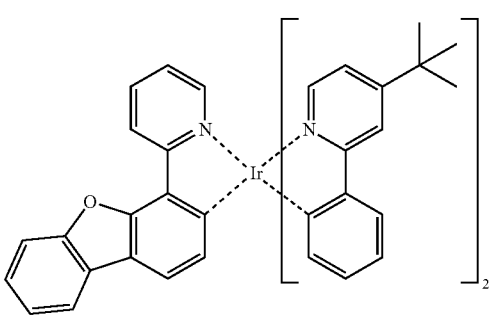
D-110

-continued
D-111
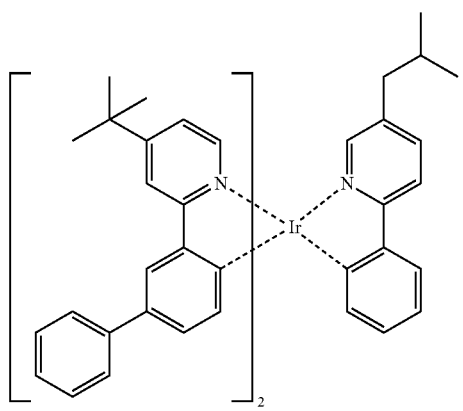
D-112
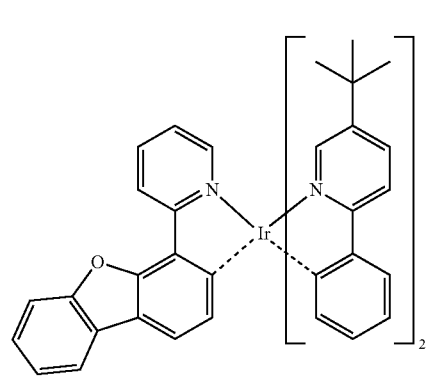
D-113
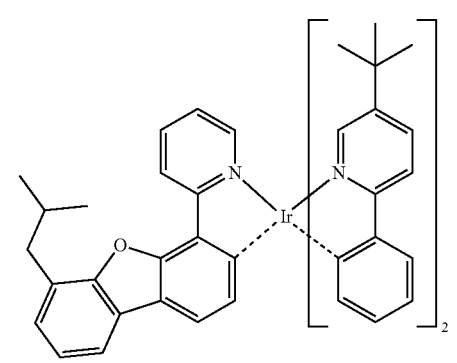
D-114
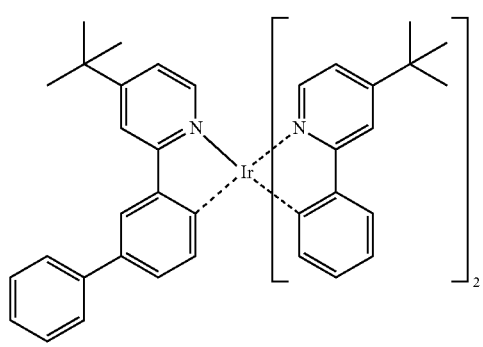
-continued
D-115
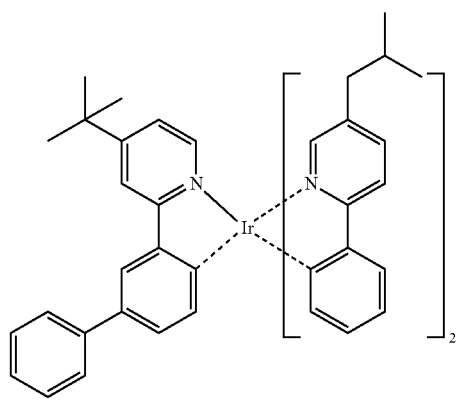
D-116
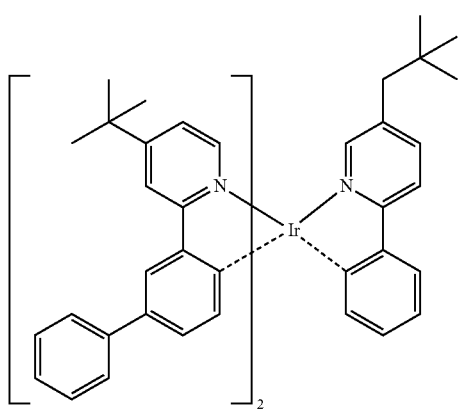
D-117
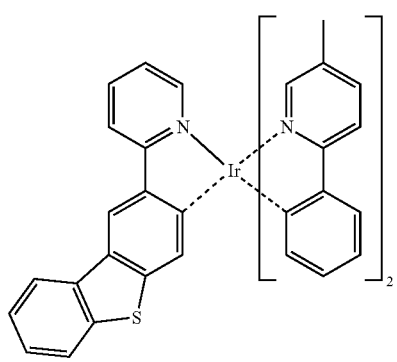
D-118
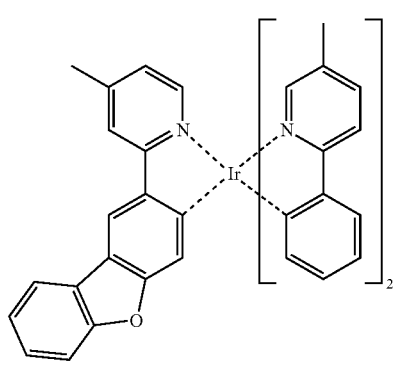

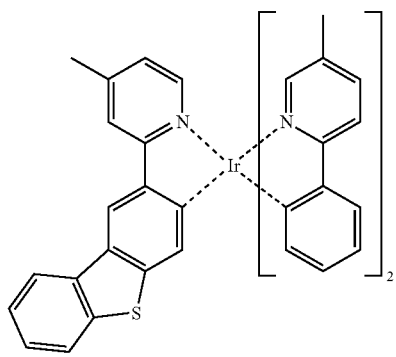
D-119
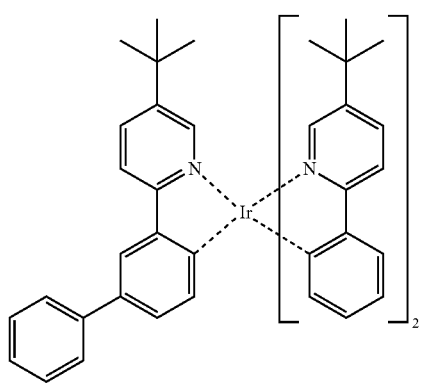
D-123
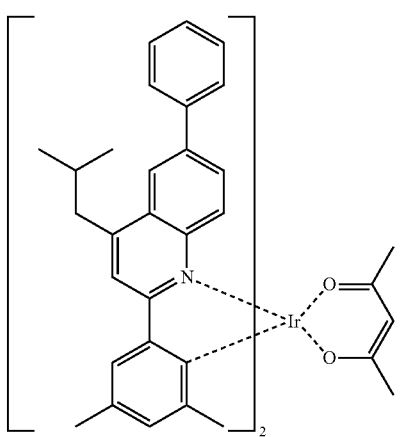
D-120
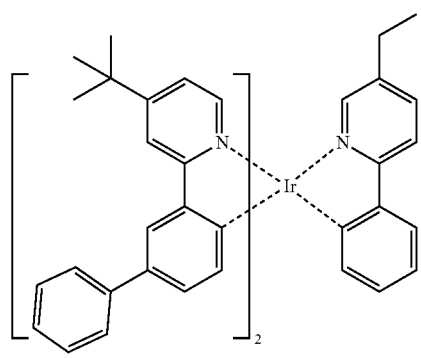
D-124
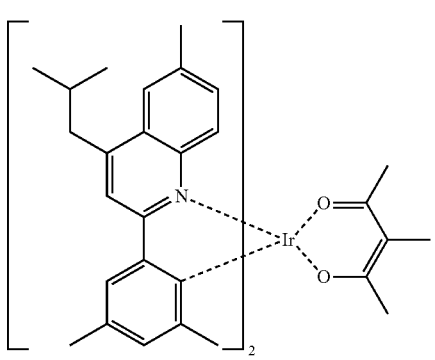
D-121
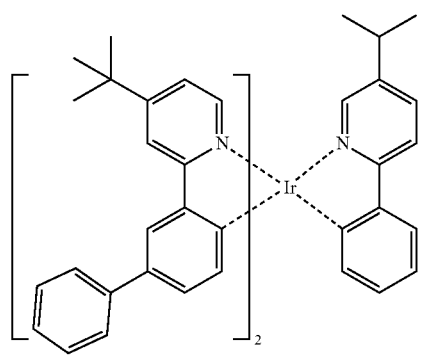
D-125
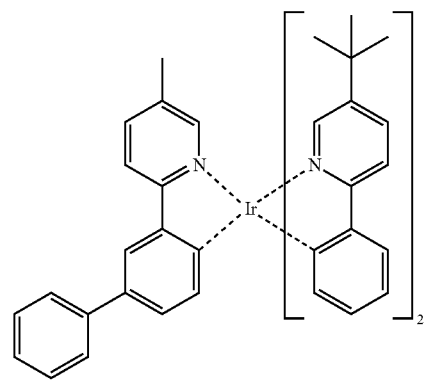
D-122
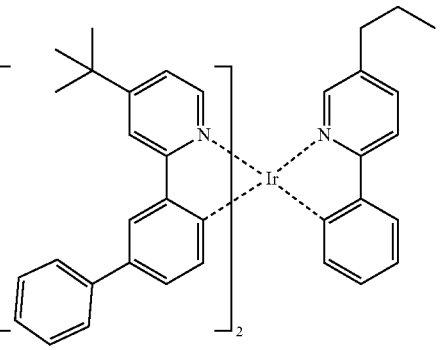
D-126

-continued
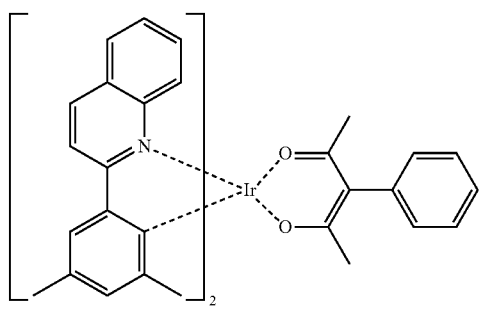
D-127
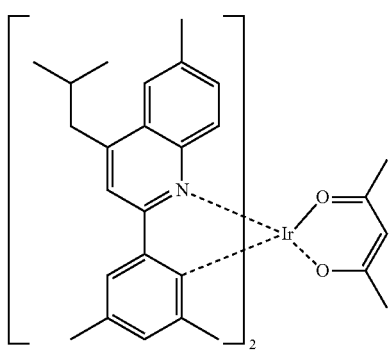
D-128
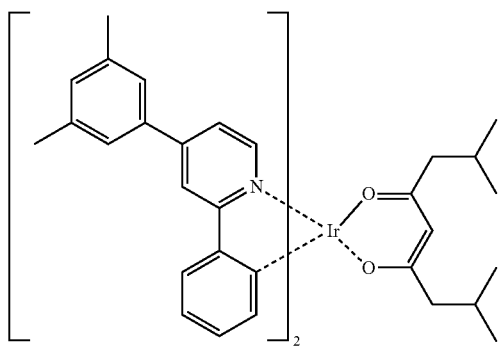
D-129
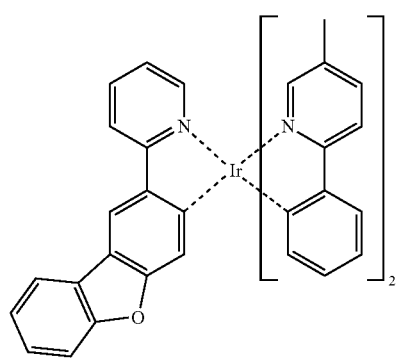
D-130
-continued
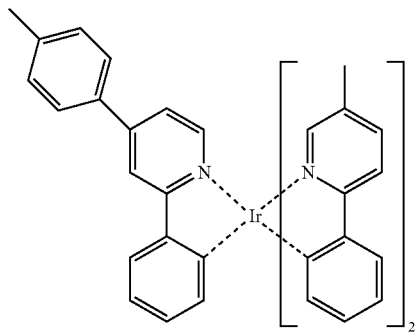
D-131
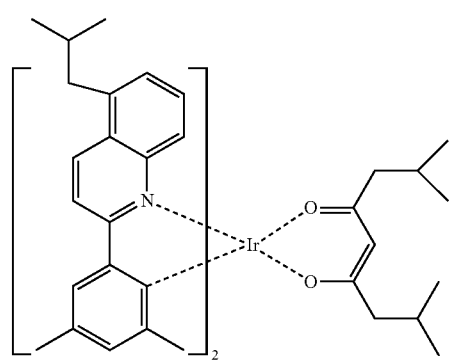
D-132
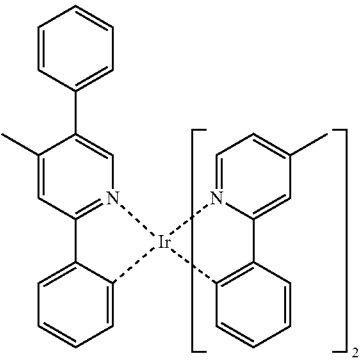
D-133
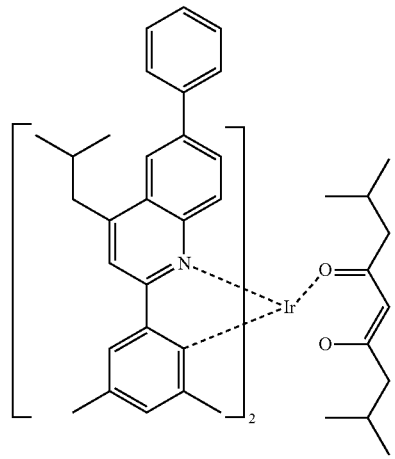
D-134

D-135
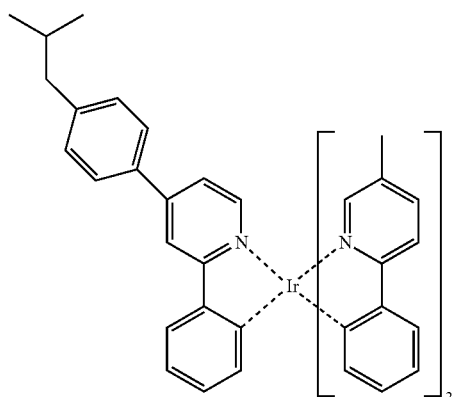
D-136
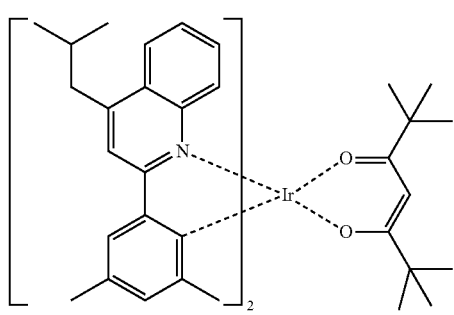
D-137
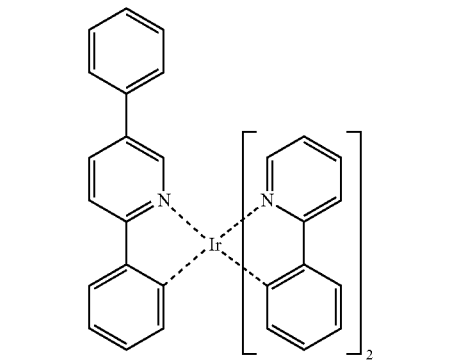
D-138
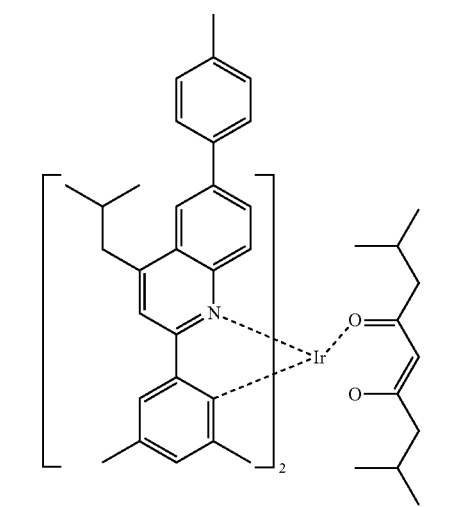
D-139
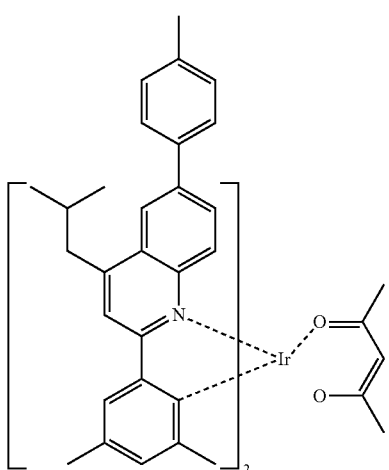
D-140
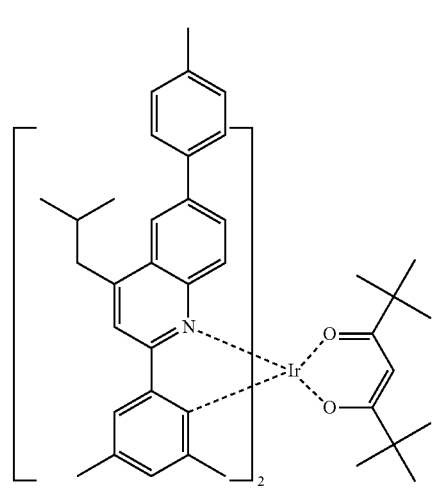
D-141
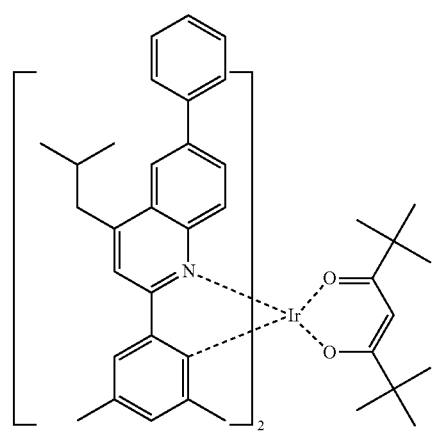

D-142 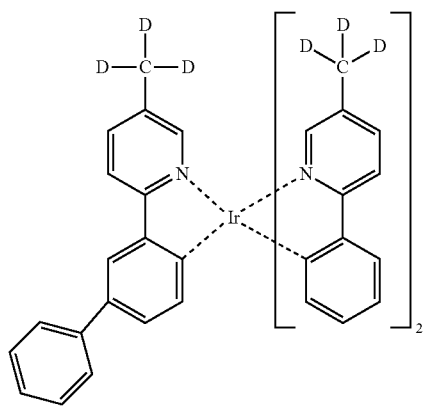
D-143 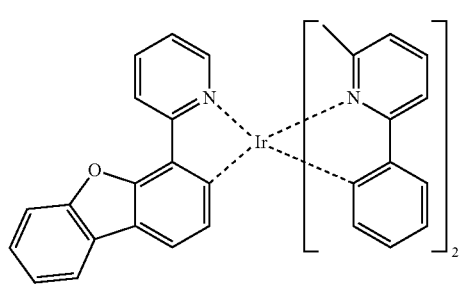
D-144 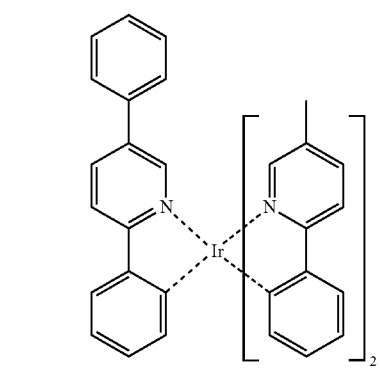
D-145 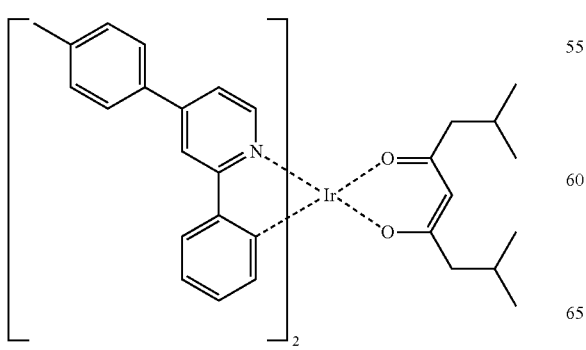
D-146 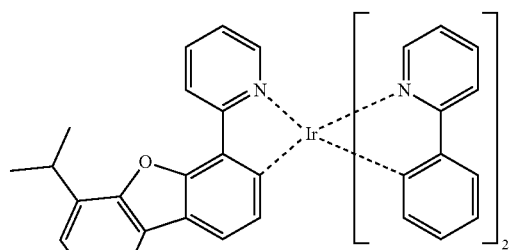
D-147 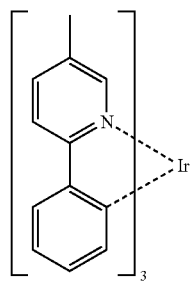
D-148 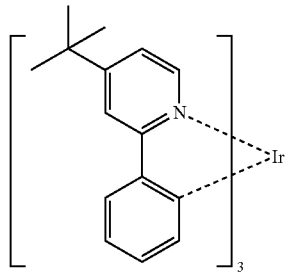
D-149 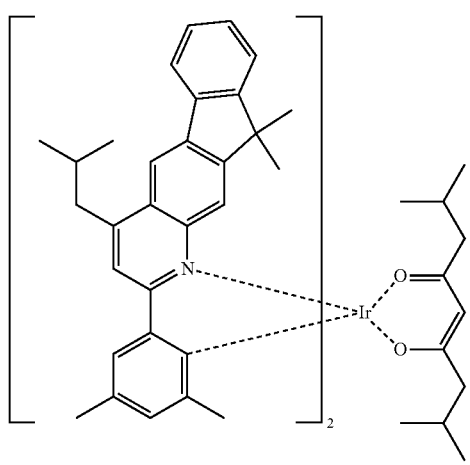

D-150
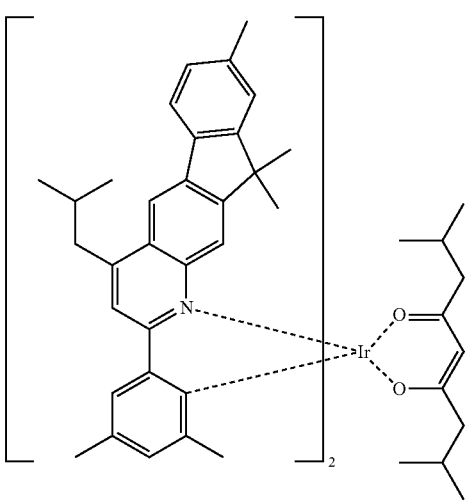
D-151
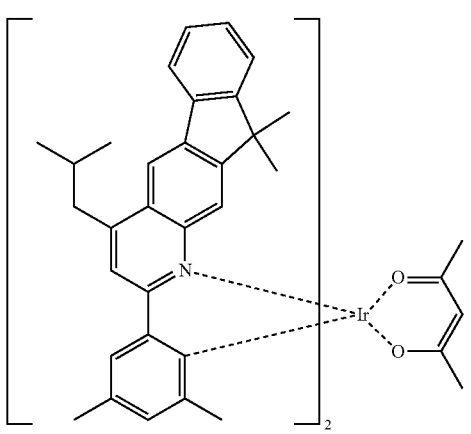
D-152
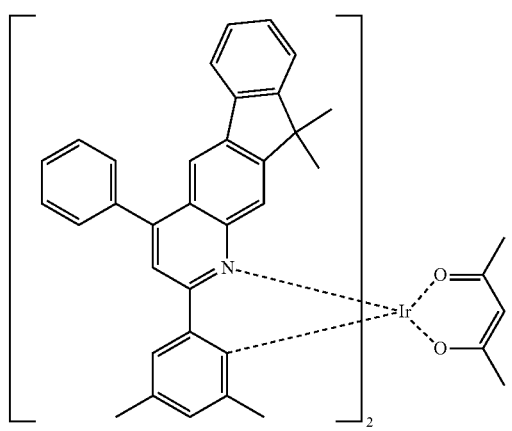
D-153
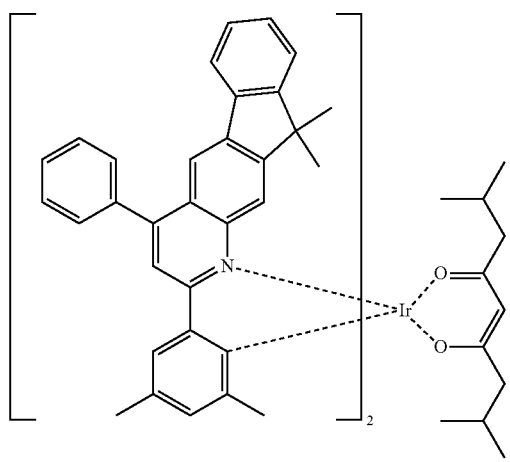
D-154
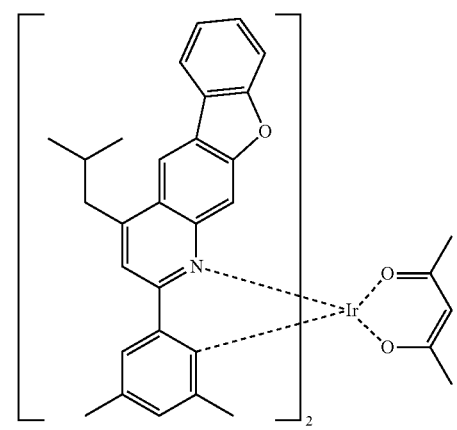
D-155
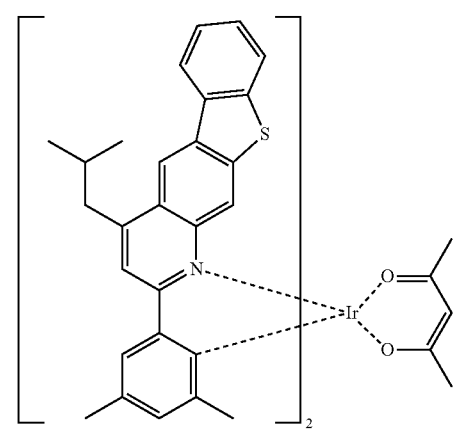

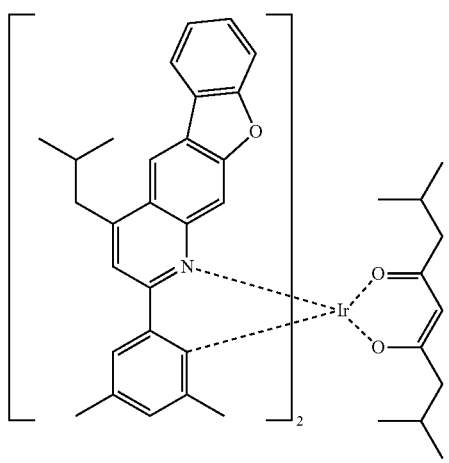

D-156

D-157

In addition, the present disclosure provides an electron transport material or an electron buffer material comprising the organic electroluminescent compound of formula 1.

The electron buffer material may control flow properties of a charge. For example, the electron buffer material may trap an electron, block an electron, or lower an energy barrier between an electron transport zone and a light-emitting layer. The electron buffer material in an organic electroluminescent device may be used for an electron buffer layer, or may be used in another zone such as an electron transport zone or a light-emitting layer, in which the electron buffer layer is formed between the light-emitting layer and the electron transport zone, or between the electron transport zone and the second electrode. The electron buffer material may further comprise conventional materials generally used in producing an organic electroluminescent device.

When the organic electroluminescent compound of formula 1 is used as an electron transport material, the electron transport material can be comprised of the organic electroluminescent compound of formula 1 alone, or can further comprise conventional materials generally included in electron transport materials.

When the compound according to the present disclosure is used as an electron transport material or an electron buffer material, a light-emitting layer comprised in the organic electroluminescent device may comprise a host and a dopant. The host compound may be a phosphorescent host compound or a fluorescent host compound, and the dopant compound may be a phosphorescent dopant compound or a fluorescent dopant compound. As the fluorescent host material, an anthracene derivative, an aluminum complex, a rubrene derivative, an arylamine derivative, etc., and preferably an anthracene derivative may be used. The specific examples of the fluorescent host material may be as follows, but are not limited thereto:

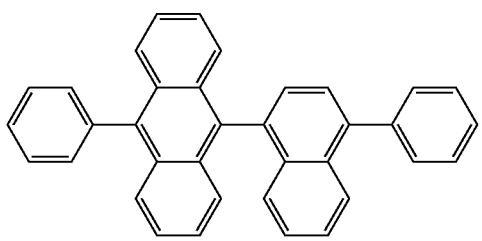

H-1

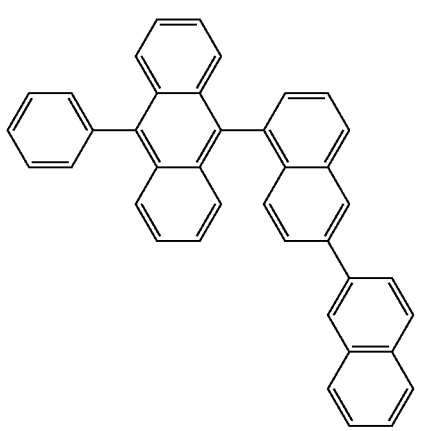

H-2

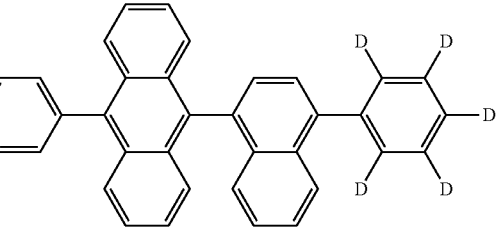

H-3

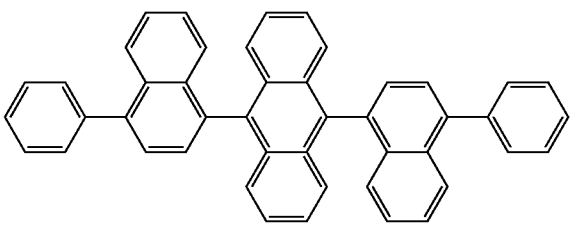

H-4

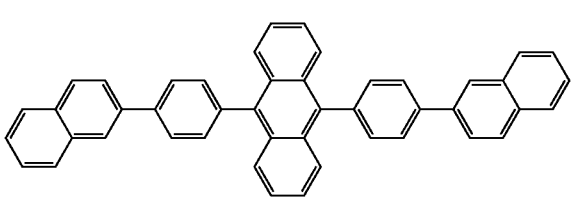

H-5

H-6
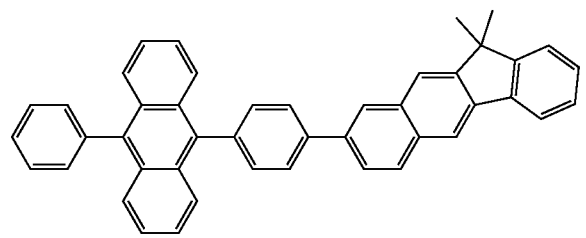
H-7
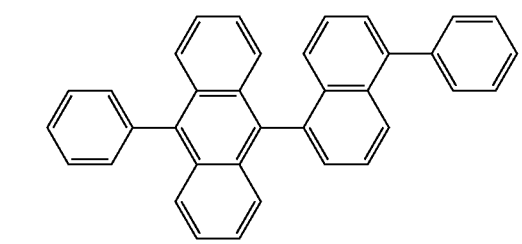
H-8
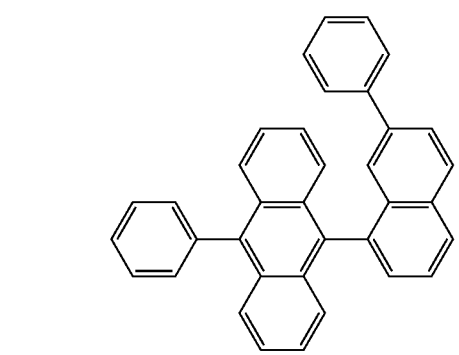
H-9
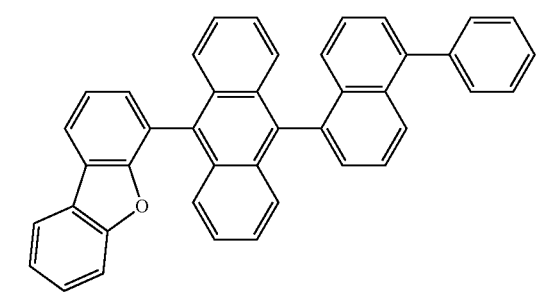
H-10
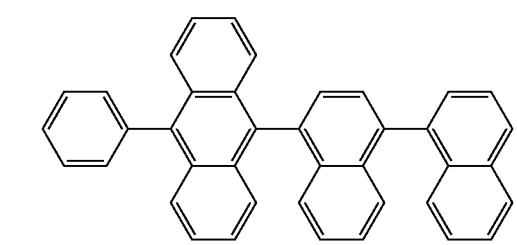
H-11
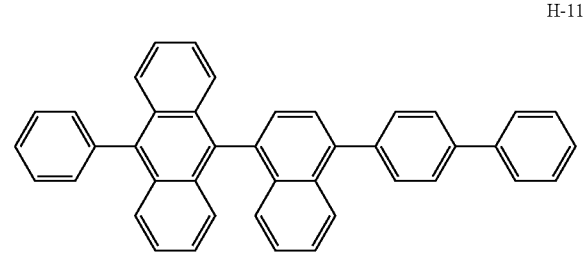
H-12
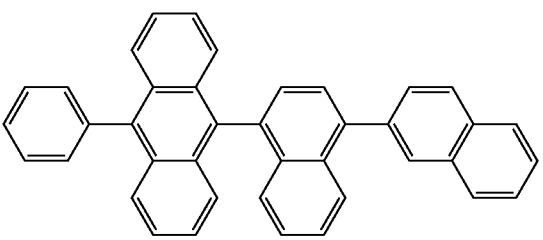
H-13
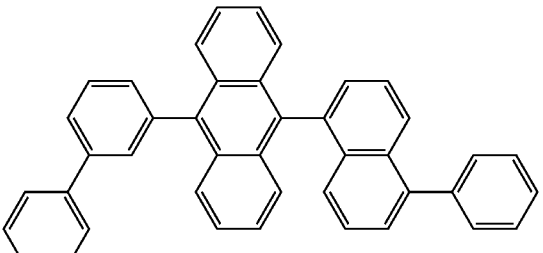
H-14
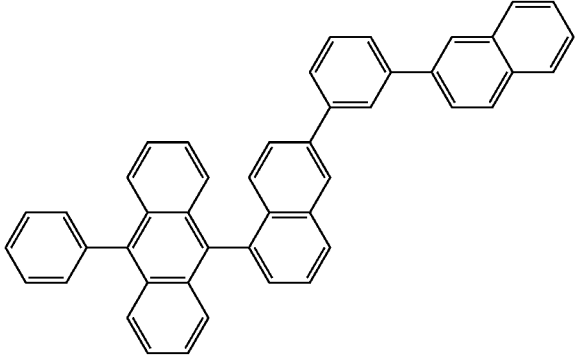
H-15
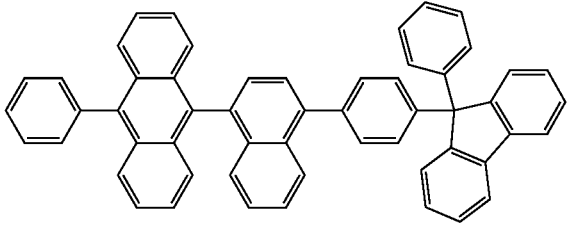
H-16

H-17
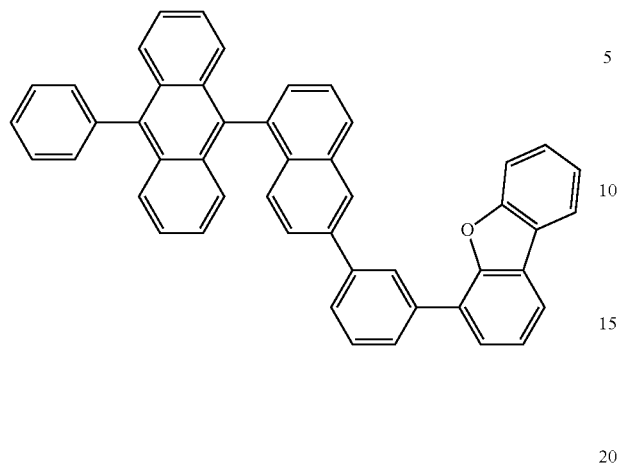
H-18
H-20
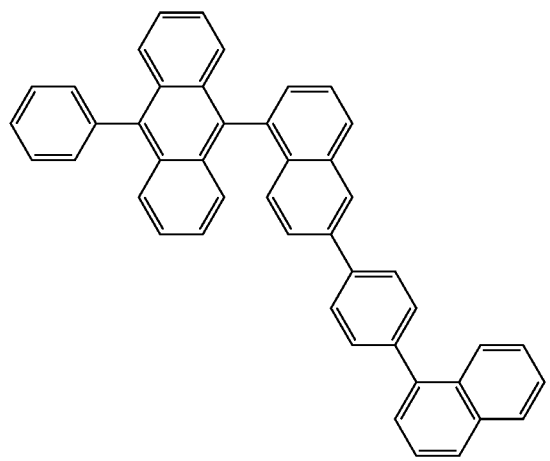
H-21
H-22
H-19
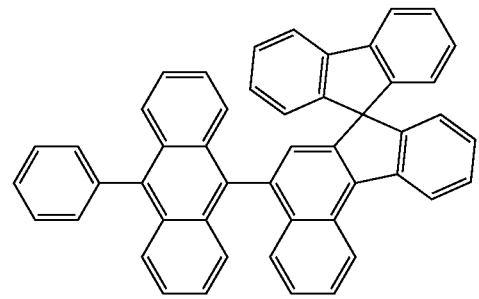
H-23
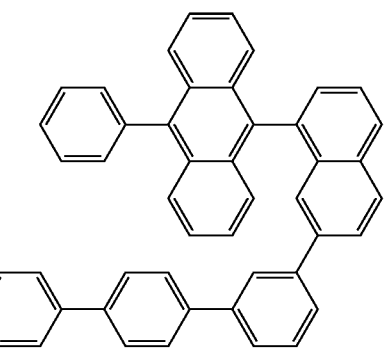

H-24
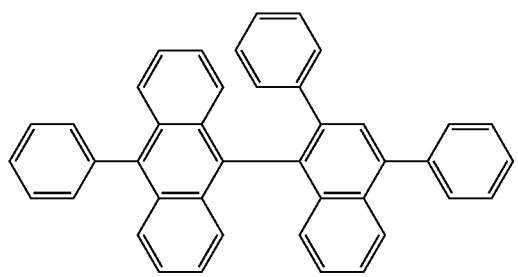
H-25
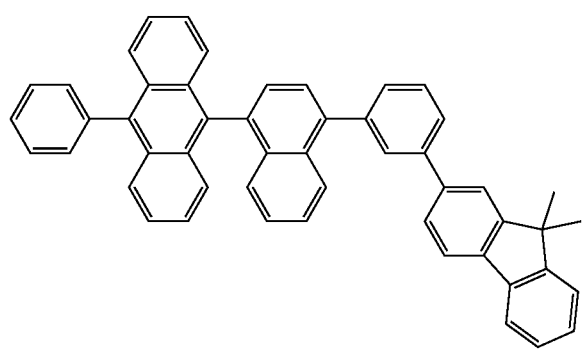
H-26
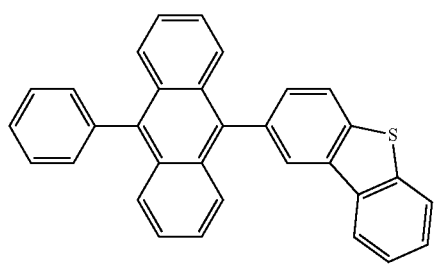
H-27
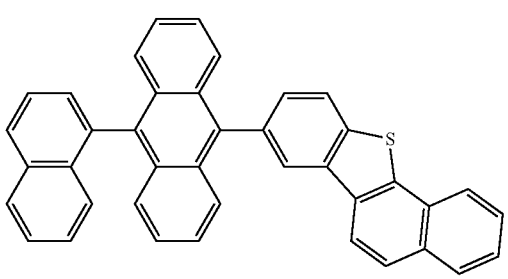
H-28
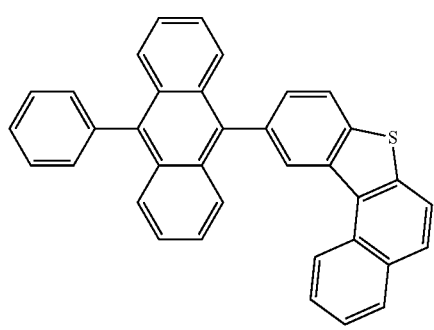
H-29
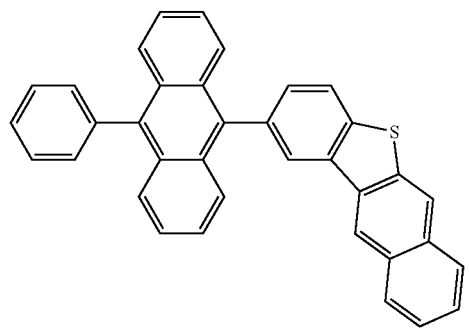
H-30
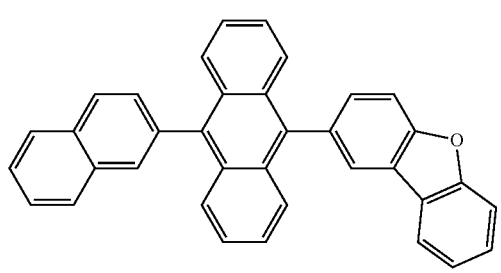
H-31
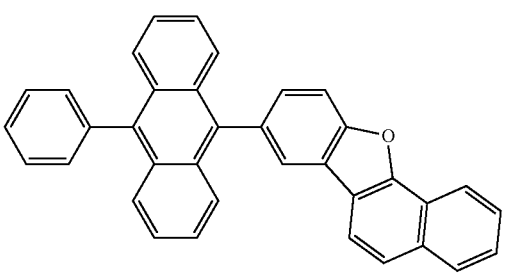
H-32
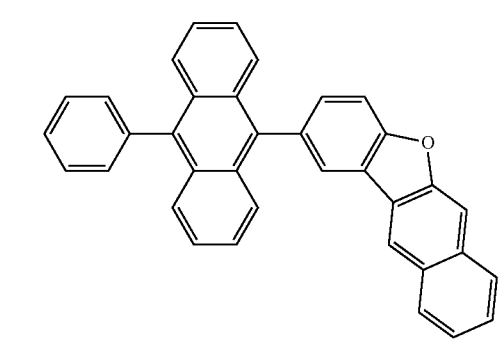
H-33
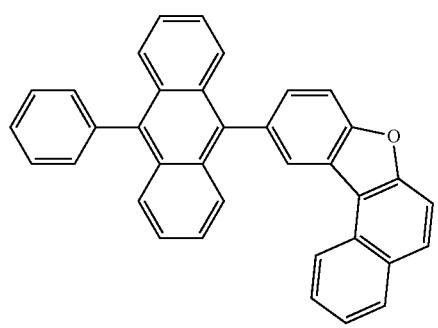

H-34
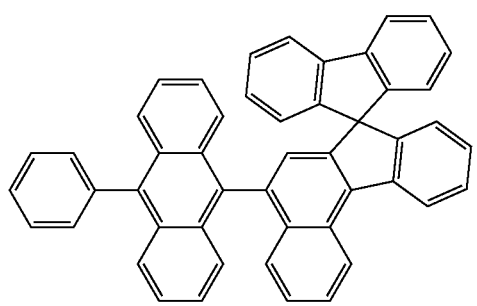
F-1
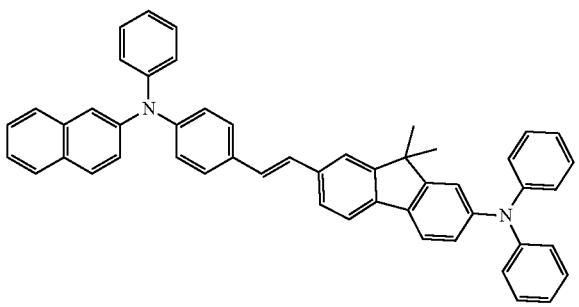
H-35
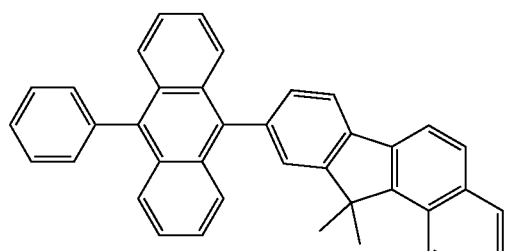
F-2
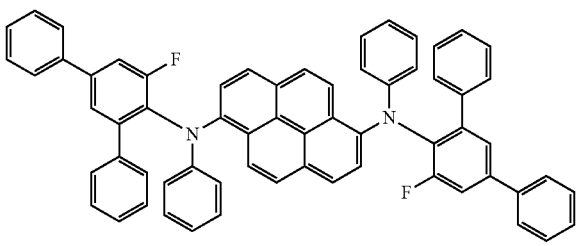
H-36
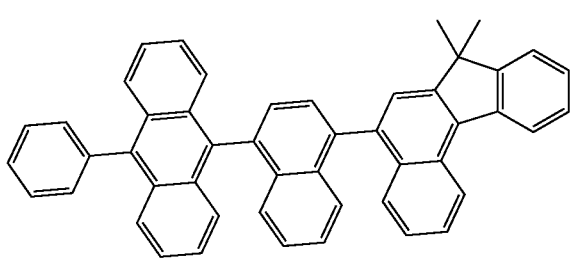
F-3
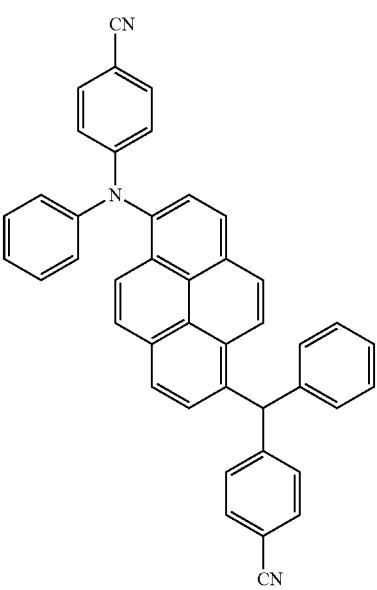
H-37
In addition, as the fluorescent dopant material, derivatives of pyrenes, aminofluorenes, aminoanthracenes, aminochrysenes, stilbenes, etc., and preferably pyrene derivatives may be used.
The specific examples of the fluorescent dopant material may be as follows, but are not limited thereto:
F-4

-continued
F-5
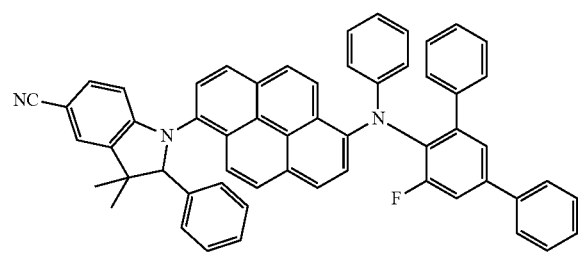
F-6
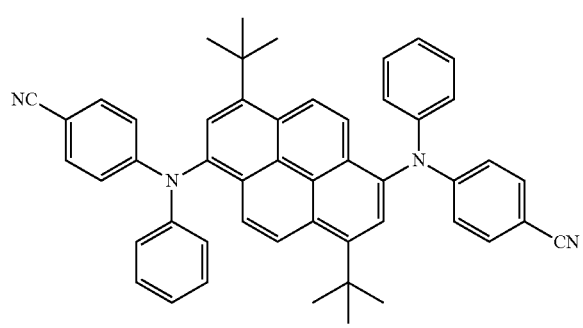
F-7
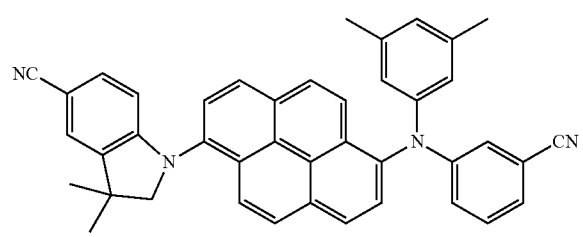
F-8
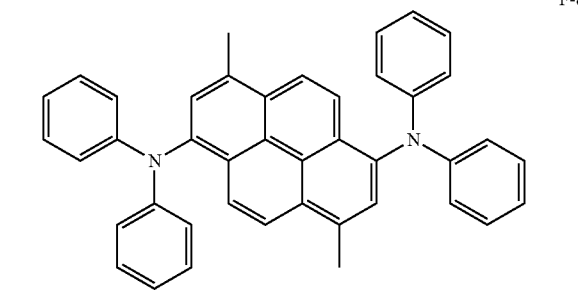
F-9
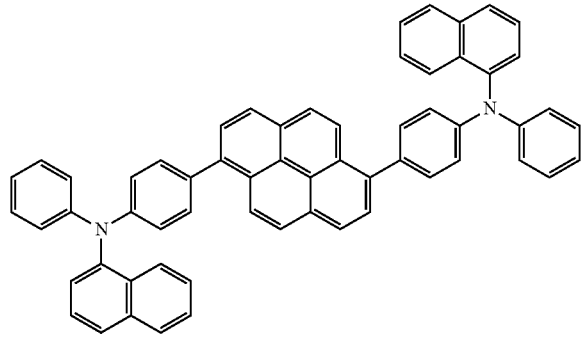
-continued
F-10
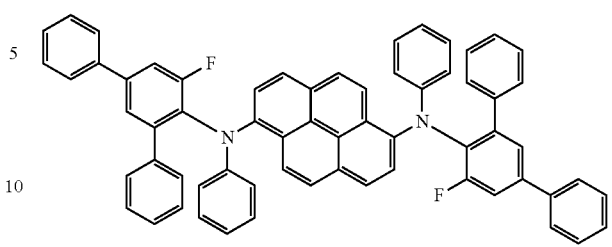
F-11
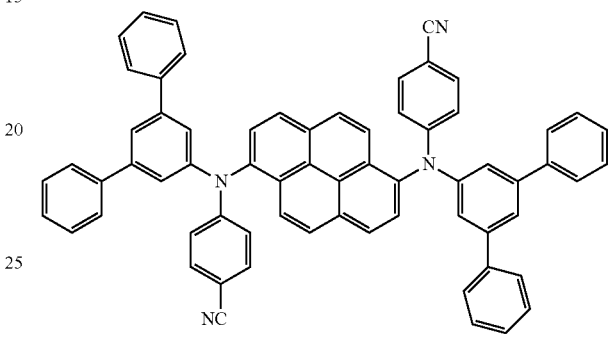
F-12
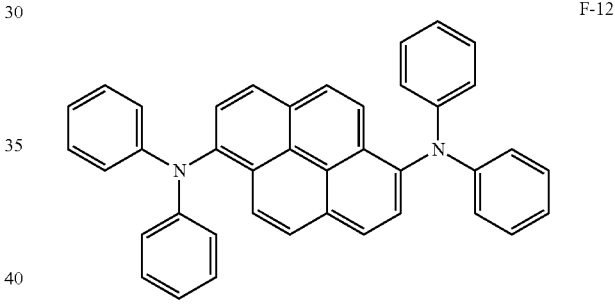
F-13
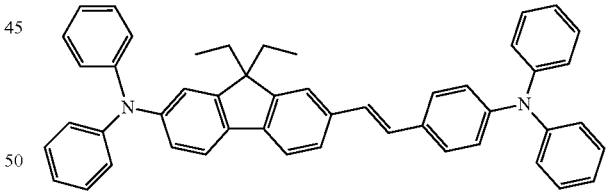
F-14
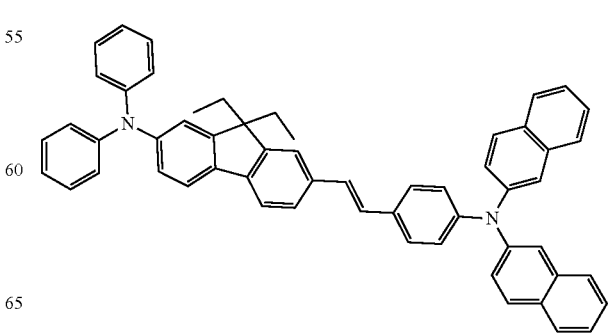

F-15
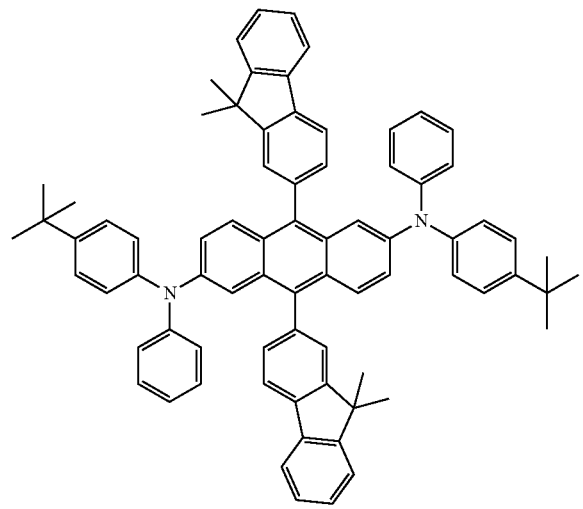
F-19
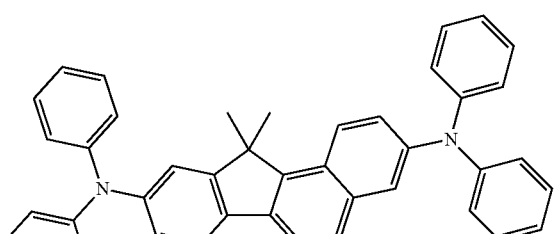
F-16
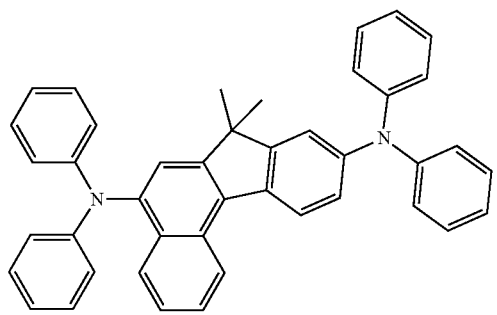
F-20
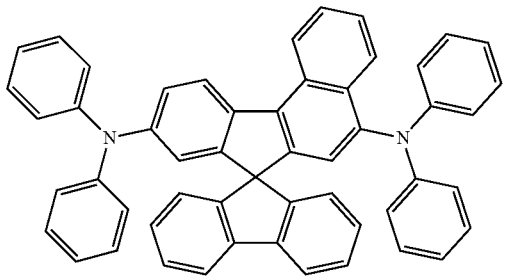
F-17
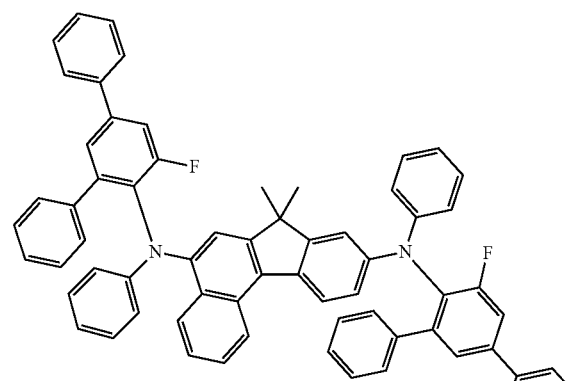
F-21
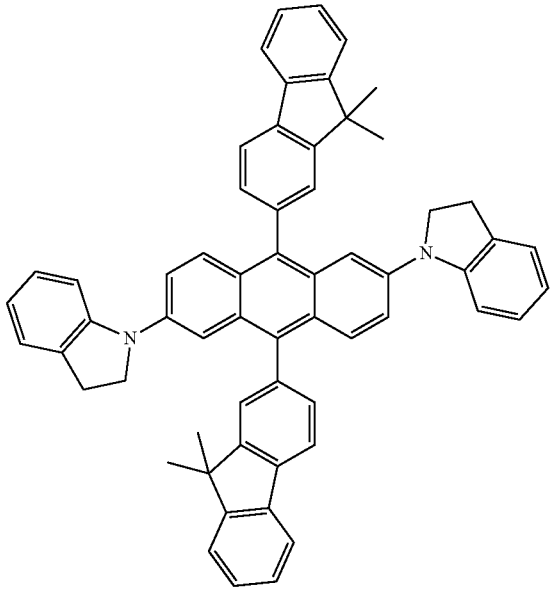
F-18
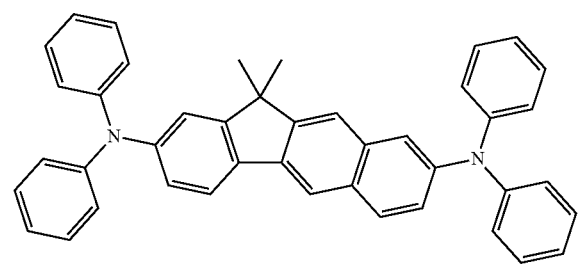

F-22

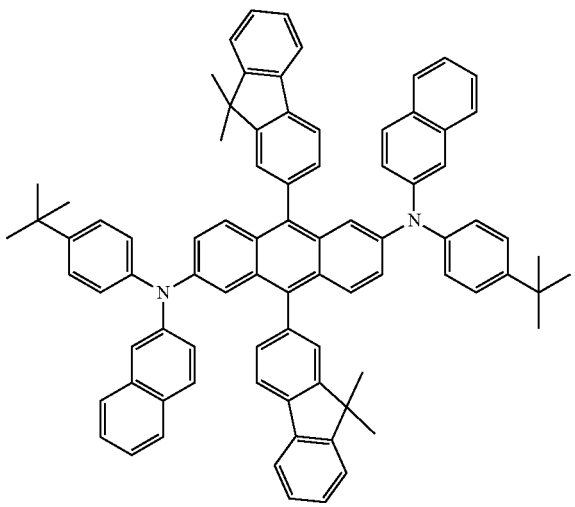

F-23

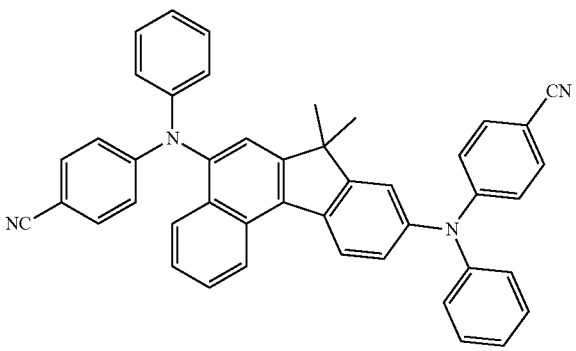

F-24

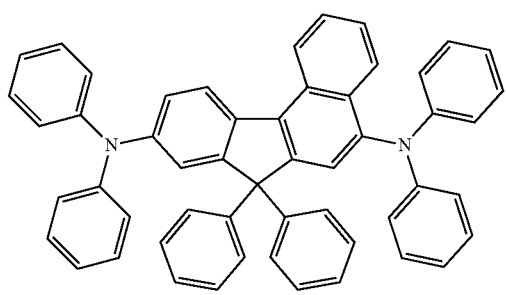

The organic electroluminescent device of the present disclosure may further comprise at least one compound selected from the group consisting of arylamine-based compounds and styrylarylamine-based compounds.

In the organic electroluminescent device of the present disclosure, the organic layer may further comprise at least one metal selected from the group consisting of metals of Group 1, metals of Group 2, transition metals of the 4th period, transition metals of the 5th period, lanthanides, and organic metals of the d-transition elements of the Periodic Table, or at least one complex compound comprising the metal.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a multi-component of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic EL device having two or more light-emitting layers and emitting white light.

In order to form each layer constituting the organic EL device of the present disclosure, dry film-forming methods such as vacuum deposition, sputtering, plasma, ion plating methods, etc., or wet film-forming methods such as spin coating, dip coating, flow coating methods, etc., can be used. The first and second host compounds of the present disclosure may be co-evaporated or mixture-evaporated.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a layer.

By using the organic electroluminescent device of the present disclosure, a display system, for example, for smartphones, tablets, notebooks, PCs, TVs, or vehicles, or a lighting system, for example, an indoor or outdoor lighting system, can be produced.

Hereinafter, the preparation method of the organic electroluminescent compounds of the present disclosure, the physical properties of the compounds, and the luminous properties of the organic electroluminescent device comprising the compounds will be explained in detail with reference to the representative compounds of the present disclosure.

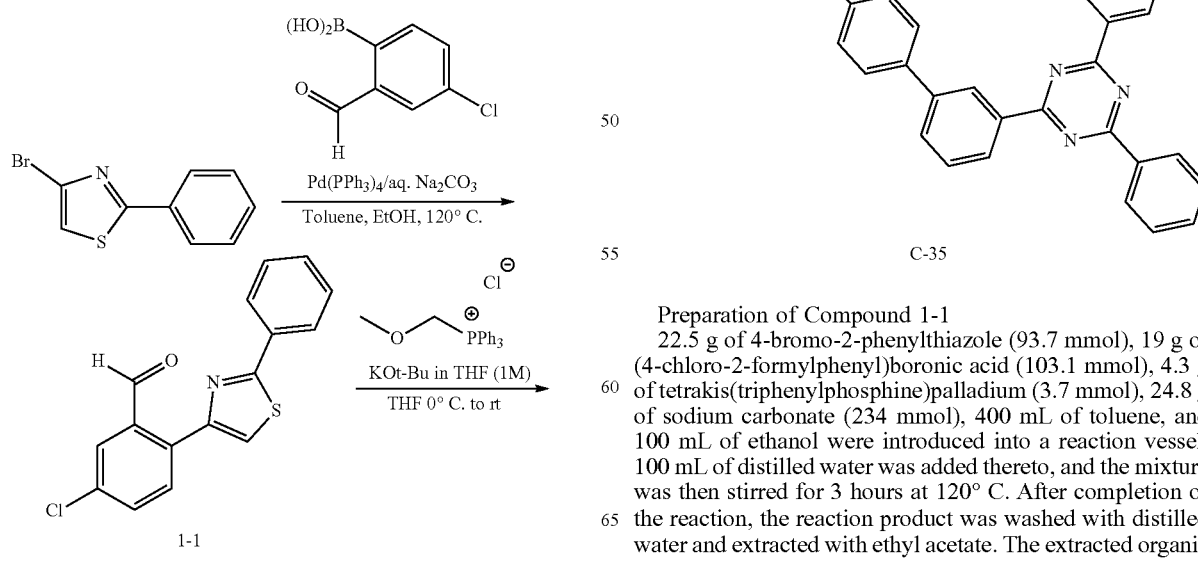

Preparation of Compound 1-1

22.5 g of 4-bromo-2-phenylthiazole (93.7 mmol), 19 g of (4-chloro-2-formylphenyl)boronic acid (103.1 mmol), 4.3 g of tetrakis(triphenylphosphine)palladium (3.7 mmol), 24.8 g of sodium carbonate (234 mmol), 400 mL of toluene, and 100 mL of ethanol were introduced into a reaction vessel, 100 mL of distilled water was added thereto, and the mixture was then stirred for 3 hours at 120° C. After completion of the reaction, the reaction product was washed with distilled water and extracted with ethyl acetate. The extracted organic layer was then dried with magnesium sulfate. The solvent was removed with a rotary evaporator, and the resulting product was purified by column chromatography to obtain 20.7 g of compound 1-1 (yield: 74%).

Preparation of Compound 1-2

19.7 g of compound 1-1 (65.7 mmol), 33.8 g of (methoxymethyl)phosphonium chloride (98.6 mmol), and 350 mL of tetrahydrofuran were introduced into a reaction vessel, and 100 mL of 1 M potassium tert-butoxide was added dropwise thereto at 0° C. The reaction temperature was then slowly raised to room temperature, and the mixture was stirred for an additional 2 hours. After completion of the reaction, the reaction product was extracted with ethyl acetate. The extracted organic layer was then dried with magnesium sulfate. The solvent was removed with a rotary evaporator, and the resulting product was purified by column chromatography to obtain 16.3 g of compound 1-2 (yield: 76%).

Preparation of Compound 1-3

15.6 g of compound 1-2 (47.7 mmol) was dissolved in chlorobenzene in a reaction vessel, and 1.7 mL of Eaton's reagent was slowly added dropwise thereto. The mixture was then stirred under reflux for an additional 2 hours. After completion of the reaction, the reaction product was washed with distilled water and extracted with ethyl acetate. The extracted organic layer was then dried with magnesium sulfate. The solvent was removed with a rotary evaporator, and the resulting product was purified by column chromatography to obtain 10.5 g of compound 1-3 (yield: 71%).

Preparation of Compound 1-4

10.0 g of compound 1-3 (33.8 mmol), 10.3 g of bis (pinacholato)diborane (40.6 mmol), 1.2 g of tris(dibenzylideneacetone)dipalladium (1.4 mmol), 1.1 g of 2-dicyclohexylphosphino-2',6'-dimethoxybiphenyl (s-Phos) (2.8 mmol), 9.9 g of potassium acetate (101.4 mmol), and 200 mL of 1,4-dioxane were introduced into a reaction vessel, and the mixture was stirred under reflux for 4 hours. After completion of the reaction, the reaction product was washed with distilled water and extracted with ethyl acetate. The extracted organic layer was then dried with magnesium sulfate. The solvent was removed with a rotary evaporator, and the resulting product was purified by column chromatography to obtain 13.1 g of compound 1-4 (yield: 100%).

Preparation of Compound C-35

13.1 g of compound 1-4 (33.8 mmol), 12 g of 2-(3-bromophenyl)-4,6-diphenyl-1,3,5-triazine (30.7 mmol), 2.0 g of tetrakis(triphenylphosphine)palladium (1.7 mmol), 11.9 g of sodium carbonate (86 mmol), 120 mL of toluene, and 40 mL of ethanol were introduced into a reaction vessel, 40 mL of distilled water was added thereto, and the mixture was then stirred for 3 hours at 120° C. After completion of the reaction, the reaction product was washed with distilled water and extracted with ethyl acetate. The extracted organic layer was then dried with magnesium sulfate. The solvent was removed with a rotary evaporator, and the resulting product was purified by column chromatography to obtain 20.7 g of compound C-35 (yield: 78%).

|  | MW | UV | PL | M.P. |
|---|---|---|---|---|
| C-35 | 568.70 | 290 nm | 427 nm | 282° C. |

Example 2: Preparation of compound C-249

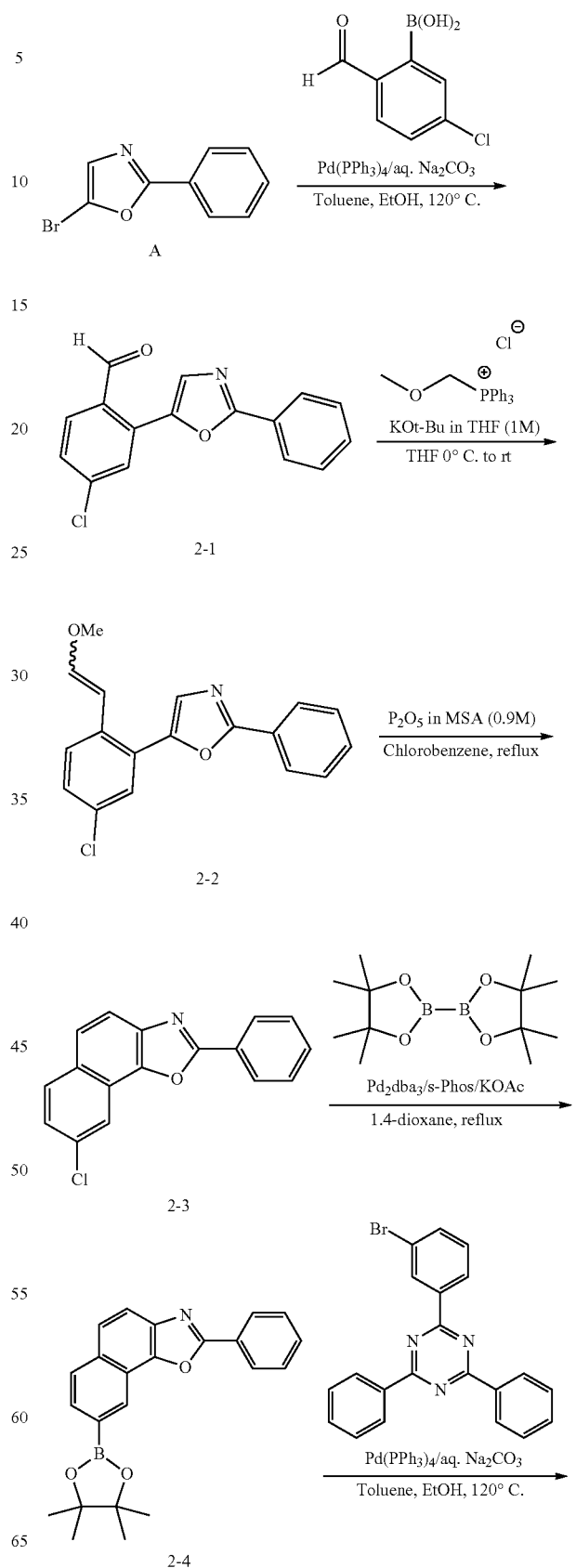

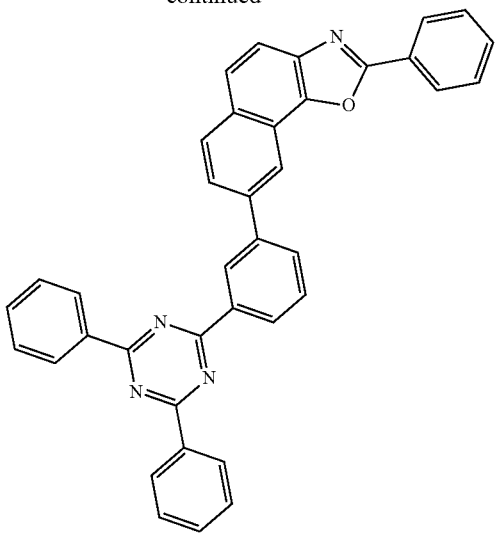

C-249

Preparation of Compound 2-1

30 g of compound A (134 mmol), 27 g of (5-chloro-2-formylphenyl)boronic acid (147 mmol), 6.2 g of tetrakis(triphenylphosphine)palladium (5 mmol), 35.5 g of sodium carbonate (335 mmol), 270 mL of toluene, and 67 mL of ethanol were introduced into a reaction vessel, 67 mL of distilled water was added thereto, and the mixture was then stirred for 3 hours at 120° C. After completion of the reaction, the reaction product was washed with distilled water and extracted with ethyl acetate. The extracted organic layer was then dried with magnesium sulfate. The solvent was removed with a rotary evaporator, and the resulting product was purified by column chromatography to obtain 22.2 g of compound 2-1 (yield: 58%).

Preparation of Compound 2-2

22.2 g of compound 2-1 (78 mmol), 40.2 g of (methoxymethyl)phosphonium chloride (117 mmol), and 355 mL of tetrahydrofuran were introduced into a reaction vessel, and 117 mL of 1 M potassium tert-butoxide was added dropwise thereto at 0° C. The reaction temperature was then slowly raised to room temperature, and the mixture was stirred for an additional 2 hours. After completion of the reaction, the reaction product was extracted with ethyl acetate. The extracted organic layer was then dried with magnesium sulfate. The solvent was removed with a rotary evaporator, and the resulting product was purified by column chromatography to obtain 10.1 g of compound 2-2 (yield: 41%).

Preparation of Compound 2-3

10 g of compound 2-2 (32 mmol) was dissolved in chlorobenzene in a reaction vessel, and 1.7 mL of Eaton's reagent was slowly added dropwise thereto. The mixture was stirred under reflux for an additional 2 hours. After completion of the reaction, the reaction product was washed with distilled water and extracted with ethyl acetate. The extracted organic layer was then dried with magnesium sulfate. The solvent was removed with a rotary evaporator, and the resulting product was purified by column chromatography to obtain 7.4 g of compound 2-3 (yield: 82%).

Preparation of Compound 2-4

7.4 g of compound 2-3 (26 mmol), 0.9 g of s-Phos (2 mmol), 7.8 g of potassium acetate (79 mmol), and 156 mL of 1,4-dioxane were introduced into a reaction vessel, and the mixture was stirred under reflux for 4 hours. After completion of the reaction, the reaction product was washed with distilled water and extracted with ethyl acetate. The extracted organic layer was then dried with magnesium sulfate. The solvent was removed with a rotary evaporator, and the resulting product was purified by column chromatography to obtain 6.1 g of compound 2-4 (yield: 62%).

Preparation of Compound C-249

3 g of compound 2-4 (8 mmol), 2.9 g of 2-(3-bromophenyl)-4,6-diphenyl-1,3,5-triazine (7 mmol), 0.4 g of tetrakis(triphenylphosphine)palladium (0.4 mmol), 2 g of sodium carbonate (18 mmol), 27 mL of toluene, and 9 mL of ethanol were introduced into a reaction vessel, 9 mL of distilled water was added thereto, and the mixture was then stirred for 3 hours at 120° C. After completion of the reaction, the reaction product was washed with distilled water and extracted with ethyl acetate. The extracted organic layer was then dried with magnesium sulfate. The solvent was removed with a rotary evaporator, and the resulting product was purified by column chromatography to obtain 2.9 g of compound C-249 (yield: 71%).

|  | MW | UV | PL | M.P. |
|---|---|---|---|---|
| C-249 | 552.64 | 296 nm | 389 nm | 276° C. |

Example 3: Perparation of compound C-258

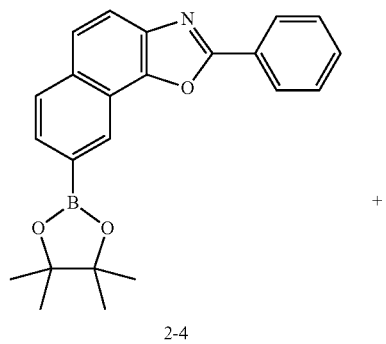

2-4

+

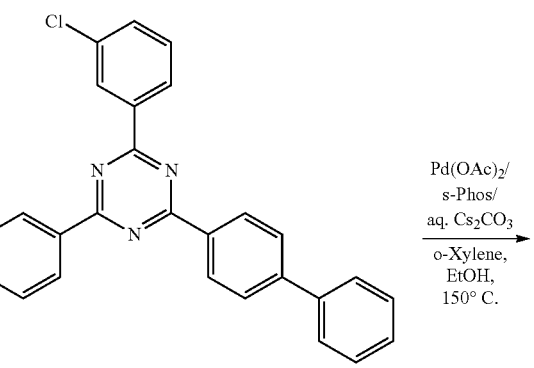

Pd(OAc)$_2$/
s-Phos/
aq. Cs$_2$CO$_3$
o-Xylene,
EtOH,
150° C.

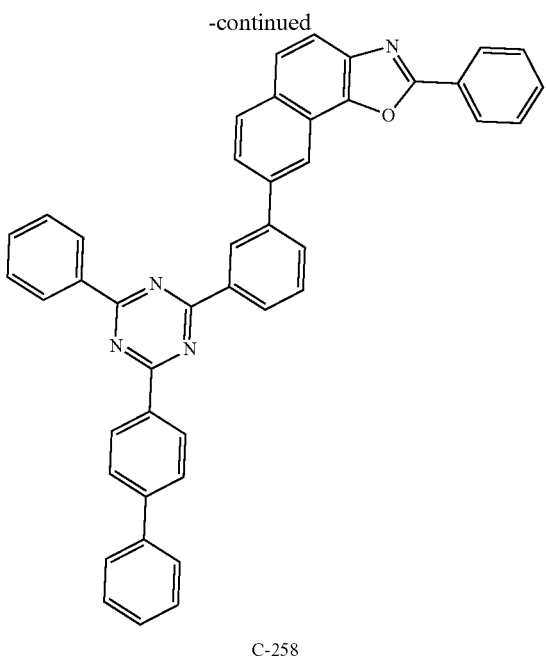

C-258

Preparation of Compound C-258

2.6 g of compound 2-4 (7 mmol), 2.5 g of 2-([1.1'-biphenyl]-4-yl)-4-[3-chlorophenyl]-6-diphenyl-1,3,5-thiazine (6 mmol), 0.13 g of palladium(II) acetate (0.6 mmol), 0.5 g of s-Phos (1 mmol), 5.7 g of cesium carbonate (18 mmol), 30 mL of o-xylene, and 15 mL of ethanol were introduced into a reaction vessel, 15 mL of distilled water was added thereto, and the mixture was then stirred for 3 hours at 150° C. After completion of the reaction, the reaction product was washed with distilled water and extracted with ethyl acetate. The extracted organic layer was then dried with magnesium sulfate. The solvent was removed with a rotary evaporator, and the resulting product was purified by column chromatography to obtain 3 g of compound C-258 (yield: 81%).

|   | MW | UV | PL | M.P. |
| --- | --- | --- | --- | --- |
| C-258 | 628.74 | 324 nm | 391 nm | 331° C. |

Comparative Example 1: Producing a Blue Light-Emitting OLED Device not Comprising an Electron Buffer Layer An OLED device was produced as follows: A transparent electrode indium tin oxide (ITO) thin film (10 Ω/sq) on a glass substrate for an OLED (GEOMATEC CO., LTD., Japan) was subjected to an ultrasonic washing with acetone, ethanol, and distilled water, sequentially, and then was stored in isopropanol. Next, the ITO substrate was mounted on a substrate holder of a vacuum vapor deposition apparatus. $N^4,N^{4'}$-diphenyl-$N^4,N^{4'}$-bis(9-phenyl-9H-carbazol-3-yl)-[1,1'-biphenyl]-4,4'-diamine (Compound HI-1) was introduced into a cell of the vacuum vapor deposition apparatus, and the pressure in the chamber of the apparatus was then controlled to $10^{-7}$ torr. Thereafter, an electric current was applied to the cell to evaporate the introduced material, thereby forming a first hole injection layer having a thickness of 60 nm on the ITO substrate. 1,4,5,8,9,12-hexaazatriphenylen-hexacarbonitrile (HAT-CN) (Compound HI-2) was then introduced into another cell of the vacuum vapor deposition apparatus, and an electric current was applied to the cell to evaporate the introduced material, thereby forming a second hole injection layer having a thickness of 5 nm on the first hole injection layer. N-([1,1'-biphenyl]-4-yl)-9,9-dimethyl-N-(4-(9-phenyl-9H-carbazol-3-yl)phenyl)-9H-fluorene-2-amine (Compound HT-1) was introduced into another cell of the vacuum vapor deposition apparatus. Thereafter, an electric current was applied to the cell to evaporate the introduced material, thereby forming a first hole transport layer having a thickness of 20 nm on the second hole injection layer. 9-(naphthalen-2-yl)-3-(4-(9-phenyl-9H-carbazol-3-yl)phenyl)-9H-carbazole (Compound HT-2) was then introduced into another cell of the vacuum vapor deposition apparatus, and an electric current was applied to the cell to evaporate the introduced material, thereby forming a second hole transport layer having a thickness of 5 nm on the first hole transport layer. After forming the hole injection layers and the hole transport layers, a light-emitting layer was then deposited as follows. Compound H-1 as a host was introduced into one cell of the vacuum vapor deposition apparatus and compound F-2 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, 2-(3-phenanthren-9-yl)-5-(pyridin-3-yl)phenyl)-4,6-diphenyl-1,3,5-triazine (compound ETL-1) as an electron transport material was introduced into one cell of the vacuum vapor deposition apparatus, and lithium quinolate (compound EIL-1) was introduced into another cell of the vacuum vapor deposition apparatus. The two materials were evaporated at the same rate and doped in a doping amount of 50 wt %, respectively, to form an electron transport layer having a thickness of 35 nm on the light-emitting layer. After depositing lithium quinolate as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at $10^{-6}$ torr.

The driving voltage, luminous efficiency, and CIE color coordinates at a luminance of 1,000 nits of the produced OLED device are provided in Table 1 below.

Comparative Example 2 and Device Examples 1-1 and 1-2: Producing a Blue Light-Emitting OLED Device Comprising an Electron Buffer Layer OLED devices were produced in the same manner as in Comparative Example 1, except that the thickness of the electron transport layer was reduced to 30 nm, and an electron buffer layer having a thickness of 5 nm was inserted between the light-emitting layer and the electron transport layer. The driving voltage, luminous efficiency, the CIE color coordinates at a luminance of 1,000 nits of the OLED devices produced in Comparative Example 2, and Device Examples 1-1 and 1-2 are provided in Table 1 below.

TABLE 1

|  | Electron Buffer Material | Voltage (V) | Luminous Efficiency (cd/A) | Color Coordinate (x) | Color Coordinate (y) |
| --- | --- | --- | --- | --- | --- |
| Comparative Example 1 | — | 4.2 | 5.9 | 139 | 87 |
| Comparative Example 2 | Compound 1 | 4.3 | 5.8 | 139 | 88 |
| Device Example 1-1 | C-35 | 4.1 | 6.5 | 139 | 87 |
| Device Example 1-2 | C-249 | 4.1 | 6.5 | 139 | 88 |

From Table 1 above, it can be seen that the OLED device comprising the organic electroluminescent compound of the present disclosure, wherein a heteroaryl is bonded to a carbon position of a benzene ring, which is not directly fused with an oxazole in a naphthoxazole structure, via an arylene as a linker, as an electron buffer material provides lower driving voltage and higher luminous efficiency, compared to the OLED device comprising a conventional compound, which is different from the compound of the present disclosure only in the position of the substituents, i.e., wherein a heteroaryl is bonded to a carbon position of a benzene ring, which is directly fused with an oxazole in a naphthoxazole structure, via an arylene as a linker.

Comparative Examples 3 and 4 and Device Example 2: Producing a Blue Light-Emitting OLED Device Comprising the Compound of the Present Disclosure as an Electron Transport Material OLED devices were produced in the same manner as in Comparative Example 1, except that the material of the electron transport layer was changed. The driving voltage, luminous efficiency, and CIE color coordinates at a luminance of 1,000 nits of the OLED devices produced in Comparative Examples 3 and 4, and Device Example 2 are provided in Table 2 below.

TABLE 2

|  | Electron Transport Material | Voltage (V) | Luminous Efficiency (cd/A) | Color Coordinate (x) | Color Coordinate (y) |
| --- | --- | --- | --- | --- | --- |
| Comparative Example 3 | ETL-2 | 4.3 | 5.5 | 141 | 92 |
| Comparative Example 4 | Compound 1 | 3.9 | 6.1 | 140 | 90 |
| Device Example 2 | C-35 | 4.1 | 6.5 | 140 | 88 |

From Table 2 above, it can be seen that the OLED device comprising the organic electroluminescent compound of the present disclosure, wherein a heteroaryl is bonded to a carbon position of a benzene ring, which is not directly fused with an oxazole in a naphthoxazole structure, via an arylene as a linker, as an electron transport material provides superior effects in the aspects of luminous efficiency and color coordinates, compared to the OLED device comprising a conventional compound, which is different from the compound of the present disclosure only in the position of the substituents, i.e., wherein a heteroaryl is bonded to a carbon position of a benzene ring, which is directly fused with an oxazole in a naphthoxazole structure, via an arylene as a linker.

The compounds used in the Device Examples and the Comparative Examples are provided in Table 3 below.

TABLE 3

Hole Injection Layer/
Hole Transport Layer

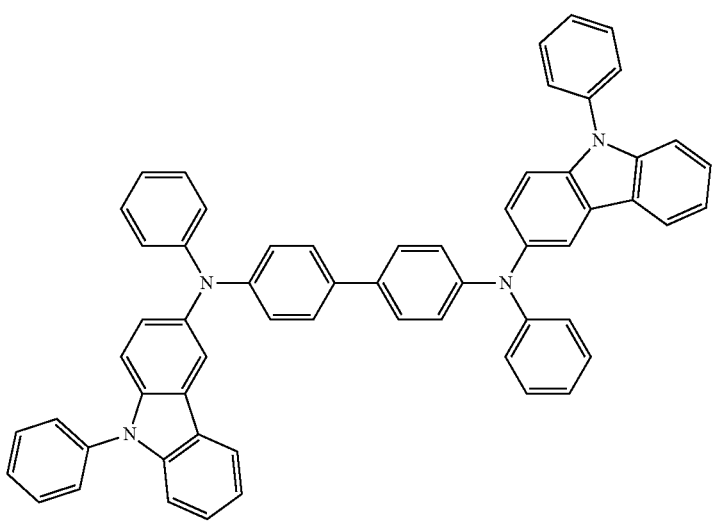

HI-1

TABLE 3-continued
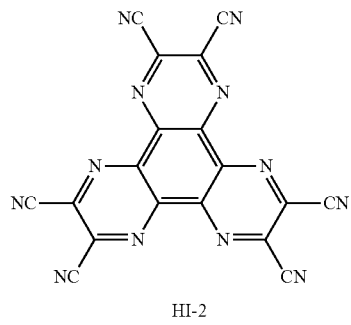
HI-2
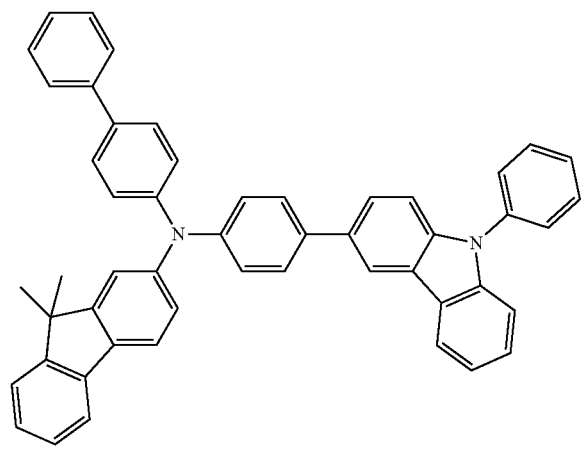
HT-1
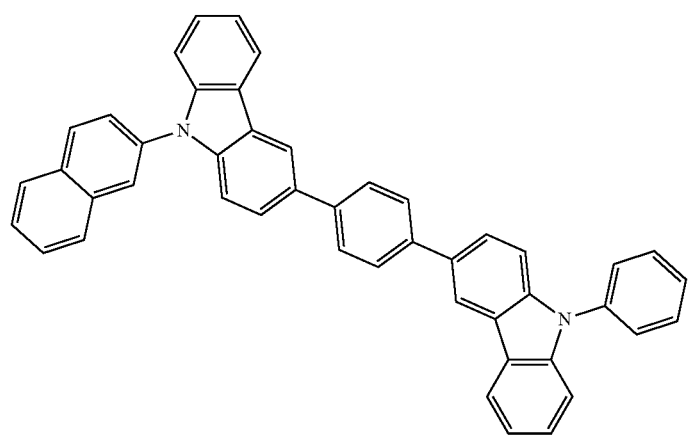
HT-2

TABLE 3-continued
Light-Emitting Layer
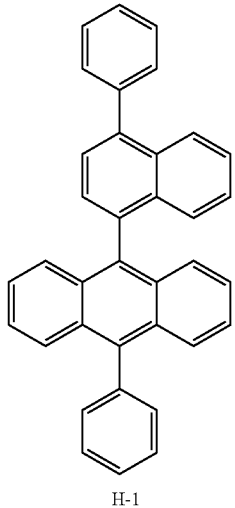
H-1
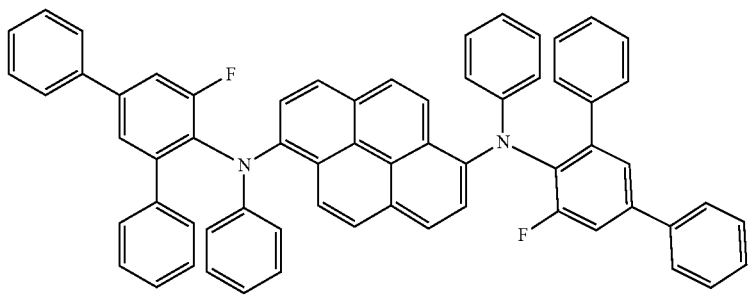
F-2
Electron Transport Layer/ Electron Buffer Layer
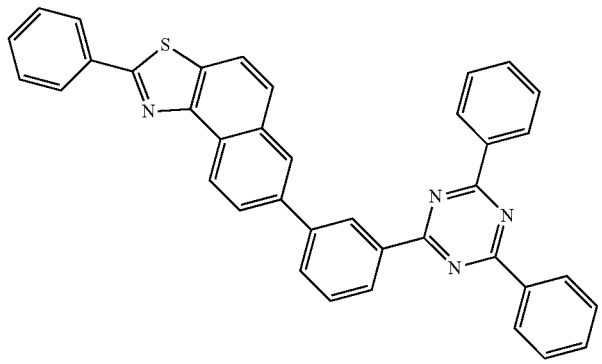
C-35
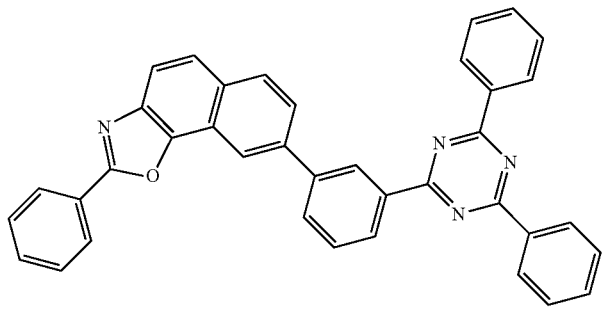
C-249

TABLE 3-continued
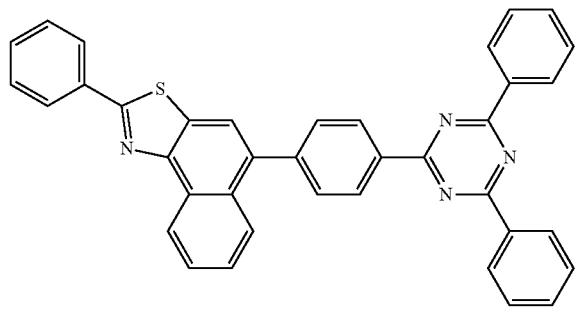
Compound 1
Electron Transport Layer/ Electron Injection Layer
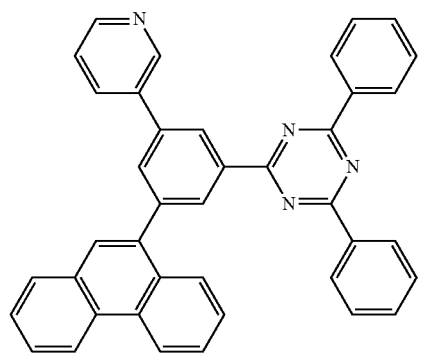
ETL-1
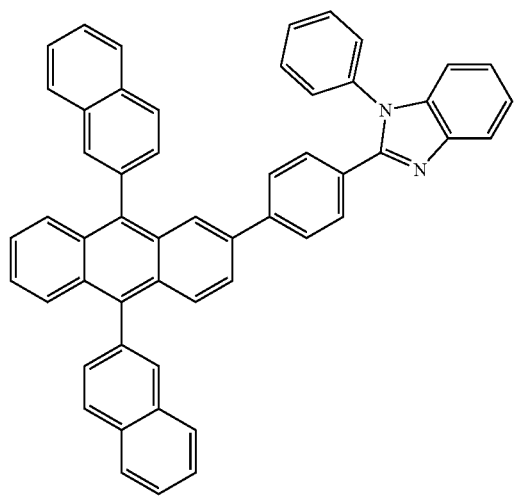
ETL-2
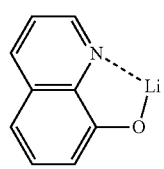
EIL-1

The invention claimed is:

1. An organic electroluminescent compound represented by the following formula 2:

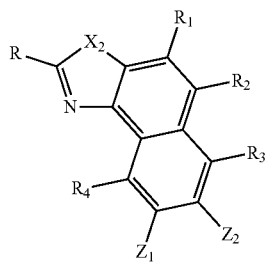

(2)

wherein
$X_2$ represents O, or S;
$Z_1$ and $Z_2$ each independently represent hydrogen, deuterium, or $-L_1$-Het, with the proviso that, at least one of $Z_1$ and $Z_2$ represents $-L_1$-Het;
R represents a substituted or unsubstituted (C6-C30)aryl, or a substituted or unsubstituted 3- to 30-membered heteroaryl containing at least one heteroatom selected from N, O and S;
$R_1$ to $R_4$ each independently represent hydrogen, deuterium, a substituted or unsubstituted (C1-C10)alkyl, a substituted or unsubstituted (C6-C30)aryl, or a substituted or unsubstituted 3- to 30-membered heteroaryl containing at least one heteroatom selected from N, O and S;
$L_1$ represents a direct bond, a substituted or unsubstituted (C6-C30)arylene, or a substituted or unsubstituted 3- to 30-membered heteroarylene containing at least one heteroatom selected from N, O and S;
Het represents a substituted or unsubstituted 3- to 30-membered heteroaryl containing at least one heteroatom selected from N, O and S.

2. The organic electroluminescent compound according to claim 1, wherein formula 2 is represented by any one of the following formulae 4 and 5:

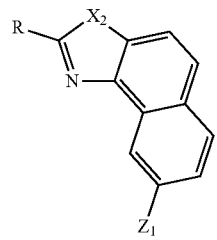

(4)

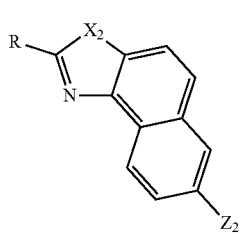

(5)

wherein $X_2$, $Z_1$, $Z_2$, and R are as defined in claim 1.

3. The organic electroluminescent compound according to claim 1, wherein substituents of the substituted alkyl, the substituted aryl(ene), and the substituted heteroaryl(ene) in R, $R_1$ to $R_4$, $L_1$, and Het each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a 3- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

4. The organic electroluminescent compound according to claim 1, wherein
$X_2$ represents O or S;
$Z_1$ and $Z_2$ each independently represent hydrogen or $-L_1$-Het, with the proviso that at least one of $Z_1$ and $Z_2$ represents $-L_1$-Het;
R represents a substituted or unsubstituted (C6-C18)aryl, or a substituted or unsubstituted 5- to 18-membered heteroaryl containing at least one heteroatom selected from N, O and S;
$R_1$ to $R_4$ each independently represent hydrogen;
$L_1$ represents a direct bond, a substituted or unsubstituted (C6-C18)arylene, or a substituted or unsubstituted 5- to 18-membered heteroarylene containing at least one heteroatom selected from N, O and S; and
Het represents a substituted or unsubstituted 5- to 18-membered heteroaryl containing at least one heteroatom selected from N, O and S.

5. The organic electroluminescent compound according to claim 1, wherein
$X_2$ represents O, or S;
$Z_1$ and $Z_2$ each independently represent hydrogen or $-L_1$-Het, with the proviso that at least one of $Z_1$ and $Z_2$ represents $-L_1$-Het;
R represents an unsubstituted (C6-C18)aryl, or an unsubstituted 5- to 18-membered heteroaryl containing at least one heteroatom selected from N, O and S;
$R_1$ to $R_4$ each independently represent hydrogen;
$L_1$ represents a direct bond, a (C6-C18)arylene unsubstituted or substituted with a (C1-C6)alkyl, or an unsubstituted 5- to 18-membered heteroarylene containing at least one heteroatom selected from N, O and S; and
Het represents a 5- to 18-membered heteroaryl unsubstituted or substituted with a (C6-C12)aryl, containing at least one heteroatom selected from N, O and S.

6. The organic electroluminescent compound according to claim 1, wherein Het represents a substituted or unsubstituted pyridine, a substituted or unsubstituted pyrimidine, a substituted or unsubstituted triazine, a substituted or unsubstituted quinoline, a substituted or unsubstituted isoquinoline, a substituted or unsubstituted quinazoline, a substituted or unsubstituted quinoxaline, a substituted or unsubstituted triazole, a substituted or unsubstituted pyrazole, a substituted or unsubstituted benzofuran, a substituted or unsubstituted dibenzofuran, a substituted or unsubstituted benzothiophene, or a substituted or unsubstituted dibenzothiophene.

7. The organic electroluminescent compound according to claim 1, wherein the compound represented by formula 1 is selected from the group consisting of:
C-1
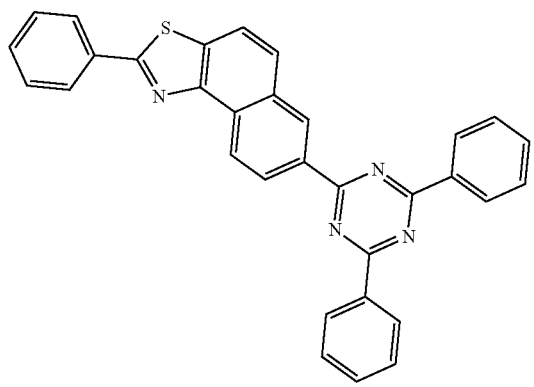
C-2
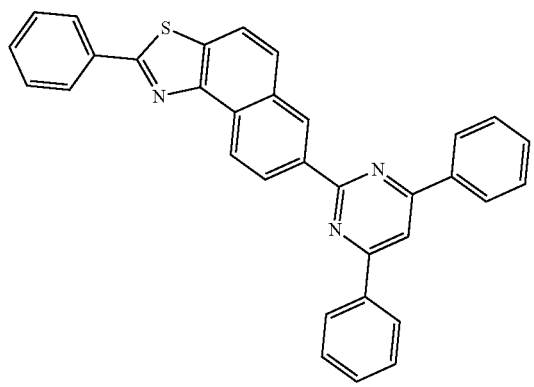
C-3
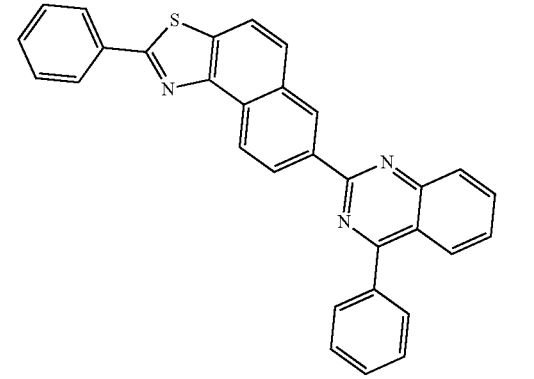
C-4
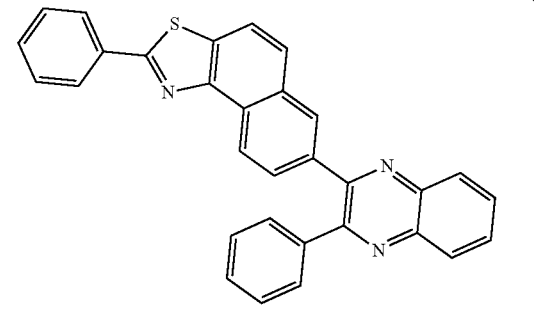
C-5
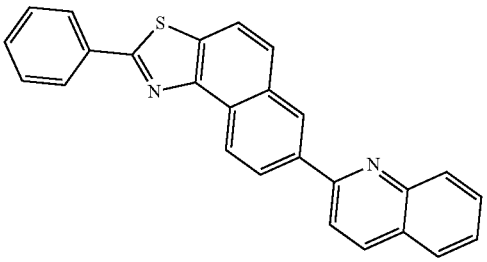
C-6
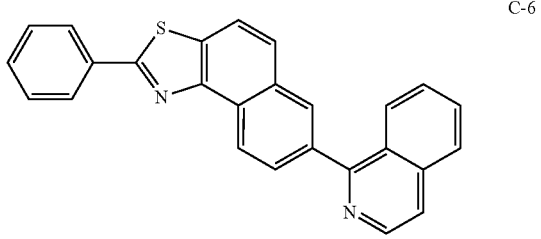
C-7
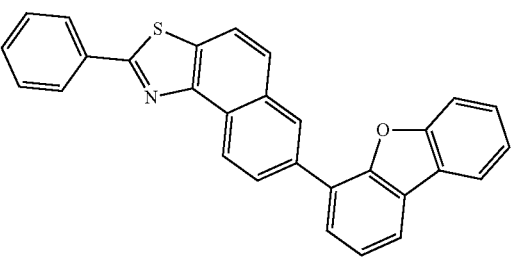
C-8
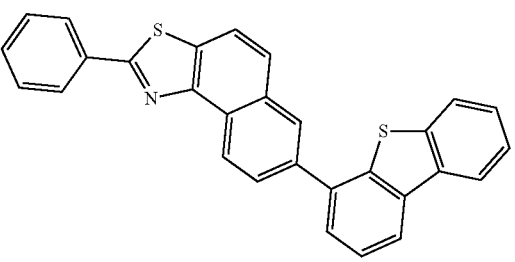
C-9
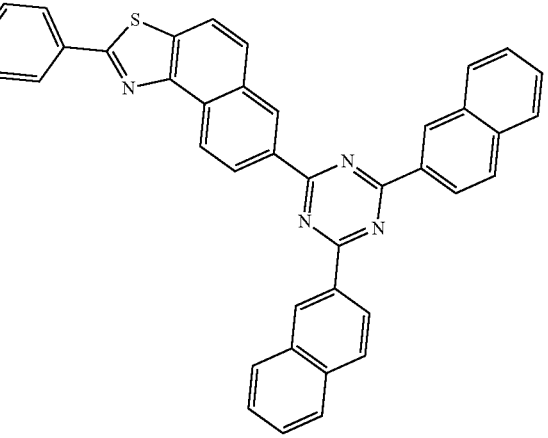

-continued
C-10
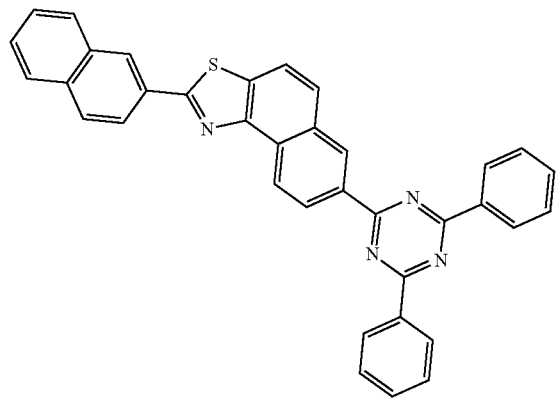
C-11
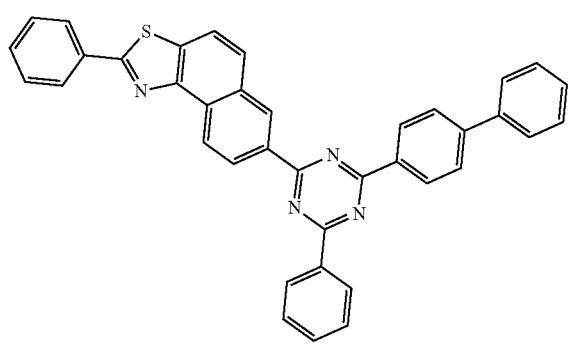
C-12
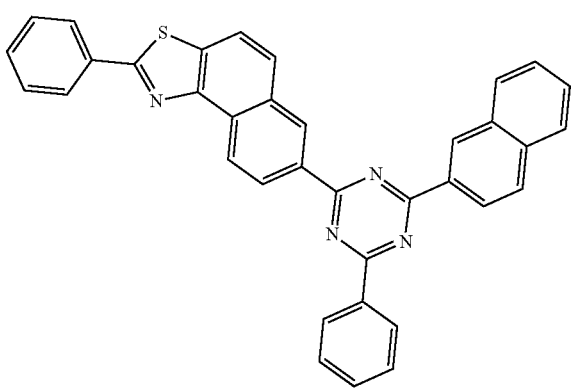
C-13
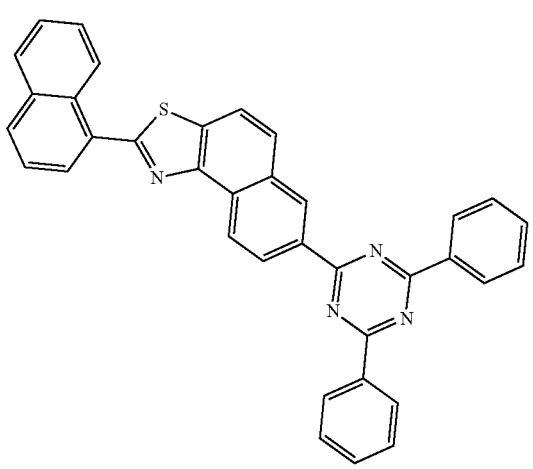
-continued
C-14
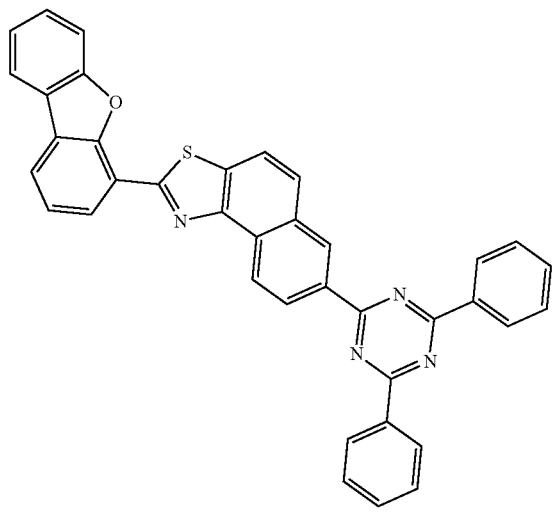
C-15
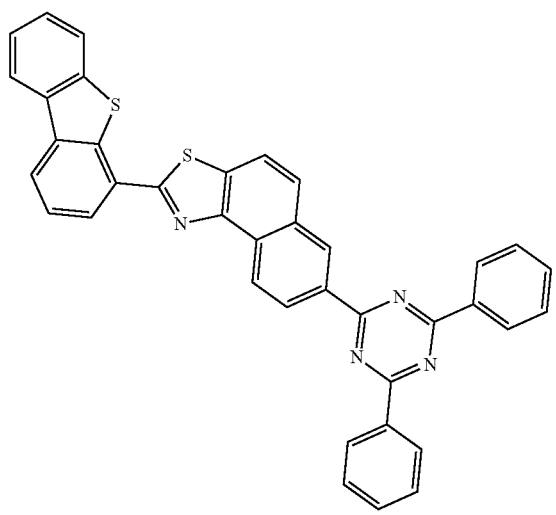
C-16
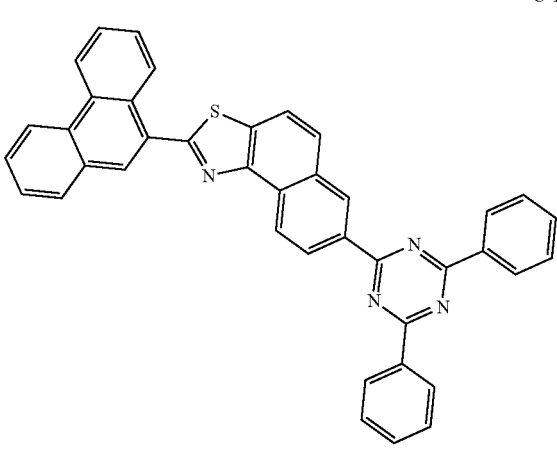

C-17
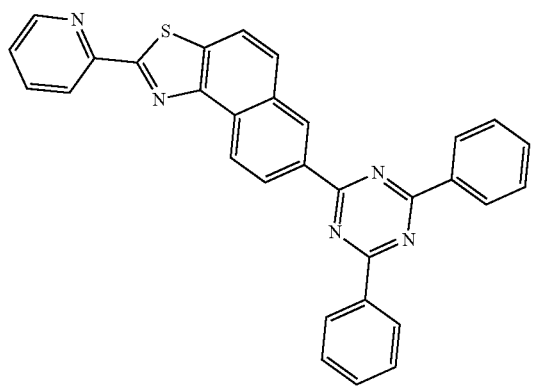
C-18
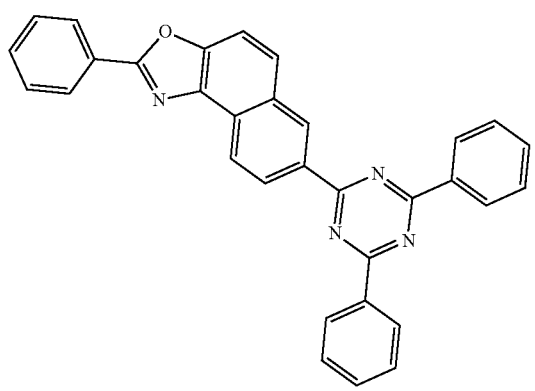
C-19
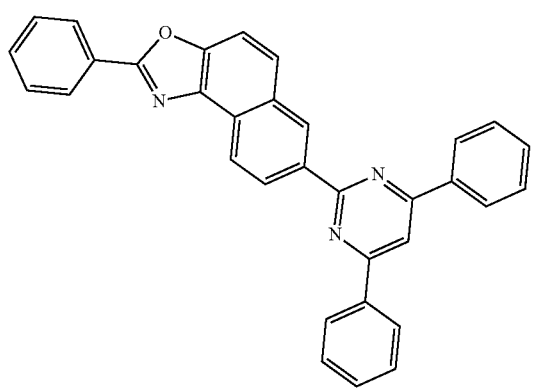
C-20
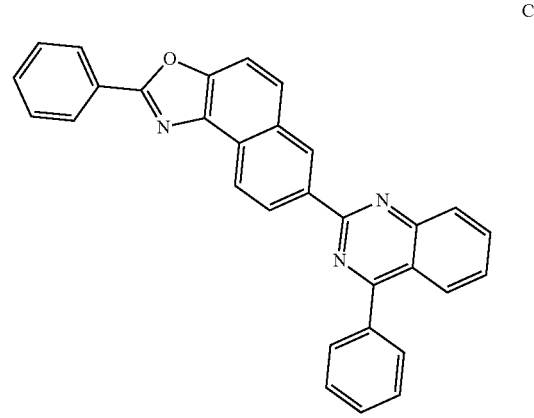
C-21
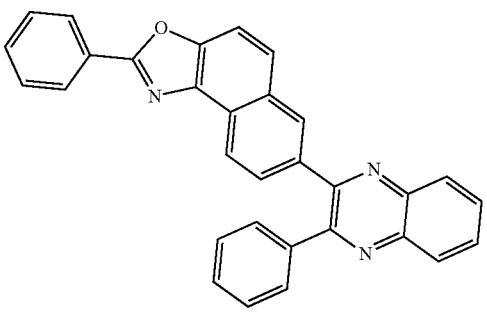
C-22
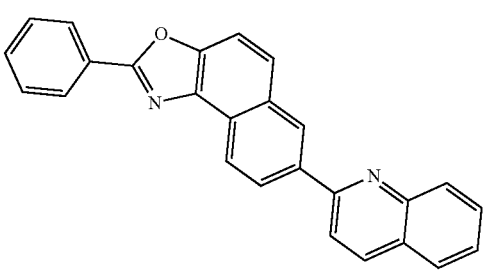
C-23
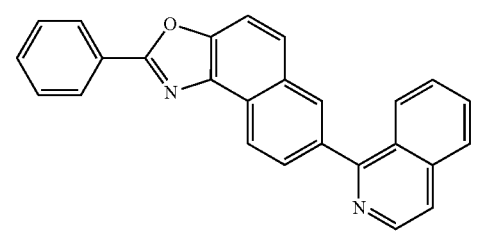
C-24
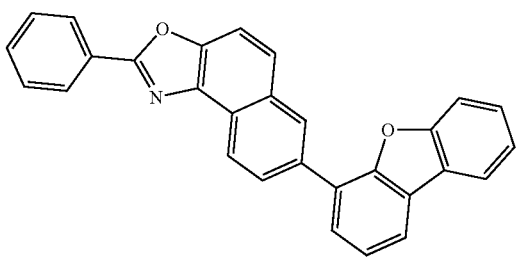
C-25
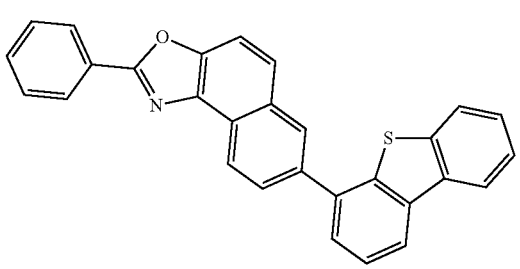

C-26
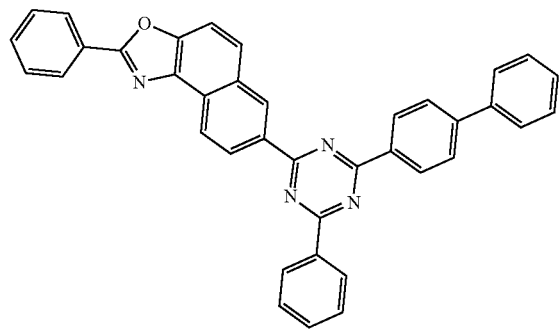
C-27
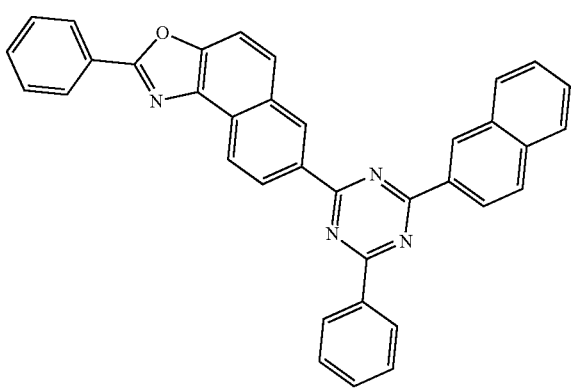
C-28
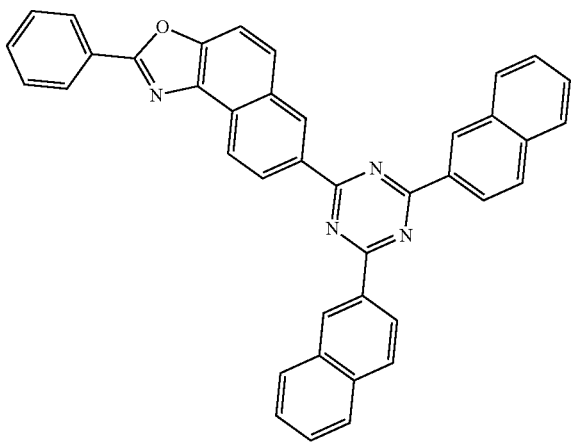
C-29
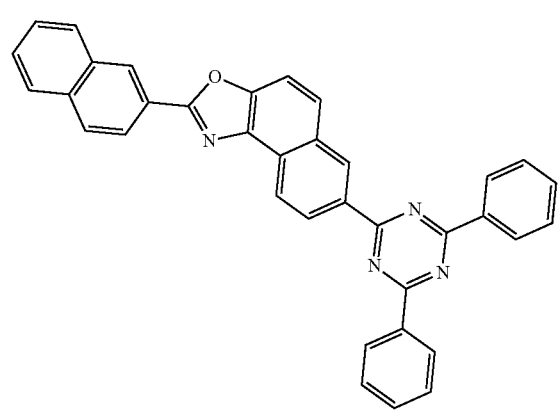
C-30
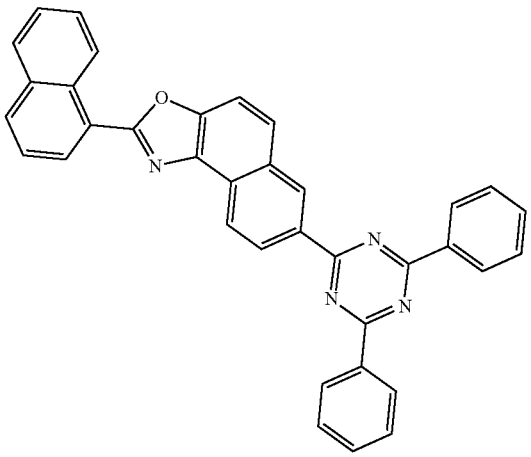
C-31
C-32

233
-continued
C-33
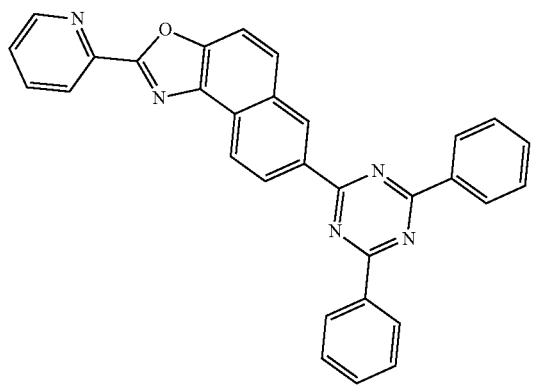
C-34
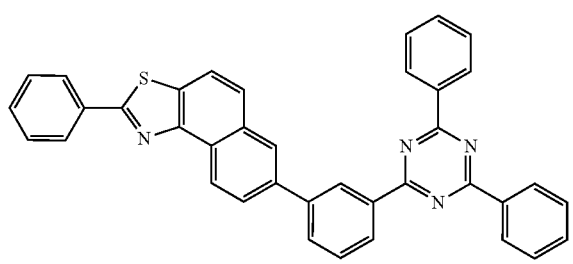
C-35
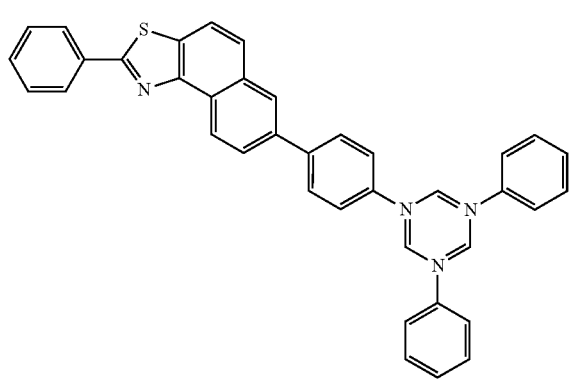
C-36
234
-continued
C-37
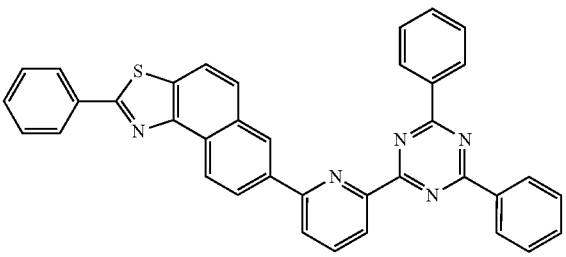
C-38
C-39
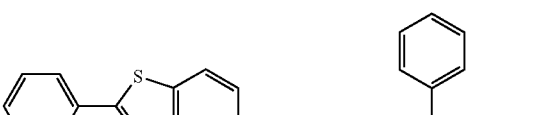
C-40
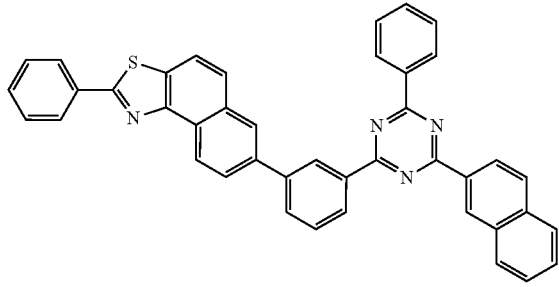

-continued
C-41
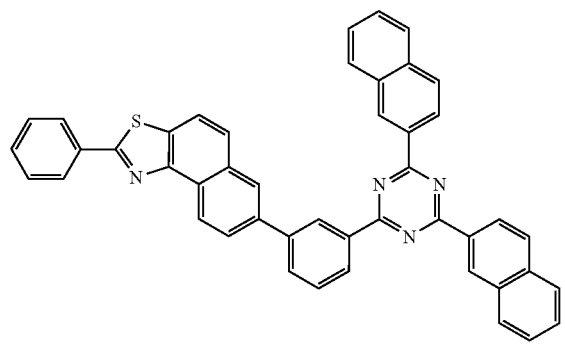
C-42
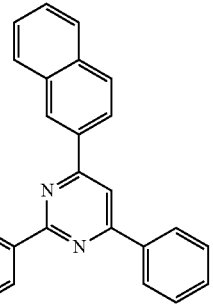
C-43
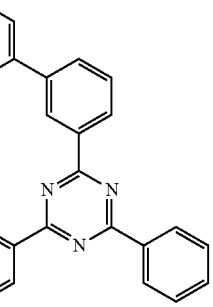
C-44
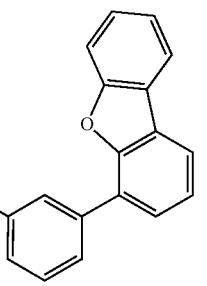
-continued
C-45
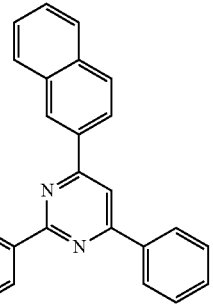
C-46
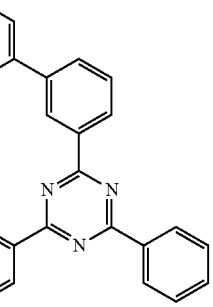
C-47
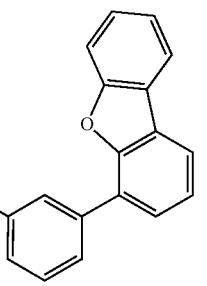
C-48
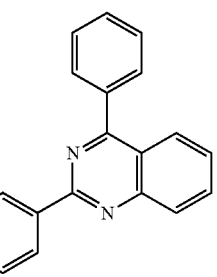
C-49
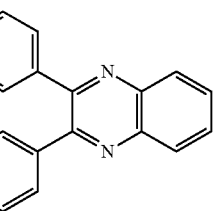

-continued
C-50
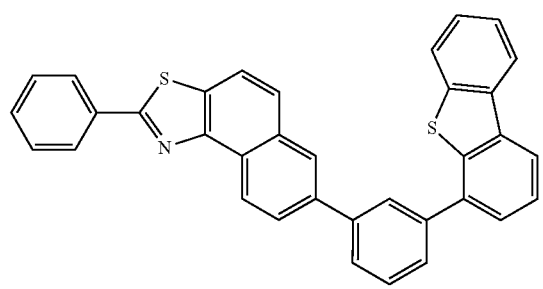
C-51
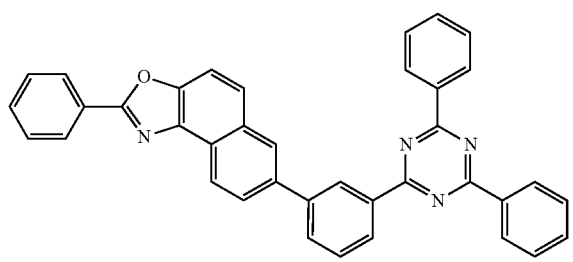
C-52
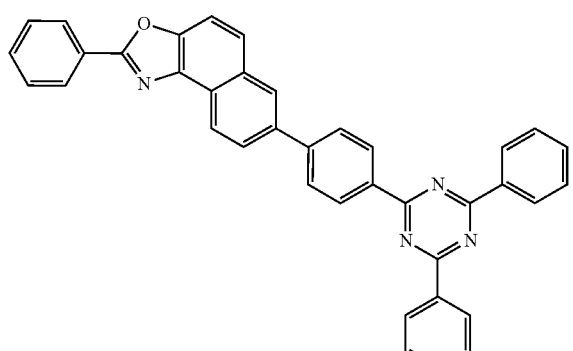
C-53
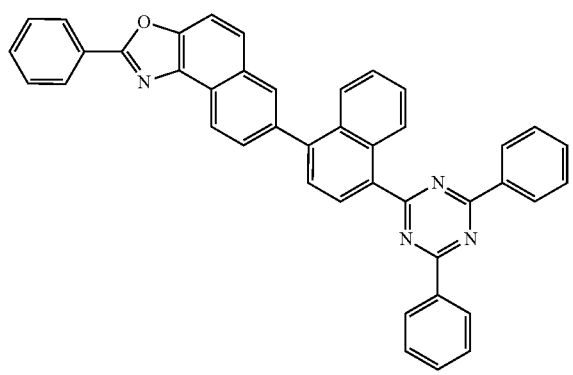
C-54
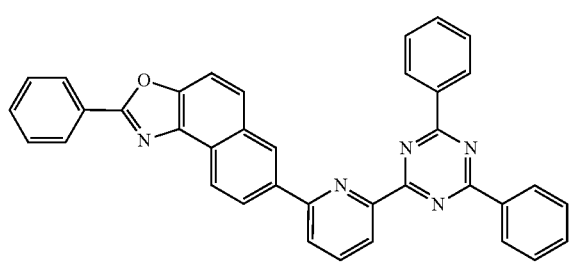
-continued
C-55
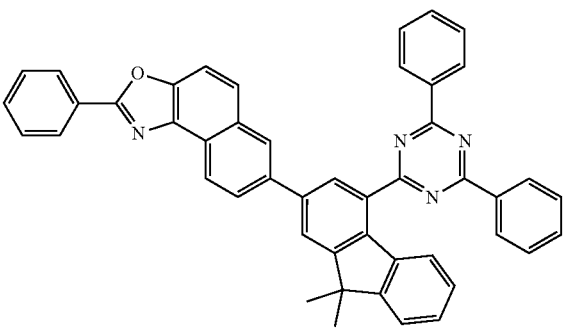
C-56
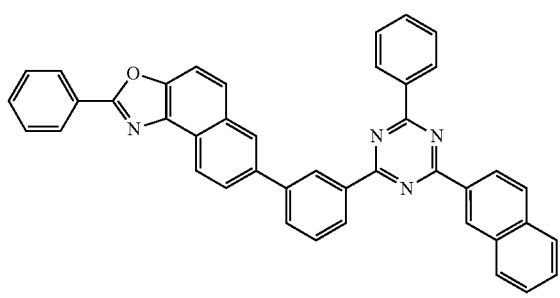
C-57
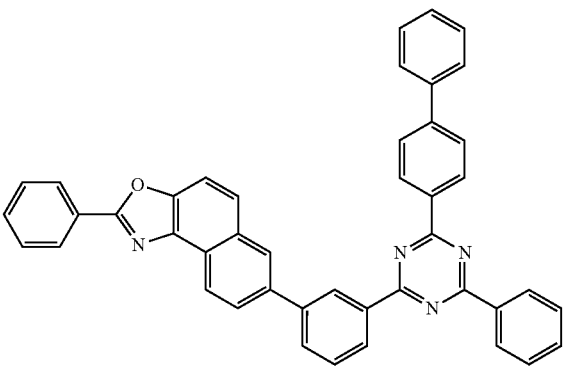
C-58
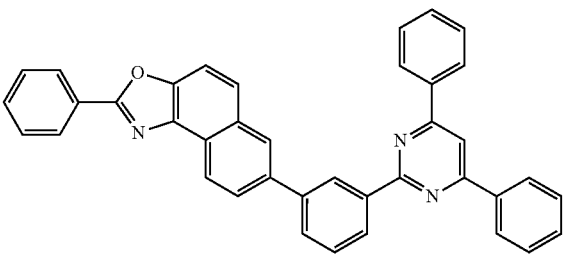

-continued
C-59
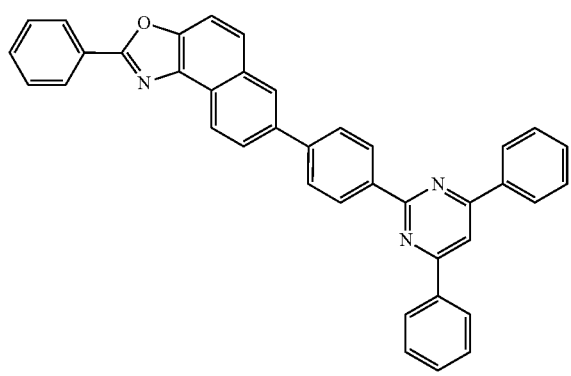
C-60
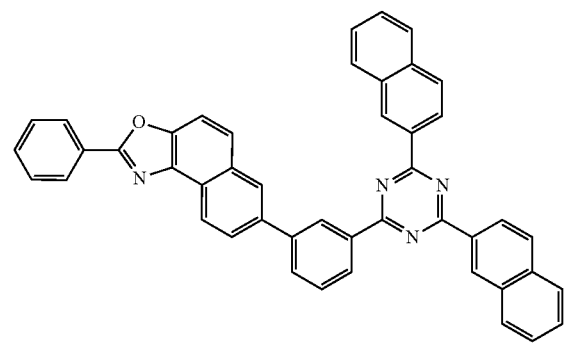
C-61
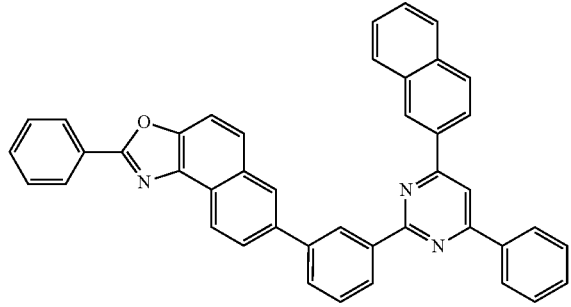
C-62
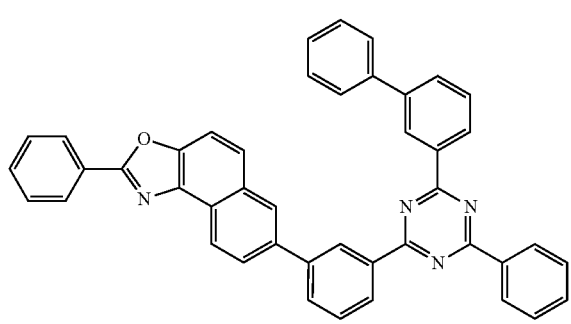
-continued
C-63
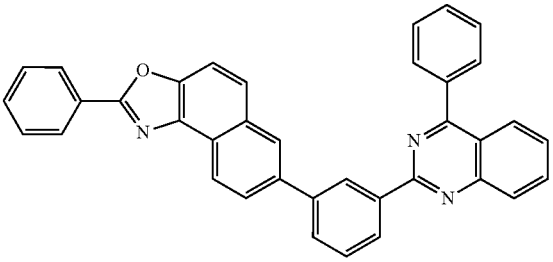
C-64
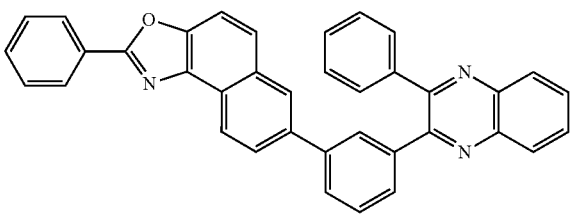
C-65
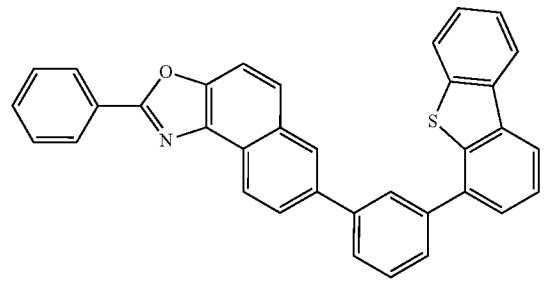
C-66
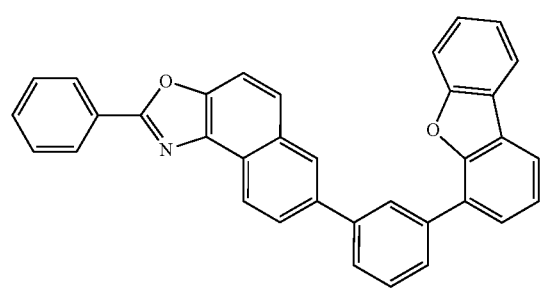
C-133

C-134
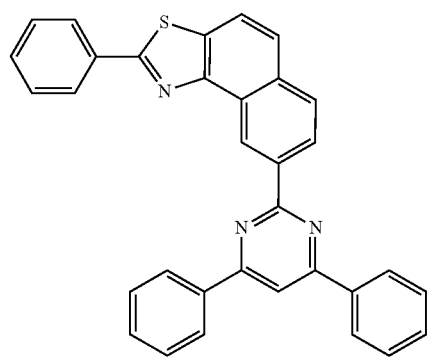
C-135
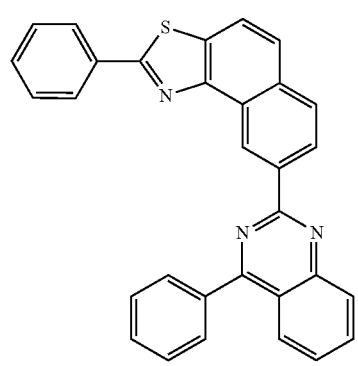
C-136
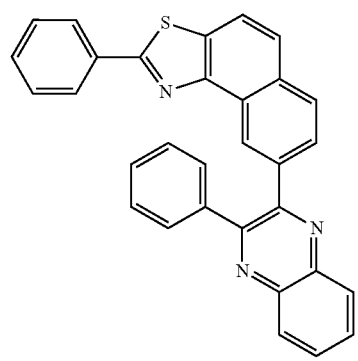
C-137
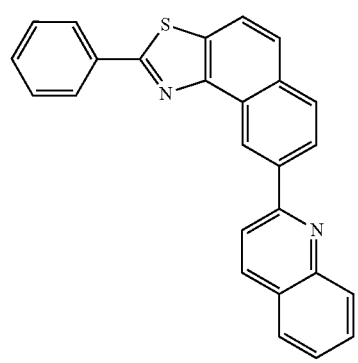
C-138
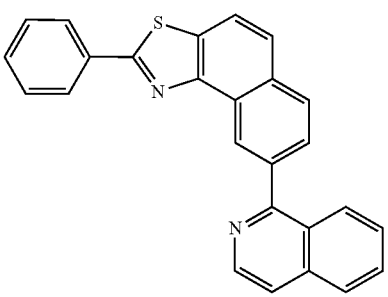
C-139
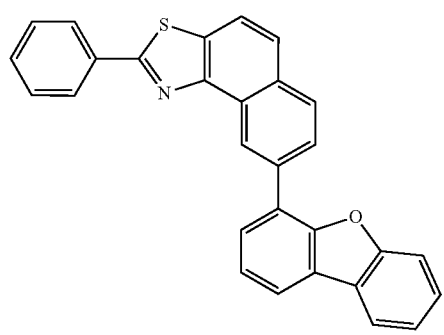
C-140
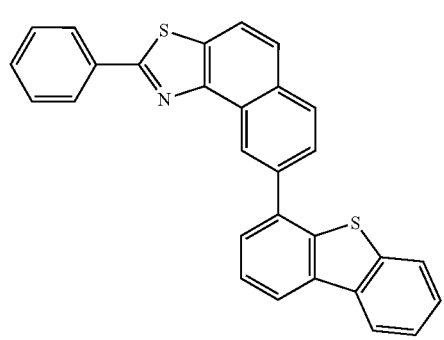
C-141
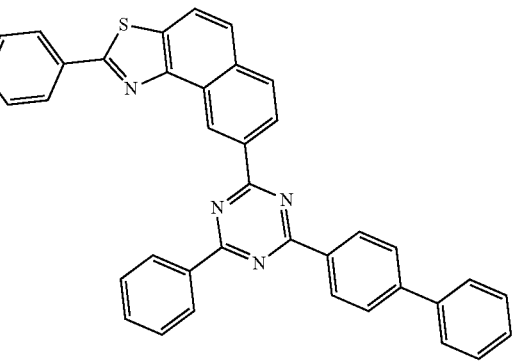

C-142
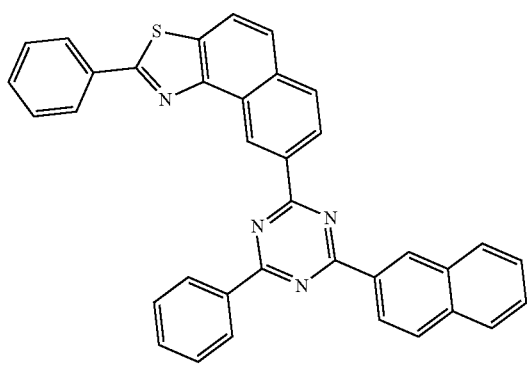
C-143
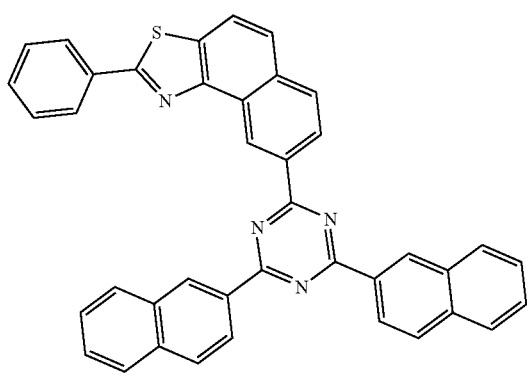
C-144
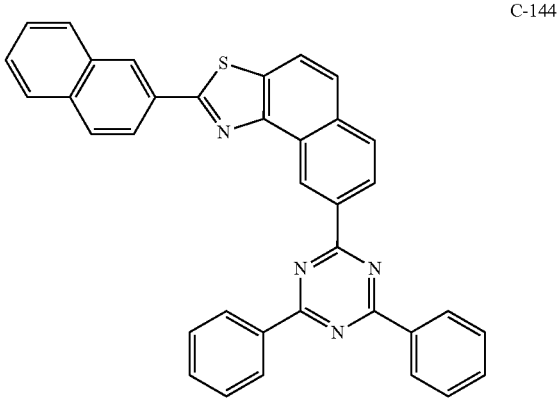
C-145
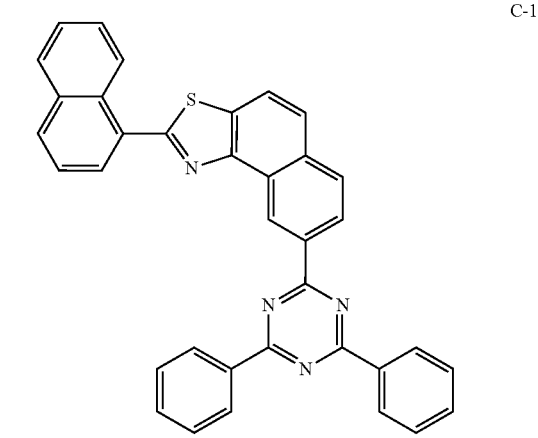
C-146
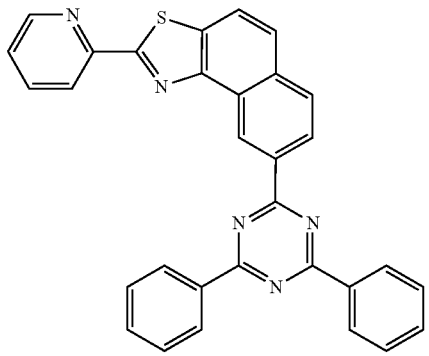
C-147
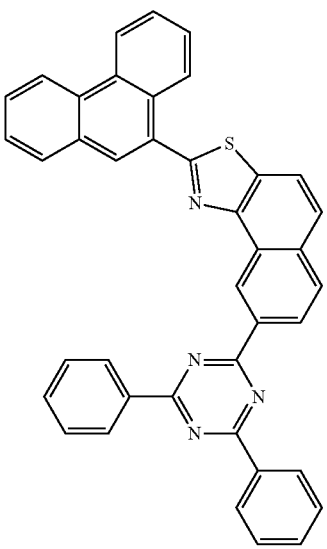
C-148
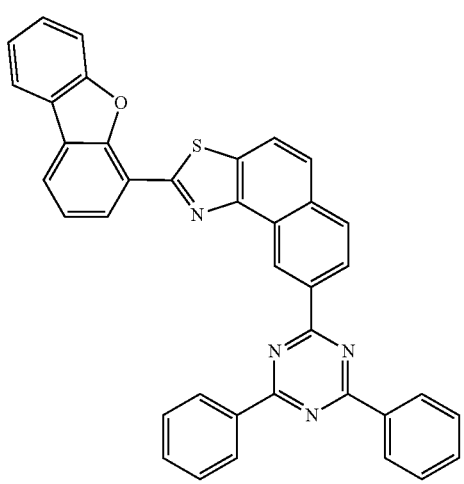

C-149
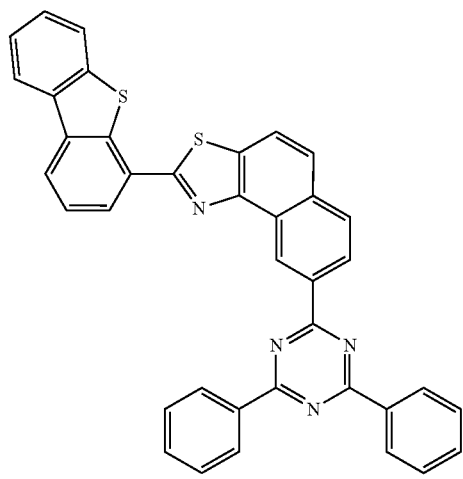
C-150
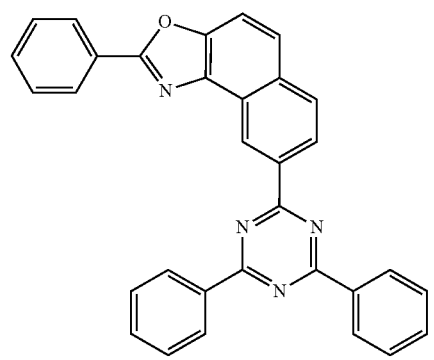
C-151
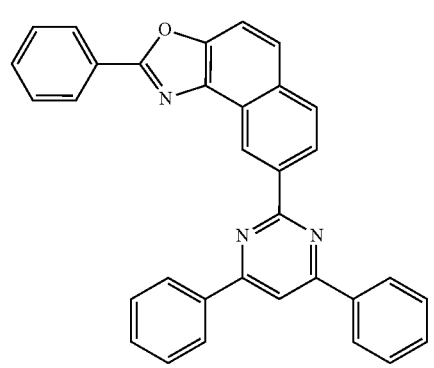
C-152
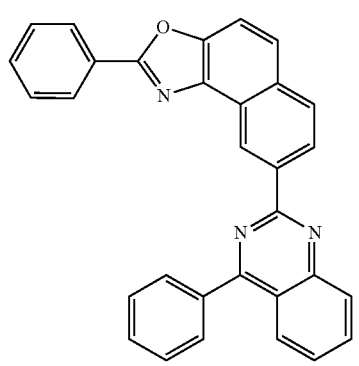
C-153
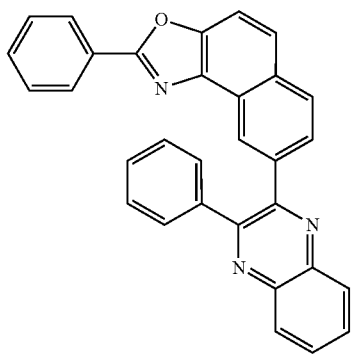
C-154
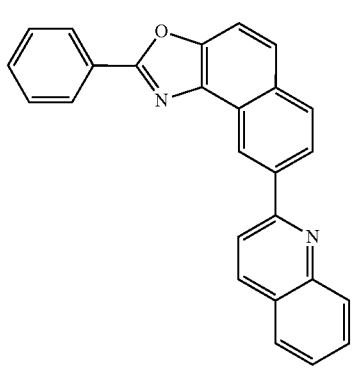
C-155
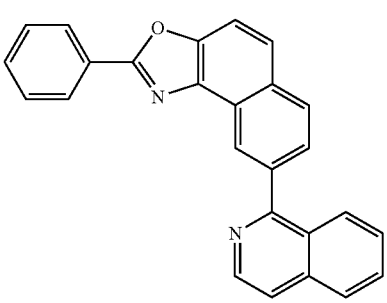
C-156
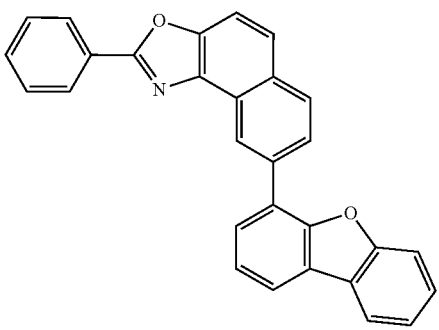

C-157
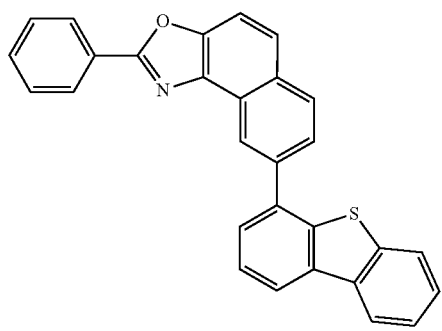
C-158
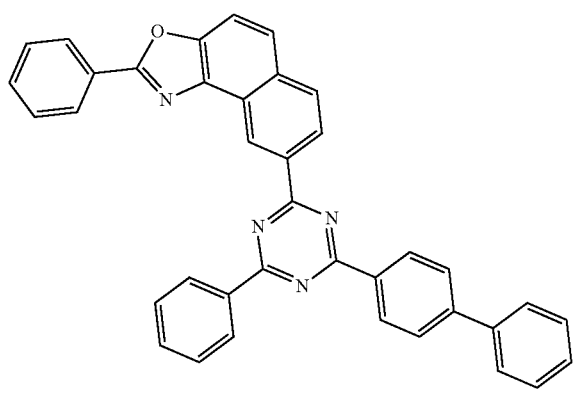
C-159
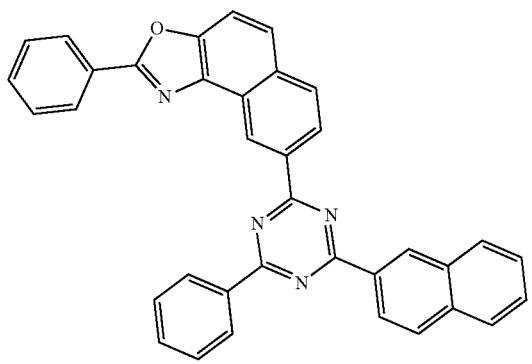
C-160
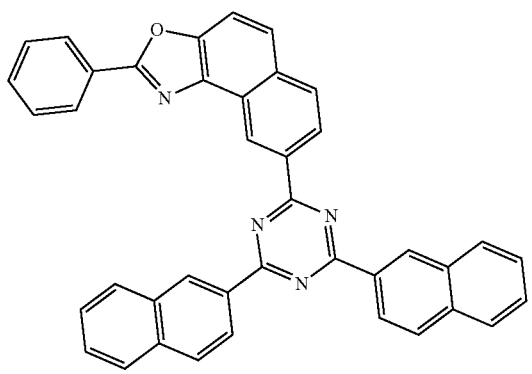
C-161
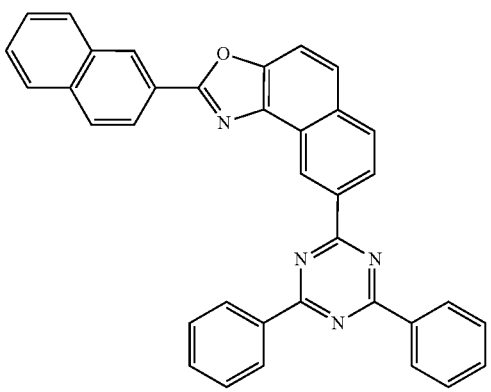
C-162
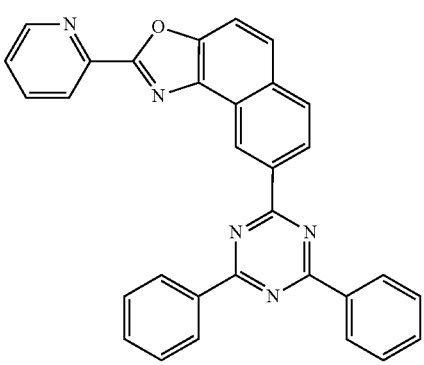
C-163
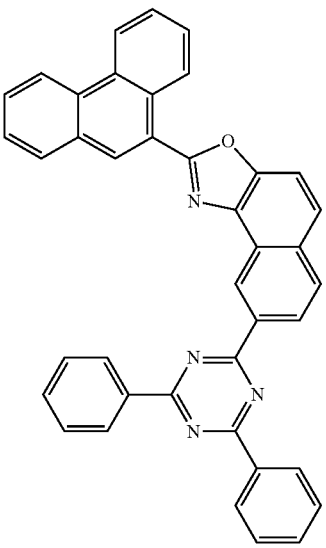

C-164
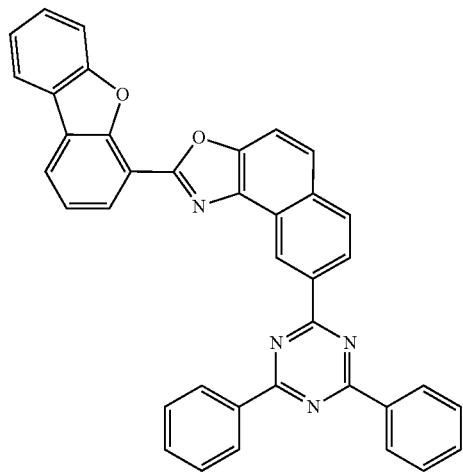
C-165
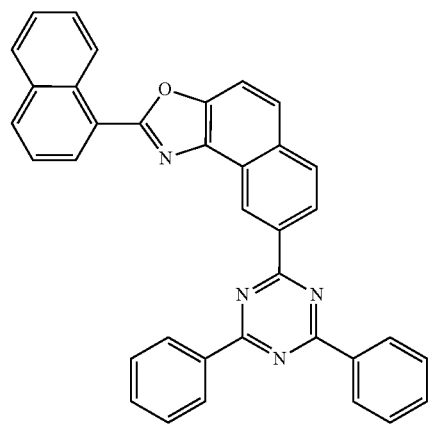
C-166
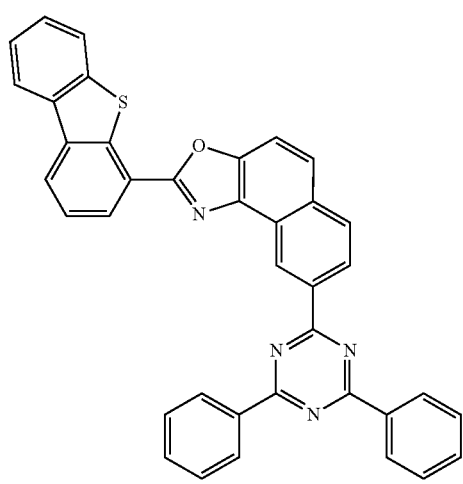
C-167
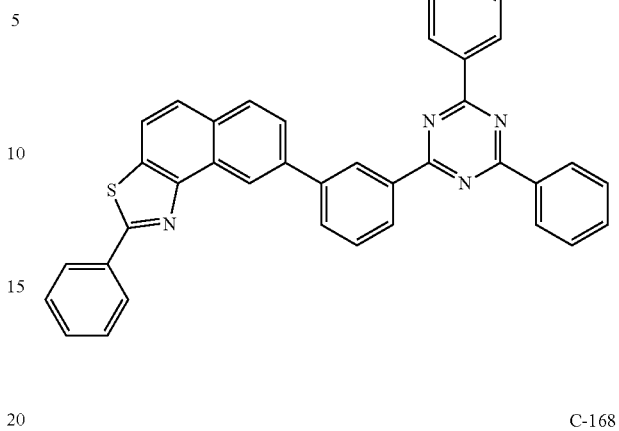
C-168
C-169
C-170
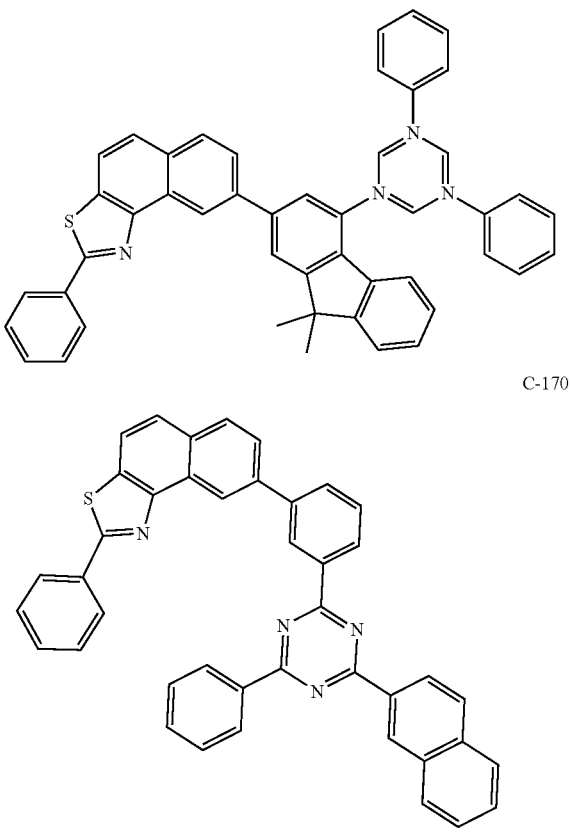

C-171
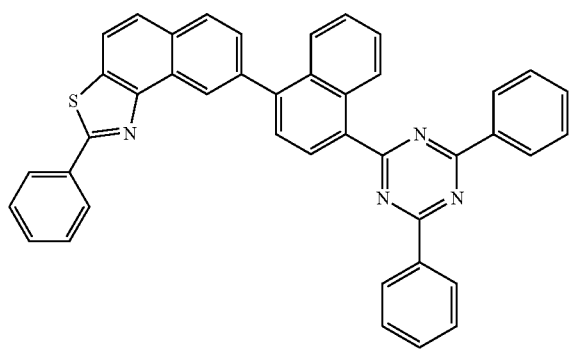
C-172
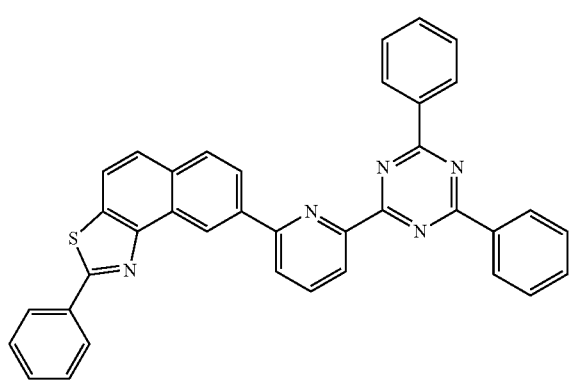
C-173
C-174
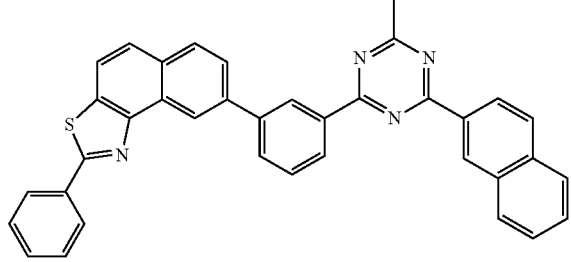
C-175
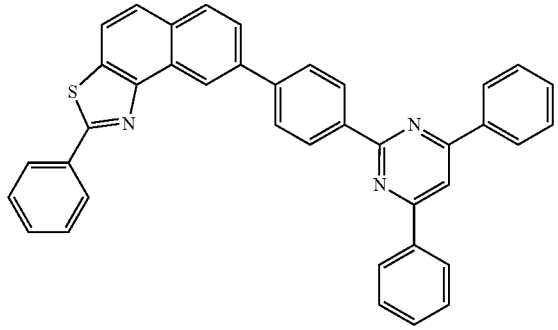
C-176
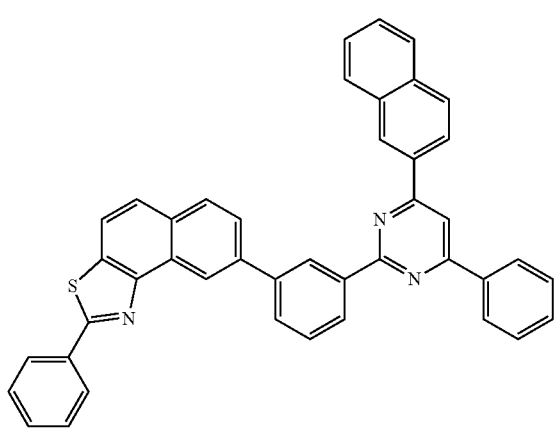
C-177
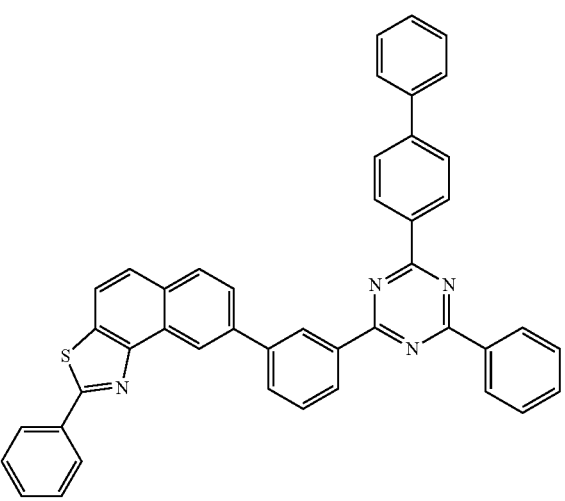

-continued
C-178
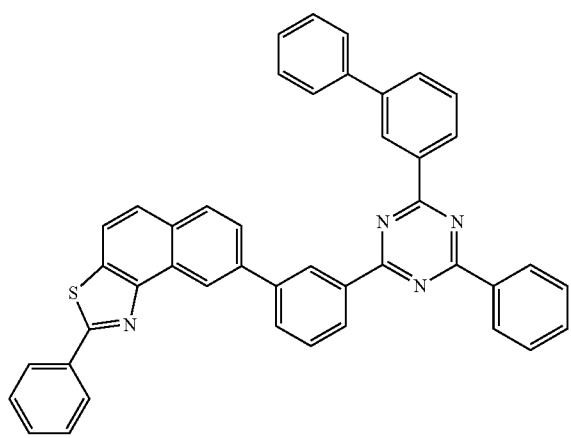
C-182
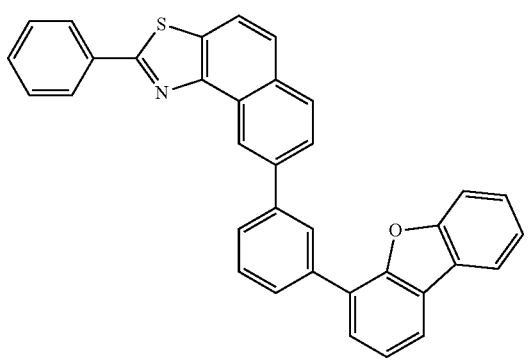
C-179
C-183
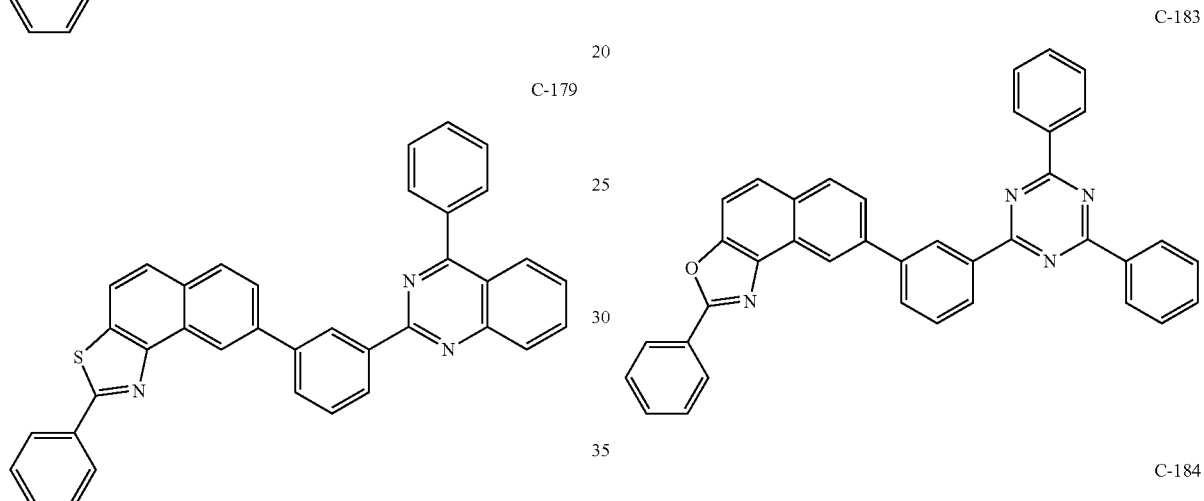
C-180
C-184
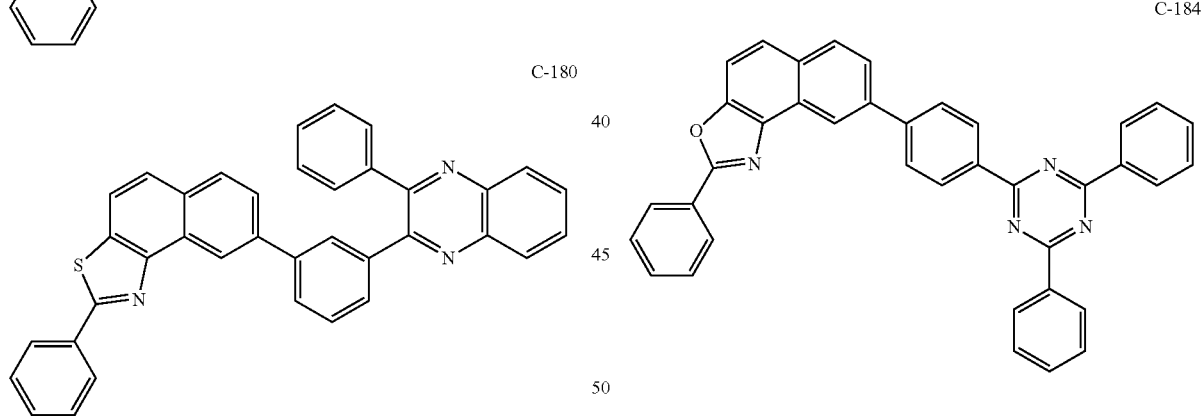
C-181
C-185
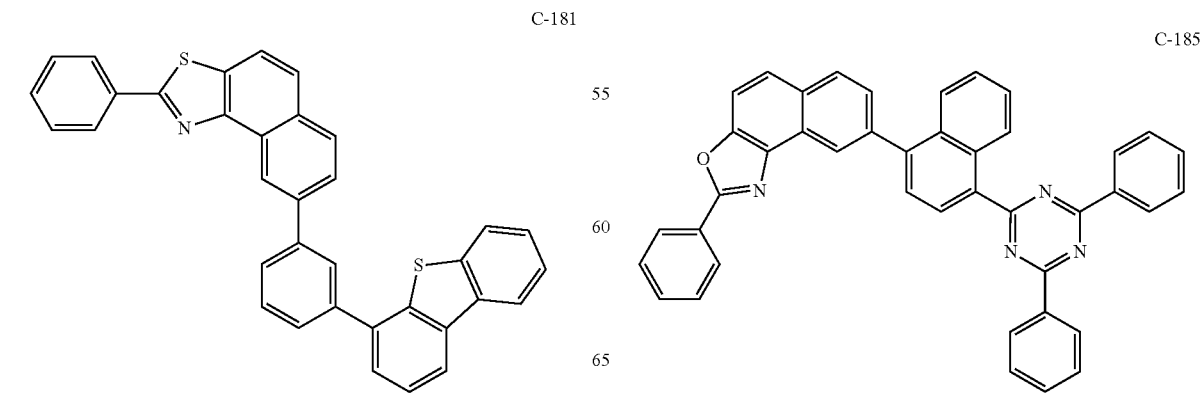

-continued
C-186
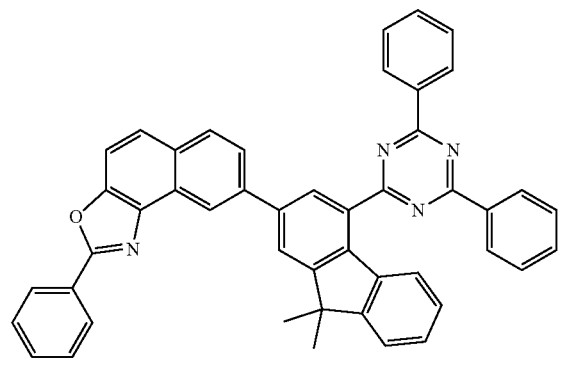
C-187
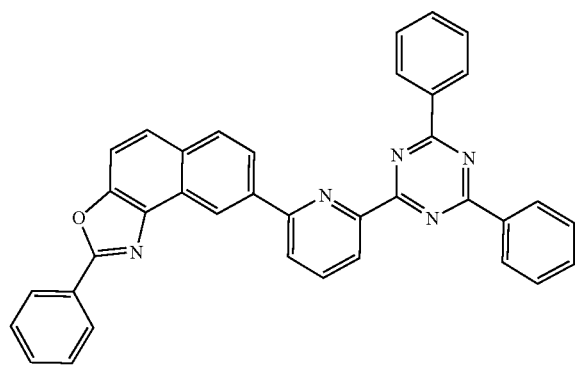
C-188
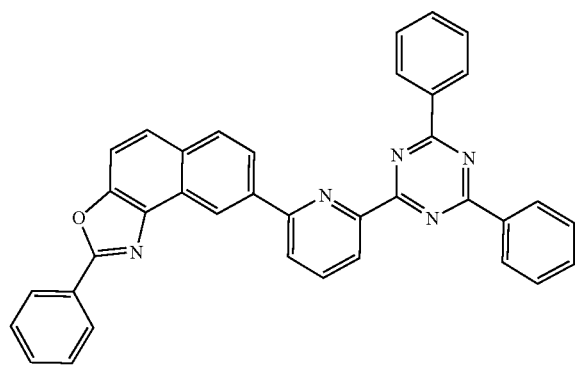
-continued
C-189
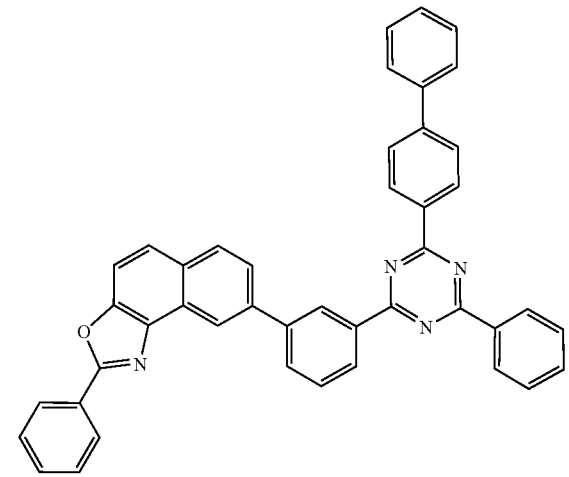
C-190
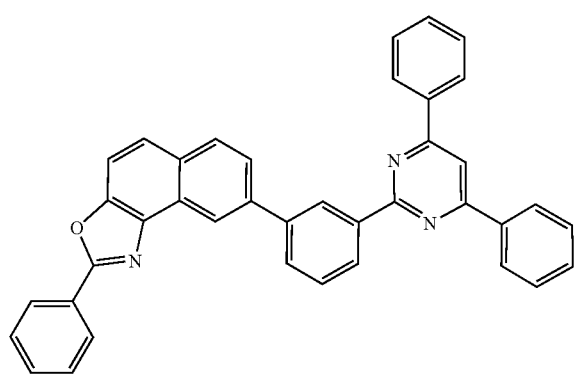
C-191
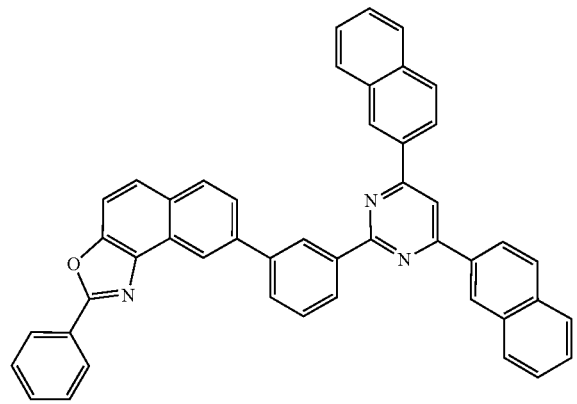

-continued
C-192
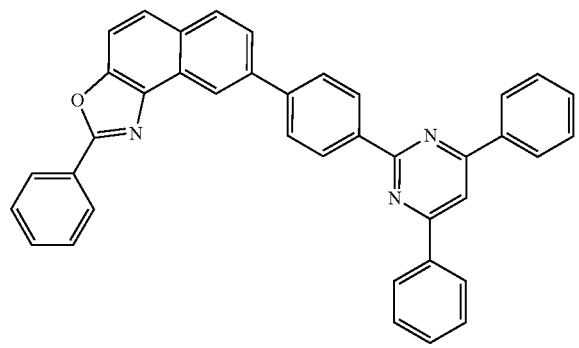
C-193
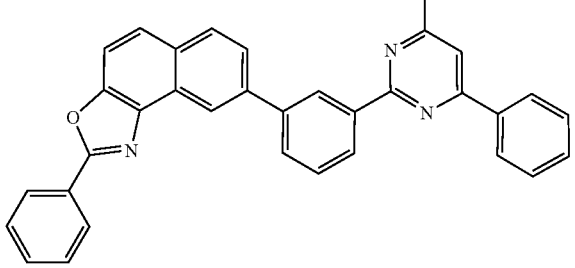
C-194
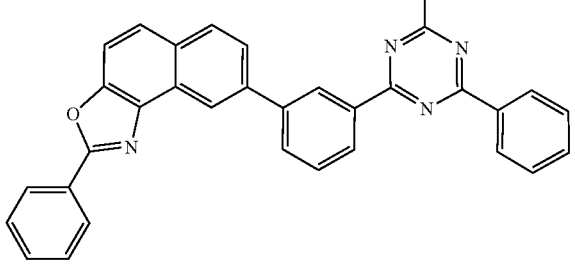
-continued
C-195
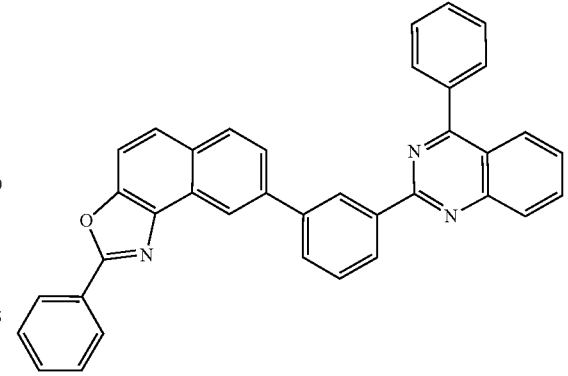
C-196
C-197
C-198
8. An organic electroluminescent device comprising the organic electroluminescent compound according to claim 1.
9. The organic electroluminescent device according to claim 8, wherein the organic electroluminescent compound according to claim 1 is comprised in at least one of an electron transport material, an electron buffer material, and a phosphorescent host material.

* * * * *